US012668808B2

(12) United States Patent　　　　(10) Patent No.:　US 12,668,808 B2
Brower-Toland et al.　　　　　　　(45) Date of Patent:　Jun. 30, 2026

(54) COMPOSITIONS AND METHODS FOR SITE DIRECTED GENOMIC MODIFICATION

(71) Applicant: Monsanto Technology LLC, St. Louis, MO (US)

(72) Inventors: Brent Brower-Toland, St. Louis, MO (US); Andrei Y. Kouranov, Chesterfield, MO (US); Rosemarie Kuehn, St. Louis, MO (US); Richard J. Lawrence, Kirkwood, MO (US); Ervin D. Nagy, Lake St. Louis, MO (US); Linda Rymarquis, High Ridge, MO (US); Veena Veena, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 309 days.

(21) Appl. No.: 18/596,328

(22) Filed: Mar. 5, 2024

(65) Prior Publication Data

US 2024/0209385 A1　　Jun. 27, 2024

Related U.S. Application Data

(62) Division of application No. 18/146,434, filed on Dec. 26, 2022, now Pat. No. 11,952,578, which is a division of application No. 17/503,235, filed on Oct. 15, 2021, now Pat. No. 11,566,254, which is a division of application No. 15/120,110, filed as application No. PCT/US2015/018104 on Feb. 27, 2015, now Pat. No. 11,186,843.

(60) Provisional application No. 61/945,700, filed on Feb. 27, 2014.

(51) Int. Cl.
*C12N 15/82*　　　(2006.01)
(52) U.S. Cl.
CPC ..... *C12N 15/8213* (2013.01); *C12N 15/8216* (2013.01)
(58) Field of Classification Search
None
See application file for complete search history.

(56) References Cited

U.S. PATENT DOCUMENTS

| | | | |
|---|---|---|---|
| 8,697,359 | B1 | 4/2014 | Zhang |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 8,945,839 | B2 | 2/2015 | Zhang |
| 9,840,713 | B2 | 12/2017 | Zhang |
| 10,519,457 | B2 | 12/2019 | Li et al. |
| 2012/0095080 | A1 | 4/2012 | Rossi et al. |
| 2014/0068797 | A1 | 3/2014 | Doudna et al. |
| 2014/0170753 | A1 | 6/2014 | Zhang |
| 2014/0227787 | A1 | 8/2014 | Zhang |
| 2014/0242664 | A1 | 8/2014 | Zhang et al. |
| 2014/0273231 | A1 | 9/2014 | Cong et al. |
| 2014/0273232 | A1 | 9/2014 | Zhang et al. |
| 2014/0273234 | A1 | 9/2014 | Zhang et al. |
| 2014/0302563 | A1 | 10/2014 | Doudna et al. |
| 2015/0067922 | A1* | 3/2015 | Yang .................. C12N 15/8289<br>435/468 |
| 2015/0082478 | A1 | 3/2015 | Cigan et al. |

FOREIGN PATENT DOCUMENTS

| | | |
|---|---|---|
| WO | 2013176772 | 11/2013 |
| WO | 2014018423 | 1/2014 |
| WO | 2014065596 | 5/2014 |
| WO | 2014150624 | 9/2014 |
| WO | 2014191518 | 12/2014 |
| WO | 2014191521 | 12/2014 |
| WO | 2014194190 | 12/2014 |
| WO | 2015026887 | 2/2015 |

OTHER PUBLICATIONS

Belhaj et al., "Plant genome editing made easy: targeted mutagenesis in model and crop plants using the CRISPR/Cas system," Plant Methods 9:39, 2013.
Cho et al.,"Targeted genonne engineering in human cells with the Cas9 RNA-guided endonuclease," Nat Biotechnol, 31:230-232, 2013.
Cong et al., "Multiplex genome engineering using CRISPR/Cas Systems," Science, 339:819-823, 2013.
Connelly et al., "Small nuclear RNA genes transcribed by either RNA polymerase II or RNA polymerase III in monocot plants share three promoter elements and use a strategy to regulate gene expression different from that used by their dicot plant counterparts," Mol Cell Biol, 14(9):5910-5919, 1994.
Doudna et al., "The new frontier of genome engineering with CRISPR-Cas9," Science, 346:1258096, 2014.
EBI Accession No. X51447, dated Mar. 13, 1990.
EBI Accession No. Z17301, dated Oct. 16, 1992.
Esvelt et al., "Concerning RNA-guided gene drives for the alteration of wild populations," Elife, 3:e03401, 2014.
(Continued)

*Primary Examiner* — Cynthia E Collins
(74) *Attorney, Agent, or Firm* — Dentons US LLP; Jan Desomer

(57) ABSTRACT

The disclosure provides novel corn, tomato, and soybean U6, U3, U2, U5, and 7SL snRNA promoters which are useful for CRISPR/Cas-mediated targeted gene modifications in plants. The disclosure also provides methods for us for U6, U3, U2, U5, and 7SL promoters in driving expression of sgRNA polynucleotides which function in a CRISPR/Cas system of targeted gene modification in plants. The disclosure also provides methods of genome modification by insertion of blunt-end DNA fragments at a site of genomic cleavage.

14 Claims, 27 Drawing Sheets

Specification includes a Sequence Listing.

(56)  References Cited

OTHER PUBLICATIONS

Gaj et al., "ZFN, TALEN, and CRISPR/Cas-based methods for genome engineering," Trends Biotechnol, 31:397-405, 2013.

GenBank CG438579.1 OGTBE38TV ZM_0.7_1.5_KB *Zea mays* genomic clone ZMMBMa0854H03, genomic survey sequence [online] Sep. 17, 2003 [retrieved Jul. 13, 2015]. Available at: http://www.ncbi.nlm.nih.gov/nucgss/CG438579.

GenBank CP000494.1 *Bradyrhizobium* sp. BTAi1, complete genome [Showing 3.19kb region from base 4149455 to 4152649] [online] Jan. 14, 2014 [retrieved Jul. 13, 2015]. Available at: http:/www.ncbi.nlm.nih.gov/nuccore/146403799?from=4149455&to41526498,sat=4&sat_key=105750 108.

Hale et al., "Essential features and rational design of CRISPR RNAs that function with the Cas RAMP module complex to cleave RNAs," Mol Cell, 45:292-302, 2012.

International Search Report and Written Opinion for PCT/US15/18104 dated Jul. 31, 2015.

Jiang et al., "Demonstration of CRISPR/Cas9/sgRNA-mediated targeted gene modification in *Arabidopsis*, tobacco, sorghum and rice," Nucl Acids Res, 41(20):e188, 2013.

Jinek et al., "A programmable dual-RNA-guided DNA endonuclease in adaptive bacterial immunity," Science, 337:816-821, 2012.

Li et al., "Heritable gene targeting in the mouse and rat using a CRISPR-Cas system," Nat Biotechnol, 31:681-683, 2013.

Li et al., "Multiplex and homologous recombination-mediated genome editing in *Arabidopsis* and Nicotiana benthamiana using guide RNA and Cas9," Nat Biotechnol, 31(8):688-691, 2013.

Li et al., "Simultaneous generation and germline transmission of multiple gene mutations in rat using CRISPR-Cas systems," Nature Biotechnol, 31:684-686, 2013.

Liang et al., "Targeted mutagenesis in Zea mays using TALENs and the CRISPR/Cas system," J Genet Genomics, 41:63-68, 2014.

Long et al., "Prevention of muscular dystrophy in mice by CRISPR/Cas9-mediated editing of germline DNA," Science, 345:1184-1188, 2014.

Mali et a/., "RNA-guided human genome engineering via Cas9," Science, 339:823-826, 2013.

Marshallsay et al, "Characterization of the U3 and U6 snRNA genes from wheat: U3 snRNA genes in monocot plants are transcribed by RNA polymerase III," Plant Mol Biol, 19:973-983, 1992.

Nekrasov et al., "Targeted mutagenesis in the model plant Nicotiana benthamiana using Cas9 RNA-guided endonuclease," Nat Biotechnol, 31(8):691-693, 2013.

Owor et al., "A rep-based hairpin inhibits replication of diverse maize streak virus isolates in a transient assay", J Gen Virol. Oct. 2011; 92(Pt 10):2458-65. Epub. Jun. 8, 2011. (Year: 2011).

Partial Supplementary European Search Report regarding European Application No. EP 15755923, dated Jun. 21, 2017.

Patron, "How to Knock-Out Plant Genes Using RNA-Guided CAS9," TSL Plasmids & Molecular Tools, <http://synbio.tsl.ac.uk/how-to-assemble-case9crispr-constructs-for-use-in-plants/> Retrieved from the internet on Jun. 1, 2017.

Qi et al., "RNA processing enables predictable programming of gene expression," Nat Biotechnol, 30:1002-1006, 2012.

Qu et al., "Artificial MicroRNA-Mediated Virus Resistance in Plants," Journal of Virology 81(12):6690-6699, 2007.

Sampson et al., "A CRISPR/Cas system mediates bacterial innate immune evasion and virulence," Nature, 497:254-257, 2013.

Shan, et al., "Targeted genome modification of crop plants using a CRISPR-Cas system," Nat Biotechnol, 31 (8):686-688, 2013.

Sugano et al., "CRISPR/Cas9-Mediated Targeted Mutagenesis in the Liverwort *Marchantia polymorpha* L.," Plant & Cell Physiology 55(3):475-481, 2014.

Van der Oost, "New tool for genome surgery," Science, 339:768-770, 2013.

Veretnik et al., "Nucleotide sequence of a maize U6 gene," Nucleic Acids Research 18(12):3661, 1990.

Wang et al., "Hairpin RNAs derived from RNA polymerase II and polymerase III promoter-directed transgenes are processed differently in plants", RNA, May 2008; 14(5):903-13. Epub. Mar. 26, 2008. (Year: 2008).

Wang et al., "One-step generation of mice carrying mutations in multiple genes by CRISPR/Cas-mediated genome engineering," Cell, 153:910-918, 2013.

Watson et al., "RNA silencing platforms in plants," FESS Letters 579:5982-5987, 2005.

Westra et al., "The CRISPRs, they are a-changin': how prokaryotes generate adaptive immunity," Annu Rev Genet, 46:311-339, 2012.

Xie et al., "RNA-Guided Genome Editing in Plants Using a CRISPR-Cas System," Molecular Plant 6(6):1975-1983, 2013.

* cited by examiner

```
                    260        280             300
                     |          |               |
ZmU6_Ch3   AA-TAGGAGA TAATGTCAA- ------GC  GTTGACGGTG CACATATATT  246
ZmU6_Ch8   AG-TAGGACA CAGTGTCAGC GC----CGC GTTGACGGAG AATATTTGCA  272
ZmU6_Ch2   GC-CAAGACC CAGGACCAGA AAGGGGGCAC GTTCACAGCG GATGCTGATG  234
ZmU6_Ch1   AAGCGTAATT TATAGGGCAC TAGTAGGACT GTCGACTGTG CGCTCGGCCC  280
Consensus  AA-NAGGACA NAGTGTCANC NAG---GCGC GTTGACCGTG CANANTNANN
```

Conservation 100%
        0%

Sequence logo 2.0bits
      0.0bits

```
                    320        340
                     |          |
ZmU6_Ch3   TGTTTTTTA AAGG----C  GTAGTGGCGT GTGTG--C-A AAAACAT---  285
ZmU6_Ch8   AAAAAGTAAA AGAGAAAGTC ATAGCGGCGT ATGTG--CCA AAAACTT---  317
ZmU6_Ch2   GGTTAGATCG ACTGATCGAG GAAGAGGAGA GCTTAATTAA GAAACGC---  281
ZmU6_Ch1   GGATAATGCG TCAAAAGCGA AGACGTGCAC GTGGGATGGG AAAACACGAA  330
Consensus  GGNTAGTTCN ACAGAANGNC NTAGNGGCGT GTGTGATCNA AAAACACAN---
```

Conservation 100%
        0%

Sequence logo 2.0bits
      0.0bits

Chromosome | Oligo

SEQ ID NO:123    CATGCCCTCTTAGGCAGTAGCCGGCCAGCATTTGAATTAAGGGATAACAGGGTAATATAGGGTAACTATAACG
SEQ ID NO:124    CATGCCCTCTTAGGCAGTAGCCGGCCAGCATTTGAATTAAGGGATAACAGGGTAATATAGGGTAACTATAACG
SEQ ID NO:125    CATGCCCTCTTAGGCAGTAGCCGGCCAGCATTT————AAGGGATAACAGGGTAATATAGGGTAACTATAACG

FIG.10A

L70c_DNA insert without micro-homology

Chromosome | Oligo

SEQ ID NO:126    AAAGCAACACTTAATCGGCTCTCAAGAAGTCCTCAAGGGATAACAGGGTAATATAGCGTAACTATAACGGTCC
SEQ ID NO:127    AAAGCAACACTTAATCGGCTCTCAAGAAGTCCTCAAGGGATAACAGGGTAATATAGCGTAACTATAACGGTCC
SEQ ID NO:128    AAAGCAACACTTAATCGGCTCTCAAGAAGTCCTCAA———————————GTAACTATAACGGTCC

FIG.10B

L70c _DNA insert with 3 bp micro-homology

Chromosome | Oligo

SEQ ID NO:129    AAAGCAACACTTAATCGGCTCTCAAGAAGTCCTCAAGGGATAACAGGGTAATATAGCGTAACTATAACGGTCC
SEQ ID NO:130    AAAGCAACACTTAATCGGCTCTCAAGAAGTCCTCAAGGGATAACAGGGTAATATAGCGTAACTATAA——GTCC
SEQ ID NO:131    AAAGCAACACTTAATCGGCTCTCAAGAAGTCCTCAA——GATAACAGGGTAATATAGCGTAACTATAA——GTCC

FIG.10C 230 bp     90 bp     230 bp

LHA–L70.4     DNA fragment     RHA–L70.4

1027 bp     90 bp     230 bp

LHA–L70.4     DNA fragment     RHA–L70.4

L70f

SEQ ID NO:144  CTATCTAGTGAAGATGTAATACTCTATGGTCTGTTTAAGGGATAACAGGGTAATATAGCGTAACTATA
SEQ ID NO:145  CTATCTAGTGAAGATGTAATACTCTATGGTCTGT-------------GGGTAATATAGCGTAACTATA

1

COMPOSITIONS AND METHODS FOR SITE DIRECTED GENOMIC MODIFICATION

CROSS REFERENCE TO RELATED APPLICATIONS

This application is a divisional of U.S. patent application Ser. No. 18/146,434, filed Dec. 26, 2022, which is a divisional of U.S. patent application Ser. No. 17/503,235, filed Oct. 15, 2021, now U.S. Pat. No. 11,566,254, which is a divisional of U.S. patent application Ser. No. 15/120,110, filed Aug. 18, 2016, now U.S. Pat. No. 11,186,843, which is a 371 National Stage application of International Application Serial No. PCT/US2015/018104, filed Feb. 27, 2015, which claims the priority of U.S. Provisional Appl. Ser. No. 61/945,700, filed Feb. 27, 2014, the entire disclosure of which is incorporated herein by reference.

INCORPORATION OF SEQUENCE LISTING

The sequence listing that is contained in the file named "MONS350USD3_ST26.xml", which is 382 kilobytes (measured in MS-WINDOWS) and created on Feb. 28, 2024, is filed herewith by electronic submission and incorporated herein by reference.

BACKGROUND

Field

The disclosure relates to the field of biotechnology. More specifically, the disclosure provides a method of introducing recombinant blunt-end double-strand DNA fragments into the genome of a plant by introducing a double-strand break in the genome and novel plant promoters beneficial for the expression of, for instance, non-protein-coding small RNAs for CRISPR-mediated genome modification.

Description of Related Art

Site-specific recombination has potential for application across a wide range of biotechnology-related fields. Meganucleases, zinc finger nucleases (ZFNs), and transcription activator-like effector nucleases (TALENs) containing a DNA-binding domain and a DNA-cleavage domain enable genome modification. While meganucleases, ZFNs, and TALENs, are effective and specific, these technologies require generation through protein engineering of one or more components for each genomic site chosen for modification. Recent advances in application of clustered, regularly interspaced, short palindromic repeats (CRISPR) have illustrated a method of genome modification that may be as robust as the comparable systems (meganucleases, ZFNs, and TALENs), yet has the advantage of being quick to engineer.

The Clustered Regularly Interspersed Short Palindromic Repeats (CRISPRs) system constitutes an adaptive immune system in prokaryotes that targets endonucleolytic cleavage of invading phage. The system is composed of a protein component (Cas) and a guide RNA (gRNA) that targets the protein to a specific locus for endonucleolytic cleavage. This system has been successfully engineered to target specific loci for endonucleolytic cleavage of mammalian, zebrafish, drosophila, nematode, bacteria, yeast, and plant genomes.

SUMMARY

In one aspect the invention provides a recombinant DNA construct comprising a snRNA promoter selected from the group consisting of: a U6 promoter, a U3 promoter, a U2 promoter, a U5 promoter, and a 7SL promoter; operably linked to a sequence encoding a single-guide RNA (sgRNA), wherein the sequence of said snRNA promoter comprises SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO:12, SEQ ID NO: 13, SEQ ID NO:14, SEQ ID NO:15, SEQ ID NO:16, SEQ ID NO:17, SEQ ID NO:18, SEQ ID NO:19, SEQ ID NO:20, SEQ ID NOs: 146-149, SEQ ID NOs: 160-201, or SEQ ID NOs:247-283; or a fragment thereof, wherein the fragment is at least 140 bp in length.

In one embodiment the sequence of said U6 promoter may comprise any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO:11, SEQ ID NO: 12, SEQ ID NO: 13, SEQ ID NO:14, SEQ ID NO:15, SEQ ID NO:16, SEQ ID NO:17, SEQ ID NO:18, SEQ ID NO:19, SEQ ID NO:20, SEQ ID NOs: 146-149, SEQ ID NOs: 160-166, SEQ ID NOs:200-201, or SEQ ID NO:283, or a fragment thereof, wherein the fragment is at least 140 bp in length. In a further embodiment, the sequence of said U6 promoter may comprise SEQ ID NO:7. In another embodiment the sequence of said U6 promoter may comprise a sequence selected from the group consisting of: SEQ ID NO: 17, SEQ ID NO:18, SEQ ID NO: 19, and SEQ ID NO:20. In yet another embodiment the sequence of said U3 promoter may comprise any of SEQ ID NOs: 167-171 or SEQ ID NOs: 178-182, or a fragment thereof; wherein the fragment is at least 140 bp in length. In still yet another embodiment the sequence of said U2 promoter comprises any of SEQ ID NOs: 183-187, SEQ ID NOs: 192-199, or SEQ ID NOs:247-275, or a fragment thereof; wherein the fragment is at least 140 bp in length. In another embodiment the sequence of said U5 promoter comprises any of SEQ ID NOs:188-191, or SEQ ID NOs: 276-282, or a fragment thereof; wherein the fragment is at least 140 bp in length. In a further embodiment the sequence of said 7SL promoter comprises any of SEQ ID NOs: 172-177, or a fragment thereof; wherein the fragment is at least 140 bp in length. The recombinant DNA construct may further comprise a transcription termination sequence.

The recombinant DNA construct may also further comprise a sequence encoding a promoter operably linked to a sequence encoding a clustered, regularly interspaced, short palindromic repeats (CRISPR)-associated Cas endonuclease gene product. In certain embodiments of the recombinant DNA construct, the Cas endonuclease gene product may be further operably linked to a nuclear localization sequence (NLS). Further, in certain embodiments of the contemplated recombinant DNA construct, the sequence encoding said Cas endonuclease may be selected from the group consisting of SEQ ID NO:27, SEQ ID NO:68, and SEQ ID NO:97, SEQ ID NO:119, and SEQ ID NO:136.

Another aspect of the invention provides a recombinant DNA construct comprising a snRNA promoter selected from the group consisting of: a U6 promoter, a U3 promoter, a U2 promoter, a U5 promoter, and a 7SL promoter; operably linked to a sequence specifying a non-coding RNA, wherein the sequence of said snRNA promoter comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO: 12, SEQ ID NO: 13, SEQ ID NO: 14, SEQ ID NO:15, SEQ ID NO: 16, SEQ ID NO: 17, SEQ ID NO: 18, SEQ ID NO: 19, SEQ ID NO:20, SEQ ID NOs: 146-149, SEQ ID NOs:

160-201 or SEQ ID NOs:247-283, or a fragment thereof, wherein the fragment is at least 140 bp in length. In some embodiments the non-coding RNA is selected from the group consisting of: a microRNA (miRNA), a miRNA precursor, a small interfering RNA (siRNA), a small RNA (22-26 nt in length) and precursor encoding same, a hetero-chromatic siRNA (hc-siRNA), a Piwi-interacting RNA (piRNA), a hairpin double strand RNA (hairpin dsRNA), a trans-acting siRNA (ta-siRNA), and a naturally occurring antisense siRNA (nat-siRNA).

Certain embodiments if the invention further comprise such a recombinant DNA construct, wherein the sequence of said U3 promoter comprises any of SEQ ID NOs: 167-171 and SEQ ID NOs: 178-182, or a fragment thereof; wherein the fragment is at least 140 bp in length. In another embodi-ment of the recombinant DNA construct, the sequence of said U2 promoter comprises any of SEQ ID NOs: 183-187, SEQ ID NOs: 192-199, or SEQ ID NOs:247-275, or a fragment thereof; wherein the fragment is at least 140 bp in length. In yet another embodiment of the recombinant DNA construct, the sequence of said U5 promoter comprises any of SEQ ID NOs:188-191, or SEQ ID NOs:276-282, or a fragment thereof; wherein the fragment is at least 140 bp in length. Still further, the invention provides an embodiment wherein the sequence of said U6 promoter may comprise any of SEQ ID NOs: 1-20, SEQ ID NOs: 146-149, SEQ ID NOs: 160-166, SEQ ID NOs:200-201, or SEQ ID NO:283, or a fragment thereof; wherein the fragment is at least 140 bp in length. Another embodiment comprises the recombi-nant DNA construct wherein the sequence of said 7SL promoter comprises any of SEQ ID NOs: 172-177, or a fragment thereof; wherein the fragment is at least 140 bp in length.

Another aspect of the invention provides a cell compris-ing a recombinant DNA construct as described above. In certain embodiments the cell is a plant cell.

The invention further provides a method of introducing a double-strand break in the genome of a cell, comprising introducing in said cell: a) at least one recombinant DNA construct of claim 1; and b) a second recombinant DNA construct comprising a sequence encoding a promoter oper-ably linked to a sequence encoding a clustered, regularly interspaced, short palindromic repeats (CRISPR)-associated Cas endonuclease gene product operably linked to a nuclear localization sequence (NLS). In one embodiment of such a method, the sequence of the U6 promoter comprises SEQ ID NO:7. In another embodiment of the method, the U6 pro-moter comprises a sequence selected from the group con-sisting of: SEQ ID NO:17, SEQ ID NO:18, SEQ ID NO: 19, and SEQ ID NO:20. In yet another embodiment of the method, the sequence encoding said Cas endonuclease is selected from the group consisting of SEQ ID NO:27, SEQ ID NO:68, and SEQ ID NO:97, SEQ ID NO:119, and SEQ ID NO: 136.

The invention further provides a method of introducing a double-strand break in the genome of a cell, comprising introducing to said cell at least one recombinant DNA construct which comprises a recombinant DNA construct comprising a snRNA promoter selected from the group consisting of: a U6 promoter, a U3 promoter, a U2 promoter, a U5 promoter, and a 7SL promoter; operably linked to a sequence encoding a single-guide RNA (sgRNA), wherein the sequence of said snRNA promoter comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO: 12, SEQ ID NO: 13, SEQ ID NO: 14, SEQ ID NO: 15, SEQ ID NO:16, SEQ ID NO:17, SEQ ID NO:18, SEQ ID NO: 19, SEQ ID NO:20, SEQ ID NOs: 146-149, SEQ ID NOs: 160-201, or SEQ ID NOs:247-283; or a fragment thereof, wherein the fragment is at least 140 bp in length, and also further comprises a sequence encoding a promoter operably linked to a sequence encoding a clustered, regularly inter-spaced, short palindromic repeats (CRISPR)-associated Cas endonuclease gene product.

In certain embodiments of the method, the sequence of said U6 promoter comprises SEQ ID NO:7. In other embodi-ments the U6 promoter comprises a sequence selected from the group consisting of: SEQ ID NO:17, SEQ ID NO:18, SEQ ID NO:19, and SEQ ID NO:20. In some embodiments of the method the sequence encoding the Cas endonuclease is selected from the group consisting of SEQ ID NO:27, SEQ ID NO:68, and SEQ ID NO:97, SEQ ID NO: 119, and SEQ ID NO:136.

Another aspect of the invention provides a method of genome modification comprising: a) introducing a double-strand break at a selected site in the genome of a plant cell, and b) introducing into said plant cell a recombinant blunt-end double-strand DNA fragment, wherein said recombinant blunt-end double-strand DNA fragment is incorporated into said double strand break by endogenous DNA repair. The method may comprise genome modification such as produc-tion of a modified linkage block, linking two or more QTLs, disrupting linkage of two or more QTLs, gene insertion, gene replacement, gene conversion, deleting or disrupting a gene, transgenic event selection, transgenic trait donor selec-tion, transgene replacement, or targeted insertion of at least one nucleic acid of interest. In some embodiments of the method the double stranded break is introduced by an endonuclease. In certain embodiments the endonuclease may be selected from the group consisting of: a TALEN endonuclease; a CRISPR endonuclease; a meganuclease comprising a "LAGLIDADG," (SEQ ID NO:284) "GIY-YIG," "His-Cys box," or HNH sequence motif; and a Zinc finger nuclease. In particular embodiments the endonuclease is a TALEN endonuclease and TALEN expression con-structs are introduced into the plant cell, wherein about 0.1 pmol of each TALEN expression construct is introduced into the plant cell. Further, in the method the plant cell may be a protoplast or may have been, or is being, grown in a plant cell culture. In certain embodiments of the method the plant cell is selected from the group consisting of: a soybean plant cell; a corn plant cell; a rice plant cell; a wheat plant cell; a turfgrass plant cell; a cotton plant cell; and a canola plant cell. In other embodiments of the method the recombinant blunt-end double-strand DNA fragment does not comprise a region of homology to the selected site in the genome.

Embodiments of the method are contemplated wherein about 0.03 to about 0.3 fmol of recombinant blunt-end double-strand DNA fragment is introduced into said plant cell. In particular embodiments about 0.15 fmol of recom-binant blunt-end double-strand DNA fragment is introduced into said plant cell. Further, the blunt-end double-strand DNA fragment may comprise on the 5' end, or the 3' end, or both the 5' and 3' ends, a region with microhomology to a sequence comprising one or both ends of said double-strand break in the genome. Some embodiments comprise a method wherein the region of microhomology is selected from a sequence 1 bp, 2 bp, 3 bp, 4, bp, 5 bp, 6 bp, 7 bp, 8 bp, 9 bp, or 10 bp in length. In a particular embodiment of the method the region of microhomology is 3 bp in length.

The method may comprise introduction of a double-strand break in step a) as described above, by providing said cell with an endonuclease designed to target a selected target site in the genome of said cell. Further, the endonuclease may be provided by at least one recombinant DNA construct encoding the endonuclease. In an embodiment, the endonuclease is provided by delivering an mRNA encoding the endonuclease or the endonuclease to the plant cell. In particular embodiments The endonuclease is selected from the group consisting of: a TALEN endonuclease; a Zinc finger endonuclease; a meganuclease; and a CRISPR endonuclease. Additional embodiments may comprise introduction of a double-strand break in step a) by providing said cell with a recombinant DNA construct encoding a promoter operably linked to a sequence encoding a clustered, regularly interspaced, short palindromic repeats (CRISPR)-associated Cas endonuclease gene product and a recombinant DNA construct comprising a U6, U3, U2, U5, or 7SL promoter operably linked to a sequence encoding a single-guide RNA (sgRNA) designed to target a selected target site in the chromosome of said cell. In particular embodiments the Cas endonuclease gene product may be further operably linked to at least one nuclear localization sequence (NLS).

In certain embodiments of the method the sequence of said U6, U3, U2, U5, or 7SL promoter may comprise SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NOs: 146-149, SEQ ID NOs: 160-201 or SEQ ID NOs:247-283, or a fragment thereof; wherein the fragment is at least 140 bp in length and comprises a transcription termination sequence. In particular embodiments the U6 promoter may comprise a sequence selected from the group consisting of: SEQ ID NOs: 1-20, SEQ ID NOs: 146-149, SEQ ID NOs: 160-166, SEQ ID NOs:200-201, and SEQ ID NO:283, or a fragment thereof; wherein the fragment is at least 140 bp in length comprising a transcription termination sequence. In alternative embodiments the U6 promoter may comprise a sequence selected from the group consisting of: SEQ ID NO:17, SEQ ID NO:18, SEQ ID NO: 19, and SEQ ID NO:20. In further embodiments the sequence of said U3 promoter may comprise any of SEQ ID NOs: 167-171 or SEQ ID NOs:178-182, or a fragment thereof; wherein the fragment is at least 140 bp in length. In still further embodiments the sequence of said U5 promoter comprises any of SEQ ID NOs: 188-191, or SEQ ID NOs:276-282, or a fragment thereof; wherein the fragment is at least 140 bp in length. Additionally, the sequence of said U2 promoter may comprise any of SEQ ID NOs: 183-187, SEQ ID NOs: 192-199, or SEQ ID NOs:247-275, or a fragment thereof; wherein the fragment is at least 140 bp in length. In yet other embodiments the sequence of said 7SL promoter comprises any of SEQ ID NOs: 172-177, or a fragment thereof, wherein the fragment is at least 140 bp in length.

Embodiments are also contemplated wherein the recombinant DNA construct encoding a promoter operably linked to a sequence encoding a clustered, regularly interspaced, short palindromic repeats (CRISPR)-associated Cas endonuclease gene product, and the recombinant DNA construct comprising a U6, U3, U2, U5, or 7SL promoter operably linked to a sequence encoding a single-guide RNA (sgRNA) is designed to target a selected target site in the chromosome of said cell, are on the same construct. Other embodiments of the method may comprise use of a recombinant DNA construct encoding a promoter operably linked to a sequence encoding a clustered, regularly interspaced, short palindromic repeats (CRISPR)-associated Cas endonuclease gene product and the recombinant DNA construct comprising a U6, U3, U2, U5, or 7SL promoter is operably linked to a sequence encoding a single-guide RNA (sgRNA) designed to target a selected target site in the chromosome of said cell are on at least two constructs.

A further aspect of the invention comprises a plant cell comprising a targeted recombinant sited-directed integration of a blunt-end double-strand DNA fragment. Further provided are a plant, plant part, or plant seed comprising a targeted recombinant sited-directed integration of a blunt-end double-strand DNA fragment.

A still further aspect of the invention comprises: a method of genome modification comprising: a) introducing a double-strand break in the genome of a plant cell by introducing a double-strand break in the genome of a cell, comprising introducing in said cell: a) at least one recombinant DNA construct of claim 1; and b) a second recombinant DNA construct comprising a sequence encoding a promoter operably linked to a sequence encoding a clustered, regularly interspaced, short palindromic repeats (CRISPR)-associated Cas endonuclease gene product operably linked to a nuclear localization sequence (NLS); and b) introducing into said plant cell a recombinant blunt-end double-strand DNA fragment, wherein said recombinant blunt-end double-strand DNA fragment is incorporated into said double strand break by endogenous DNA repair.

A further aspect of the invention comprises a method of genome modification comprising: a) introducing a double-strand break in the genome of a plant cell as described above, and b) introducing into said plant cell a recombinant blunt-end double-strand DNA fragment, wherein said recombinant blunt-end double-strand DNA fragment is incorporated into said double strand break by endogenous DNA repair.

Yet another aspect of the invention comprises a recombinant DNA construct comprising at least a first expression cassette comprising a U6, U3, U2, U5, or 7SL promoter operably linked to a sequence encoding a single-guide RNA (sgRNA), wherein the sequence of said promoter comprises any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO:11, SEQ ID NO:12, SEQ ID NO: 13, SEQ ID NO: 14, SEQ ID NO: 15, SEQ ID NO: 16, SEQ ID NO:17, SEQ ID NO: 18, SEQ ID NO: 19, SEQ ID NO:20, SEQ ID NOs: 146-149, SEQ ID NOs: 160-201, or SEQ ID NOs:247-283, or a fragment thereof; wherein the fragment is at least 140 bp in length. In certain embodiments the recombinant DNA construct further comprises at least a second expression cassette, wherein the sequence encoding the first sgRNA is distinct from the sequence encoding the second sgRNA. The recombinant DNA construct may also comprise a construct wherein the promoter operably linked to the sequence encoding the first sgRNA is distinct from the promoter operably linked to the sequence encoding the second sgRNA. In certain embodiments the construct comprises flanking left and right homology arms (HA) which are each about 200-1200 bp in length. In particular embodiments the homology arms are about 230 to about 1003 bp in length.

Another aspect of the invention provides a method of quantifying the activity of a nuclease by detecting integrated DNA fragments by determining the rate of homologous recombination (HR) mediated targeted integration by use of using digital PCR or quantitative PCR.

Yet another aspect of the invention comprises a recombinant DNA construct comprising: a) a first snRNA promoter selected from the group consisting of: a U6 promoter, a U3 promoter, a U2 promoter, a U5 promoter, and a 7SL promoter; operably linked to a sequence encoding a non-coding RNA, and b) a second snRNA promoter selected from the group consisting of: a U6 promoter, a U3 promoter, a U2 promoter, a U5 promoter, and a 7SL promoter; operably linked to a sequence encoding a non-coding RNA, wherein the first snRNA promoter and the second snRNA promoter are different. In certain embodiments the sequence encoding the first snRNA promoter and the sequence encoding the second snRNA promoter each comprise SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO:20, SEQ ID NOs: 146-149, SEQ ID NOs: 160-201, or SEQ ID NOs:247-283, or a fragment thereof; wherein the fragment is at least 140 bp in length. Further, a recombinant DNA construct, wherein the first and second snRNA promoter are U6 promoters and the sequences encoding the first and second snRNA promoters are each selected from the group consisting of: SEQ ID NOs: 1-8, SEQ ID NOs: 17-20, and SEQ ID NOs:200-201 is also provided in certain embodiments.

Thus, a recombinant DNA construct wherein the first and second snRNA promoter are U6 promoters and the sequences encoding the first and second snRNA promoters are each selected from the group consisting of: SEQ ID NOs: 12-16, SEQ ID NOs: 160-166, and SEQ ID NO:283, is also provided. Alternatively, a recombinant DNA construct, wherein the first and second snRNA promoter are U6 promoters and the sequences encoding the first and second snRNA promoters are each selected from the group consisting of: SEQ ID NOs:9-11 and SEQ ID NO:146-149, is provided.

A recombinant DNA construct, wherein the first and second snRNA promoter are U2 promoters and the sequences encoding the first and second snRNA promoters are each selected from the group consisting of SEQ ID NOs: 183-187 and SEQ ID NOs:192-199 is also contemplated. Additionally, certain embodiments of the invention comprise a recombinant DNA construct wherein the first and second snRNA promoter are U2 promoters and the sequences encoding the first and second snRNA promoters are each selected from the group consisting of SEQ ID NOs:247-275.

Yet other embodiments comprise a recombinant DNA construct, wherein the first and second snRNA promoter are U3 promoters and the sequences encoding the first and second snRNA promoters are each selected from the group consisting of SEQ ID NOs:178-182. Still other embodiments of the invention comprise a recombinant DNA construct, wherein the first and second snRNA promoter are U3 promoters and the sequences encoding the first and second snRNA promoters are each selected from the group consisting of SEQ ID NOs: 167-171.

Alternatively, the recombinant DNA construct may comprise first and second snRNA promoter which are U5 promoters and wherein the sequences encoding the first and second snRNA promoters are each selected from the group consisting of SEQ ID NOs: 188-191. Alternatively provided are recombinant DNA constructs wherein the first and second snRNA promoter are U5 promoters and the sequences encoding the first and second snRNA promoters are each selected from the group consisting of SEQ ID NOs:276-282.

Certain embodiments of the invention provide a recombinant DNA construct wherein the first and second snRNA promoter are 7SL promoters and the sequences encoding the first and second snRNA promoters are each selected from the group consisting of SEQ ID NOs: 175-177. In other embodiments the recombinant DNA construct wherein the first and second snRNA promoter are 7SL promoters and the sequences encoding the first and second snRNA promoters are each selected from the group consisting of SEQ ID NOs: 172-174.

Also contemplated are embodiments wherein the recombinant DNA construct comprises a first snRNA promoter which is a U6 promoter and a second snRNA promoter is also present and is selected from the group consisting of: a U3 promoter, a U2 promoter, a U5 promoter, and a 7SL promoter. Other embodiments include a recombinant DNA construct wherein the first snRNA promoter is a U3 promoter and the second snRNA promoter is selected from the group consisting of: a U6 promoter, a U2 promoter, a U5 promoter, and a 7SL promoter. Alternatively in the recombinant DNA construct, the first snRNA promoter is a U2 promoter and the second snRNA promoter may be selected from the group consisting of: a U6 promoter, a U3 promoter, a U5 promoter, and a 7SL promoter; or the first snRNA promoter is a U5 promoter and the second snRNA promoter is selected from the group consisting of: a U6 promoter, a U2 promoter, a U3 promoter, and a 7SL promoter. Further, the recombinant DNA construct may comprise a first snRNA promoter which is a 7SL promoter and the second snRNA promoter may be selected from the group consisting of: a U6 promoter, a U2 promoter, a U3 promoter, and a U5 promoter.

Other contemplated embodiments of the invention include a recombinant DNA construct as described above, wherein the sequences encoding the first and second snRNA promoters are each selected from the group consisting of: SEQ ID NOs:1-8, SEQ ID NOs:17-20, SEQ ID NOs:200-201, SEQ ID NOs: 183-187, SEQ ID NOs: 192-199, SEQ ID NOs: 178-182, SEQ ID NOs: 188-191, and SEQ ID NOs: 175-177. In certain embodiments of the recombinant DNA construct, the sequences encoding the first and second snRNA promoters are each selected from the group consisting of: SEQ ID NOs: 12-16, SEQ ID NOs: 160-166, SEQ ID NO:283, SEQ ID NOs:247-275, SEQ ID NOs: 167-171, SEQ ID NOs: 276-282, and SEQ ID NOs: 172-174.

The recombinant DNA construct may further comprise a sequence specifying one or more additional snRNA promoters selected from the group consisting of: a U6 promoter, a U3 promoter, a U2 promoter, a U5 promoter, and a 7SL promoter; operably linked to a sequence encoding a non-coding RNA, wherein the first snRNA promoter, the second snRNA promoter, and each of the one or more additional snRNA promoters are different. In particular embodiments of the recombinant DNA construct, the sequence specifying said one or more additional snRNA promoters is selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NOs: 146-149, SEQ ID NOs: 160-201, or SEQ ID NOs:247-283; or a fragment thereof, wherein the fragment is at least 140 bp in length. Further, the recombinant DNA construct may comprise 3, 4, 5, 6, 7, 8, 9 or 10 snRNA promoters.

In some embodiments of the recombinant DNA construct, the non-coding RNAs are sgRNAs targeting different selected target sites in a chromosome of a plant cell. The recombinant DNA constructs may further comprise a sequence encoding a promoter operably linked to a sequence encoding a clustered, regularly interspaced, short palindromic repeats (CRISPR)-associated Cas endonuclease gene product.

Yet another aspect of the invention provides a method of genome modification comprising: a) introducing double-strand breaks at two or more selected sites in the genome of a plant cell by providing said cell with a clustered, regularly interspaced, short palindromic repeats (CRISPR)-associated Cas endonuclease and a recombinant DNA construct wherein the non-coding RNAs are sgRNAs targeting different selected target sites in a chromosome of a plant cell, and b) introducing into said plant cell one or more exogenous double-strand DNA fragment; wherein said exogenous double-strand DNA fragments are incorporated into said double strand breaks by endogenous DNA repair. In some embodiments said one or more exogenous double-strand DNA fragments are blunt-ended. In certain embodiments of the method, said one or more exogenous double-strand DNA fragments comprise a region of homology to a selected site in the genome. In other embodiments the exogenous double-strand DNA fragments comprise regions of homology to different selected sites in the genome.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 1A) and (FIG. 1B) The sequence consensus, and (SEQ ID NOs:285-292) percent conservation are presented below the alignments. (FIG. 1B) The thick arrow indicates the transcription start site; upstream from the transcriptional start site are a 'TATA Box', an Upstream Sequence Element (USE), and Monocot-Specific Promoter (MSP) elements, each marked with heavy lined boxes; the stretch of seven thymidine bases (poly-T) at the 3' end is the transcription termination signal. The sequences in FIG. 1.A and FIG. 1.B correspond the following: ZmU6_Ch1 represented by SEQ ID NO:98; ZmU6_Ch2 represented by SEQ ID NO:99; ZmU6_Ch3 represented by SEQ ID NO:100; ZmU6_Ch8 represented by SEQ ID NO: 101.

(FIG. 5B) blunt-end oligonucleotide without microhomology used for insertion at a corn genomic target site (SEQ ID NO:293 pre-insertion and SEQ ID NOs:294 and 295 after insertion; (FIG. 5C) blunt-end oligonucleotide with microhomology ends used for insertion at a corn genomic target site (SEQ ID NO:293 pre-insertion and SEQ ID NOs:294 and 295 after insertion; (FIG. 5D) fragment analysis profile of PCR amplicons spanning the oligo-chromosome junction in test (upper panel) and negative control samples (bottom panel) of the oligonucleotide integration assay (where the arrow indicates the expected peak); and (FIG. 5E) DNA sequences of oligonucleotide-chromosome junctions (SEQ ID NOs:294 and 295) at the Zm_L70c corn genomic target site confirming integrations of both full-length (integration 1; SEQ ID NO:103) and truncated oligonucleotides (integration 2; SEQ ID NO: 104), the expected sequence (template) is presented as SEQ ID NO:102.

(FIG. 7B) a CRISPR/Cas multiplex system to evaluate gene linkage of multiple QTL candidate genes. Where likelihood of odds (LOD) is a statistical measure for genetic linkage; an LOD of 3 means that it is 1000× more likely that a QTL exists in the interval than that there is no QTL.

FIGS. 10A-10C. Sequence confirmation for targeted integrations of blunt-end, double-strand DNA fragments into chromosomes of corn protoplasts transformed with CRISPR/Cas9 and sgRNA expression constructs. For all panels FIGS. 10A, 10B, 10C, the top sequence is the expected sequence of one junction of the target site and the blunt-end double-strand DNA fragment (underlined sequence) included in the experiment. FIG. 10A. Corn chromosome site Zm7 targeted by CRISPR/Cas9 constructs and with blunt-end double-strand DNA fragment formed by annealed DNA fragments represented by SEQ ID NO:115 and SEQ ID NO:116. FIG. 10B. Corn chromosome site L70c targeted by CRISPR/Cas9 constructs and with blunt-end double-strand DNA fragment without micro-homology sequences formed by annealed DNA fragments represented by SEQ ID NO:45 and SEQ ID NO:46. FIG. 10C. Corn chromosome site L70c targeted by CRISPR/Cas9 constructs and with blunt-end double-strand DNA fragment with 3 bp micro-homology sequences at each end of the DNA fragment formed by annealed DNA fragments represented by SEQ ID NO:121 and SEQ ID NO:122.

FIG. 13A. Schematic for HR-cassette construct for targeting the corn chromosome site Zm7 with LHA and RHA of 240 and 230 bp in length, respectively. FIG. 13B. Schematic for HR-cassette construct for targeting the corn chromosome site Zm7 with LHA and RHA of 240 and 1003 bp in length, respectively.

FIG. 14A. Schematic for HR-cassette construct for targeting the corn chromosome site L70.4 with both the LHA and RHA 230 bp in length. FIG. 14B. Schematic for HR-cassette construct for targeting the corn chromosome site L70.4 with LHA and RHA of 1027 bp and 230 bp in length, respectively.

FIG. 15A. Graphical presentation of data showing percent targeted integration rates in transfected corn protoplasts using StCas9 CRISPR constructs targeting native corn chromosomal target sites L70c, L70f, and L70g. The controls lacked a StCas9 expression cassette construct in the transfection mixture. FIG. 15B. Sequence alignment of expected integration of the blunt-end, double-strand DNA fragment at the L70f target site (SEQ ID NO: 144) and one example of target site integration with indel of the DNA fragment sequence (SEQ ID NO:145).

FIG. 16A. Chromosomal integration rates using constructs with the corn chromosome 8 U6 promoter or one of three separate chimeric U6 promoters driving sgRNA expression in CRISPR/Cas9 system to target three different corn chromosomal target sites. Targeted integration was measured by ddPCR assay using MGB TaqMan probes. FIG. 16B. Chromosomal integration rates using constructs with the corn chromosome 8 U6 promoter or one of three separate chimeric U6 promoters driving sgRNA expression in CRISPR/Cas9 system to target three different corn chromosomal target sites. Targeted integration was measured by ddPCR assay using EvaGreen® intercalating dye.

FIG. 17A. Schematic of PCR screening strategy to detect CRISPR/Cas9 induced mutation by NHEJ at tomato invertase inhibitor target site 2 (TS2), resulting in mutation of restriction endonuclease site SmlI. FIG. 17B. Photograph of PCR amplicons run on an agarose gel showing undigested amplicons and SmlI digested amplicons to detect CRISPR/Cas9 induced mutation at tomato invertase inhibitor target site 2. FIG. 17C. Multiple sequence alignment of sequences of PCR amplicons from CRISPR/Cas9 induced mutation by NHEJ at the tomato invertase inhibitor target site 2.

FIG. 18A. Graphical representation of data showing normalized GUS mRNA levels from soybean cotyledon protoplast assays with recombinant expression constructs with U6, U3, and 7SL promoters. FIG. 18B. Graphical representation of data showing normalized GUS mRNA levels from corn leaf protoplast assays with recombinant expression constructs with U6, U3, 7SL, U2, or U5 promoters.

DETAILED DESCRIPTION

Figure 1A:
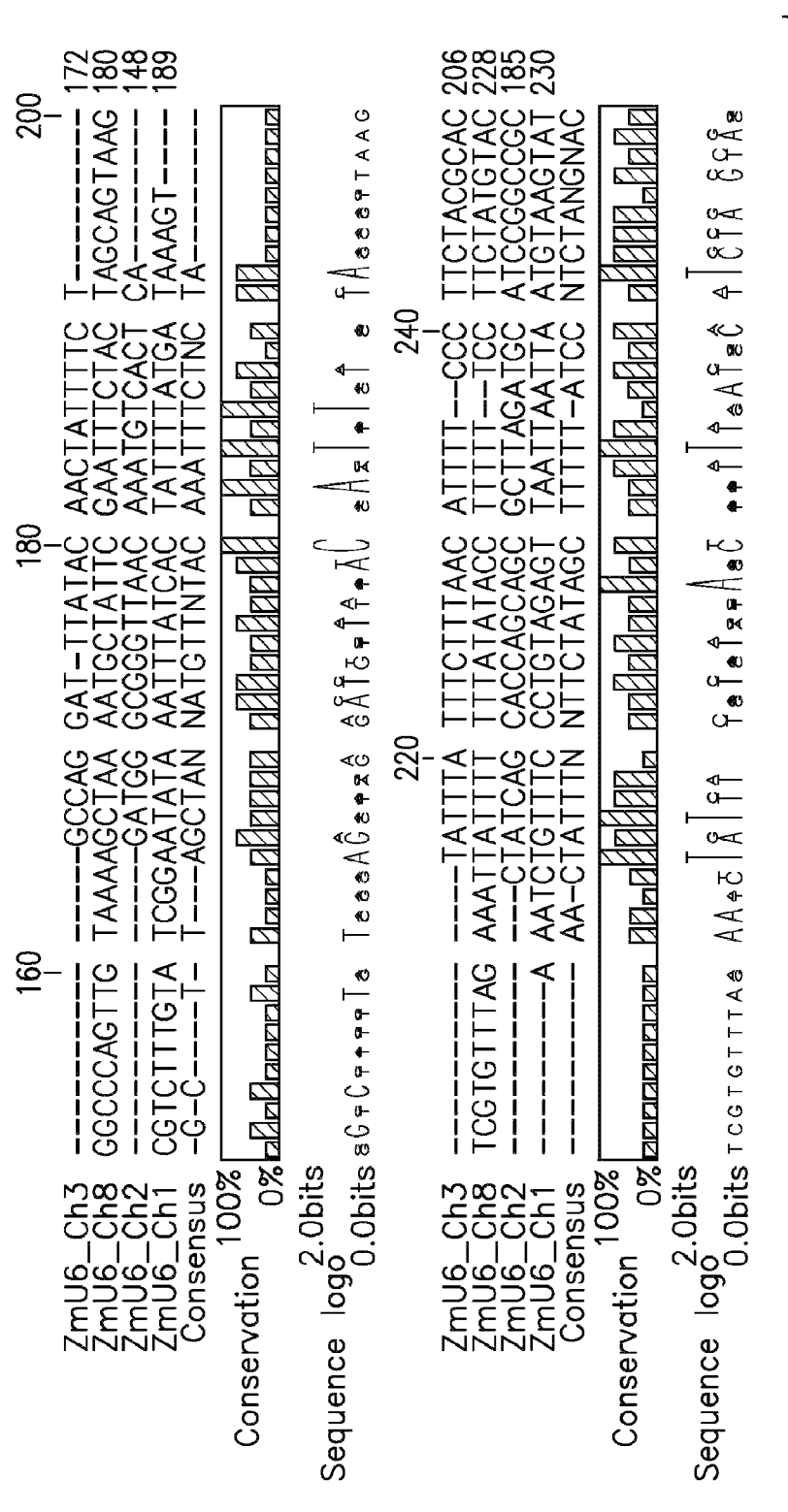
FIGS. 1A-1B: Nucleotide sequence alignment of four native corn U6 small nuclear RNA (snRNA) genes, including their putative promoters from chromosomes 1, 2, 3, and 8.

The disclosure provides novel promoters from *Zea mays* and other plants, and methods for their use that include targeted gene modification of a plant genome using transgenic expression of a gene, or genes, involved in the Clustered Regularly Interspersed Short Palindromic Repeats (CRISPR) system found in many bacteria. For instance, the disclosure provides, in one embodiment, DNA constructs encoding at least one expression cassette including a U6 promoter disclosed herein and a sequence encoding a single-guide RNA (sgRNA). Methods for causing a CRISPR system to modify a target genome are also provided, as are the genomic complements of a plant modified by the use of such a system. The disclosure thus provides tools and methods that allow one to insert, remove, or modify genes, loci, linkage blocks, and chromosomes within a plant. Also disclosed are U3, U2, U5 and 7SL promoters and methods for their use that include targeted gene modification of a plant genome.

The disclosure provides, in another embodiment, DNA constructs encoding at least one expression cassette including a promoter disclosed herein and a sequence encoding a non-protein-coding small RNA (npcRNA). These constructs are useful for targeting nuclear expression of the npcRNA molecules.

The CRISPR system constitutes an adaptive immune system in prokaryotes that targets endonucleolytic cleavage of the DNA and RNA of invading phage (reviewed in Westra et al., Annu Rev Genet, 46:311-39, 2012). There are three known types of CRISPR systems, Type I, Type II, and Type III. The CRISPR systems rely on small RNAs for sequence-specific detection and targeting of foreign nucleic acids for destruction. The components of the bacterial CRISPR systems are CRISPR-associated (Cas) genes and CRISPR array (s) consisting of genome-target sequences (protospacers) interspersed with short palindromic repeats. Transcription of the protospacer/repeat elements into precursor CRISPR RNA (pre-crRNA) molecules is followed by enzymatic cleavage triggered by hybridization between a trans-acting CRISPR RNA (tracrRNA) molecule and a pre-crRNA palindromic repeat. The resulting crRNA:tracrRNA molecules, consisting of one copy of the spacer and one repeat, complex with a Cas nuclease. The CRISPR/Cas complex is then directed to DNA sequences (protospacer) complementary to the crRNA spacer sequence, where this RNA-Cas protein complex silences the target DNA through enzymatic cleavage of both strands (double-strand break; DSB).

The native bacterial type II CRISPR system requires four molecular components for targeted cleavage of exogenous DNAs: a Cas endonuclease (e.g., Cas9), the house-keeping RNaseIII, CRISPR RNA (crRNA) and trans-acting CRISPR RNA (tracrRNA). The latter two components form a dsRNA complex and bind to Cas9 resulting in an RNA-guided DNA endonuclease complex. For targeted genome modifications in eukaryotes, this system was simplified to two components: the Cas9 endonuclease and a chimeric crRNA-tracrRNA, called guide-RNA (gRNA) or, alternatively, single-guide RNA (sgRNA). Experiments initially conducted in eukaryotic systems determined that the RNaseIII component was not necessary to achieve targeted DNA cleavage. The minimal two component system of Cas9 with the sgRNA, as the only unique component, enables this CRISPR system of targeted genome modification to be more cost effective and flexible than other targeting platforms such as meganucleases, Zn-finger nucleases, or TALE-nucleases which require protein engineering for modification at each targeted DNA site. Additionally, the case of design and production of sgRNAs provides the CRISPR system with several advantages for application of targeted genome modification. For example, the CRISPR/Cas complex components (Cas endonuclease, sgRNA, and, optionally, exogenous DNA for integration into the genome) designed for one or more genomic target sites can be multiplexed in one transformation, or the introduction of the CRISPR/Cas complex components can be spatially and/or temporally separated.

Expression Strategies for sgRNAs

The disclosure provides, in certain embodiments, novel combinations of promoters and a sequence encoding a sgRNA, to allow for specifically introducing a double-stranded DNA cleavage event into endogenous DNA (i.e., a genome). In one embodiment, a U6 promoter from corn is operably linked to a sgRNA-encoding gene, in order to constitutively express the sgRNA in transformed cells. This may be desirable, for example, when the resulting sgRNA transcripts are retained in the nucleus and will thus be optimally located within the cell to guide nuclear processes. This may also be desirable, for example, when the activity of the CRISPR is low or the frequency of finding and cleaving the target site is low. It may also be desirable when a promoter for a specific cell type, such as the germ line, is not known for a given species of interest. In another embodiment, a U3, U2, U5, or 7SL promoter is operably linked to a sgRNA-encoding gene, for expression of an sgRNA in transformed cells.

In another embodiment, a chimeric promoter comprising all or a portion of any of the U6 promoters provided herein can be used to express a sgRNA. Alternatively, a U3, U2, U5, or 7SL chimeric promoter comprising all or a portion of any of these promoters, may be utilized. For example, the 5' portion of the U6 promoter from corn chromosome 1 (SEQ ID NO:1), including one MSP element, operably linked to the 3' portion of the U6 promoter from corn chromosome 8 (SEQ ID NO:7), including a USE element and a TATA box (SEQ ID NO:17), cloned upstream of a sgRNA, may be used to induce CRISPR-mediated cleavage under different environmental conditions.

Multiple U6 promoters with differing sequence may be utilized to minimize problems in vector stability, which is typically associated with sequence repeats. Further, highly repetitive regions in chromosomes may lead to genetic instability and silencing. Therefore, use of multiple U6 (or other disclosed) promoters in the CRISPR/Cas system of targeted gene modification may facilitate vector stacking of multiple sgRNA cassettes in the same transformation construct, wherein the differing sgRNA transcript levels are to be optimized for efficient targeting of a single target site. Chimeric U6 promoters can result in new, functional versions with improved or otherwise modified expression levels, and four representative chimeric corn U6 promoters have been designed (SEQ ID NO:17, SEQ ID NO: 18, SEQ ID NO: 19, and SEQ ID NO:20).

The disclosed U6 promoters may also drive expression of other non-protein-coding RNA (npcRNA). Non-limiting examples of non-protein-coding small RNA include a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), and a naturally occurring antisense siRNA (nat-siRNA).

Promoters and transcriptional elements for additional small nuclear RNA (snRNA) genes, similar to U6 promoters and which may be transcribed by RNA polymerase II or RNA polymerase III, can also be identified, such as U3, U2, U5, and 7SL promoters. These alternate promoters can be useful in cassette design, especially where these additional elements may facilitate nuclear retention of the CRISPR system transcripts. Additional gene transcription elements that can be useful in CRISPR cassette design include intron-embedded elements and transcriptional elements of plant specific RNA polymerase IV and V promoters.

Expression Strategies for Cas-Associated Genes

The disclosure provides novel promoters for use in sequence-specific or sequence-directed CRISPR-mediated cleavage for molecular breeding by providing transcription of, for example, a sgRNA including a spacer sequence used to target a protospacer sequence within a genomic target site for endonuclease cleavage by at least one Cas protein, wherein the genomic target site is native or transgenic. In addition, CRISPR systems can be customized to catalyze cleavage at one or more genomic target sites. In certain embodiments, such a custom CRISPR system would have properties making it amenable to genetic modification such that the system's Cas endonuclease protein(s) recognition, binding and/or catalytic activity could be manipulated.

One aspect of this disclosure is to introduce into a plant cell an expression vector comprising one or more cassettes encoding a U6 corn promoter, or other disclosed promoter such as an U3, U2, U5 or 7SL promoter, operably linked to a sgRNA, including a copy of a spacer sequence complementary to a protospacer sequence within a genomic target site, and an expression vector encoding a Cas-associated gene to modify the plant cell in such a way that the plant cell, or a plant comprised of such cells, will subsequently exhibit a beneficial trait. In one non-limiting example, the trait is a trait such as improved yield, resistance to biotic or abiotic stress, herbicide tolerance, or other improvements in agronomic performance. The ability to generate such a plant cell derived therefrom depends on introducing the CRISPR system using transformation vectors and cassettes described herein.

The expression vector encoding a Cas-associated gene may comprise a promoter. In certain embodiments, the promoter is a constitutive promoter, a tissue specific promoter, a developmentally regulated promoter, or a cell cycle regulated promoter. Certain contemplated promoters include ones that only express in the germline or reproductive cells, among others. Such developmentally regulated promoters have the advantage of limiting the expression of the CRISPR system to only those cells in which DNA is inherited in subsequent generations. Therefore, a CRISPR-mediated genetic modification (i.e., chromosomal or episomal dsDNA cleavage) is limited only to cells that are involved in transmitting their genome from one generation to the next. This might be useful if broader expression of the CRISPR system were genotoxic or had other unwanted effects. Examples of such promoters include the promoters of genes encoding DNA ligases, recombinases, replicases, and so on.

Endonucleases are enzymes that cleave the phosphodiester bond within a polynucleotide chain. Examples of endonucleases that cleave only at specific nucleotide sequences are well known in the art and can include, for instance, restriction endonucleases. However, the need for targeted genome engineering as an alternative to classical plant breeding requires highly customizable tools for genome editing. The CRISPR-associated type II prokaryotic adaptive immune system provides such an alternative. As such, the DNA constructs provided herein can recognize a specific nucleotide sequence of interest within a target host genome and allow for mutation or integration at that site. In a particular embodiment, the DNA constructs contain one or more corn U6 promoter, or chimeras thereof, that express high levels of a sequence encoding a sgRNA. A DNA construct that expresses a sgRNA that targets a Cas-associated gene product with endonuclease activity to a specific genomic sequence, such that the specific genomic sequence is cleaved and produces a double-stranded break which is repaired by a double strand break repair pathway, which may include, for example, non-homologous end-joining, homologous recombination, synthesis-dependent strand annealing (SDSA), single-strand annealing (SSA), or a combination thereof thereby disrupting the native locus, may be particularly useful.

In one embodiment, a CRISPR system comprises at least one Cas-associated gene encoding a CRISPR endonuclease and one sgRNA comprising a copy of a spacer sequence complementary to a protospacer sequence within an endogenous genomic target site.

In particular embodiments, a Cas-associated gene can include any type II CRISPR system endonuclease. Such a Cas-associated gene product would have properties making it amenable to genetic modification such that its nuclease activity and its recognition and binding of crRNA, tracrRNA, and/or sgRNA could be manipulated.

The present disclosure also provides for use of CRISPR-mediated double-stranded DNA cleavage to genetically alter expression and/or activity of a gene or gene product of interest in a tissue- or cell-type specific manner to improve productivity or provide another beneficial trait, wherein the nucleic acid of interest may be endogenous or transgenic in nature. Thus, in one embodiment, a CRISPR system is engineered to mediate disruption at specific sites in a gene of interest. Genes of interest include those for which altered expression level/protein activity is desired. These DNA cleavage events can be either in coding sequences or in regulatory elements within the gene.

This disclosure provides for the introduction of a type II CRISPR system into a cell. Exemplary type II Cas-associated genes include natural and engineered (i.e., modified, including codon-optimized) nucleotide sequences encoding polypeptides with nuclease activity such as Cas9 from *Streptococcus pyogenes, Streptococcus thermophilus*, or *Bradyrhizobium* sp.

The catalytically active CRISPR-associate gene (e.g., Cas9 endonuclease) can be introduced into, or produced by, a target cell. Various methods may be used to carry this out, as disclosed herein.

Transient Expression of CRISPRs

In some embodiments, the sgRNA and/or Cas-associated gene is transiently introduced into a cell. In certain embodiments, the introduced sgRNA and/or Cas-associated gene is provided in sufficient quantity to modify the cell but does not persist after a contemplated period of time has passed or after one or more cell divisions. In such embodiments, no further steps are needed to remove or segregate the sgRNA and/or Cas-associated gene from the modified cell. In yet other embodiments of this disclosure, double-stranded DNA fragments are also transiently introduced into a cell along with sgRNA and/or Cas-associated gene. In such embodiments, the introduced double-stranded DNA fragments are provided in sufficient quantity to modify the cell but do not persist after a contemplated period of time has passed or after one or more cell divisions.

In another embodiment, mRNA encoding the Cas-associated gene is introduced into a cell. In such embodiments, the mRNA is translated to produce the type II CRISPR system endonuclease in sufficient quantity to modify the cell (in the presence of at least one sgRNA) but does not persist after a contemplated period of time has passed or after one or more cell divisions. In such embodiments, no further steps are needed to remove or segregate the Cas-associated gene from the modified cell.

In one embodiment of this disclosure, a catalytically active Cas-associated gene product is prepared in vitro prior to introduction to a cell, including a prokaryotic or eukaryotic cell. The method of preparing a Cas-associated gene product depends on its type and properties and would be known by one of skill in the art. For example, if the Cas-associated gene product is a large monomeric DNA nuclease, the active form of the Cas-associated gene product can be produced via bacterial expression, in vitro translation, via yeast cells, in insect cells, or by other protein production techniques described in the art. After expression, the Cas-associated gene product is isolated, refolded if needed, purified and optionally treated to remove any purification tags, such as a His-tag. Once crude, partially purified, or more completely purified Cas-associated gene products are obtained, the protein may be introduced to, for example, a plant cell via electroporation, by bombardment with Cas-associated gene product coated particles, by chemical transfection or by some other means of transport across a cell membrane. Methods for introducing nucleic acids into bacterial and animal cells are similarly well known in the art. The protein can also be delivered using nanoparticles, which can deliver a combination of active protein and nucleic acid. Once a sufficient quantity of the Cas-associated gene product is introduced so that an effective amount of in vivo nuclease activity is present, along with the appropriate sgRNA, the protospacer sequences within the episomal or genomic target sites are cleaved. It is also recognized that one skilled in the art might create a Cas-associated gene product that is inactive but is activated in vivo by native processing machinery; such a Cas-associated gene product is also contemplated by this disclosure.

In another embodiment, a construct that will transiently express a sgRNA and/or Cas-associated gene is created and introduced into a cell. In yet another embodiment, the vector will produce sufficient quantities of the sgRNAs and/or Cas-associated gene in order for the desired episomal or genomic target site or sites to be effectively modified by CRISPR-mediated cleavage. For instance, the disclosure contemplates preparation of a vector that can be bombarded, electroporated, chemically transfected or transported by some other means across the plant cell membrane. Such a vector could have several useful properties. For instance, in one embodiment, the vector can replicate in a bacterial host such that the vector can be produced and purified in sufficient quantities for transient expression. In another embodiment, the vector can encode a drug resistance gene to allow selection for the vector in a host, or the vector can also comprise an expression cassette to provide for the expression of the sgRNA and/or Cas-associated gene in a plant. In a further embodiment, the expression cassette could contain a promoter region, a 5' untranslated region, an optional intron to aid expression, a multiple cloning site to allow facile introduction of a sequence encoding sgRNAs and/or Cas-associated gene, and a 3' UTR. In particular embodiments, the promoters in the expression cassette would be U6 promoters from *Zea mays* In yet other embodiments, the promoters would be chimeric U6 promoters from *Zea mays*. In some embodiments, it can be beneficial to include unique restriction sites at one or at each end of the expression cassette to allow the production and isolation of a linear expression cassette, which can then be free of other vector elements. The untranslated leader regions, in certain embodiments, can be plant-derived untranslated regions. Use of an intron, which can be plant-derived, is contemplated when the expression cassette is being transformed or transfected into a monocot cell.

In other embodiments, one or more elements in the vector include a spacer complementary to a protospacer contained within an episomal or genomic target site. This facilitates CRISPR-mediated modification within the expression cassette, enabling removal and/or insertion of elements such as promoters and transgenes.

In another approach, a transient expression vector may be introduced into a cell using a bacterial or viral vector host. For example, *Agrobacterium* is one such bacterial vector that can be used to introduce a transient expression vector into a host cell. When using a bacterial, viral or other vector host system, the transient expression vector is contained within the host vector system. For example, if the *Agrobacterium* host system is used, the transient expression cassette would be flanked by one or more T-DNA borders and cloned into a binary vector. Many such vector systems have been identified in the art (reviewed in Hellens et al., 2000).

In embodiments whereby the sgRNA and/or Cas-associated gene is transiently introduced in sufficient quantities to modify a cell, a method of selecting the modified cell may be employed. In one such method, a second nucleic acid molecule containing a selectable marker is co-introduced with the transient sgRNA and/or Cas-associated gene. In this embodiment, the co-introduced marker may be part of a molecular strategy to introduce the marker at a target site. For example, the co-introduced marker may be used to disrupt a target gene by inserting between genomic target sites. In another embodiment, the co-introduced nucleic acid may be used to produce a visual marker protein such that transfected cells can be cell-sorted or isolated by some other means. In yet another embodiment, the co-introduced marker may randomly integrate or be directed via a second sgRNA:Cas-protein complex to integrate at a site independent of the primary genomic target site. In still yet another embodiment, the co-introduced molecule may be targeted to a specific locus via a double strand break repair pathway, which may include, for example, non-homologous end-joining, homologous recombination, synthesis-dependent strand annealing (SDSA), single-strand annealing (SSA), or a combination thereof, at the genomic target site(s). In the above embodiments, the co-introduced marker may be used to identify or select for cells that have likely been exposed to the sgRNA and/or Cas-associated gene and therefore are likely to have been modified by the CRISPR.

Stable Expression of CRISPRs

In another embodiment, a CRISPR expression vector is stably transformed into a cell so as to cleave a DNA sequence at or near a genomic target site in the host genome with a sgRNA and Cas-associated gene product encoded within the vector. In this embodiment, the design of the transformation vector provides flexibility for when and under what conditions the sgRNA and/or Cas-associated gene is expressed. Furthermore, the transformation vector can be designed to comprise a selectable or visible marker that will provide a means to isolate or efficiently select cell lines that contain and/or have been modified by the CRISPR.

Cell transformation systems have been described in the art and descriptions include a variety of transformation vectors. For example, for plant transformations, two principal methods include *Agrobacterium*-mediated transformation and particle gun bombardment-mediated (i.e., biolistic) transformation. In both cases, the CRISPR is introduced via an expression cassette. The cassette may contain one or more of the following elements: a promoter element that can be used to express the sgRNA and/or Cas-associated gene; a 5' untranslated region to enhance expression; an intron element to further enhance expression in certain cell types, such as monocot cells; a multiple-cloning site to provide convenient restriction sites for inserting the sgRNA and/or Cas-associated gene sequences and other desired elements; and a 3' untranslated region to provide for efficient termination of the expressed transcript. In particular embodiments, the promoters in the expression cassette would be U6 promoters from *Zea mays*. In yet other embodiments, the promoters would be chimeric U6 promoters from *Zea mays*.

For particle bombardment or with protoplast transformation, the expression cassette can be an isolated linear fragment or may be part of a larger construct that might contain bacterial replication elements, bacterial selectable markers or other elements. The sgRNA and/or Cas-associated gene expression cassette(s) may be physically linked to a marker cassette or may be mixed with a second nucleic acid molecule encoding a marker cassette. The marker cassette is comprised of necessary elements to express a visual or selectable marker that allows for efficient selection of transformed cells. In the case of *Agrobacterium*-mediated transformation, the expression cassette may be adjacent to or between flanking T-DNA borders and contained within a binary vector. In another embodiment, the expression cassette may be outside of the T-DNA. The presence of the expression cassette in a cell may be manipulated by positive or negative selection regime(s). Furthermore, a selectable marker cassette may also be within or adjacent to the same T-DNA borders or may be somewhere else within a second T-DNA on the binary vector (e.g., a 2 T-DNA system).

In another embodiment, cells that have been modified by a CRISPR, either transiently or stably, are carried forward along with unmodified cells. The cells can be sub-divided into independent clonally derived lines or can be used to regenerate independently derived plants. Individual plants or clonal populations regenerated from such cells can be used to generate independently derived lines. At any of these stages a molecular assay can be employed to screen for cells, plants or lines that have been modified. Cells, plants or lines that have been modified continue to be propagated and unmodified cells, plants or lines are discarded. In these embodiments, the presence of an active CRISPR in a cell is essential to ensure the efficiency of the overall process.

Transformation Methods

Methods for transforming or transfecting a cell are well known in the art. Methods for plant transformation using *Agrobacterium* or DNA coated particles are well known in the art and are incorporated herein. Suitable methods for transformation of host cells for use with the current disclosure are believed to include virtually any method by which DNA can be introduced into a cell, for example by *Agrobacterium*-mediated transformation (U.S. Pat. Nos. 5,563,055; 5,591,616; 5,693,512; 5,824,877; 5,981,840; and 6,384,301) and by acceleration of DNA coated particles (U.S. Pat. Nos. 5,015,580; 5,550,318; 5,538,880; 6,160,208; 6,399,861; and 6,403,865), etc. Through the application of techniques such as these, the cells of virtually any species may be stably transformed.

Various methods for selecting transformed cells have been described. For example, one might utilize a drug resistance marker such as a neomycin phosphotransferase protein to confer resistance to kanamycin or to use 5-enolpyruvyl shikimate phosphate synthase to confer tolerance to glyphosate. In another embodiment, a carotenoid synthase is used to create an orange pigment that can be visually identified. These three exemplary approaches can each be used effectively to isolate a cell or plant or tissue thereof that has been transformed and/or modified by a CRISPR.

When a nucleic acid sequence encoding a selectable or screenable marker is inserted into a genomic target site, the marker can be used to detect the presence or absence of a CRISPR or its activity. This may be useful once a cell has been modified by a CRISPR, and recovery of a genetically modified cell that no longer contains the CRISPR, or a regenerated plant from such a modified cell, is desired. In other embodiments, the marker may be intentionally designed to integrate at the genomic target site, such that it can be used to follow a modified cell independently of the CRISPR. The marker can be a gene that provides a visually detectable phenotype, such as in the seed, to allow rapid identification of seeds that carry or lack a CRISPR expression cassette.

This disclosure provides for a means to regenerate a plant from a cell with a repaired double-stranded break within a protospacer sequence at a genomic target site. The regenerant can then be used to propagate additional plants.

The disclosure additionally provides novel plant transformation vectors and expression cassettes which include novel U6 promoters, and U3, U2, U5 and 7SL promoters, and combinations thereof, with CRISPR-associated gene(s) and sgRNA expression cassettes. The disclosure further provides methods of obtaining a plant cell, a whole plant, and a seed or embryo that have been specifically modified using CRISPR-mediated cleavage. This disclosure also relates to a novel plant cell containing a CRISPR-associated Cas endonuclease expression construct and sgRNA expression cassettes.

Targeting Using Blunt-End Oligonucleotides

In certain embodiments, the CRISPR/Cas9 system can be utilized for targeting insertion of a blunt-end double-stranded DNA fragment into a genomic target site of interest. CRISPR-mediated endonuclease activity can introduce a double stand break (DSB) in the protospacer of the selected genomic target site and DNA repair, such as microhomology-driven non-homologous end-joining DNA repair, results in insertion of the blunt-end double-stranded DNA fragment into the DSB. Blunt-end double-stranded DNA fragments can be designed with 1-10 bp of microhomology, on both the 5' and 3' ends of the DNA fragment, that correspond to the 5' and 3' flanking sequence at the cut site of the protospacer in the genomic target site.

Use of Custom CRISPRs in Molecular Breeding

In some embodiments, genome knowledge is utilized for targeted genetic alteration of a genome. At least one sgRNA can be designed to target at least one region of a genome to disrupt that region from the genome. This aspect of the disclosure may be especially useful for genetic alterations. The resulting plant could have a modified phenotype or other property depending on the gene or genes that have been altered. Previously characterized mutant alleles or introduced transgenes can be targeted for CRISPR-mediated modification, enabling creation of improved mutants or transgenic lines.

In another embodiment, a gene targeted for deletion or disruption may be a transgene that was previously introduced into the target plant or cell. This has the advantage of allowing an improved version of a transgene to be introduced or by allowing disruption of a selectable marker encoding sequence. In yet another embodiment, a gene targeted for disruption via CRISPR is at least one transgene that was introduced on the same vector or expression cassette as (an) other transgene(s) of interest, and resides at the same locus as another transgene. It is understood by those skilled in the art that this type of CRISPR-mediated modification may result in deletion or insertion of additional sequences. Thus it may, in certain embodiments, be preferable to generate a plurality of plants or cells in which a deletion has occurred, and to screen such plants or cells using standard techniques to identify specific plants or cells that have minimal alterations in their genomes following CRISPR-mediated modification. Such screens may utilize genotypic and/or phenotypic information. In such embodiments, a specific transgene may be disrupted while leaving the remaining transgene(s) intact. This avoids having to create a new transgenic line containing the desired transgenes without the undesired transgene.

In another aspect, the present disclosure includes methods for inserting a DNA fragment of interest into a specific site of a plant's genome, wherein the DNA fragment of interest is from the genome of the plant or is heterologous with respect to the plant. This disclosure allows one to select or target a particular region of the genome for nucleic acid (i.e., transgene) stacking (i.e., mega-locus). A targeted region of the genome may thus display linkage of at least one transgene to a haplotype of interest associated with at least one phenotypic trait, and may also result in the development of a linkage block to facilitate transgene stacking and transgenic trait integration, and/or development of a linkage block while also allowing for conventional trait integration.

Use of Custom CRISPRs in Trait Integration

Directed insertion, in at least one genomic protospacer site, of DNA fragments of interest, via CRISPR-mediated cleavage allows for targeted integration of multiple nucleic acids of interest (i.e., a trait stack) to be added to the genome of a plant in either the same site or different sites. Sites for targeted integration can be selected based on knowledge of the underlying breeding value, transgene performance in that location, underlying recombination rate in that location, existing transgenes in that linkage block, or other factors. Once the stacked plant is assembled, it can be used as a trait donor for crosses to germplasm being advanced in a breeding pipeline or be directly advanced in the breeding pipeline.

The present disclosure includes methods for inserting at least one nucleic acid of interest into at least one site, wherein the nucleic acid of interest is from the genome of a plant, such as a QTL or allele, or is transgenic in origin. A targeted region of the genome may thus display linkage of at least one transgene to a haplotype of interest associated with at least one phenotypic trait (as described in U.S. Patent Application Publication No. 2006/0282911), development of a linkage block to facilitate transgene stacking and transgenic trait integration, development of a linkage block to facilitate QTL or haplotype stacking and conventional trait integration, and so on.

In another embodiment of this disclosure, multiple unique sgRNAs can be used to modify multiple alleles at specific loci within one linkage block contained on one chromosome by making use of knowledge of genomic sequence information and the ability to design custom sgRNAs as described in the art. A sgRNA that is specific for, or can be directed to, a genomic target site that is upstream of the locus containing the non-target allele is designed or engineered as necessary. A second sgRNA that is specific for, or can be directed to, a genomic target site that is downstream of the target locus containing the non-target allele is also designed or engineered. The sgRNAs may be designed such that they complement genomic regions where there is no homology to the non-target locus containing the target allele. Both sgRNAs may be introduced into a cell using one of the methods described above.

The ability to execute targeted integration relies on the action of the sgRNA:Cas-protein complex and the endonuclease activity of the Cas-associated gene product. This advantage provides methods for engineering plants of interest, including a plant or cell, comprising at least one genomic modification.

A custom sgRNA can be utilized in a CRISPR system to generate at least one trait donor to create a custom genomic modification event that is then crossed into at least one second plant of interest, including a plant, wherein CRISPR delivery can be coupled with the sgRNA of interest to be used for genome editing. In other aspects one or more plants of interest are directly transformed with the CRISPR system and at least one double-stranded DNA fragment of interest for directed insertion. It is recognized that this method may be executed in various cell, tissue, and developmental types, including gametes of plants. It is further anticipated that one or more of the elements described herein may be combined with use of promoters specific to particular cells, tissues, plant parts and/or developmental stages, such as a meiosis-specific promoter.

In addition, the disclosure contemplates the targeting of a transgenic element already existing within a genome for deletion or disruption. This allows, for instance, an improved version of a transgene to be introduced, or allows selectable marker removal. In yet another embodiment, a gene targeted for disruption via CRISPR-mediated cleavage is at least one transgene that was introduced on the same vector or expression cassette as (an) other transgene(s) of interest, and resides at the same locus as another transgene.

In one aspect, the disclosure thus provides a method for modifying a locus of interest in a cell comprising (a) identifying at least one locus of interest within a DNA sequence; (b) creating a modified nucleotide sequence, in or proximal to the locus of interest, that includes a protospacer sequence within a genomic target site for a first sgRNA according to the disclosure; (c) introducing into at least one cell the sgRNA and Cas-associated gene, wherein the sgRNA and/or Cas-associated gene is expressed transiently or stably; (d) assaying the cell for a CRISPR-mediated modification in the DNA making up or flanking the locus of interest; and (e) identifying the cell or a progeny cell thereof as comprising a modification in said locus of interest.

Another aspect provides a method for modifying multiple loci of interest in a cell comprising (a) identifying multiple loci of interest within a genome; (b) identifying multiple genomic protospacer sites within each locus of interest; (c) introducing into at least one cell multiple sgRNA and at least one Cas-associated gene according to the disclosure, wherein the cell comprises the genomic protospacer sites and the sgRNA and Cas-associated gene is expressed transiently or stably and creates a modified locus, or loci, that includes at least one CRISPR-mediated cleavage event; (d) assaying the cell for CRISPR-mediated modifications in the DNA making up or flanking each locus of interest; and (e) identifying a cell or a progeny cell thereof which comprises a modified nucleotide sequence at said loci of interest.

The disclosure further contemplates sequential modification of a locus of interest, by two or more sgRNAs and Cas-associated gene(s) according to the disclosure. Genes or other sequences added by the action of such a first CRISPR-mediated genomic modification may be retained, further modified, or removed by the action of a second CRISPR-mediated genomic modification.

The present invention thus includes a method for modifying a locus of interest in a crop plant such as maize (corn; *Zea mays*), soybean (*Glycine max*), cotton (*Gossypium hirsutum; Gossypium* sp.), peanut (*Arachis hypogaea*), barley (*Hordeum vulgare*); oats (*Avena sativa*); orchard grass (*Dactylis glomerata*); rice (*Oryza sativa*, including indica and *japonica* varieties); sorghum (*Sorghum bicolor*); sugar cane (*Saccharum* sp.); tall fescue (*Festuca arundinacea*); turf-grass species (e.g. species: *Agrostis stolonifera, Poa pratensis, Stenotaphrum secundatum*); wheat (*Triticum aestivum*); alfalfa (*Medicago sativa*); members of the genus *Brassica*, including broccoli, cabbage, carrot, cauliflower, Chinese cabbage; cucumber, dry bean, eggplant, tobacco, fennel, garden beans, gourd, leek, lettuce, melon, okra, onion, pea, pepper, pumpkin, radish, spinach, squash, sweet corn, tomato, watermelon, ornamental plants, and other fruit, vegetable, tuber, oilseed, and root crops, wherein oilseed crops include soybean, canola, oil seed rape, oil palm, sunflower, olive, corn, cottonseed, peanut, flaxseed, safflower, and coconut.

The genome modification may comprise a modified linkage block, the linking of two or more QTLs, disrupting linkage of two or more QTLs, gene insertion, gene replacement, gene conversion, deleting or disrupting a gene, transgenic event selection, transgenic trait donor selection, transgene replacement, or targeted insertion of at least one nucleic acid of interest.

Definitions

The definitions and methods provided define the present disclosure and guide those of ordinary skill in the art in the practice of the present disclosure. Unless otherwise noted, terms are to be understood according to conventional usage by those of ordinary skill in the relevant art. Definitions of common terms in molecular biology may also be found in Alberts et al., Molecular Biology of The Cell, 5th Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed., Oxford University Press: New York, 2247; and Lewin, Genes IX, Oxford University Press: New York, 2007. The nomenclature for DNA bases as set forth at 37 CFR § 1.822 is used.

As used herein, "CRISPR-associated genes" refers to nucleic acid sequences that encode polypeptide components of clustered regularly interspersed short palindromic repeats (CRISPR)-associated systems (Cas). Examples include, but are not limited to, Cas3 and Cas9, which encode endonucleases from the CRISPR type I and type II systems, respectively.

As used herein, "single-guide RNA (sgRNA)" refers to a crRNA:tracrRNA fused hybrid single-stranded RNA molecule encoded by a customizable DNA element that, generally, comprises a copy of a spacer sequence which is complementary to the protospacer sequence of the genomic target site, and a binding domain for an associated-Cas endonuclease of the CRISPR complex.

As used herein, "genomic target site" refers to a protospacer and a protospacer adjacent motif (PAM) located in a host genome selected for targeted mutation and/or double-strand break.

As used herein, "protospacer" refers to a short DNA sequence (12 to 40 bp) that can be targeted for mutation, and/or double-strand break, mediated by enzymatic cleavage with a CRISPR system endonuclease guided by complementary base-pairing with the spacer sequence in the crRNA or sgRNA.

As used herein, "protospacer adjacent motif (PAM)" includes a 3 to 8 bp sequence immediately adjacent to the protospacer sequence in the genomic target site.

As used herein, "microhomology" refers to the presence of the same short sequence (1 to 10 bp) of bases in different polynucleotide molecules.

As used herein, "codon-optimized" refers to a polynucleotide sequence that has been modified to exploit the codon usage bias of a particular plant. The modified polynucleotide sequence still encodes the same, or substantially similar polypeptide as the original sequence but uses codon nucleotide triplets that are found in greater frequency in a particular plant.

As used herein, "non-protein-coding RNA (npcRNA)" refers to a non-coding RNA (ncRNA) which is a precursor small non-protein coding RNA, or a fully processed non-protein coding RNA, which are functional RNA molecules that are not translated into a protein.

As used herein, the term "chimeric" refers to the product of the fusion of portions of two or more different polynucleotide molecules, or to a gene expression element produced through the manipulation of known elements or other polynucleotide molecules. Novel chimeric regulatory elements can be designed or engineered by a number of methods. In one embodiment of the present disclosure, a chimeric promoter may be produced by fusing the 5' portion of a U6 promoter from corn chromosome 1, which includes at least one Monocot-Specific Promoter (MSP) element, to the 3' portion of the U6 promoter from corn chromosome 8, which includes an Upstream Sequence Element (USE) and a TATA Box. The resultant chimeric promoter may have novel expression properties relative to the first or second promoters.

As used herein, "promoter" refers to a nucleic acid sequence located upstream or 5' to a translational start codon of an open reading frame (or protein-coding region) of a gene and that is involved in recognition and binding of RNA polymerase I, II, or III and other proteins (trans-acting transcription factors) to initiate transcription. A "plant promoter" is a native or non-native promoter that is functional in plant cells. Constitutive promoters are functional in most or all tissues of a plant throughout plant development. Tissue-, organ- or cell-specific promoters are expressed only or predominantly in a particular tissue, organ, or cell type, respectively. Rather than being expressed "specifically" in a given tissue, plant part, or cell type, a promoter may display "enhanced" expression, i.e., a higher level of expression, in one cell type, tissue, or plant part of the plant compared to other parts of the plant. Temporally regulated promoters are functional only or predominantly during certain periods of plant development or at certain times of day, as in the case of genes associated with circadian rhythm, for example. Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

As used herein, an "expression cassette" refers to a polynucleotide sequence comprising at least a first polynucleotide sequence capable of initiating transcription of an operably linked second polynucleotide sequence and optionally a transcription termination sequence operably linked to the second polynucleotide sequence.

A palindromic sequence is a nucleic acid sequence that is the same whether read 5' to 3' on one strand or 3' to 5' on the complementary strand with which it forms a double helix. A nucleotide sequence is said to be a palindrome if it is equal to its reverse complement. A palindromic sequence can form a hairpin.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability.

Having described the present disclosure in detail, it will be apparent that modifications, variations, and equivalent embodiments are possible without departing from the scope of the present disclosure defined in the appended claims. Furthermore, it should be appreciated that all examples in the present disclosure are provided as non-limiting examples.

EXAMPLES

The following examples are included to demonstrate embodiments of the disclosure. It should be appreciated by those of skill in the art that many changes can be made in the specific embodiments which are disclosed and still obtain a like or similar result without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

Example 1

Identification of Promoters to Express sgRNA

Figure 1B:
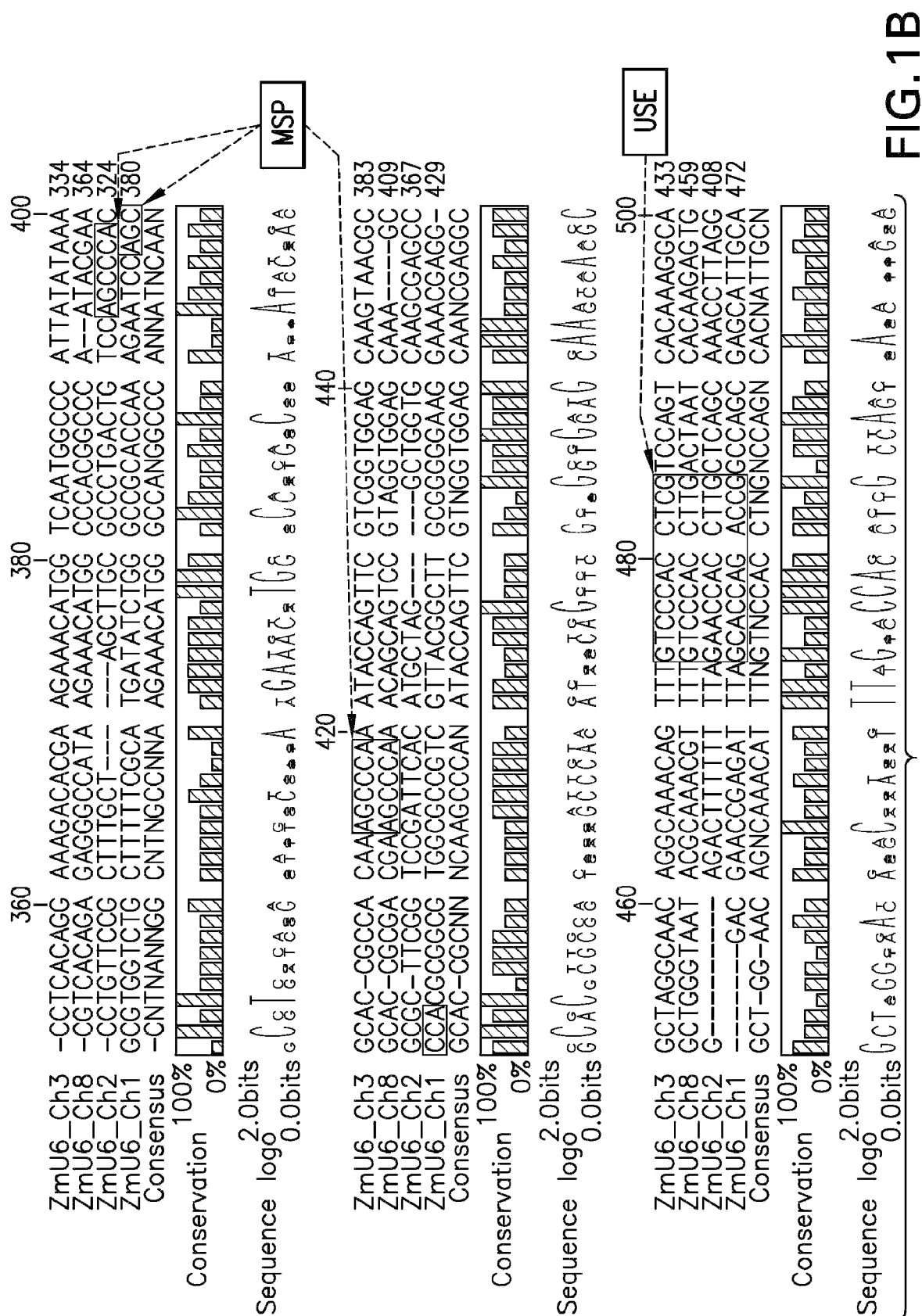
Figure 1B:
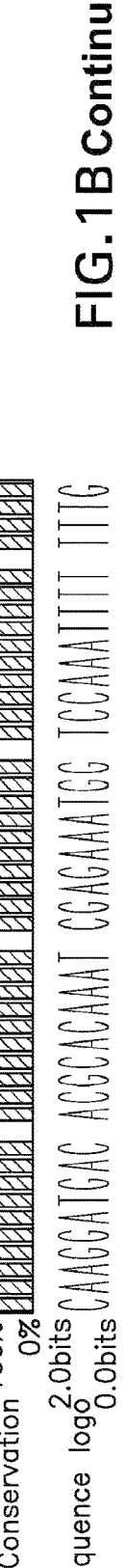

To enable genome engineering in corn, soy, and tomato using the CRISPR-based gene targeting system, novel U6 promoters native to these three genomes were identified. After BLAST searching for the highly conserved U6 gene in corn, soy, and tomato genomes, 200-600 bp of sequence upstream of these putative U6 genes was selected to test for promoter function (Table 1). Four U6 promoters were identified from the corn B73 genome, one each on chromosome 1 (SEQ ID NO:1), chromosome 2 (SEQ ID NO:3), chromosome 3 (SEQ ID NO:5), and chromosome 8 (SEQ ID NO:7). A multiple sequence alignment of these four corn U6 promoters and corresponding U6 genes was compiled as shown in FIGS. 1A and B. For each of these corn U6 promoters, conserved U6 promoter motifs (e.g., TATA Box, Upstream Sequence Element (USE), and Monocot-Specific Promoter (MSP) elements (Connelly, Mol. Cell Biol. 14:5910-5919, 1994) are present (FIG. 1B). A guanine nucleobase following the poly-T tracts was conserved among these four genes, and may have a significant role in transcription. The sequence consensus, and percent conservation are presented below the alignment (FIG. 1). Based on the multiple sequence alignment, the conserved motifs of these U6 promoters were within the 140 bp proximal to the transcription start site. Based on the proximity of these conserved U6 promoter motifs, 200 bp of the proximal upstream sequence from the transcription start site for each of the corn chromosome U6 promoters, chromosome 1 (SEQ ID NO:2), chromosome 2 (SEQ ID NO:4), chromosome 3 (SEQ ID NO:6), and chromosome 8 (SEQ ID NO:8) was selected for testing for efficient promoter activity in sgRNA expression cassettes.

In addition to the four corn U6 promoters, chimeric U6 promoters were designed. Four chimeric corn U6 promoters were designed using differing combinations of the corn U6 promoters from chromosome 1, 2, and 8, with each chimeric promoter being 397 bp in length. The breakpoints of the chimeras were determined so that the conserved elements (e.g., USE, MSP, and TATA box) of different chromosomal origins were mixed in the new chimeric U6 promoters but retained their relative spacing to the native corn U6 promoters. For example, the 5' end of the U6 promoter including MSP and USE were derived from one chromosome, while the 3' end including the TATA box and one or more MSP elements were derived from a second chromosome. Although the corn U6 promoter from chromosome 2 was not a very strong promoter in its native form, it included more than one MSP element. Consequently, chimeras that include mainly chromosome 1 and/or 8 sequence can also include one or more chromosome 2 MSP elements. Specifically, the 5' portion of chimera 1 (SEQ ID NO:17) is derived from the U6 promoter from corn chromosome 1 (SEQ ID NO:1), including one MSP element, and the 3' portion of this chimera is derived from the U6 promoter from corn chromosome 8 (SEQ ID NO:7), including a USE element and a TATA box. Similarly, the 5' portion of chimera 2 (SEQ ID NO:18) is derived from the U6 promoter from corn chromosome 1 (SEQ ID NO:1), including one MSP element, and the 3' portion of this chimera is derived from the U6 promoter from corn chromosome 8 (SEQ ID NO:7), including a second MSP element, a USE element, and a TATA box. The 5' portion of chimera 3 (SEQ ID NO:19) is derived from the U6 promoter from corn chromosome 8 (SEQ ID NO:7), including one MSP element, and the 3' portion of this chimera is derived from the U6 promoter from corn chromosome 1 (SEQ ID NO:1), including a second MSP element, a USE element, and a TATA box. Additionally, for chimera 3, there is a 3 bp deletion beginning at bp 100 of SEQ ID NO:7, and the 5' end of the chimera begins with 5'-AAG-3'. Chimera 4 (SEQ ID NO:20) was derived from the U6 promoter from corn chromosome 8 (SEQ ID NO:7), including the MSP element, the USE element and the TATA box. However, this chimera also includes two additional MSP elements (for a total of 3 MSP elements) derived from the U6 promoter of corn chromosomes 1 and 2.

27

TABLE 1

U6 promoters from corn (*Zea mays*), tomato (*Solanum lycopersicum*),
and soybean (*Glycine max*), their chromosomal source and length.

| SEQ ID NO. | Source | Chromosome | Length (bp) |
|---|---|---|---|
| 1 | *Zea mays* | 1 | 397 |
| 2 | *Zea mays* | 1 | 200 |
| 3 | *Zea mays* | 2 | 397 |
| 4 | *Zea mays* | 2 | 200 |
| 5 | *Zea mays* | 3 | 397 |
| 6 | *Zea mays* | 3 | 200 |
| 7 | *Zea mays* | 8 | 397 |
| 8 | *Zea mays* | 8 | 200 |
| 9 | *Solanum lycopersicum* | 10 | 540 |
| 10 | *Solanum lycopersicum* | 1 | 600 |
| 11 | *Solanum lycopersicum* | 7 | 540 |
| 12 | Glycine max | 6 | 540 |
| 13 | Glycine max | 16 | 540 |
| 14 | Glycine max | 19 | 540 |
| 15 | Glycine max | 4 | 540 |
| 16 | Glycine max | 19 | 420 |
| 17 | *Zea mays* | Chimeric: 1 + 8 | 397 |
| 18 | *Zea mays* | Chimeric: 1 + 8 | 397 |
| 19 | *Zea mays* | Chimeric: 8 + 1 | 397 |
| 20 | *Zea mays* | Chimeric: 8 + 2 + 1 + 8 | 397 |

Example 2

Identification of Cas9 Genes to Enable Genome Engineering in Plants

The *S. pyogenes* Cas9 sequence (SEQ ID NO:28 is the polypeptide sequence of Cas9 with NLS, and SEQ ID NO:96 is the polypeptide sequence of Cas9 without NLS) was used for CRISPR-mediated site-directed targeting of a reporter construct in immature corn embryos. For expression, the codon-optimized nucleotide sequence of Cas9 was designed into an expression vector capable of expression in a plant. This Cas9 expression vector contained a 35S promoter driving expression of the Cas9 open reading frame, a NLS sequence incorporated into the 3' end of the Cas9 coding region, and a Nos transcription termination sequence (SEQ ID NO:29).

A Cas9 protein (SEQ ID NO:26), and a monocot codon-optimized version of the nucleotide sequence encoding the same (SEQ ID NO:27), were identified from the plant-related bacteria *Bradyrhizobium*, and can be useful for increasing the robustness of CRISPR/Cas-mediated genome modification in plants. A Cas9 protein (SEQ ID NO:69) and a monocot codon-optimized version thereof (SEQ ID NO:68), were identified from *Streptococcus thermophilus*, and can be useful for increasing the robustness of CRISPR/Cas-mediated genome modification in plants. Additional Cas9 genes from plant-related bacteria (e.g., symbiotic or pathogenic bacteria) can also be identified.

Example 3

Single-Guide RNA Cassette Design

A set of single-guide RNA (sgRNA) expression cassettes were designed to target a protospacer in corn genomic target site referred to as Zm7 (5'-GCCGGCCAGCATTTGAAA-CATGG-3', SEQ ID NO:22). The different expression cassettes included one of the 397 bp U6 promoters from corn: chromosome 1 (SEQ ID NO:30), chromosome 2 (SEQ ID NO:32), chromosome 3 (SEQ ID NO:34), or chromosome 8 (SEQ ID NO:36); or one of the 200 bp U6 promoter from corn: chromosome 1 (SEQ ID NO:31), chromosome 2 (SEQ ID NO:33), chromosome 3 (SEQ ID NO:35), or chromosome 8 (SEQ ID NO:37). Each expression cassette also contained, i) the U6 poly-T terminator conserved in each of the four corn U6 genes; ii) a sgRNA including a copy of the spacer sequence 5'-GCCGGCCAGCATTTGAAACA-3' (SEQ ID NO:23) corresponding to the protospacer of the Zm7 genomic target site (SEQ ID NO:22); and iii) the conserved 3' domain of a sgRNA providing the Cas endonuclease binding domain, and ending with the U6 poly-T tract (SEQ ID NO:21).

Similarly, a set of sgRNA cassettes were designed with one of the four corn U6 397 bp promoters (SEQ ID NO:30, SEQ ID NO:32, SEQ ID NO:34, or SEQ ID NO:36; see Table 2), and the spacer sequence of the sgRNA complementary to the protospacer of the corn genomic target site referred to as Zm231 (SEQ ID NO:24). Table 3 lists the corresponding SEQ ID NOs for the DNA and RNA sequences of the sgRNAs containing the Zm7, Zm231, and Zm14 target sites. A negative control sgRNA cassette was designed with the corn U6 397 bp promoter from corn chromosome 8 (SEQ ID NO:36) and spacer sequence of the sgRNA complementary to the protospacer of the corn genomic target site referred to as Zm14 (SEQ ID NO:24). This negative control sgRNA cassette was designed with a spacer sequence of the sgRNA that is non-complementary to the protospacer sequence of the Zm231 corn genomic target site. Inclusion of a sgRNA comprising the spacer sequence complementary to the Zm14 corn genomic target site will not result in CRISPR/Cas-mediated cleavage of the protospacer sequence of the Zm231 corn target protospacer site. These Zm231 and Zm14 sgRNA cassettes are represented by SEQ ID NO:38, SEQ ID NO:39, SEQ ID NO:40, SEQ ID NO:41, and SEQ ID NO:42 (Table 2). Each of these sgRNA cassettes also contains at the 3' end of the sgRNA sequence a U6 poly-T tract.

TABLE 2

Cassettes with the indicated corn (*Zea mays*)
U6 promoters and sgRNA containing spacers
complementary to the protospacer sequence
of the indicated corn genomic target sites.

| SEQ ID NO. | U6 Promoter from Chromosome | U6 Promoter Length (bp) | Genomic target site |
|---|---|---|---|
| 30 | 1 | 397 | Zm7 |
| 31 | 1 | 200 | Zm7 |
| 32 | 2 | 397 | Zm7 |
| 33 | 2 | 200 | Zm7 |
| 34 | 3 | 397 | Zm7 |
| 35 | 3 | 200 | Zm7 |
| 36 | 8 | 397 | Zm7 |
| 37 | 8 | 200 | Zm7 |
| 38 | 1 | 397 | Zm231 |
| 39 | 2 | 397 | Zm231 |
| 40 | 3 | 397 | Zm231 |
| 41 | 8 | 397 | Zm231 |
| 42 | 8 | 397 | Zm14 |

TABLE 3

DNA and RNA sequences of *Streptococcus*
*pyogenes* sgRNAs containing spacer sequences
complementary to the protospacer sequence of the
corn genomic target sites Zm7, Zm231, and Zm14.

SEQ ID NO.

| DNA | RNA | Genomic target site |
|---|---|---|
| 76 | 79 | Zm7 |
| 77 | 80 | Zm231 |
| 78 | 81 | Zm14 |

Example 4

CRISPR Activity in Corn—Modified GUS Reporter Assay

To determine the activity of CRISPR/Cas-mediated gene-targeting efficiency in corn, a system for the transient expression of a reporter gene in immature corn embryos was used. In addition to the sgRNA cassettes described above, the design incorporated an expression cassette containing the Cas9 endonuclease of *Streptococcus pyogenes* (SEQ ID NO:28) containing a nuclear localization signal (NLS) sequence and was codon-optimized for expression in corn.

Figure 2:
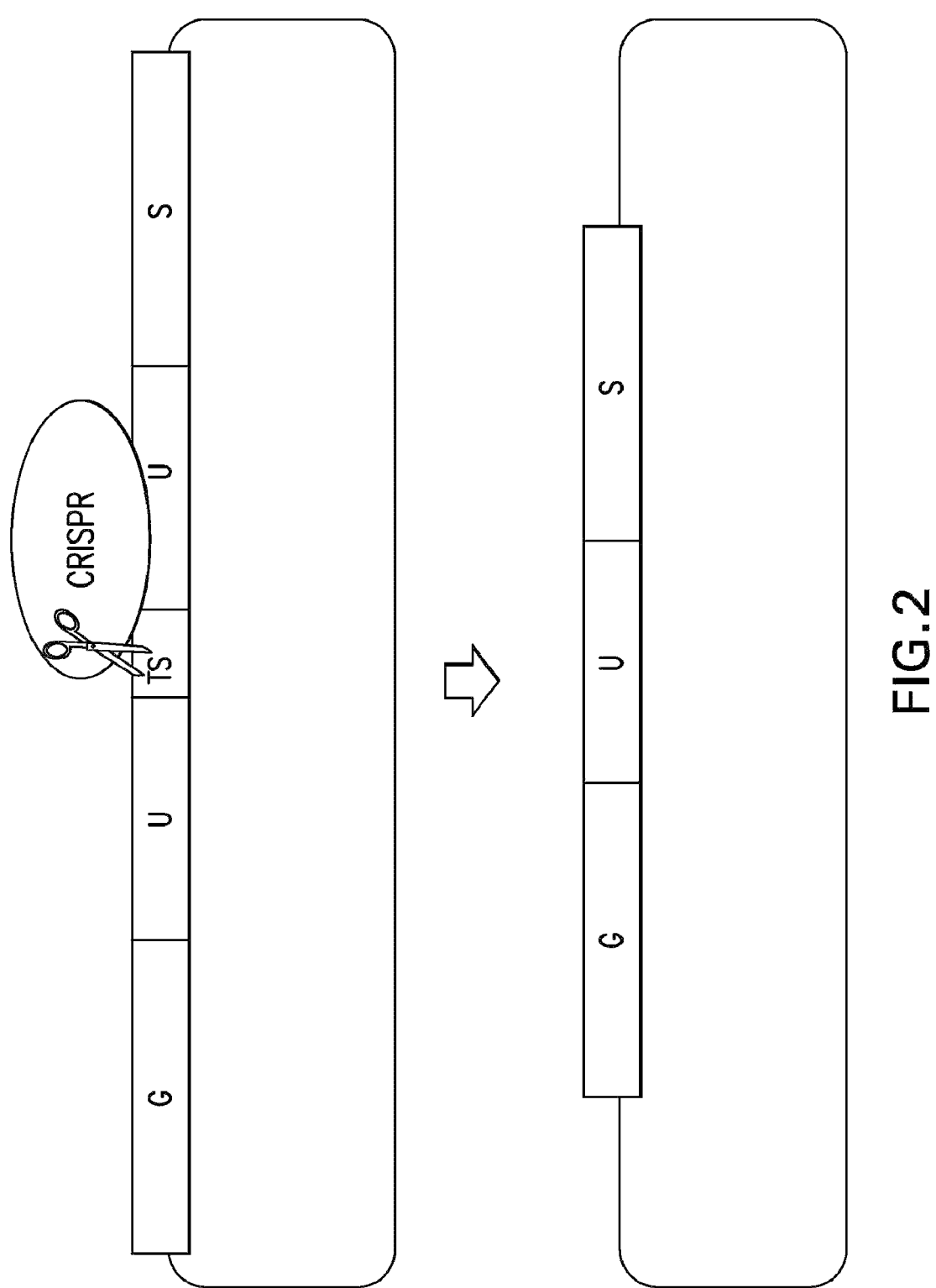
FIG. 2: Illustration of a modified GUS (β-glucuronidase) reporter gene harboring a direct repeat of the coding sequence (GUUS) interrupted by a target site (TS) for CRISPR cleavage.

The reporter gene construct for these experiments was a cassette containing a modified β-glucuronidase (GUS) coding sequence with a corn genomic target site (protospacer and PAM) for targeted CRISPR cleavage (e.g., the Zm7 (SEQ ID NO:22), Zm231 (SEQ ID NO:44), or Zm14 (SEQ ID NO:43)) engineered into the reporter gene and surrounded by an internal direct repeat of the GUS coding sequence (FIG. 2). When co-delivered with expression vectors for CRISPR components, if the CRISPR system cleaves the protospacer sequence, the endogenous plant single-strand annealing (SSA) pathway of homologous recombination DNA repair will reconstitute a functional GUS gene. These modified GUS reporter constructs were named GU-Zm7-US, GU-Zm231-US, or GU-Zm14-US, referring to the corn genomic target site inserted into the GUS gene, Zm7, Zm231, and Zm14, respectively. One of the modified GUS reporter gene cassettes was co-delivered with expression vectors for the other CRISPR components (e.g., one of the sgRNA cassettes) and the expression cassette encoding the Cas9 endonuclease (SEQ ID NO:28). Expression cassettes were mixed and co-coated on 0.6 μM gold particles using standard protocols. 3-day old pre-cultured immature corn embryos were then bombarded with these prepared gold particles. Embryos were maintained in culture for 3-5 days after bombardment and then processed for histochemical staining using X-Gluc (5-bromo-4-chloro-3-indolyl glucuronide) and standard laboratory protocols.

Figure 3:
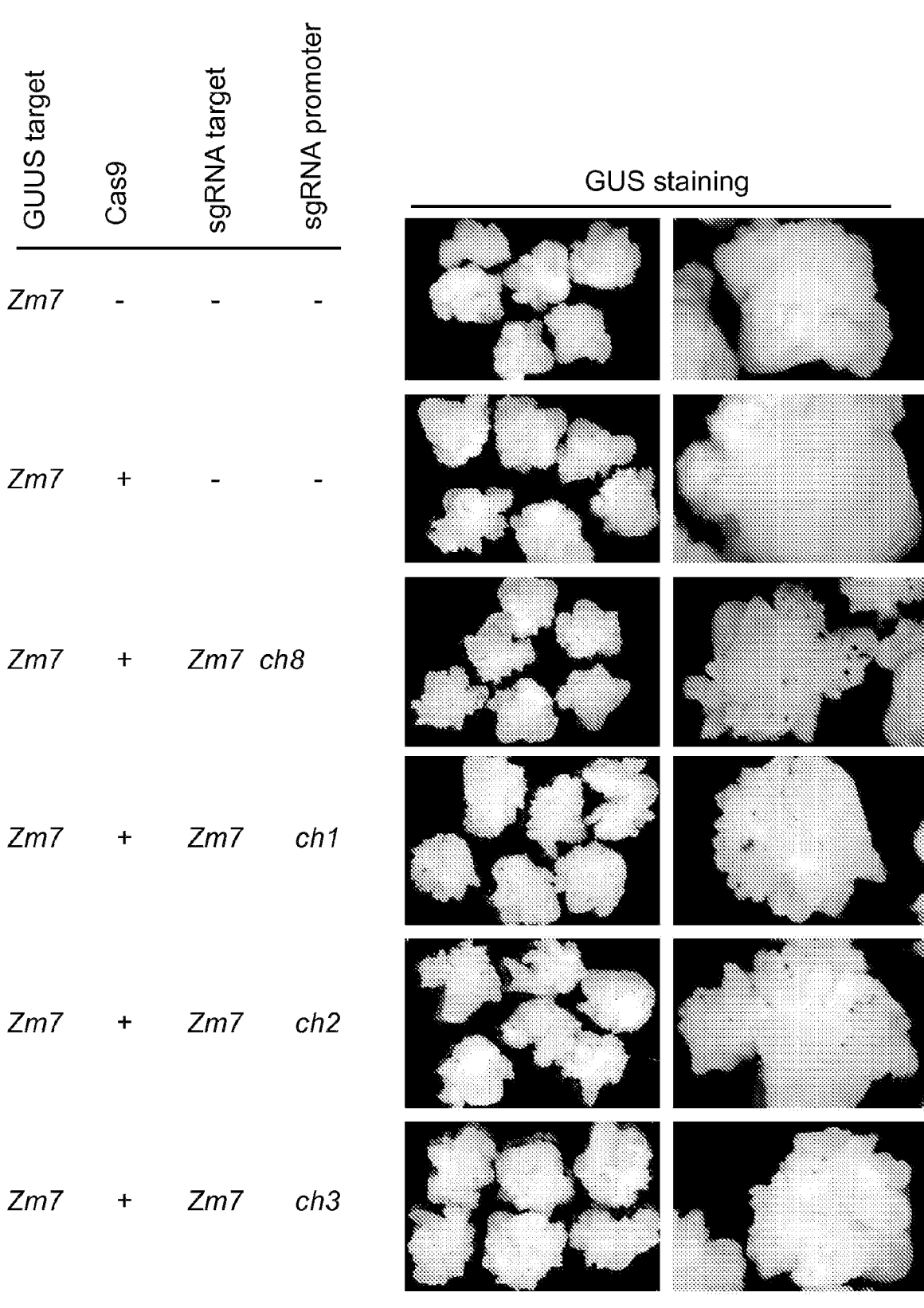
FIG. 3: GUS activities detected in corn callus after co-bombardment of a GUUS reporter construct together with CRISPR constructs designed for introducing a double-stranded break (DSB) at the Zm7 genomic target site.
Figure 4:
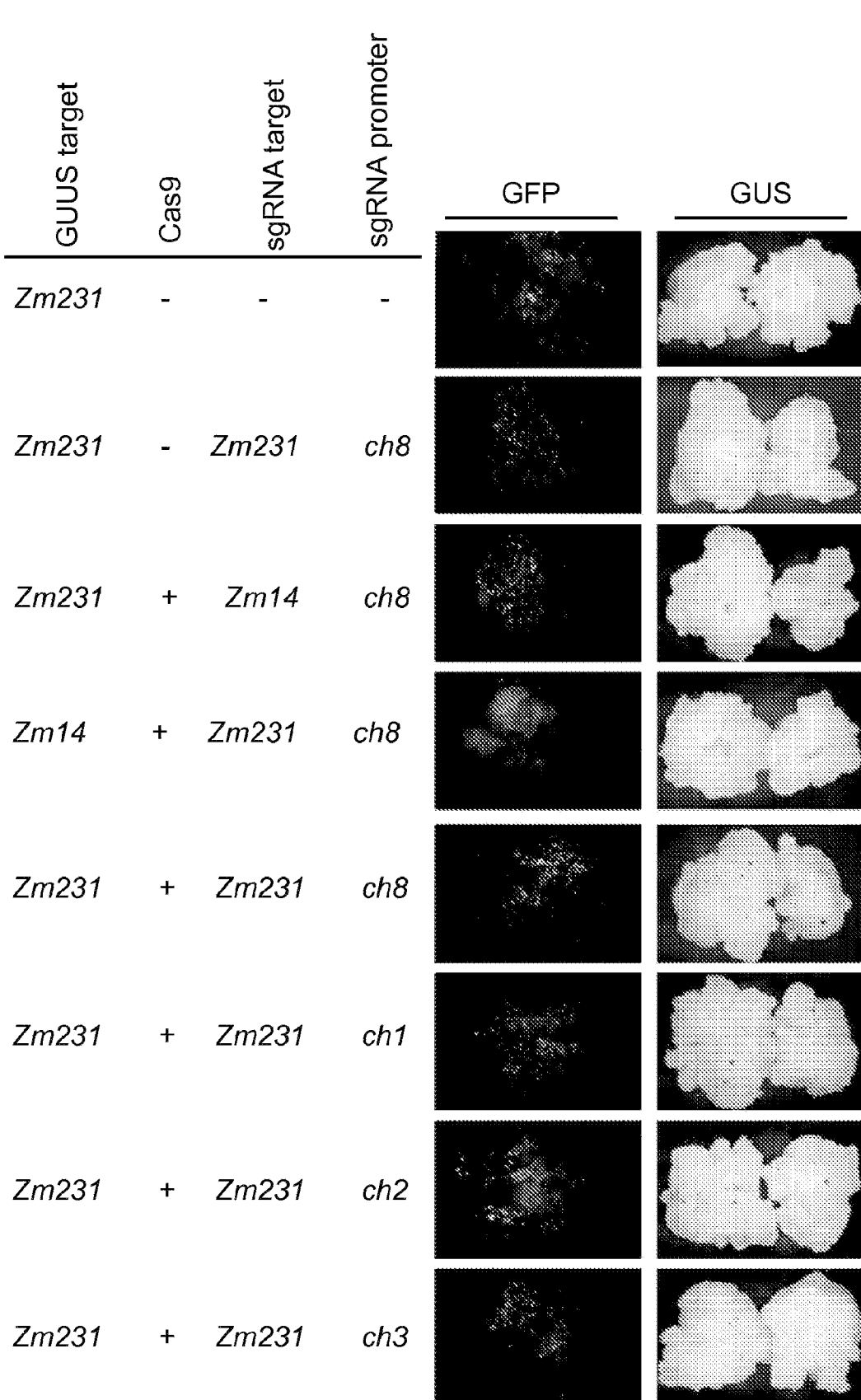
FIG. 4: GUS activity detected in corn callus after co-bombardment of a GUUS reporter construct together with CRISPR constructs designed for introducing a DSB at the Zm231 genomic target site. A different genomic target and single-guide RNA (sgRNA) spacer sequence, Zm14, were used as negative control. Also shown are fluorescence microscopy images of representative calli which were co-bombarded with a green fluorescent protein (GFP) expression vector with the GUUS reporter construct, Cas9 expression vector and vectors containing the various sgRNA cassettes.

If CRISPR-mediated Cas9 endonuclease activity occurs at the protospacer site in the modified reporter gene construct, then GUS activity is detected as blue foci using histochemical staining and X-Gluc (FIGS. 3 and 4).

Separate expression cassettes were designed to contain one of four corn U6 promoters (from chromosomes 1, 2, 3, and 8) driving expression of a sgRNA containing a spacer sequence complementary to the protospacer of the corn Zm7 genomic target site (FIG. 3). To prepare samples for the expression assay, 0.6 μM gold particles were coated with 0.6 pmol of one of the Zm7-sgRNA constructs and 0.3 pmol of each of the other constructs (Cas9 expression cassette and the Zm7-modified reporter construct (GU-Zm7-US)). Once the coated gold particles were prepared, ¼ of the mixture was used for bombardment of 3-day old immature corn embryos using standard protocols. More than 50 immature corn calli were bombarded for each set of constructs evaluated, and staining was done 5 days post-bombardment. Following staining, photographs of representative calli (overview of several calli and a close-up view of a single callus) were taken (FIG. 3). The modified reporter construct GU-Zm7-US was designed to contain the Zm7 genomic target site (SEQ ID NO:22), and the sgRNA was designed to contain a copy of the Zm7 spacer (SEQ ID NO:23). The Zm7-sgRNA spacer was incorporated into expression cassettes with one of the four 397 bp corn U6 promoters from chromosome 1 (SEQ ID NO:30), chromosome 2 (SEQ ID NO:32), chromosome 3 (SEQ ID NO:34), or chromosome 8 (SEQ ID NO:36). Negative controls used in the transformation included the modified reporter construct GU-Zm7-US with the Zm7 genomic target site and: (1) lacking both the Cas9 endonuclease expression cassette and the Zm7-sgRNA expression cassette; or (2) lacking just the Zm7-sgRNA expression cassette (FIG. 3). For both of these controls no blue sectors were detected, indicating no CRISPR-mediated cleavage of the modified reporter construct had occurred. The results from evaluation of the four different 397 bp corn U6 promoters in driving expression of the Zm7-sgRNA cassette showed that while all four 397 bp corn U6 promoters worked (i.e., blue sectors detected in the calli), the efficacy of the different promoters varied (as evidenced by the size and number of blue sectors in the calli). The U6 promoter from corn chromosome 8 showed the most efficacy, followed by the U6 promoter from chromosome 1. The U6 promoters from chromosomes 2 and 3 showed similar efficacy to each other (Chr 8>Chr 1>Chr2≈Chr3).

The specificity of the CRISPR/Cas9 system in this corn expression system was evaluated by testing mismatches between the protospacer sequence within the genomic target site in the modified GUUS reporter gene construct and the spacer sequence included in the varying sgRNA constructs (FIG. 4). As in the experiment described above, 0.6 μM gold particles were coated with one or more constructs; 0.3 pmol of the individual modified GUUS reporter construct (GUUS target), 0.16 pmol of the Cas9 endonuclease expression cassette, 0.3 pmol of the individual sgRNA cassettes, and 0.03 pmol of a transformation control construct expressing green fluorescent protein (GFP) (FIG. 4). Once the coated gold particles were prepared, ¼ of the mixture was used for bombardment of 3-day old immature corn embryos using standard protocols. More than 50 immature corn calli were bombarded for each set of constructs evaluated. Tissue was maintained in culture for 3 days post-bombardment. Determination of GFP expression by fluorescence microscopy was done on day 1 and again on day 3 to validate uniform bombardment and transformation. After the fluorescence microscopy on day 3, the calli were processed for X-Gluc staining and fluorescent and light micrographs of representative calli were taken (FIG. 4). The fluorescent staining for all calli indicated good transformation.

Negative controls used in the transformation included the modified reporter construct GU-Zm231-US with the Zm231 genomic target site (1) lacking both the Cas9 endonuclease expression cassette and any sgRNA expression cassette; or (2) having a Zm231-sgRNA expression cassette with a corn U6 promoter from chromosome 8, but lacking the Cas9 endonuclease expression cassette (FIG. 4). Both of these controls showed no blue sectors detected with X-Gluc staining, indicating no CRISPR-mediated cleavage of the modified reporter construct had occurred (FIG. 4).

The specificity of the CRISPR/Cas9 system was also evaluated using controls including a mismatch between the protospacer site in the modified GUUS reporter construct and the sgRNA spacer sequence. Specifically, the mismatch was between the modified reporter construct GU-Zm231-US with the Zm231 genomic target site and (1) the sgRNA expression cassette with the Zm14 spacer and a corn U6 promoter from chromosome 8; or (2) the sgRNA expression cassette with the Zm231 spacer sequence and a corn U6 promoter from chromosome 8 (FIG. 4).

Finally, the 397 bp corn U6 promoters (chromosome 1, 2, 3, and 8) were each used to generate sgRNA expression cassettes with the Zm231 genomic target site. These were each co-transformed with the modified reporter construct GU-Zm231-US made with the Zm231 genomic target site. Results indicated that when the sgRNA spacer sequence and the genomic target site of the reporter construct were mismatched, there was very little GUS activity detected. By contrast, when the sgRNA spacer sequence and the genomic target site of the reporter construct were matched, many large blue foci were detected (FIG. 4). The U6 promoter from corn chromosome 8 may have higher efficacy (based on the assumption that efficacy correlates to blue foci which were more numerous, larger in size, and darker in staining intensity), followed by the U6 promoter from corn chromosome 1. The U6 promoters from corn chromosomes 2 and 3 showed similar efficacy to each other (Chr 8>Chr 1>Chr2≈Chr3).

The sgRNA driven by the U6 promoter from corn chromosome 8 consistently showed high activity. These findings suggest that different corn U6 promoters have differing activities, and further highlights the usefulness of the U6 promoter derived from corn chromosome 8 in the CRISPR/Cas system of targeted genome modification.

Example 5

Blunt-End Oligonucleotide Integration

The CRISPR/Cas9 system was evaluated for targeting efficacy of insertion of a blunt-end double-stranded DNA fragment into one of three genomic target sites, identified as Zm_L70a (SEQ ID NO:47), Zm_L70c (SEQ ID NO:59), and Zm_L70d (SEQ ID NO:61) within the corn genome. Each of these three genomic target sites is unique in the corn genome. If the CRISPR components are capable of endonuclease activity and introduce a double strand break (DSB) in the protospacer of the selected genomic target site, then the endogenous corn non-homologous end-joining DNA repair system will insert the blunt-end double-stranded DNA fragment into the DSB.

Figure 5A:
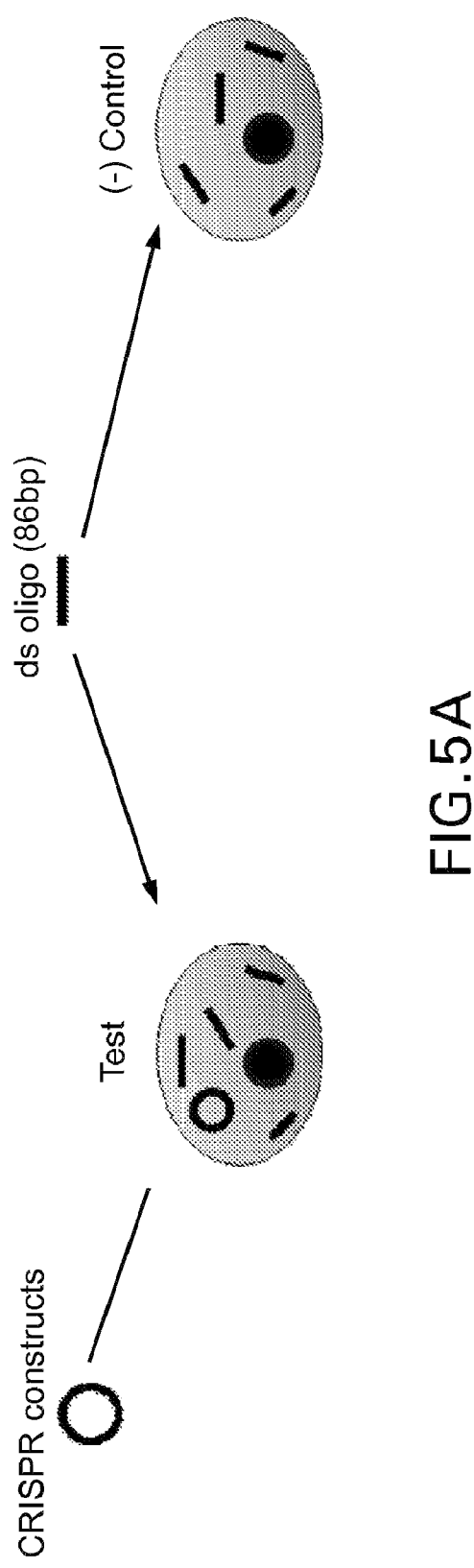
FIGS. 5A-5E: Illustrations of (FIG. 5A) oligonucleotide integration assay.
Figure 5B:
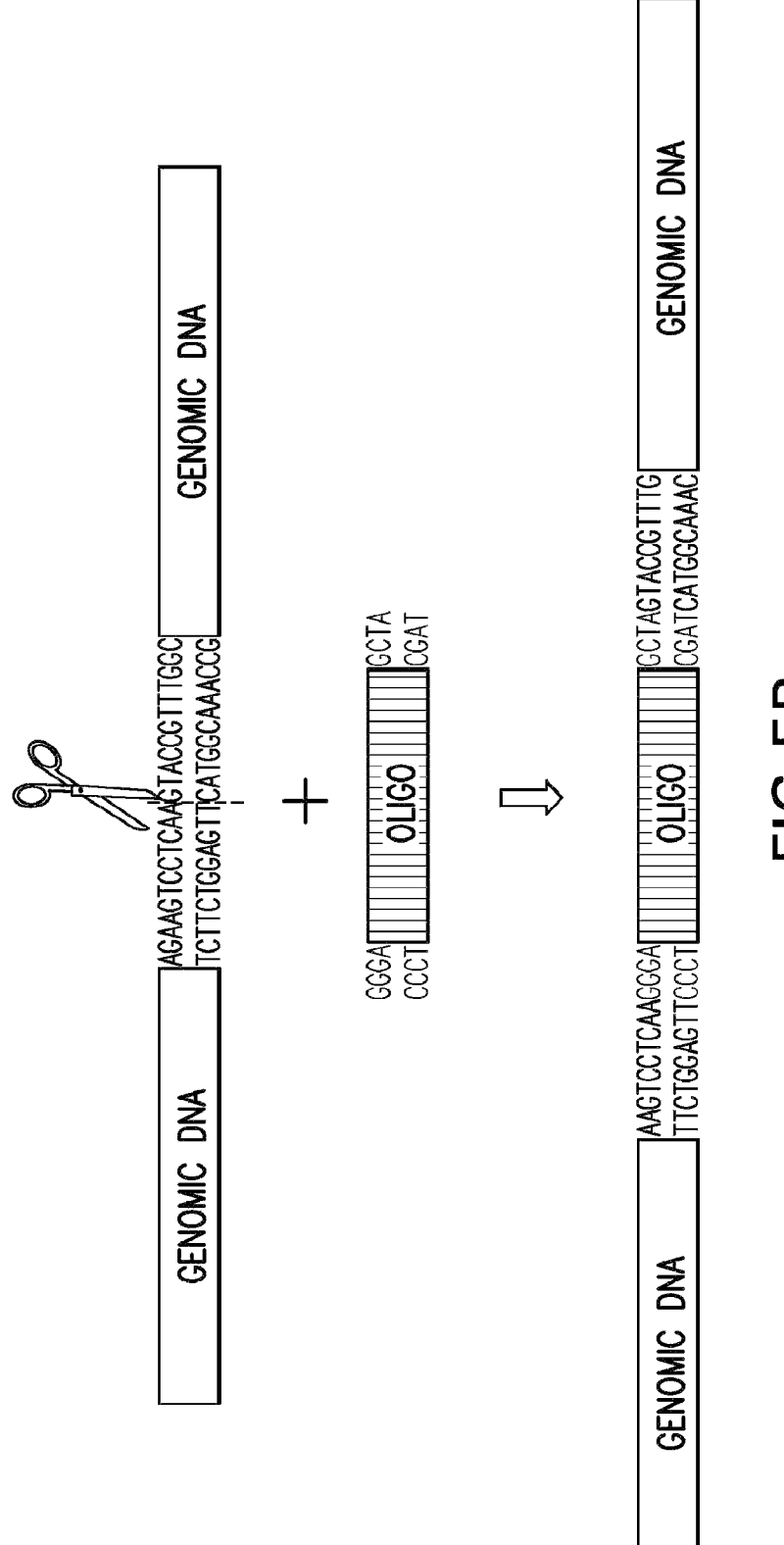
Figure 5C:
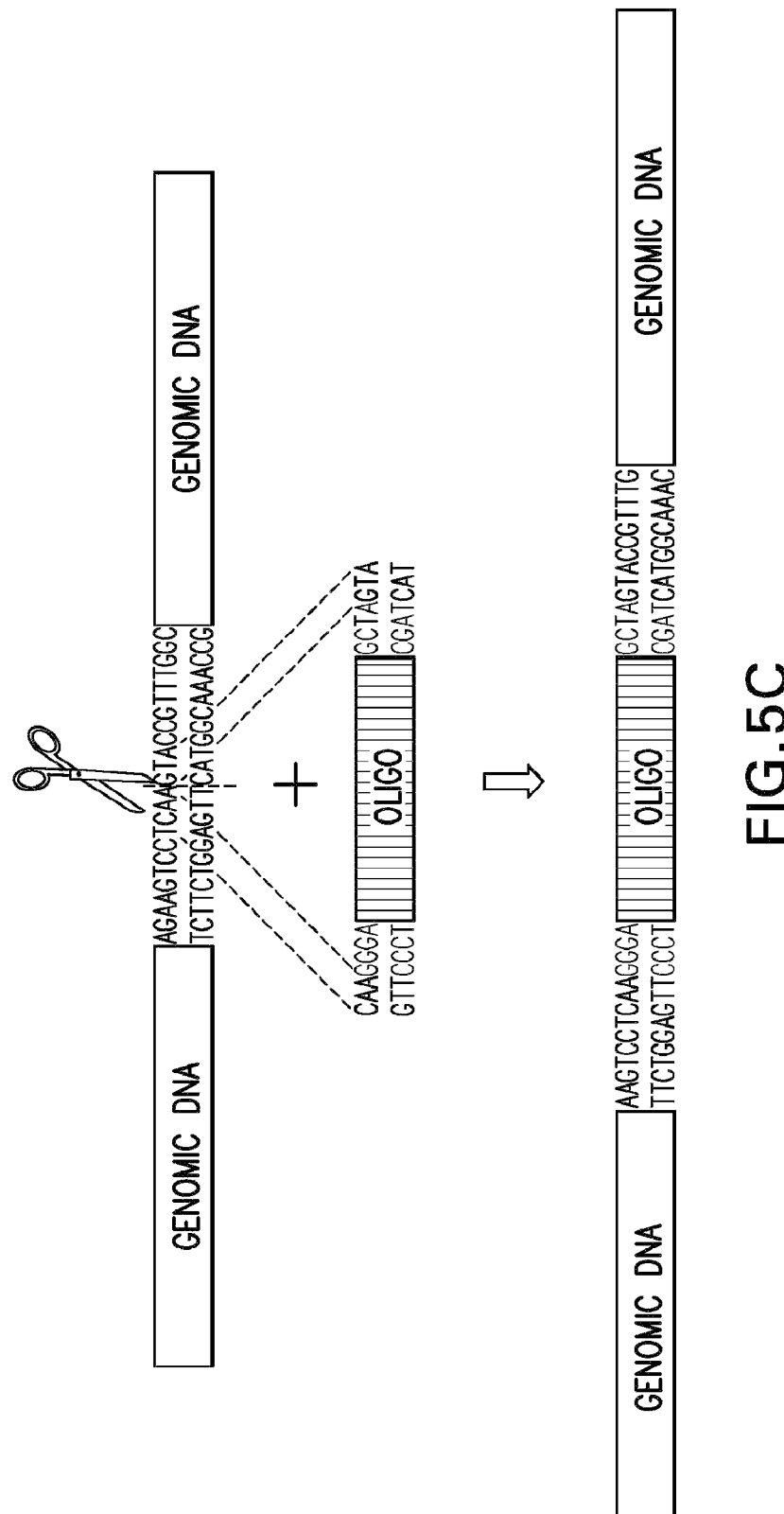

Complementary oligonucleotides were pre-annealed to form blunt-ended double-stranded DNA fragments, and these were co-transformed with CRISPR constructs into corn protoplasts (FIG. 5A). The oligonucleotide pairs were designed to either (1) not contain microhomology regions (see FIG. 5B), or (2) contain on each end (5' and 3') a 3 bp microhomology to the corresponding 5' and 3' flanking sequence at the cut site of the protospacer in the genomic target site (FIG. 5C). The microhomology sequences may promote blunt-end double-strand DNA fragment integrations through a mechanism of microhomology-driven non-homologous end-joining at the genomic target site. The two sequences of the oligonucleotide pair without microhomology sequence were SEQ ID NO:45 and SEQ ID NO:46. The three pairs of oligonucleotides, each containing microhomology to their respective genomic target site, were annealed in pairwise combinations of the following oligonucleotides: (1) SEQ ID NO:62 and SEQ ID NO:63 (microhomology to Zm_L70a); (2) SEQ ID NO:64 and SEQ ID NO:65 (microhomology to Zm_L70c); and (3) SEQ ID NO:66 and SEQ ID NO:67 (microhomology to Zm_L70d) to form blunt-end double-strand DNA fragments.

For these blunt-end double-strand DNA fragment integration assays, the CRISPR constructs used included the Cas9 endonuclease expression cassette described above, and one of three sgRNA expression cassettes. The three sgRNA expression cassettes were each driven by the 397 bp version of the U6 promoter from corn chromosome 8 (SEQ ID NO:7) and contained the spacer sequence corresponding to the genomic target sites: Zm_L70a (SEQ ID NO:48), Zm_L70c (SEQ ID NO:58), and Zm_L70d (SEQ ID NO:60). Differing combinations of the CRISPR components and oligonucleotides for these assays were mixed as follows:

0.6 pmol of the Cas9 expression cassette, 1.6 pmol of one of the sgRNA expression cassettes, and 35 pmol of the pre-annealed, oligonucleotide pair, and, using a standard PEG-mediated protocol, transformed into aliquots of corn leaf protoplast suspensions containing about 320,000 cells. Two days later, corn protoplasts were harvested and analyzed for insertion of the blunt-end double-strand DNA fragment into the particular L70 genomic target site targeted by the unique sgRNA selected in each case (Table 4). The negative control was the omission of the Cas9 expression cassette during the corn protoplast transformation.

To detect the insertion of the blunt-end double strand DNA fragment into the corn chromosome, DNA was extracted and high-throughput thermal amplification (PCR) was done with multiple pairs of primers (Table 5). As the blunt-end double strand DNA fragment may insert into the CRISPR cleaved chromosomal DNA in either orientation, primers were designed to one strand of the blunt-end double strand DNA fragment and to both flanking genomic regions, with each primer pair spanning the junction of the insertion site. The PCR amplicons were separated on a fragment analysis platform (ABI3730 DNA analyzer) from Life Technologies (Grand Island, NY). This platform, which is more sensitive than gel-based electrophoresis methods and has single-bp resolution, confirmed whether the amplicons originated from the template of interest and whether they were specific to the experimental treatment conditions.

TABLE 4

DNA and RNA sequences of *Streptococcus pyogenes* sgRNA containing spacer sequences complementary to the protospacer sequence of the corn genomic target sites L70a, L70c, L70d.

| SEQ ID NO. | | |
| --- | --- | --- |
| DNA | RNA | Genomic target site |
| 82 | 85 | Zm_L70a |
| 83 | 86 | Zm_L70c |
| 84 | 87 | Zm_L70d |

Figure 5D:
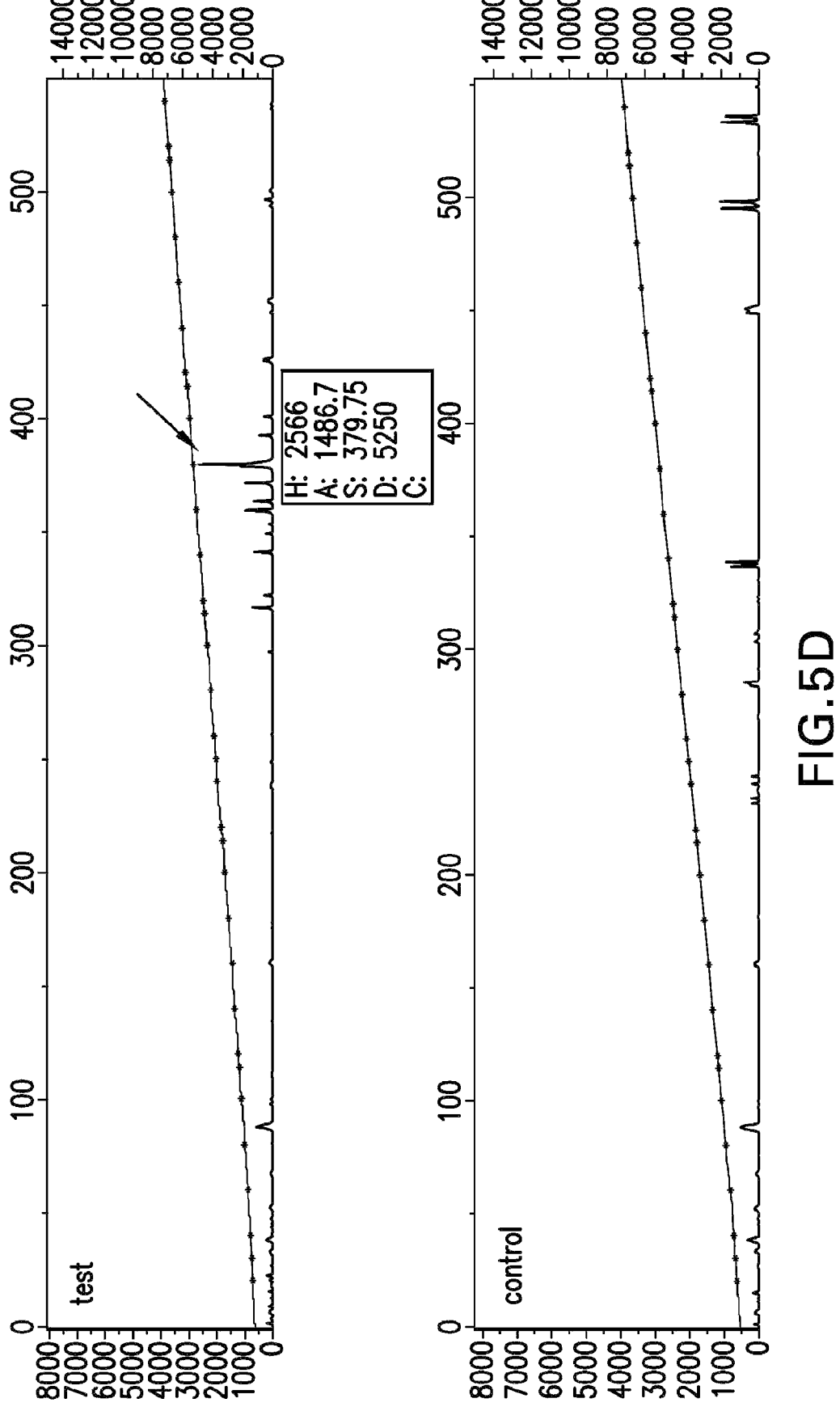

One representative fragment analysis profile is shown in FIG. 5D (Experiment T3, Table 5). Amplification of DNA extracted from corn protoplasts transformed with Cas9, sgRNA containing spacer sequences complementary to the protospacer sequence of the Zm_L70c corn genomic target site (SEQ ID NO:83), and the blunt-end double-stranded DNA fragment without microhomology, using primers at the Zm_L70c genomic target site (SEQ ID NO:49, primer specific for the inserted blunt-end double-strand DNA fragment, and SEQ ID NO:55, primer specific for flanking genomic DNA) revealed a major peak of the expected size and several additional peaks of similar sizes (arrow) (FIG. 5D, top panel). By contrast, no amplification products were seen from DNA extracted from the negative control transformations (FIG. 5D, bottom panel). This PCR profile was consistent with double-stranded breaks repaired erroneously by non-homologous end-joining, resulting in introduction of short indels at the site of repair.

Figure 5E:
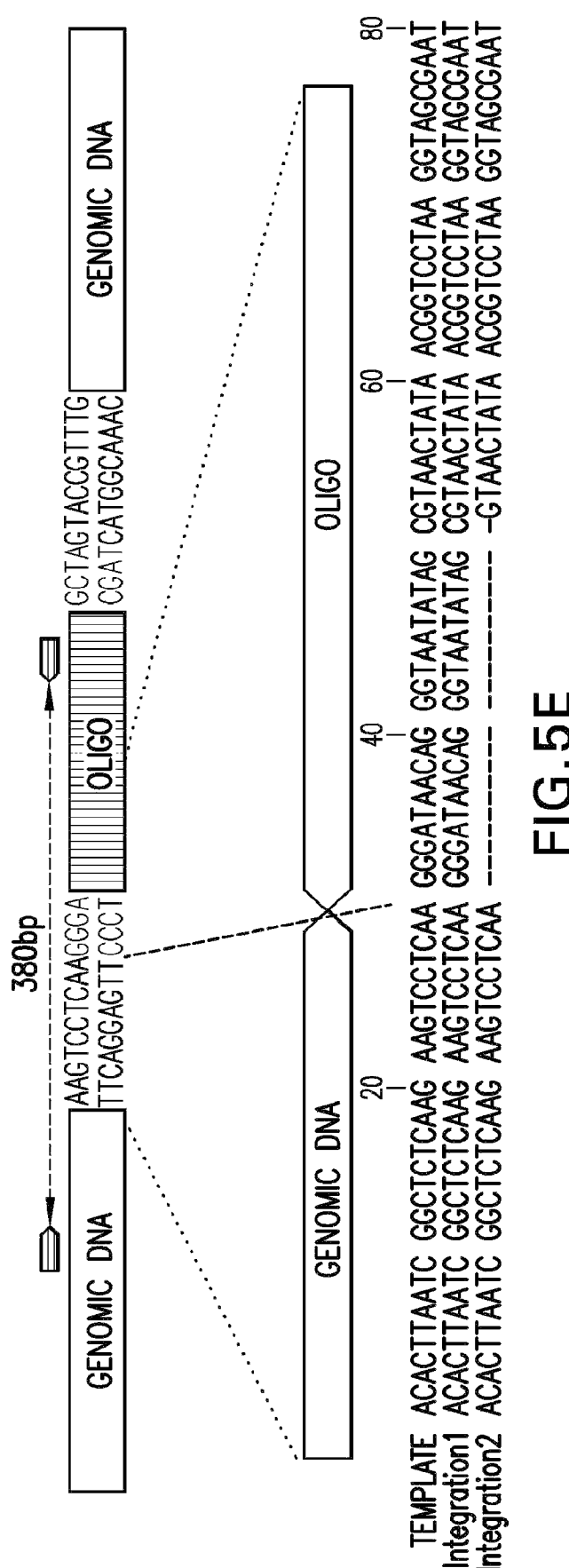

To confirm that the blunt-end double-strand DNA fragment was incorporated at the genomic target site, the PCR amplicons were cloned and sequenced (Table 5). Negative controls lacking Cas9 proteins did not produce PCR products. Seven of the ten experiments showed the expected pattern: a positive PCR product of the expected size for the test samples, and no PCR product for control samples. The seven experiments showing a positive PCR product included experiments demonstrating integrations occurring for both blunt-end double-strand DNA fragments with and without microhomology. Experiments T1 and T7 failed to detect targeted integrations in either test or control samples. PCR products from six of the experiments were cloned and sequenced, confirming the expected DNA fragment-chromosome junctions for blunt-end double-strand DNA fragment integration. Sequencing results showed the presence of both full-length and truncated DNA fragments (indels) present at the site of blunt-end double-strand DNA fragment integration (see, e.g., FIG. 5E, Experiment T1). Sequences were consistent with the fragment analysis (FIG. 5D) and demonstrated that CRISPR/Cas9 can target native, sequence-specific, chromosomal loci for cleavage in corn protoplasts. These results also demonstrated successful blunt-end double-strand DNA fragment integration with and without regions of microhomology.

Figure 6:
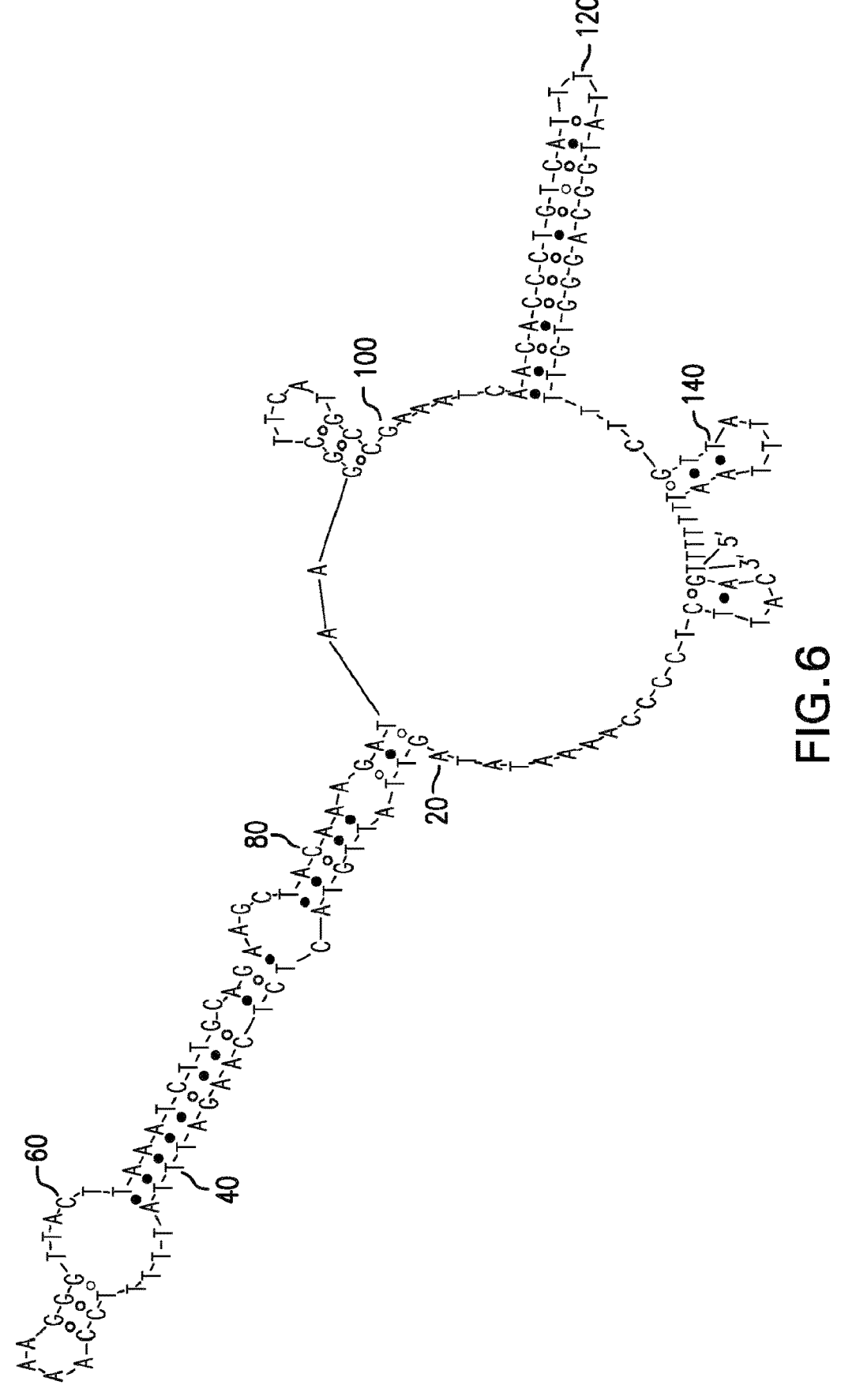
FIG. 6: Illustration of a sgRNA including a spacer sequence complementary to a native corn genomic target site and an artificial loop (5'-CCAAAAGG-3'; SEQ ID NO:105) and its predicted secondary structure designed for *Streptococcus thermophilus* Cas9-mediated targeting (SEQ ID NO:110).

Zm_L70e (SEQ ID NO:72), Zm_L70f (SEQ ID:73), Zm_L70g (SEQ ID NO:74), or Zm_L70h (SEQ ID NO:75). The seven nucleotides at the 3' end of each of these genomic target sites represent the *S. thermophilus*-specific protospacer adjacent motif (PAM, 5'-NNAGAAW-3'; SEQ ID NO:106). FIG. 6 shows the predicted secondary structure of this *S. thermophilus* sgRNA (SEQ ID NO:70) with a copy of the spacer sequence (SEQ ID NO:71) complementary to the protospacer sequence of the corn Zm_L70h genomic target site (SEQ ID NO:75) and stem-loop linker (5'-CCAAAAGG-3'; SEQ ID NO:105). Table 6 lists the corresponding SEQ ID NOs for the DNA and RNA sequences encoding *S. thermophilus* sgRNAs containing spacer sequences complementary to the protospacer sequence of the corn genomic target sites Zm_L70e, Zm_L70f, Zm_L70g, and Zm_L70h.

TABLE 5

Blunt-end oligonucleotide insertion assay.

| Experiment | Treatments | Genomic protospacer/ target site | Micro-homology | Orientation | Primer pairs (SEQ ID NOs) | Expected amplicon size (bp) | Expected amplicon | Sequenced amplicon |
|---|---|---|---|---|---|---|---|---|
| T1 | test | L70a | – | + | 50/49 | 408 | – | – |
| | (–) control | L70a | – | + | 50/49 | N/A | – | – |
| T2 | test | L70a | – | – | 51/49 | 324 | + | + |
| | (–) control | L70a | – | – | 51/49 | N/A | – | – |
| T3 | test | L70c | – | + | 55/49 | 384 | + | + |
| | (–) control | L70c | – | + | 55/49 | N/A | – | – |
| T4 | test | L70c | – | – | 54/49 | 411 | + | + |
| | (–) control | L70c | – | – | 54/49 | N/A | – | – |
| T5 | test | L70c | + | + | 55/49 | 384 | + | + |
| | (–) control | L70c | + | + | 55/49 | N/A | – | – |
| T6 | test | L70c | + | – | 54/49 | 411 | + | – |
| | (–) control | L70c | + | – | 54/49 | N/A | – | – |
| T7 | test | L70d | – | + | 56/49 | 359 | – | – |
| | (–) control | L70d | – | + | 56/49 | N/A | – | – |
| T8 | test | L70d | – | – | 57/49 | 356 | + | + |
| | (–) control | L70d | – | – | 57/49 | N/A | – | – |
| T9 | test | L70d | + | + | 56/49 | 359 | + | + |
| | (–) control | L70d | + | + | 56/49 | N/A | – | – |
| T10 | test | L70d | + | – | 57/49 | 356 | + | – |
| | (–) control | L70d | + | – | 57/49 | N/A | * | – |

Where * = sample contaminated.

Example 6

Targeted Genome Modification with CRISPR/Cas9 Complex Genes from *Streptococcus thermophilus*

It may be desirable to accomplish CRISPR-mediated genome modification of some plants (e.g., crop plants) with CRISPR complex genes derived from *Streptococcus thermophilus* instead of *S. pyogenes*. The inventors have developed an expression cassette encoding a codon-optimized nucleotide sequence with two nuclear localization signals (NLS) (SEQ ID NO:136) of the Cas9 protein from *S. thermophilus* (SEQ ID NO:69). The StCas9 was designed to encode both an N-terminal and a C-terminal nuclear-localization signal (NLS) (SEQ ID NO:120) at amino acid position 2-11 and 1133-1142 (SEQ ID NO:135). Additionally, the DNA expression cassette (SEQ ID NO:136) included an intron at nucleotide position 507-695. A series of unique *S. thermophilus* single-guide RNAs (sgRNA) have been designed. The *S. thermophilus* sgRNA was designed to link the native *S. thermophilus* crRNA and tracrRNA with a stem loop (5'-CCAAAAGG-3'; SEQ ID NO:105), and to contain the spacer sequence complementary to the protospacer of the corn genomic target sites selected from

TABLE 6

DNA and RNA sequences of *Streptococcus thermophilus* sgRNA containing spacer sequences complementary to the protospacer sequence of the corn genomic target sites Zm_L70e, Zm_L70f, Zm_L70g, and Zm_L70h.

| SEQ ID NO. | | |
|---|---|---|
| DNA | RNA | Genomic target site |
| 107 | 111 | Zm_L70e |
| 108 | 112 | Zm_L70f |
| 109 | 113 | Zm_L70g |
| 110 | 114 | Zm_L70h |

The assay for *S. thermophilus* Cas9 mediated genome modification was essentially as described in example 5. Specifically, 320,000 corn protoplasts were transfected with 0.8 pmol *S. thermophilus* Cas9 (SEQ ID NO:136) expression construct, and 1.6 pmol of one of the sgRNA expression constructs driven by the 397 bp version of the U6 promoter from corn chromosome 8 (SEQ ID NO:7) containing the spacer sequence corresponding to the genomic target sites: sgRNA construct for site L70e (SEQ ID NO:107), sgRNA construct for site L70f (SEQ ID NO:108, and sgRNA construct for site L70g (SEQ ID NO:109), and 50 pmol of a pre-annealed blunt-end double-strand DNA fragment encoded by SEQ ID NO: 115 and SEQ ID NO: 116. To test for transformation efficiency, 2.5 ug of a construct encoding green fluorescent protein (GFP) was included. At the time of harvesting, an aliquot of the transfected protoplasts was collected to calculate transfection frequency on the PE Operetta® Imaging System (PerkinElmer, Waltham, MA) which calculates the ratio of GFP positive cells per total cells. Omission of the StCas9 expression cassette during the corn protoplast transformation served as the negative control. Protoplasts were harvested 48 hours post transfection and analyzed for insertion of the blunt-end double-strand DNA fragment into the L70e, or L70f, or L70g genomic target site by quantitative, high-throughput PCR analysis using a BioRad QX200™ Droplet Digital™ PCR (ddPCR™) system (BioRad, Hercules, CA) and TaqMan® probes. To determine the percent targeted integration rate, one set of TaqMan primers and probes was used with the ddPCR system to detect the template copy number of a junction of the inserted blunt-end double-strand DNA fragment at the chromosomal target site. The junction specific primers and probe for corn chromosomal sites L70e, L70f, L70g, and L70h are indicated in Table 7. To normalize the amount of DNA in the transfected protoplast aliquot, the ddPCR system was used with a second set of TaqMan primers and a probe (primers encoded by SEQ ID NO:132 and SEQ ID NO:134; probe encoded by SEQ ID NO:133) to determine the template copy number of a site unique in the corn genome and outside of the target site. The calculation for the percent targeted integration rate was the target site specific template copy number divided by the corn genome specific template copy number divided by the transformation frequency as determined by GFP-positive vs. total cell counts using the PE Operetta® Imaging System (PerkinElmer, Waltham, MA). The data points presented in the graph were determined by averaging four biological replicates. The results are presented in FIG. 15 and show that the percent integration rate for each of the sites L70e, L70f, and L70g was higher than the corresponding control.

PCR amplicons corresponding to targeted junctions from the protoplast experiments were sequenced to confirm the integration of the blunt-end double-strand DNA fragments into the selected target sites. FIG. 15B shows an alignment of the expected integration of the blunt-end, double-strand DNA fragment at the L70f target site (SEQ ID NO:144) and one example of target site integration (SEQ ID NO:145) with deletion of some of the sequence of the DNA fragment. Although these sequencing results show indels, the results confirm that the DNA fragment was integrated at the L70f target site.

TABLE 7

| SEQ ID NOs for primers and probes for PCR amplification of junction at corn chromosomal target sites with inserted DNA fragment. | | | |
|---|---|---|---|
| Site | SEQ ID NO: of Genomic specific primer | SEQ ID NO: of Probe | SEQ ID NO: of Inserted DNA specific primer |
| L70e | 139 | 138 | 137 |
| L70f | 140 | 138 | 137 |
| L70g | 141 | 138 | 137 |
| L70h | 142 | 138 | 137 |

Example 7

Targeting Multiple Unique Genomic Sites by sgRNA Multiplexing

Figure 7A:
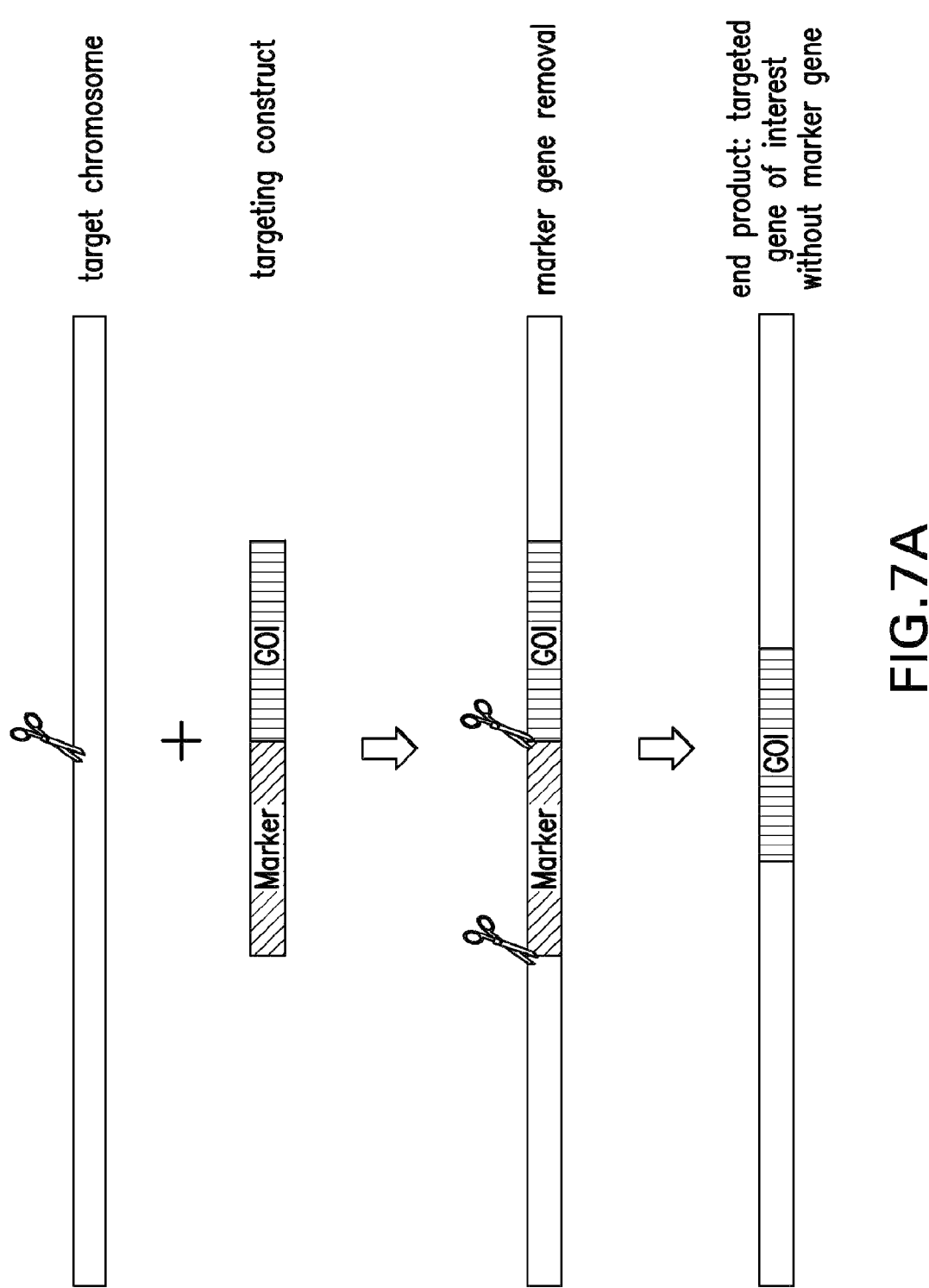
FIGS. 7A-7B: Illustrations of (FIG. 7A) selectable marker gene removal by multiplex CRISPR activity following targeted integration of the gene of interest (GOI)

A key advantage of the CRISPR system, as compared to other genome engineering platforms, is that multiple sgRNAs directed to separate and unique genomic target sites can be delivered as individual components to effect targeting. Alternatively, multiple sgRNAs directed to separate and unique genomic target sites can be multiplexed (i.e., stacked) in a single expression vector to effect targeting. An example of an application that can require multiple targeted endonucleolytic cleavages includes marker-gene removal from a transgenic event (FIG. 7A). The CRISPR system can be used to remove the selectable marker from the transgenic insert, leaving behind the gene of interest.

Figure 7B:
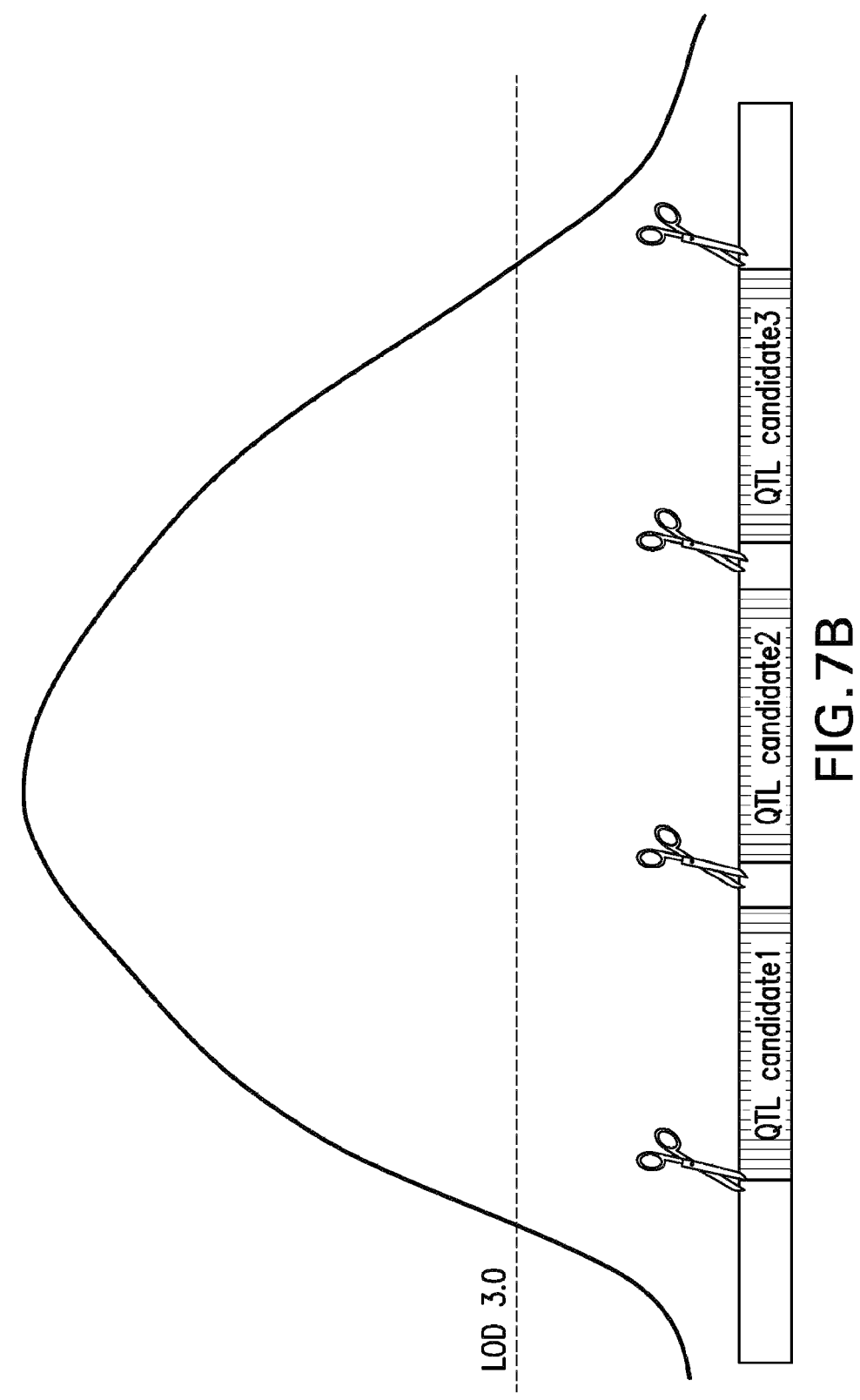

Another example of an application in which such a CRISPR/Cas system can be useful is when there is a requirement for multiple targeted endonucleolytic cleavages, such as when the identification of causal genes behind a quantitative trait is hampered by lack of meiotic recombinations in the QTL regions that would separate the gene candidates from each other. This can be circumvented by transformation with several CRISPR constructs targeting the genes of interests simultaneously. These constructs would either knock out the gene candidates by frame shift mutations or remove them by deletion. Such transformations can also lead to random combinations of intact and mutant loci that would allow for identification of casual genes (FIG. 7B).

Example 8

Integration Rates as a Function of Blunt-End DNA Fragment Concentration and Time The corn protoplast system essentially as described in Example 5 was used to determine the optimal concentration of blunt-end double-strand DNA fragment to be included in the assay mixture to achieve the highest percentage targeting integration rate. For these assays the expression construct encoding the *S. pyogenes* Cas9 was modified to include an intron from position 469-657 in the coding region (SEQ ID NO:119). Additionally, the protein sequence (SEQ ID NO:118) contained two NLS sequences (SEQ ID NO:120), one at the amino-terminal end (amino acids 2 to 11 of SEQ ID NO: 118) and one at the carboxy-terminal end (amino acids 1379 to 1388 of SEQ ID NO:118).

Figure 8:
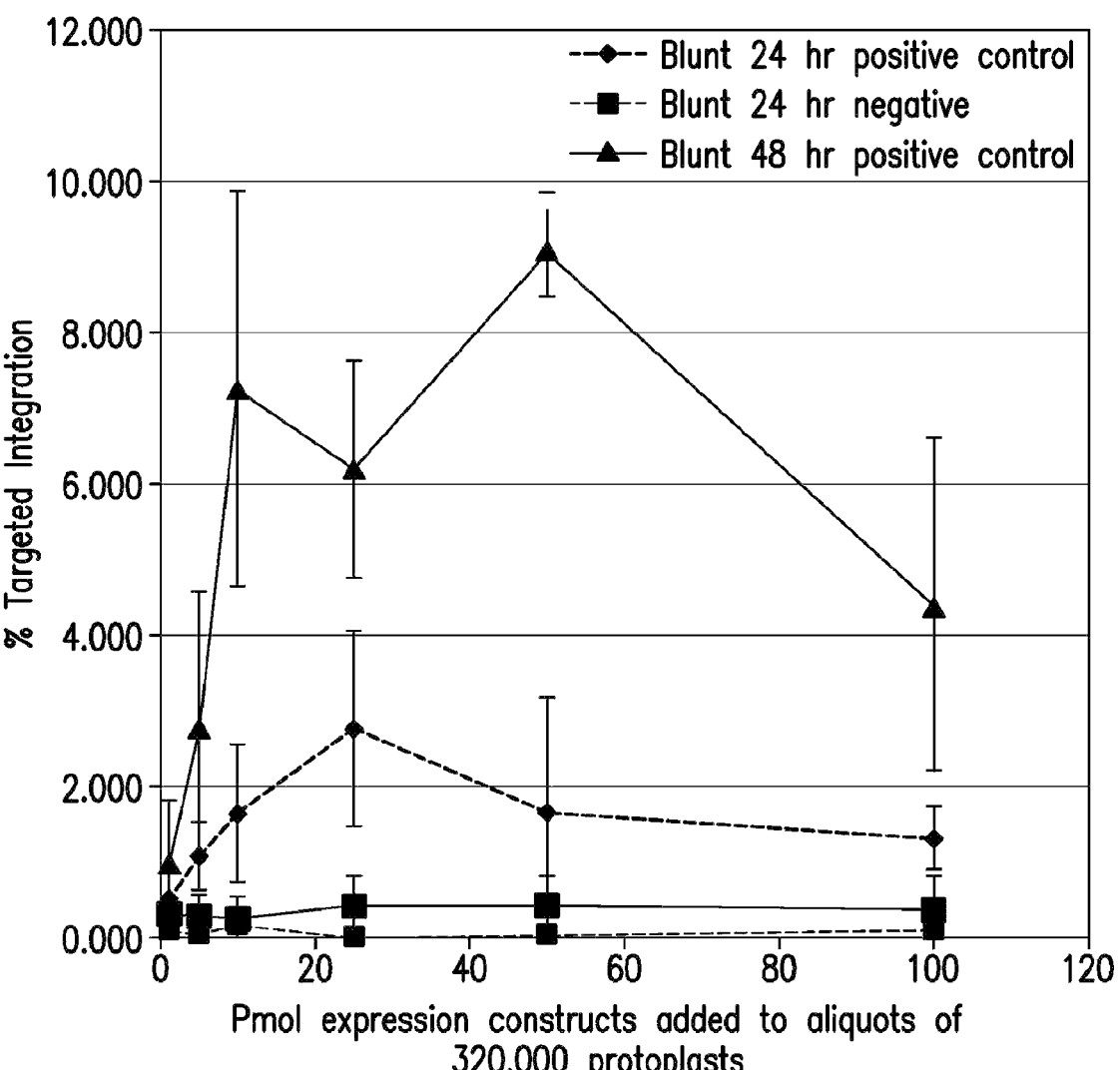
FIG. 8. Graphical presentation of data showing percentage targeted integration rates (Y-axis) detected at 24 and 48 hours post-transformation of corn protoplasts using CRISPR constructs targeting a native chromosomal target (Zm7) in corn and a titration of the pmol of blunt-end, double-stranded DNA fragment added to the transfection mixture (X-axis). The negative controls were run without added Cas9 expression constructs.

For the assay, 320,000 corn protoplasts were transfected with 0.8 pmol *S. pyogenes* Cas9 (SEQ ID NO:119) expression construct, and 1.6 pmol of sgRNA expression construct driven by the 397 bp version of the U6 promoter from corn chromosome 8 (SEQ ID NO:7) containing the spacer sequence corresponding to the genomic target sites: Zm7 (SEQ ID NO:23), and a pre-annealed blunt-end double-strand DNA fragment (SEQ ID NO:115 and SEQ ID NO:116) at 1, 5, 10, 25, 50, and 100 pmol. For transformation efficiency, 2.5 ug of a construct encoding green fluorescent protein (GFP) was included and the number of GFP positive protoplasts per 320,000 corn protoplasts was determined. Omission of the Cas9 expression cassette during the corn protoplast transformation served as the negative control. Protoplasts were harvested at 24 hours and 48 hours post transfection and analyzed for insertion of the blunt-end double-strand DNA fragment into the Zm7 genomic target site by quantitative, high-throughput PCR analysis using a BioRad QX200™ Droplet Digital™ PCR (ddPCR™) system (BioRad, Hercules, CA) and Taqman® probes. To determine the percent targeted integration rate, one set of Taqman primers (represented by SEQ ID NO:137 and SEQ ID NO:143) and a probe (represented by SEQ ID NO:138) was used with the ddPCR system to detect the template copy number of a junction of the inserted blunt-end double-strand DNA fragment at the chromosomal Zm7 target site. To normalize the amount of DNA in the transfected protoplast aliquot, the ddPCR system was used with a second set of Taqman primers and a probe (primers encoded by SEQ ID NO:132 and SEQ ID NO:134; probe encoded by SEQ ID NO: 133) to determine the template copy number of a site unique in the corn genome and outside of the target site. The calculation for the percent targeted integration rate was the target site specific template copy number divided by the corn genome specific template copy number divided by the transformation frequency as determined by GFP-positive vs. total cell counts using the PE Operetta Imaging System (PerkinElmer, Waltham, MA). The data points presented in the graph were determined by averaging four biological replicates. The results are presented in FIG. 8 and show that the peak for percentage targeted integration rate was obtained with 50 pmol of the blunt-end, double-strand DNA fragment and incubation for 48 hours.

Example 9

Integration Rates as a Function of Cas9 Endonuclease Concentration

Figure 9:
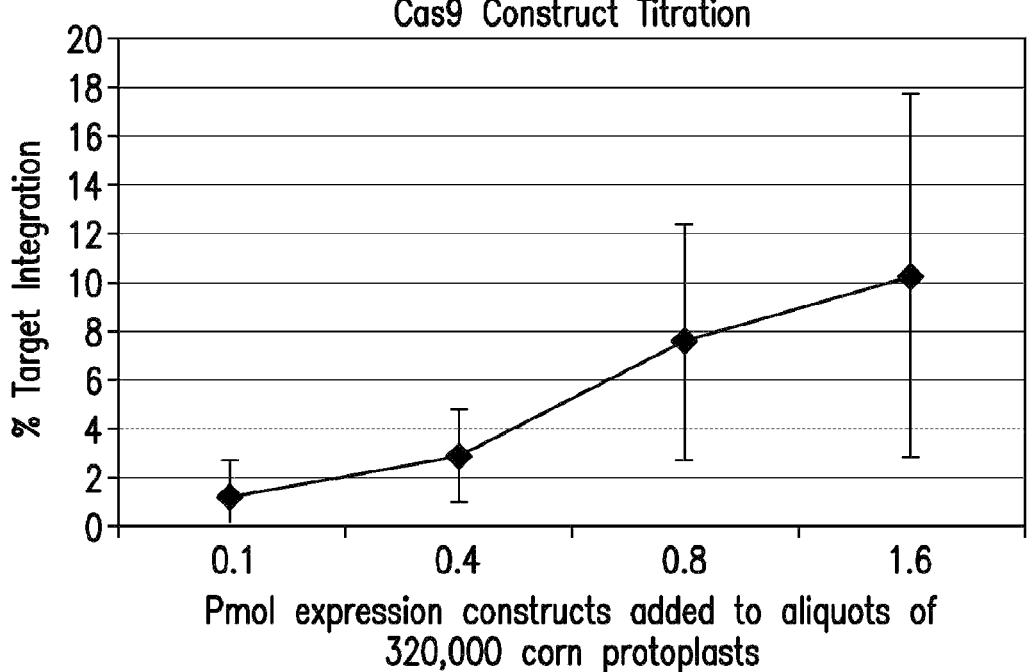
FIG. 9. Graphical presentation of the integration rate (Y-axis) as a function of the amount (in pmol) of SpCas9 expression construct added to transfection mixture of corn protoplasts (X-axis).

The corn protoplast system essentially as described in Example 8 was used to establish the optimal concentration of expression constructs encoding *S. pyogenes* Cas9 included in the protoplast transfection mixture to achieve the highest percentage targeted integration rate with the blunt-end double-strand DNA fragments. For these assays the expression construct encoding the modified *S. pyogenes* Cas9 was as described in Example 8. For the assay, 320,000 corn protoplasts were transfected with 0.1 pmol or 0.4 pmol or 0.8 pmol or 1.6 pmol of the *S. pyogenes* Cas9 (SEQ ID NO:119) expression construct, and 1.6 pmol of sgRNA expression construct driven by the 397 bp version of the U6 promoter from corn chromosome 8 (SEQ ID NO:7) containing the spacer sequence corresponding to the genomic target site Zm7 (SEQ ID NO:23), 50 pmol of pre-annealed blunt-end double-strand DNA fragment (SEQ ID NO:115 and SEQ ID NO:116), and a construct encoding GFP. The corn protoplasts were harvested 48 hours post-transfection and the percentage targeted integration was assessed as described in Example 8 using the ddPCR system and Taqman probes. The results of the analysis of the Cas9 expression construct titration are presented in FIG. 9 showing a linear increase in percentage targeted integration rate over the full-range of pmol of expression construct concentration tested.

Example 10

Sequence Confirmation of Insertion of Blunt-End Double-Strand DNA Fragments

PCR amplicons corresponding to targeted junctions from the protoplast experiments detailed in Example 5 and Example 8 were sequenced to confirm the integration of the blunt-end double-strand DNA fragments into the selected target site, Zm7 or L70c.

For the corn chromosome site Zm7 targeted by CRISPR/Cas9 constructs and with blunt-end double-strand DNA fragment formed by annealed oligonucleotides encoded by SEQ ID NO:115 and SEQ ID NO:116 (see Example 8), PCR amplicons were agarose-gel purified and sequenced. The expected sequence is presented as SEQ ID NO:123, as shown in FIG. 10A. The results from the sequencing show at least one event with a base-pair perfect insertion of the blunt-end double-strand DNA fragment into the target site (SEQ ID NO:124). The results also show events with short deletions in either the chromosome or the DNA insert side of the junction, as indicated with SEQ ID NO: 125 (see FIG. 10A).

For the corn chromosome site L70c targeted by CRISPR/Cas9 constructs and with blunt-end double-strand DNA fragment without micro-homology sequences formed by annealed oligonucleotides encoded by SEQ ID NO:45 and SEQ ID NO:46 (see Example 5), PCR amplicons were agarose-gel purified and sequenced. The expected sequence is presented as SEQ ID NO:126, as shown in FIG. 10B. The results from the sequencing show at least one event that was detected with a base-pair perfect insertion of the blunt-end double-strand DNA fragment into the target site (SEQ ID NO:127). The results also show an example of events with short deletions in either the chromosome or the DNA insert side of the junction, as indicated with SEQ ID NO:128 (see FIG. 10B).

For the corn chromosome site L70c targeted by CRISPR/Cas9 constructs and with blunt-end double-strand DNA fragment with 3 bp micro-homology sequences at each end of the DNA fragment formed by annealed oligonucleotides encoded by SEQ ID NO: 121 and SEQ ID NO:122 (see Example 5), PCR amplicons were agarose-gel purified and sequenced. The expected sequence is presented as SEQ ID NO:129, as shown in FIG. 10C. The results from the sequencing show at least one event that was detected with a base-pair perfect insertion at the junction of the blunt-end double-strand DNA fragment into the target site (SEQ ID NO:130). The results also show an example of events with short deletions in either the chromosome or the DNA insert side of the junction (SEQ ID NO: 131) and/or in the DNA insert itself (SEQ ID NO: 130 and SEQ ID NO:131), as indicated (see FIG. 10C).

These results indicate that blunt-end double-strand DNA fragments are incorporated into a double-strand break (DSB) at a target site created by a CRISPR/Cas9 system. The DNA fragments are incorporated by non-homologous end joining (NHEJ), an error-prone DNA repair mechanism that heals most somatic double-strand breaks in nature. Consistent with the endogenous NHEJ repair mechanism, the results show that blunt-end double-strand DNA fragments were incorporated with short deletions at the DSB created with CRISPR/Cas9 components, as illustrated by comparing SEQ ID NO: 123 and SEQ ID NO: 125 (FIG. 10A), and by comparing SEQ ID NO:126 and SEQ ID NO:128 (FIG. 10B), and by comparing SEQ ID NO: 129 and SEQ ID NO:131 (FIG. 10C) (with this last pair there was also a 2 bp deletion internal to the inserted DNA fragment). Blunt-end double-strand DNA fragments were incorporated in a base-pair perfect manner at the DSB created with CRISPR/Cas9 components, as illustrated by comparing SEQ ID NO:123 and SEQ ID NO: 124 (FIG. 10A), and by comparing SEQ ID NO: 126 and SEQ ID NO:127 (FIG. 10B), and by comparing SEQ ID NO: 129 and SEQ ID NO: 130 (FIG. 10C) (though in this last pair there was a 2 bp deletion internal to the inserted DNA fragment).

Example 11

Integration Rates as a Function of TALEN Endonuclease Concentration

The corn protoplast system essentially as described in Example 8 was used to establish the optimal concentration of expression constructs encoding a pair of TALEN endonucleases needed in the transfection mixture to achieve the highest percentage targeting integration rate of blunt-end double-strand DNA fragments.

Figure 11:
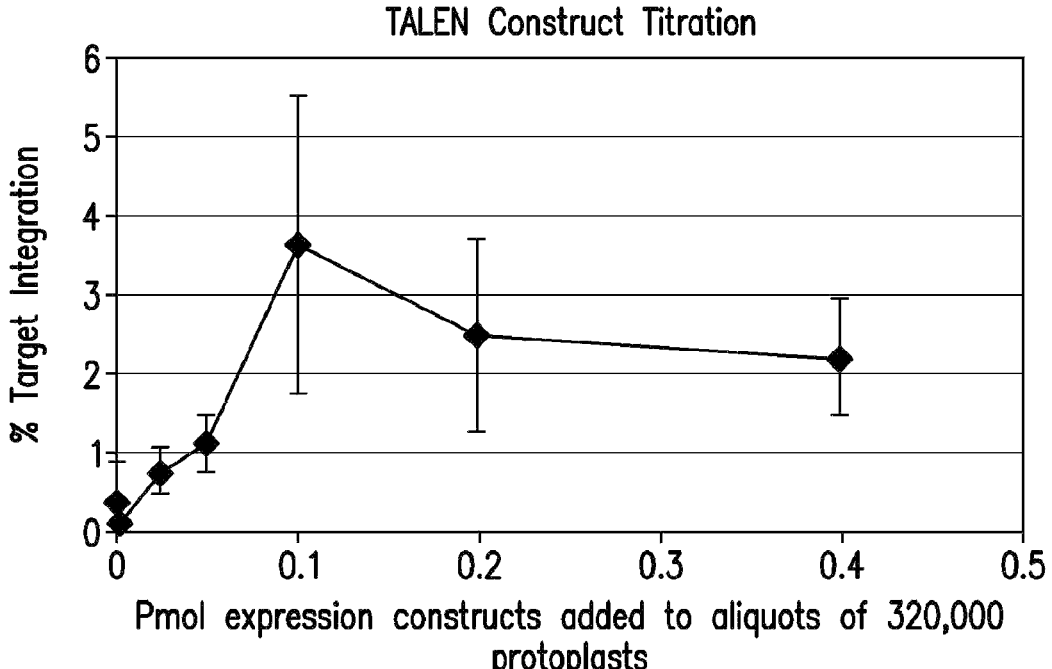
FIG. 11. Graphical presentation of the integration rate (Y-axis) as a function of the amount (in pmol) of TALEN expression constructs targeting corn chromosome site L70.4 which were added to transfection mixture of corn protoplasts (X-axis).

For these assays a pair of expression constructs with TALEN encoding cassettes was tested. The targeting site in the corn chromosome for the TALEN pair was L70.4. For the TALEN assay 0, 0.01, 0.02, 0.05, 0.1, 0.2 and 0.4 pmol of each of the constructs containing the TALEN encoding cassettes was used in the corn protoplast transformation. Also included was 50 pmol of pre-annealed blunt-end double-strand DNA fragment (SEQ ID NO:115 and SEQ ID NO:116) and 2.5 ug of the GFP encoding construct. The corn protoplasts were harvested 48 hours post-transfection and the percentage targeted integration was assessed by high-throughput PCR analysis essentially as described in previous examples. The results of the analysis of the TALEN expression construct titration are presented in FIG. 11 showing that the percentage targeted integration rate plateaus at about 0.1 pmol of each of the TALEN expression constructs included in the transfection reaction.

Example 12

Targeted Integration by Homologous Recombination—CRISPR/Cas9

Genome modification by targeted integration of a desired introduced DNA sequence will occur at sites of double strand breaks (DSB) in a chromosome. The integration of the DNA sequence is mediated by mechanisms of non-homologous end-joining (NHEJ) or homologous recombination using DNA repair mechanisms of the host cell. DSBs at specific sites in the host cell genome can be achieved using an endonuclease such as an engineered meganuclease, an engineered TALEN or a CRISPR/Cas9 system.

Figure 12B:
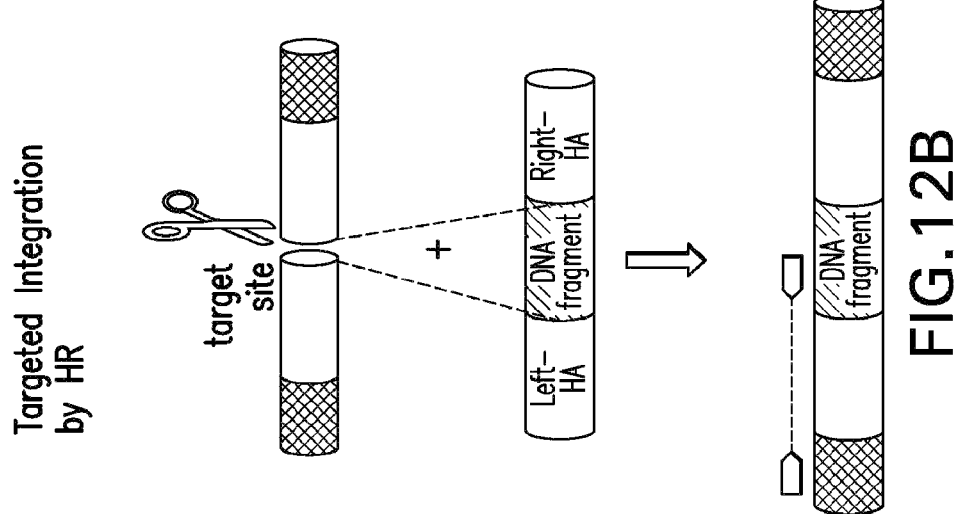
FIGS. 12A-12B. Schematic representation of NHEJ and HR-mediated targeted integration and PCR primer positions for high through-put screening. Targeted integration of a DNA fragment by non-homologous end-joining (NHEJ) is presented in FIG. 12A and targeted integration of a DNA fragment by homologous recombination (HR) is presented in FIG. 12B.
Figure 12A:
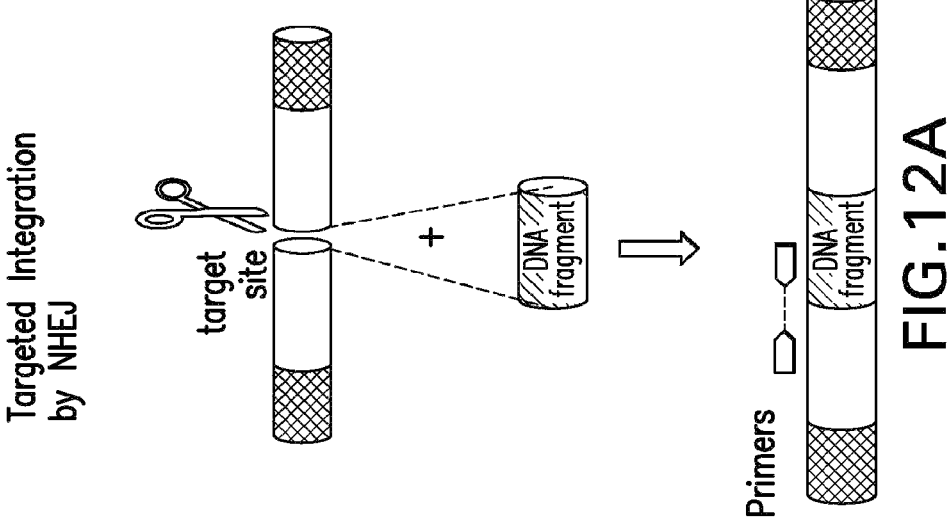

A schematic representation of a high through-put (HTP) testing method of NHEJ and HR-mediated targeted integration is presented in FIG. 12. Targeted integration of a DNA fragment by non-homologous end-joining (NHEJ) is presented in FIG. 12A and targeted integration of a DNA fragment by homologous recombination (HR) is presented in FIG. 12B. For HR, a recombinant DNA construct containing a cassette with the DNA fragment flanked with left- and right-homology arms (Left-HA and Right-HA, respectively) is introduced into the host cell. Following either NHEJ or HR targeted integration, HTP PCR analysis with primers (indicated by the short pair of arrows in FIGS. 12A and 12B) designed to detect a targeted event where one primer is internal to the inserted DNA fragment and a second primer is located in the flanking chromosomal region.

The corn protoplast system as described in the above examples was used to determine homologous recombination (HR) mediated targeted integration rates. The target site Zm7 was targeted by a CRISPR/Cas9 nuclease and the sgRNA for targeting the corn Zm7 site, as described in Example 8. In addition to the constructs encoding the CRISPR/Cas9 and sgRNA cassettes, a construct containing a cassette for homologous recombination cassette was included at either 4 ug concentration or 6 ug concentration. As described above, a construct encoding GFP was also transfected and the percentage of GFP positive cells was used in the calculation of the targeted integration rate. The controls did not contain the construct encoding the SpCas9 endonuclease.

Figure 13A:
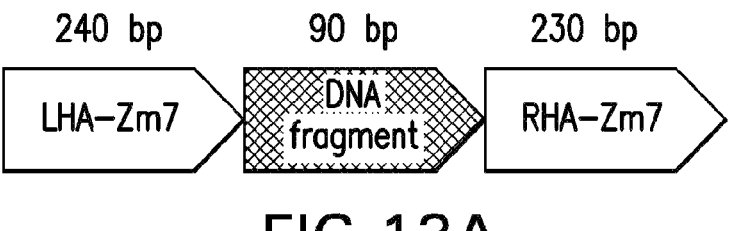
FIGS. 13A-13B. Schematic representation of the constructs used for homologous integration. The blunt-end DNA arrow indicates the 90 bp sequence corresponding to the 90 bp blunt-end, double-strand DNA fragment used for NHEJ assays, LHA refers to left-homology arm, RHA refers to right-homology arm, Zm7 refers to the target site Zm7 targeted by a CRISPR/Cas9+sgRNA. The length in bp of each of the homology arms is indicated.
Figure 13B:
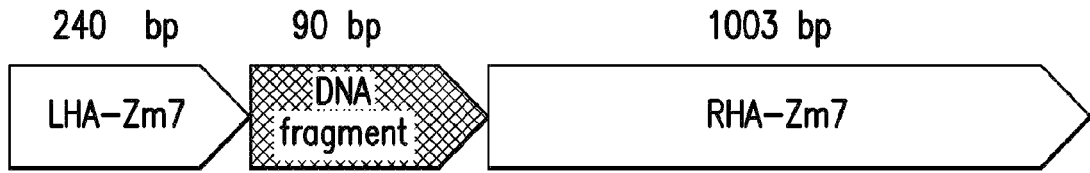

The recombinant DNA constructs containing cassettes for homologous recombination were designed to have the 90 bp sequence corresponding to the 90 bp blunt-end, double-strand DNA fragment used for NHEJ assays (encoded by sequences SEQ ID NO:115 and SEQ ID NO:116) flanked by left and right homology arms (HA). The left-HA is designed based on the sequence flanking the 5'-side of the site for the double-strand break (DSB) for targeted integration. The right-HA is designed as the sequencing flanking the 3'-side of the site for the double-strand break (DSB) for targeted integration. For the Zm7 site the left-HA was 240 bp in length, and two separate right-HA sequences were included, one of 230 bp and one of 1003 bp in length (see FIGS. 13A and 13B, respectively).

Protoplasts were transfected and harvested 48 hours later and analyzed for integration by high through-put PCR with one primer designed for the region of the DNA fragment sequence (encoded by the sequences SEQ ID NO:115 and SEQ ID NO:116) and one primer in the chromosomal region flanking the left homology arm. The size of the expected PCR amplicon with successful HR using the Zm7 targeting constructs (FIGS. 13A and 13B) was 411 bp. In conventional quantitative PCR (qPCR), amplicons longer than about 160 bp cannot be quantitatively measured, and thus, are not recommended to be used. The current experiment clearly demonstrated that significantly longer PCR amplicons can also be used in the ddPCR system, which opens up a host of new opportunities in quantitative biology.

Figure 15A:
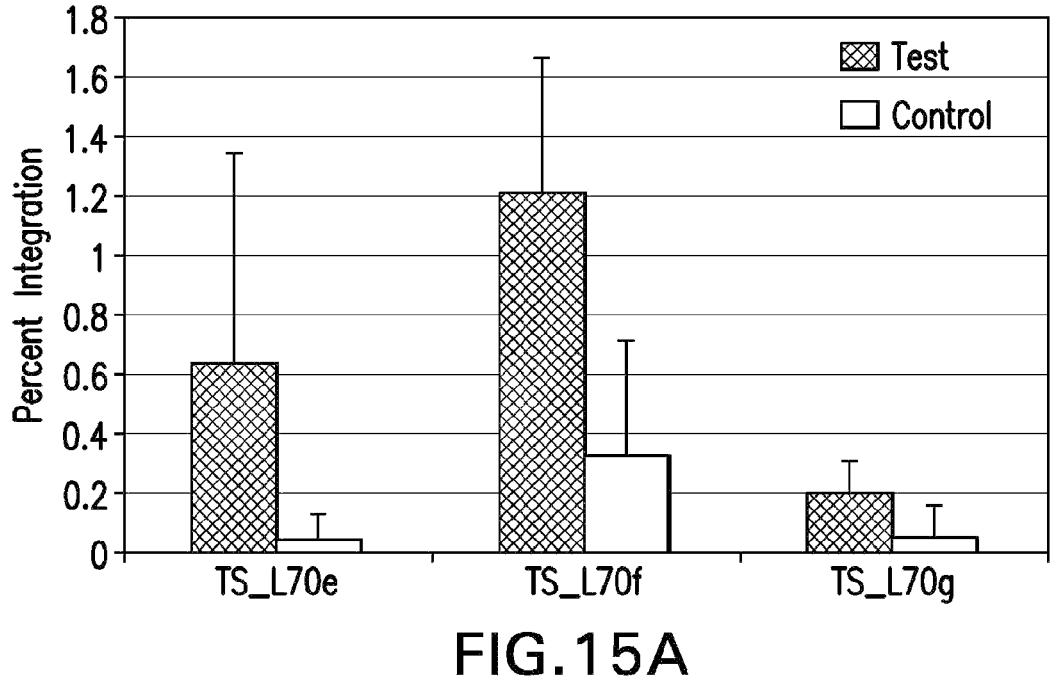
FIGS. 15A-15B.
Figure 15B:

The HR-mediated recombination rate for the corn chromosomal site Zm7 are presented in Table 8 and FIG. 15. When the left-HA and the right-HA were 240 bp and 230 bp, respectively, and the construct with the homology arm cassette was at a concentration of 4 ug or 6 ug, there was not a statistically significant difference in the percentage integration rate between the test sample and the control. When the left-HA was 240 bp and the right-HA was 1003 bp (indicated by SL in Table 8), and the construct with the homology arm cassette was at a concentration of 4 ug there was not a statistically significant difference in the percentage integration rate between the test sample and the control. In contrast, when the left-HA was 240 bp and the right-HA was 1003 bp (indicated by SL in Table 8), and the construct with the homology arm cassette was at a concentration of 6 ug there was a statistically significant ($p < 0.05$) difference in the percentage integration rate between the test sample and the control. This result shows that targeted integration can be achieved by the mechanism of HR at sites of DSB which are targeted by CRISPR/Cas9 system in a corn genome.

TABLE 8

HR-mediated integration rates in corn protoplasts with DSB mediated by a CRISPR/Cas9 system at the chromosomal site Zm7.

|  | Mean | | Std Dev | |
| --- | --- | --- | --- | --- |
|  | Test | Control | Test | Control |
| Zm7 + SS + 4 ug | 0.88346 | 0.15936 | 0.83999 | 0.17658 |
| Zm7 + SS + 6 ugl | 1.20057 | 0.15936 | 0.92889 | 0.17658 |
| Zm7 + SL + 4 ug | 1.297183 | 0.98692 | 0.791837 | 0.86133 |
| Zm7 + SL + 6 ug** | 2.32094 | 0.98692 | 1.35951 | 0.86133 |

**Test was statistically higher ($p < 0.05$) than the corresponding control based on a student's t-test.

Example 13

Targeted Integration by Homologous Recombination—TALEN

The corn protoplast system as described in the above examples was used to determine homologous recombination (HR) mediated targeted integration rates. The target site L70.4 was targeted by a pair of recombinant DNA constructs encoding a TALEN pair directed to target the corn L70.4 site, as described in Example 11. In addition to the constructs encoding the TALEN cassettes, a construct containing a cassette for homologous recombination cassette was included at either 4 ug concentration or 6 ug concentration. As described above, a construct encoding GFP was also transfected and the percentage of GFP positive cells was used in the calculation of the targeted integration rate. The controls did not contain the constructs encoding the TALENs.

Figures 14A, 14B:
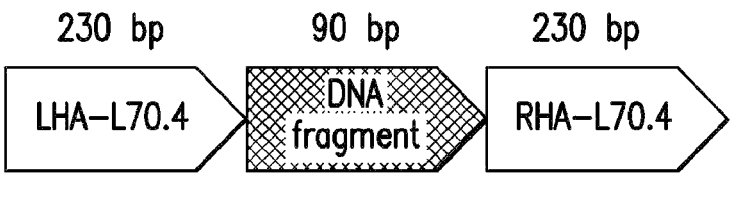
FIGS. 14A-14B. Schematic representation of the constructs used for homologous integration. In the figure, blunt-end DNA arrow indicates the 90 bp sequence corresponding to the 90 bp blunt-end, double-strand DNA fragment used for NHEJ assays, LHA refers to left-homology arm, RHA refers to right-homology arm, L70.4 refers to the target site L70.4 in the corn chromosome targeted by a TALEN pair. The length in bp of each of the homology arms is indicated.

The recombinant DNA constructs containing cassettes for homologous recombination were designed to have the 90 bp sequence corresponding to the 90 bp blunt-end, double-strand DNA fragment used for NHEJ assays (encoded by sequences SEQ ID NO:115 and SEQ ID NO:116) flanked by left and right homology arms (HA). The left-HA is designed based on the sequence flanking the 5'-side of the site for the double-strand break (DSB) for targeted integration. The right-HA is designed as the sequencing flanking the 3'-side of the site for the double-strand break (DSB) for targeted integration. For the L70.4 site the right-HA was 230 bp in length, and two separate left-HA sequences were included, one of 230 bp and one of 1027 bp in length (see FIGS. 14A and 14B, respectively).

Protoplasts were transfected and harvested 48 hours later and analyzed for integration by quantitative, high through-put PCR using the ddPCR system and Taqman probes with one primer designed for the region of the DNA fragment sequence (encoded by the sequences SEQ ID NO:115 and SEQ ID NO:116) and one primer in the chromosomal region flanking the left homologous arm. The size of the expected PCR amplicon with successful HR using the L70.4 targeting construct of FIG. 14A was 383 bp. The size of the expected PCR amplicon with successful HR using the L70.4 targeting construct of FIG. 14B was 1208 bp.

The HR-mediated recombination rate for the corn chromosomal site L70.4 with two separate template DNA constructs is presented in Table 9. When the left-HA and the right-HA were both 230 bp (indicated by SS in Table 9), and the construct with the homology arm cassette was at a concentration of 4 ug there was a statistically significant (p<0.05) difference in the percentage integration rate between the test sample and the control. When the left-HA and the right-HA were both 230 bp (indicated by SS in Table 9), and the construct with the homology arm cassette was at a concentration of 6 ug there was not a statistically significant difference in the percentage integration rate between the test sample and the control. When the left-HA was 1027 bp and the right-HA was 230 bp (indicated by LS in Table 9), and the construct with the homology arm cassette was at a concentration of 4 ug or 6 ug there was not a statistically significant difference in the percentage integration rate between the test sample and the control. This result shows that targeted integration can be achieved by the mechanism of HR at sites of DSB which are targeted by TALENs directed to a specific site in a corn genome.

TABLE 9

HR-mediated Integration Rates in corn protoplasts with DSB mediated by TALENs at the chromosomal site L70.4.

| | Mean | | Std Dev | |
|---|---|---|---|---|
| | Test | Control | Test | Control |
| L70.4 + SS + 4 ug** | 1.54833 | 0.12181 | 1.48997 | 0.14504 |
| L70.4 + SS + 6 ug | 0.28395 | 0.12181 | 0.20174 | 0.14504 |
| L70.4 + LS + 4 ug | 0.163347 | 0.38048 | 0.282926 | 0.67502 |
| L70.4 + LS + 6 ug | 0.51467 | 0.38048 | 0.23052 | 0.67502 |

**Test was statistically higher ($p < 0.05$) than the corresponding control based on a student's t-test.

Example 14

Targeting in Corn Genome with Chimeric U6 Promoters

Chimeric U6 promoters were determined to be effective at driving expression of sgRNA constructs and resulting in targeted integration of double-strand, blunt-end DNA fragments at preselected sites in corn chromosomes. These experiments were conducted using the quantitative chromosome cutting assay in corn protoplast assay as described in example 5 and example 6. The U6 promoters incorporated into the sgRNA constructs were: a) the 397 bp corn chromosome 8 U6 promoter encoded by SEQ ID NO:7, b) the 397 bp ch1:ch8 chimeric U6 promoter encoded by SEQ ID NO:18, b) the 397 bp ch8:ch1 chimeric U6 promoter encoded by SEQ ID NO:19, and c) the 397 bp ch8:ch2:ch1:ch8 chimeric U6 promoter encoded by SEQ ID NO:20. The corn chromosomal target sites were L70a, L70c, and L70d, as described in example 5. The CRISPR/Cas9 system employed an expression cassette with the *S. pyogenes* Cas9 modified to contain two NLS sequences and an intron and encoded by SEQ ID NO:119. The double-strand, blunt-end DNA fragment was encoded by SEQ ID NO:115 and SEQ ID NO:116.

In one assay, 48 hours post transfection of the corn protoplasts with the CRISPR/Cas9 system components, the quantitative assay was done with TaqMan probes. The results (see FIG. 16A) indicate that the targeted integration rate at target site L70a with the sgRNA construct containing the ch8 U6 promoter or the sgRNA construct containing the chimeric ch1:ch8 U6 promoter resulted in about the equivalent percent target integration rate. The targeted integration rate at target site L70c, the sgRNA construct containing the chimeric ch8:ch1 U6 promoter resulted in about double the target integration rate compared to sgRNA construct containing the ch8 U6 promoter. The targeted integration rate at target site L70d, the sgRNA construct containing the ch8 U6 promoter had higher targeted integration rate compared to the sgRNA construct containing the chimeric ch8:ch2:ch1:ch8 U6 promoter.

In another assay, 48 hours post transfection of the corn protoplasts with the CRISPR/Cas9 system components, the quantitative assay was done with EvaGreen® (BioRad, Hercules, CA) intercalating dye. The results (see FIG. 16B) indicate that the targeted integration rate with the sgRNA construct containing the ch8 U6 promoter was nearly the same as the targeted integration rate at target site L70a with the sgRNA construct containing the chimeric ch1:ch8 U6 promoter, and at target site L70c with the sgRNA construct containing the chimeric ch8:ch1 U6 promoter, and at target site L70d with the sgRNA construct containing the chimeric ch8:ch2:ch1:ch8 U6 promoter. These data indicate that the targeted integration rate detected by the EvaGreen intercalating dye was about ten-fold higher compared to the targeted integration rates detected using MGB TaqMan probes. This discrepancy is mostly due to differences in the chemistries of the assays. The TaqMan assay uses just two primers and an internal probe, of which one of the primers and the probe are located on the inserted DNA fragment sequence. Unfortunately, the double-strand, blunt-end DNA fragment used in the transfection often undergo degradation by endogenous exonucleases in the protoplasts, and this results in DNA fragment integrations with truncated sites where the TaqMan probe binds. These truncated integration events are not detectable by the TaqMan assay. On the other hand, the binding site for the TaqMan primer located within the inserted DNA fragment sequence is located more internally in the inserted DNA fragment and remains intact even in most truncated inserted DNA fragments. Since the assay with the intercalating Evagreen dye does not require the internal probe, and only the TaqMan primers, this assay is not affected by oligo degradations and thus can detect many more integrations than the TaqMan assay. Otherwise, the two methods of measuring the percent targeted integration showed similar patterns at the three chromosomal target sites and the three different chimeric U6 promoters driving sgRNA expression.

Figure 16A:
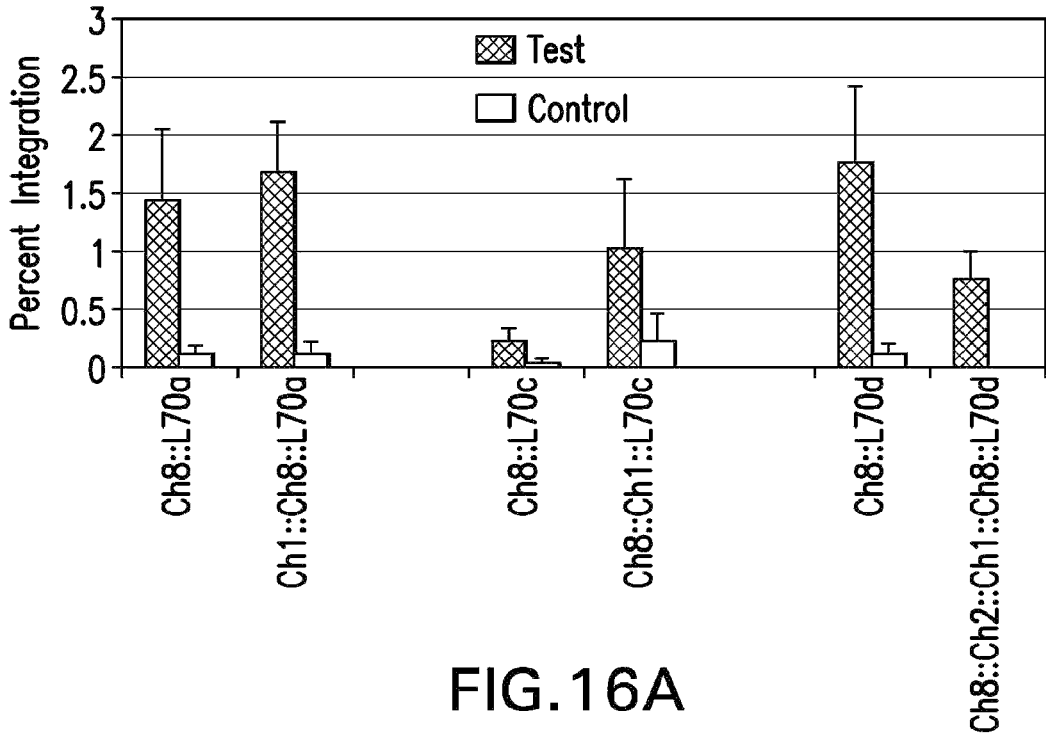
FIGS. 16A-16B.
Figure 16B:
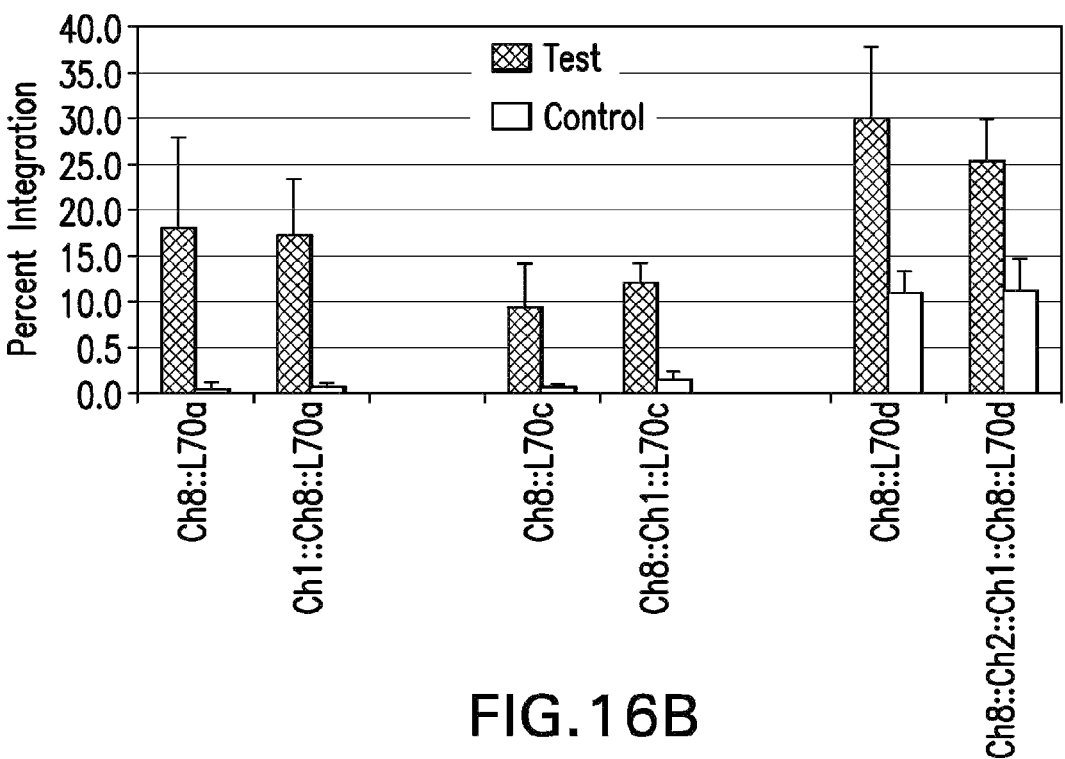

These results show that targeted integration rate at corn chromosomal site L70c when the sgRNA construct contains the Ch8::Ch1 chimeric promoter was slightly, to significantly higher compared to targeted integration rate when the sgRNA construct contains the ch8 U6 promoter (FIGS. 16A and 16B). These results also show that the targeted integration rate at corn chromosomal site L70a when the sgRNA construct contains the Ch1::Ch8 chimeric promoter is about equivalent compared to targeted integration rate when the sgRNA construct contains the ch8 U6 promoter (FIGS. 16A and 16B). Finally, these results show that the targeted integration rate at corn chromosomal site L70d when the sgRNA construct contains the ch8:ch2:ch1:ch8 chimeric promoter was lower compared to the targeted integration rate when the sgRNA construct contains the ch8 U6 promoter (FIGS. 16A and 16B). In conclusion, at least two of the three chimeric promoters were as good as, or better than, the best non-chimeric promoter in corn. These will have utility in multiplex targeting experiments, where the diversity of expression elements is indispensable.

Example 15

Targeted Mutation in Tomato Invertase Inhibitor

The CRISPR/Cas9 system was used to knock out the apoplastic invertase inhibitor gene of tomato (INVINH1) by introducing targeted frameshift point mutations following imperfect repair of the targeted double-strand breaks by NHEJ. In an earlier study, knock-down of this gene by RNAi showed elevated fruit sugar content and increased seed weight (Jin et al. *Plant Cell* 21:2072-2089, 2009). Reducing or eliminating the invertase inhibitor activity by either targeted mutagenesis or RNA interference is useful to improve yield and/or quality traits in other crop species too (Braun et al. *J Exp Bot* 65: 1713-1735, 2014).

Figures 17A, 17B, 17C:
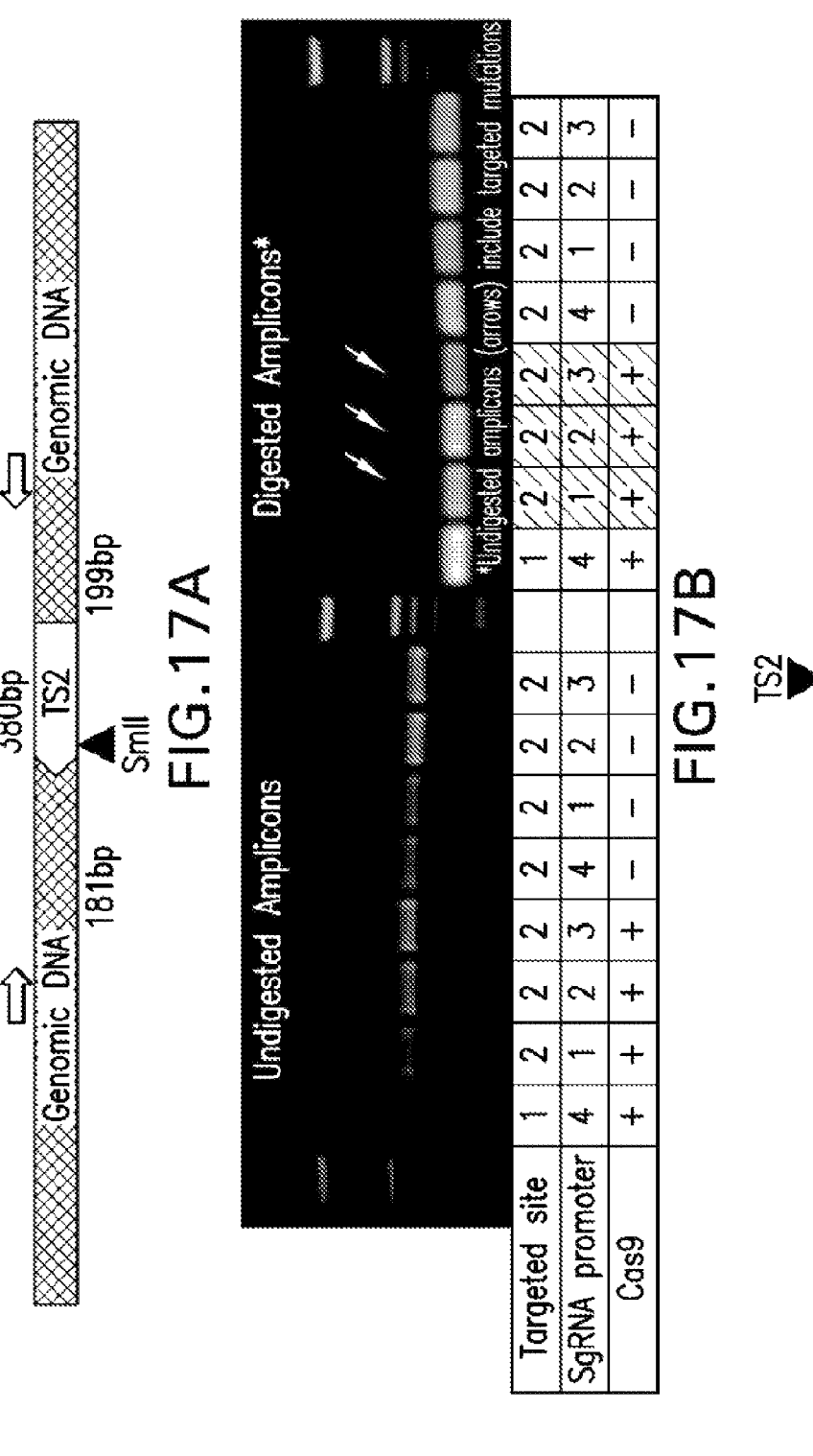
FIGS. 17A-17C.

For these experiments tomato protoplasts were transfected with an expression construct containing a cassette encoding the SpCas9 with one NLS at the C-terminus (SEQ ID NO:28), and one expression construct encoding an sgRNA cassette where expression was driven by one of 4 separate tomato U6 promoters: promoter 1 encoded by SEQ ID NO:146 (which is a fragment of SEQ ID NO: 10), promoter 2 encoded by SEQ ID NO:147 (which is a fragment of SEQ ID NO:11), promoter 3 encoded by SEQ ID NO: 148 (which is a fragment of SEQ ID NO:9), or promoter 4 encoded by SEQ ID NO:149. The sgRNA were targeted to an invertase inhibitor site (site 1) without a SmlI site or to a site (labeled site 2) in the invertase inhibitor gene with a SmlI restriction endonuclease site. The site 2 sgRNA is encoded by SEQ ID NO:150. The CRISPR/Cas9 cleavage site within target site 2 contains a SmlI restriction endonuclease site. Upon CRISPR/Cas9 induced double-strand break at target site 2, the NHEJ repair will result in indels at this site, thus effectively removing the SmlI restriction endonuclease site. This mutation of the SmlI site was leveraged during the screening for targeted events by amplifying a 380 bp amplicon (SEQ ID NO:159) and subjecting the PCR amplicon to digestion with SmlI. If the SmlI site was not mutated, then the amplicon would be digested into two fragments of 181 bp and 199 bp. If the SmlI site was mutated, then the PCR amplicon would not be digested. This PCR scheme is illustrated in FIG. 17A.

Tomato protoplasts were transfected with the CRISPR/Cas9 system targeting the tomato invertase inhibitor and harvested 48 hours later and genomic DNA extracted. Negative control for the CRISPR/Cas9 system was omission of the expression construct encoding the Cas9 endonuclease. A negative control for the target site was use of a sgRNA to target site 1, and it is not expected that the SmlI site will be mutated with this sgRNA. PCR amplification was done with primers SEQ ID NO:157 and SEQ ID NO: 158 and the resulting PCR amplicons were either undigested or digested with SmlI. The reactions were run on agarose gels and the results are shown in FIG. 17B. The negative controls of sgRNA to target site 1 and the omission of Cas9 endonuclease resulted only in PCR amplicons with the SmlI site intact. When the sgRNA was for target site 2, the SmlI site was mutated when the sgRNA cassette contained tomato U6 promoter 1, or tomato U6 promoter 2, or tomato U6 promoter 3, as evidenced by the full-length PCR amplicons (see FIG. 17B, arrows showing amplicons without a SmlI site). The sgRNA construct targeting site 2 and with U6 promoter 4 apparently did not show targeting.

To confirm that the PCR amplicons without a SmlI site were indeed due to CRISPR/Cas9 induced NHEJ mutation, these apparent mutated amplicons were gel-purified and pooled, and then they were sequenced. The multiple sequence alignment in FIG. 17C shows that these PCR amplicons without a SmlI site were from the target site 2 of the tomato invertase inhibitor and contained indels, consistent with CRISPR/Cas9 induced mutation. Specifically, in the multiple sequence alignment, SEQ ID NO: 151 represents a region of the PCR amplicon (SEQ ID NO: 159) without a mutation. SEQ ID NOs: 152 and 153 illustrate indels where there was a 1 bp insertion at the cleavage site. SEQ ID NO:154 illustrates an indel with a 3 bp deletion at the cleavage site. SEQ ID NO:155 illustrates an indel with a 4 bp deletion at the cleavage site. SEQ ID NO:156 illustrates an indel with a 6 bp deletion at the cleavage site. In conclusion, these results indicate that the CRISPR/Cas9 system using tomato U6 promoter 1 (SEQ ID NO:146), or tomato U6 promoter 2 (SEQ ID NO:147), or tomato U6 promoter 3 (SEQ ID NO:148) to drive sgRNA induces mutation at the tomato invertase inhibitor gene target site 2.

Example 16

Promoters to Drive sgRNA Expression

To identify and select additional promoters which would be useful to drive expression of sgRNAs from expression cassettes introduced into dicots and monocots, RNA polymerase II (Pol II) and RNA polymerase III (Pol III) promoters (SEQ ID NOs:160-201 and SEQ ID NOs:247-283) were identified by comparing the sequence encoding U6, U3, U5, U2 and 7SL small nuclear RNA (snRNA) against soy and corn genomes using BLAST (see Table 10). From regions of this bioinformatic alignment, 200 or more nucleotides immediately upstream of the 5' end of the coding region of the respective snRNA was used for testing as putative promoters for driving expression of sgRNA from expression cassettes introduced into plant cells.

TABLE 10

SEQ ID NO of putative promoter sequence upstream of the snRNA genes and the source (tomato or soy or corn).

| Promoter SEQ ID NO: | snRNA | Promoter Source | Promoter + GUS + Terminator SEQ ID NO | Terminator |
|---|---|---|---|---|
| 148 | Promoter 3 | tomato | 202 | poly(T)7 |
| 160 | SoyU6a | soy | 203 | poly(T)7 |
| 161 | SoyU6c | soy | 204 | poly(T)7 |
| 162 | SoyU6d | soy | 205 | poly(T)7 |
| 163 | SoyU6e | soy | 206 | poly(T)7 |
| 164 | SoyU6f | soy | 207 | poly(T)7 |
| 165 | SoyU6g | soy | 208 | poly(T)7 |
| 166 | SoyU6i | soy | 209 | poly(T)7 |
| 167 | U3a | soy | 210 | poly(T)7 |
| 168 | U3b | soy | 211 | poly(T)7 |
| 169 | U3c | soy | 212 | poly(T)7 |
| 170 | U3d | soy | 213 | poly(T)7 |
| 171 | U3e | soy | 214 | poly(T)7 |
| 172 | 7SL_CR13 | soy | 215 | poly(T)7 |
| 173 | 7SL_CR14 | soy | 216 | poly(T)7 |
| 174 | 7SL_CR10 | soy | 217 | poly(T)7 |
| 175 | 7SLCR01 | corn | 218 | poly(T)7 |
| 176 | 7SLCR07 | corn | 219 | poly(T)7 |
| 177 | 7SLCR09 | corn | 220 | poly(T)7 |
| 178 | U3CR02 | corn | 221 | poly(T)7 |
| 179 | U3CR10 | corn | 222 | poly(T)7 |
| 180 | U3CR08 | corn | 223 | poly(T)7 |
| 181 | U3CR08b | corn | 224 | poly(T)7 |
| 182 | U3CR05 | corn | 225 | poly(T)7 |
| 183 | U2snRNA_P | corn | 226 | SEQ ID NO 237 |
| 184 | U2snRNA_I | corn | 227 | SEQ ID NO 237 |
| 185 | U2snRNA_B | corn | 228 | SEQ ID NO 237 |
| 186 | U2snRNA_G | corn | 229 | SEQ ID NO 237 |
| 187 | U2snRNA_A | corn | 230 | SEQ ID NO 237 |
| 188 | U5snRNA_A | corn | 231 | SEQ ID NO 237 |
| 189 | U5snRNA_C | corn | 232 | SEQ ID NO 237 |
| 190 | U5snRNA_D | corn | 233 | SEQ ID NO 237 |
| 191 | U5snRNA_E | corn | 234 | SEQ ID NO 237 |
| 192 | U2snRNA_C | corn | — | — |
| 193 | U2snRNA_D | corn | — | — |
| 194 | U2snRNA_E | corn | — | — |
| 195 | U2snRNA_F | corn | — | — |
| 196 | U2snRNA_H | corn | — | — |
| 197 | U2snRNA_K | corn | — | — |
| 198 | U2snRNA_L | corn | — | — |
| 199 | U2snRNA_M | corn | — | — |
| 200 | U6Chr08 | corn | 235 | poly(T)7 |
| 201 | U6Chr01 | corn | 236 | poly(T)7 |
| 247 | U2CR01a | Soy | — | — |
| 248 | U2CR01b | Soy | — | — |
| 249 | U2CR02 | Soy | — | — |
| 250 | U2CR03 | Soy | — | — |
| 251 | U2CR04 | Soy | — | — |
| 252 | U2CR05a | Soy | — | — |

TABLE 10-continued

SEQ ID NO of putative promoter sequence upstream of the snRNA genes and the source (tomato or soy or corn).

| Promoter SEQ ID NO: | snRNA | Promoter Source | Promoter + GUS + Terminator SEQ ID NO | Terminator |
|---|---|---|---|---|
| 253 | U2CR05b | Soy | — | — |
| 254 | U2CR06a | Soy | — | — |
| 255 | U2CR06b | Soy | — | — |
| 256 | U2CR06v | Soy | — | — |
| 257 | U2CR07 | Soy | — | — |
| 258 | U2CR08a | Soy | — | — |
| 259 | U2CR08b | Soy | — | — |
| 260 | U2CR08c | Soy | — | — |
| 261 | U2CR10a | Soy | — | — |
| 262 | U2CR10b | Soy | — | — |
| 263 | U2CR10c | Soy | — | — |
| 264 | U2CR13 | Soy | — | — |
| 265 | U2CR14 | Soy | — | — |
| 266 | U2CR15 | Soy | — | — |
| 267 | U2CR17a | Soy | — | — |
| 268 | U2CR17b | Soy | — | — |
| 269 | U2CR17c | Soy | — | — |
| 270 | U2CR17d | Soy | — | — |
| 271 | U2CR17e | Soy | — | — |
| 272 | U2CR17f | Soy | — | — |
| 273 | U2CR19a | Soy | — | — |
| 274 | U2CR19b | Soy | — | — |
| 275 | U2CR20 | Soy | — | — |
| 276 | U5CR07 | Soy | — | — |
| 277 | U5CR10 | Soy | — | — |
| 278 | U5CR10 | Soy | — | — |
| 279 | U5CR15 | Soy | — | — |
| 280 | U5CR19 | Soy | — | — |
| 281 | U5CR20a | Soy | — | — |
| 282 | U5CR20b | Soy | — | — |
| 283 | SoyU6b | Soy | — | — |

Example 17

Normalized RNA Transcript Level Assay

To assess the efficacy of the promoters listed in Table 10 to drive expression of sgRNAs, a series of constructs were generated which contained a cassette encoding one of the putative promoters (SEQ ID NO:154, and SEQ ID NOs: 160-201) operably linked to a 221 bp fragment of a beta-glucuronidase (GUS) open reading frame and either a poly (T)7 terminator for Pol III promoters (7SL, U6, and U3) or the sequence 5'-ACAATTCAAAACAAGTTTTAT-3' (SEQ ID NO:237) for the pol II U2 and U5 promoters (Table 10). The recombinant constructs (0.5 pmol) containing the promoter-GUS fragment fusions were transfected into soy cotyledon protoplasts (SEQ ID NO:202-217 or corn leaf protoplasts (SEQ ID NO: 218-236) along with 300 ng of a plasmid serving as a transformation control encoding *Renilla luciferase* (RLUC) expressed using the CaMV promoter. The transfected protoplasts were harvested 18 hours after transfection and the RNA levels were measured via TaqMan assays using a probe and primers complementary to the GUS fragment. Internal controls used to normalized the TaqMan assay included (1) an 18S primer pair/probe set to control for RNA concentration and (2) RLUC luminescence as a transformation control.

Figure 18A:
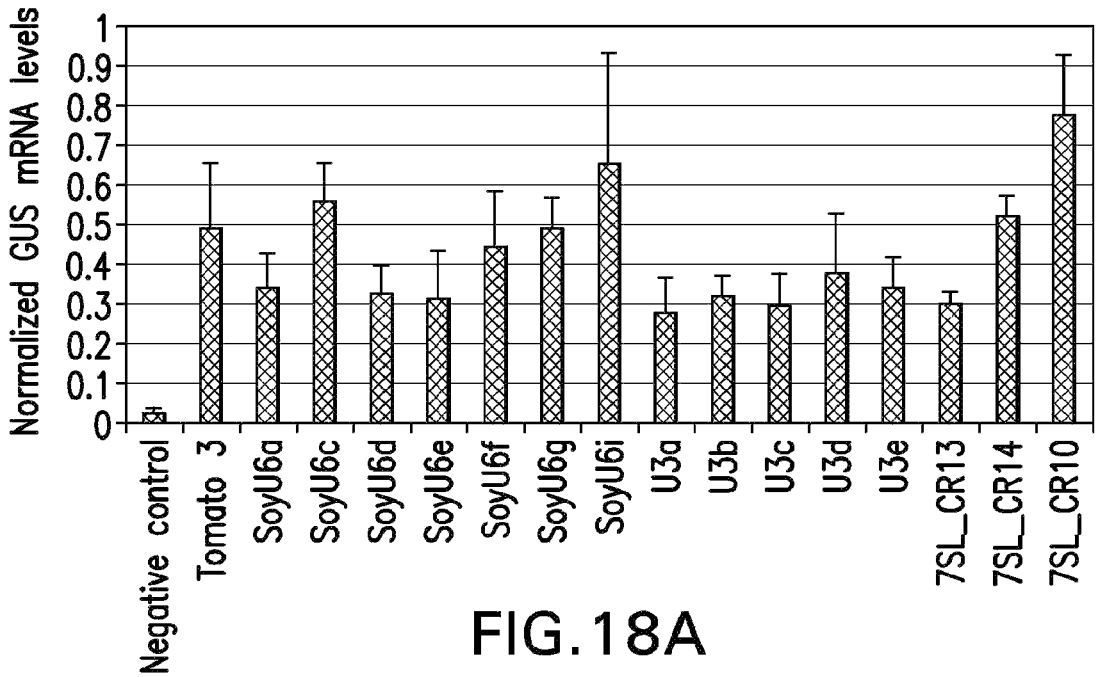
FIGS. 18A-18B.

In soy cotyledon protoplasts, all promoters tested resulted in significantly higher normalized levels of GUS mRNA than the control (no GUS construct) (One-way ANOVA student t-test p value<0.05) (FIG. 18A). The lowest level of normalized GUS mRNA was with construct (SEQ ID NO:210) containing the U3a promoter (SEQ ID NO:167). The highest level of normalized GUS mRNA was with construct (SEQ ID NO:210) containing the 7SL_CR10 promoter (SEQ ID NO:174). The level of normalized GUS mRNA with all promoters tested with this assay ranged from 11-31 times higher expression levels that the no DNA negative control. No one class of promoters (U6, U3, or 7SL) performed better than the other, although the U3 promoters were generally in the lower range of expression observed in the experiment. U3 promoters have been successfully used by Liang et al. (J. Genetics and Genomics 41:63-68, 2014) to drive sgRNAs in corn. Thus, although these data indicate that the U3 promoters may be lower than U6 or 7SL, they are still viable candidates to drive sgRNA expression in soy. These data suggest that any of the U6, U3, or 7SL promoters identified here would be good candidates for making recombinant expression constructs to drive expression of sgRNA in plant cells.

Figure 18B:
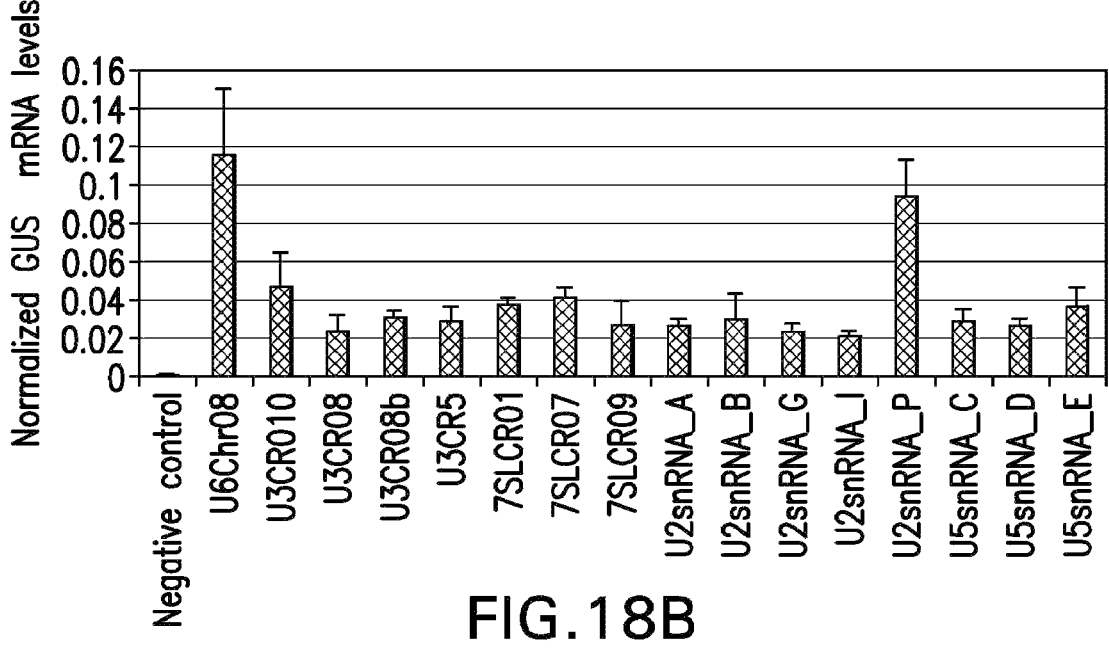

In corn leaf protoplast, all promoters tested resulted in significantly higher normalized levels of GUS mRNA compared to the control (One-way ANOVA student t-test $p$ value<0.05) with values ranging from 26 fold to 141 fold higher expression than the negative control (FIG. 18B). The U6Chr08 promoter construct (SEQ ID NO:235) resulted in the highest normalized levels of GUS mRNA expression, and U2snRNA_I promoter construct (SEQ ID NO:227) resulted in the lowest, with approximately a 5.5-fold difference in normalized levels of GUS mRNA expression between them. The U2snRNA_P promoter construct (SEQ ID NO:226) also stood out as having high normalized levels of GUS mRNA expression. All the remaining promoters were within the same relative range having less than 2 fold difference between them (FIG. 18B). These data suggest that any of the U6, U3, 7SI, U2, or U5, promoters identified here would be good candidates for making recombinant expression constructs to drive expression of sgRNA in plant cells.

Example 18

GUS Expression Assay for sgRNA Expression

To determine how the difference in sgRNA expression levels impact Cas9 activity, an assay was used that relied on activating transcription from a minimal promoter upstream of the GUS open reading frame in a reporter construct transfected into corn leaf protoplasts. For this assay, a Cas9 nuclease from *S. thermophilus* was mutated at amino acid positions D9A and H599A of the native protein sequence, effectively creating a Cas9 without endonuclease cleavage activity (also referred to as a 'dead Cas9'). Additionally, this dead Cas9 was modified to encode one NLS domain (SEQ ID NO:120) at amino acid positions 2-11 of SEQ ID NO:239 and an activation domain from a TALE protein from amino acid positions 1135-1471 of SEQ ID NO:239. The polynucleotide sequence of the dead Cas9, represented by SEQ ID NO:238, included an intron at positions 507-695. A reporter construct was constructed where the uidA (GUS) reporter gene was driven by a minimal CaMV promoter with three adjacent sgRNA binding sites (SEQ ID NO:240) at nucleotide positions 80-98, 117-135, and 154-172 of the sequence SEQ ID NO:246. Also constructed were a set of sgRNA (based on the sgRNA of Cong et al. 2013 Science 339:819) expression constructs that consisted of the one of the promoters from each class of snRNA genes, namely U6, 7SL, U2, U5, and U3 (Table 11) and which would target the dead Cas9-TALE-AD to one or more of the sgRNA binding sites of the GUS reporter construct. The U6 and 7SL promoters normally initiate transcription on a G, and the U2, U5 and U3 promoters normally initiate transcription on an A. To ensure proper transcription initiation of the sgRNA, for constructs with either a U6 or 7SL promoter, a G was inserted between the promoter and spacer sequence. For constructs with a U2, U5 or U3 promoter, an A was inserted between the promoter and spacer sequence. When the dead Cas9-TALE-AD and sgRNA complex binds the GUS reporter construct, the TALE activation domain functions as a transcription factor activating the minimal CaMV promoter resulting in higher expression of the GUS transcript, and ultimately higher levels of GUS protein expression.

TABLE 11

| SEQ ID NO corresponding to sgRNA expression constructs. | | |
| --- | --- | --- |
| Promoter + sgRNA SEQ ID NO: | Promoter | Promoter SEQ ID NO: |
| 241 | U6Chr08 | 200 |
| 242 | 7SLCR07 | 176 |
| 243 | U2snRNA_I | 184 |
| 244 | U5snRNA_E | 191 |
| 245 | U3CR08b | 181 |

Figure 19:
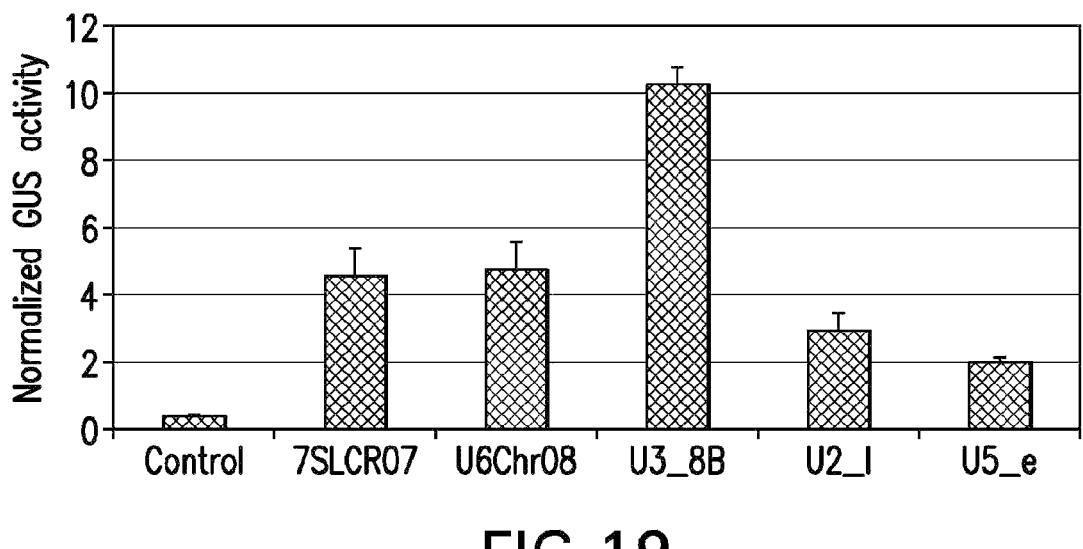
FIG. 19. Graphical representation of data from normalized GUS expression levels from corn leaf protoplast assays with, a recombinant expression constructs encoding 1) a GUS expression construct 2) a dead Cas9-TALE-AD expression construct, and 3) recombinant sgRNA expression constructs with 7SL, U6, U3, U2, or U5 promoters.

For the assay, corn leaf protoplasts were transfected with 0.8 pmol of dead Cas9-TALE-AD expression cassette, 0.5 pmol of the GUS expression cassette, 1.6 pmol of one of the sgRNA expression cassettes, 650 ng of *Luciferase* expression cassette, and 300 ng of *Renilla luciferase* (RLUC) expression cassette. The transfected protoplasts were harvested 18 hours later and GUS activity was measured using the 4-methylumbelliferyl-beta-D-glucuronide (MUG, Sigma, St. Louis, MO) fluorimetric assay, and *luciferase* and RLUC activity was measured and used as control to normalize relative to transfection controls. The activity of GUS is a readout of the how often the dead Cas9-TALE-AD binds to the reporter plasmid. Each class of snRNA promoter driving sgRNA gave higher normalized GUS activity compared to the control (FIG. 19). The U3CR08b (U3_8 B in FIG. 19) promoter resulted in the highest normalized GUS activity of about 10x over control. The two promoters 7SLCR07 and U6Chr08 both gave about the same normalized GUS activity of about 4x over control. The two promoters U2snRNA_I (Us_I in FIG. 19) and U5snRNA_E (U5_e in FIG. 19) were each at or slightly above 2x over control for normalized GUS activity. These results indicate that the 7SL, U6, U3, U2, and U5 snRNA promoters may be good to excellent candidates for use in sgRNA expression constructs for CRISPR/Cas9 system useful in genome modification.

The differences in normalized GUS expression observed using the dead Cas9-TALE-AD assay do not mirror the normalized GUS mRNA levels shown in the corn leaf protoplast assay detailed in Example 17.

What is claimed is:

1. A recombinant DNA construct comprising a U6 promoter, operably linked to a sequence encoding a single-guide RNA (sgRNA) or a sequence specifying a non-coding RNA, wherein the sequence of said U6 promoter comprises SEQ ID NO:164; or a fragment thereof, wherein the fragment is at least 140 bp in length, and wherein the U6 promoter or fragment thereof and the sgRNA or non-coding RNA come from different sources.

2. The recombinant DNA construct of claim 1, further comprising a transcription termination sequence.

3. The recombinant DNA construct of claim 1, further comprising a sequence encoding a promoter operably linked to a sequence encoding a clustered, regularly interspaced, short palindromic repeats (CRISPR)-associated Cas endonuclease gene product.

4. The recombinant DNA construct of claim 3, wherein the Cas endonuclease gene product is further operably linked to a nuclear localization sequence (NLS).

5. The recombinant DNA construct of claim 3, wherein the sequence encoding said Cas endonuclease is selected from the group consisting of SEQ ID NO: 27, SEQ ID NO: 68, SEQ ID NO:97, SEQ ID NO: 119, and SEQ ID NO:136.

6. The recombinant DNA construct of claim 1, wherein the non-coding RNA is selected from the group consisting of: a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), and a naturally occurring antisense siRNA (nat-siRNA).

7. A cell comprising the recombinant DNA construct of claim 1.

8. The cell of claim 7, wherein the cell is a plant cell.

9. A method of introducing a double-strand break in the genome of a cell, comprising introducing in said cell:

a) at least one recombinant DNA construct of claim 1; and b) a second recombinant DNA construct comprising a sequence encoding a promoter operably linked to a sequence encoding a clustered, regularly interspaced, short palindromic repeats (CRISPR)-associated Cas endonuclease gene product operably linked to a nuclear localization sequence (NLS).

10. The method of claim 9, wherein the sequence encoding said Cas endonuclease is selected from the group consisting of SEQ ID NO:27, SEQ ID NO:68, SEQ ID NO:97, SEQ ID NO:119, and SEQ ID NO:136.

11. A method of introducing a double-strand break in the genome of a cell, comprising introducing to said cell at least one recombinant DNA construct of claim 3.

12. The method of claim 11, wherein the sequence encoding the Cas endonuclease is selected from the group consisting of SEQ ID NO:27, SEQ ID NO:68, SEQ ID NO:97, SEQ ID NO:119, and SEQ ID NO:136.

13. A method of genome modification comprising:

a) introducing a double-strand break in the genome of a plant cell by the method according to claim 9; and b) introducing into said plant cell a recombinant blunt-end double-strand DNA fragment, wherein said recombinant blunt-end double-strand DNA fragment is incorporated into said double strand break by endogenous DNA repair.

14. A method of genome modification comprising:

a) introducing a double-strand break in the genome of a plant cell by the method according to claim 11; and b) introducing into said plant cell a recombinant blunt-end double-strand DNA fragment, wherein said recombinant blunt-end double-strand DNA fragment is incorporated into said double strand break by endogenous DNA repair.

* * * * *

SEQUENCE LISTING

```
Sequence total quantity: 295
SEQ ID NO: 1              moltype = DNA  length = 397
FEATURE                   Location/Qualifiers
source                    1..397
                          mol_type = genomic DNA
```

-continued

```
                              organism = Zea mays
SEQUENCE: 1
aggaaaagaa gaggtgatta ctgtacctat tcgtctttgt atcggaatat aaatttatca   60
ctatttatg ataaagtaaa tctgtttccc tgtagagtta attaattaat gtaagtataa   120
gcgtaattta tagggcacta gtaggactgt cgactgtgcg ctcggcccgg ataatgcgtc   180
aaaagcgaag acgtgcacgt gggatgggaa aacacgaagc gtggtctgct ttttcgcatg   240
atatctgggc cgcaccaaag aatccagccc acgcggcgtg gcgccgtcgt tacggcttgc   300
gggggaagga aacgagggac gaaccgagat ttagcaccag accggccagc gagcattgca   360
gacaccggct tataagttca gctgcgacta ccactcc                          397

SEQ ID NO: 2            moltype = DNA   length = 200
FEATURE                 Location/Qualifiers
source                  1..200
                        mol_type = genomic DNA
                        organism = Zea mays
SEQUENCE: 2
cgtgggatgg gaaaacacga agcgtggtct gctttttcgc atgatatctg ggccgcacca   60
aagaatccag cccacgcggc gtggcgccgt cgttacggct tgcgggggaa ggaaacgagg   120
gacgaaccga gatttagcac cagaccggcc agcgagcatt gcagacaccg gcttataagt   180
tcagctgcga ctaccactcc                                             200

SEQ ID NO: 3            moltype = DNA   length = 397
FEATURE                 Location/Qualifiers
source                  1..397
                        mol_type = genomic DNA
                        organism = Zea mays
SEQUENCE: 3
ttatatgtta ccgttgcaaa gcacgggcac tcacctagta tataatataa catcagtcgt   60
acgtaatgta ctgatgggcg ggttaacaaa tgtcactcac tatcagcacc agcagcgctt   120
agatgcatcc ggccgggcca agacccagga ccagaaagcg cgcacgttca cagcggatgc   180
tgatgggtta gatcgactga tcgaggaaga ggagagctta attaagaaac gccctgttcc   240
gctttgctag cttgcgccct gactgtccag cccacgcgct tcggtccgat tcacatgcta   300
ggctggtgca agcgagccga gactttttttt tagaaccacc ttgctcagca aaccttagga   360
acaccggctt ataagtcgaa gcgaagcgct gtgcact                          397

SEQ ID NO: 4            moltype = DNA   length = 200
FEATURE                 Location/Qualifiers
source                  1..200
                        mol_type = genomic DNA
                        organism = Zea mays
SEQUENCE: 4
tgatcgagga agaggagagc ttaattaaga aacgccctgt tccgctttgc tagcttgcgc   60
cctgactgtc cagcccacgc gcttcggtcc gattcacatg ctaggctggt gcaagcgagc   120
cgagactttt ttttagaacc accttgctca gcaaacctta ggaacaccgg cttataagtc   180
gaagcgaagc gctgtgcact                                             200

SEQ ID NO: 5            moltype = DNA   length = 397
FEATURE                 Location/Qualifiers
source                  1..397
                        mol_type = genomic DNA
                        organism = Zea mays
SEQUENCE: 5
ggattcggtg ttctttatta ggttctcgcc gaatatggtt ctcagttatg acctaacggt   60
gtccacaaga gttcgccagg atttatacaa ctattttctt atttatttct ttaacatttt   120
cccttctacg cacaatagga gataatgtca agcgttgacg gtgcacatat atttgttttt   180
ttaaaggcgt agtggcgtgt gtgcaaaaac atcctcacag gaaagacacg aagaaacatg   240
gtcaatggcc cattatataa agcaccgcca caaagcccaa ataccagttc gtcggtggag   300
caagtaacgc gctaggcaac aggcaaacag tttgtcccac ctcgtccagt cacaaaggca   360
aagcgtgact tataagccag agcggaagaa ccatacc                          397

SEQ ID NO: 6            moltype = DNA   length = 200
FEATURE                 Location/Qualifiers
source                  1..200
                        mol_type = genomic DNA
                        organism = Zea mays
SEQUENCE: 6
tgtgtgcaaa aacatcctca caggaaagac acgaagaaac atggtcaatg cccattata   60
taaagcaccg ccacaaagcc caaataccag ttcgtcggtg gagcaagtaa cgcgctaggc   120
aacaggcaaa cagtttgtcc cacctcgtcc agtcacaaag gcaaagcgtg acttataagc   180
cagagcggaa gaaccatacc                                             200

SEQ ID NO: 7            moltype = DNA   length = 397
FEATURE                 Location/Qualifiers
source                  1..397
                        mol_type = genomic DNA
                        organism = Zea mays
SEQUENCE: 7
tcgtaaaata gtggtgtcca aagaatttcc aggcccagtt gtaaaagcta aaatgctatt   60
cgaatttcta ctagcagtaa gtcgtgttta gaaattattt ttttatatac ctttttttcct   120
```

-continued

```
tctatgtaca gtaggacaca gtgtcagcgc cgcgttgacg gagaatattt gcaaaaaagt    180
aaaagagaaa gtcatagcgg cgtatgtgcc aaaaacttcg tcacagagag ggccataaga    240
aacatggccc acggcccaat acgaagcacc gcgacgaagc ccaaacagca gtccgtaggt    300
ggagcaaagc gctgggtaat acgcaaacgt tttgtcccac cttgactaat cacaagagtg    360
gagcgtacct tataaaccga gccgcaagca ccgaatt                             397

SEQ ID NO: 8          moltype = DNA   length = 200
FEATURE               Location/Qualifiers
source                1..200
                      mol_type = genomic DNA
                      organism = Zea mays
SEQUENCE: 8
cggcgtatgt gccaaaaact tcgtcacaga gagggccata agaaacatgg cccacggccc    60
aatacgaagc accgcgacga agcccaaaca gcagtccgta ggtggagcaa agcgctgggt    120
aatacgcaaa cgtttttgtcc caccttgact aatcacaaga gtggagcgta ccttataaac   180
cgagccgcaa gcaccgaatt                                                200

SEQ ID NO: 9          moltype = DNA   length = 540
FEATURE               Location/Qualifiers
source                1..540
                      mol_type = genomic DNA
                      organism = Solanum lycopersicum
SEQUENCE: 9
gttacgtaat tatatttctt agtcatattt tagttattcc atcttaacca cataggtgat    60
agtcaatatg tctatttcac atgtatggtt ccgtactata attaacaaca tattgatttg    120
aaattctatt tgtgctacat atattagaca aggaaaataa catatgttat tttgaaatca    180
cgtatatttta ctataaaatta caatgattaa caacttaaaa tatttaaatg aaaatcatat   240
taatgactct ctaaattta tctgtgtcac ataaatgaaa aacaaaaaat aacaaatatt     300
gtattcgcac gggcgcatgt gtctagttag ttataaacga agaaataagg ggctgatttc    360
gaaataaacg ttcttagaat tggaagaaat gttcagtttc taaacttgta ggactaaagc    420
aataacttt atttaattta ttttcttta tgtttctccc acatcgatca tacatataac      480
tatacagcag tataagaact ctagcgaagc aataatgctc gtcccgttgg ggacatccga    540

SEQ ID NO: 10         moltype = DNA   length = 600
FEATURE               Location/Qualifiers
source                1..600
                      mol_type = genomic DNA
                      organism = Solanum lycopersicum
SEQUENCE: 10
tataataata ctatgttaaa tatgcaacat gtattagaag tgaattaagt atgcaataga    60
tatgtattta aaaatatatt atgcttgttt gataagaagt tgatgcattg tattataagt    120
acgttagaat gtgcaataaa tatattatct atcattagaa cttgaattat aagtgaataa     180
tagattattt tttgtaatat gaattaaaag tgtattaaac atgtattaac ggtgatcaat    240
tggttaaaaa aaagtttatt attaaaatga taaatctttt taatttatag tatatttatg    300
taagttttca cgttgagtaa atagcgaaga agttgggccc aaccaagtaa aataagaagg    360
ccgggccatt acaattaagt cgtcacacaa ctgggcttca ttgaaaaaag cgcaaaaccg    420
attccaggcc cgtgttagca tgaagactca actcaaccag agatttctcc ctcatcgctt    480
acagaaaaaa gctatatgct gtttatattg cgaaatctaa cagtgtagtt tgtcccttcg    540
gggacatccg ataaaattgg aacgatacag agaagattag catgtgcccct gcgcaaggat    600

SEQ ID NO: 11         moltype = DNA   length = 540
FEATURE               Location/Qualifiers
source                1..540
                      mol_type = genomic DNA
                      organism = Solanum lycopersicum
SEQUENCE: 11
ttctccaaaa aaaaaaaga aaagaagaag caaacaaaca aatagaagca tatctcttga     60
tgtggaagga gatcaaaata ttcccaataa atacttatga gaagaagtaa ctgatttaaa    120
attttcacta atagggttcg aaaaatgaaa atgtaatacg tggaacttga atgtaaaacc    180
tcaaggaatt cttgtgtcta agaaattcaa aatctctcta aatgtataca aaagatgatt    240
tcttttacc ttatatatag taaaataaaa ttgtcggata aattcgagtg aacaccctag     300
cacccctaa atcctcccc gtagtcggcc cattacagtt aaagtccagg tacaacaaaa       360
tgggcttcga ttaagatgga ataaaaggag tccaggccca tgagcccaac aaacaagcta    420
tttctccctc atcggcgcac aaagaagctt tattctctta ttatagctga atattagcat    480
gtgtgtttgt cccttcgggg acatccgata aaattggaac gatacagaga agattagcat    540

SEQ ID NO: 12         moltype = DNA   length = 540
FEATURE               Location/Qualifiers
source                1..540
                      mol_type = genomic DNA
                      organism = Glycine max
SEQUENCE: 12
accttttaa ccgcacaaag ttttaaccag atttatataa tttattttg aatccccaat       60
acatatcatt ataacatatc aattatcaaa tatttcaata acctcatgat atggcaatga    120
atacatcttc ttctcaatga acagagattc ctgaaaaaga ttaggaaagt gaaagcatac    180
tcgtttgcaa tgtaaaactg atacttcccc aaaatcatca tattccaaat atgccctggt    240
gttactgacc aaaaccagaa aaaagaaacg gaagacatat acgtctaaac ggagaaattt    300
caaaaaacaa aaattggatc atttctcgat ttgtgggtgt catcttgtgc agggcatgct    360
aatcttctct ttaccctttc ccacaagact cagcgcatgt tgtctcgtct catccaagtc    420
```

-continued

```
ccacaccgcc taaacttaac acaatattag tatttataat gacatacaac attcaagatg    480
ttgtcccttc ggggacatcc gataaaattg gaacgataca gagaagatta gcatggcccc    540

SEQ ID NO: 13            moltype = DNA   length = 540
FEATURE                  Location/Qualifiers
source                   1..540
                         mol_type = genomic DNA
                         organism = Glycine max
SEQUENCE: 13
cattataaaa agtaaaatat aactactttg ttttttaata aaaaaaattc aatgggagat     60
actatggatt caattacctt actgatttta tttcatatgt gccagaagta tttcagttta    120
ttttgaaaaa tcagaaaaaa aatgtctgga ataaaatata ataagcgata ctaataaata    180
attgaacaag ataaatggta aaatgtcaaa tcaaaactag gctacagagt gcagagcaga    240
gtcatgatga atgacccgcta gttctactta ctacaccgat tcttgtgtac ataaaaatat    300
tttaaaataa ttgaatcttt ctttagccag ctttgacaac aatgtacacc gttcgtactt    360
cttactggta ggcaatgctt cttgtttgct ttcggtggaa ggtgtatata ctcaacatta    420
cttctttttc agcgtgtttt cttacgggag tcccacaccg cccaaaacta atacagtatt    480
cttgtttata aagaagtgca ccacttcaat tgttgtccct cggggacat ccgataaaat    540

SEQ ID NO: 14            moltype = DNA   length = 540
FEATURE                  Location/Qualifiers
source                   1..540
                         mol_type = genomic DNA
                         organism = Glycine max
SEQUENCE: 14
atattcataa tttttttttt ttgttttttt atacaaggac ggctgattca atcatcacac     60
cacacgtcat attaaaaaaa tatagtagat ttatttttaaa atagagagaa tcgttaagaa    120
aaaaataaat agtaaagtaa atgaaaaccc aaataatatc attattatgt caataagtcg    180
gagaggatag taatcaaatg gtctatgagg tggtggttca ttcaacatat agcacctatt    240
cattgttcct aaaacataat ttaagaacaa aaacttaaat taataata ataataaaag    300
agtacatcga agtatctgtg ttctctatcc ttctgactaa cattcatgtt gtttgtattc    360
agcaaagggc cgtgcaggat ttgtgcgtcg cgctccggtt agttattgca gtgaccgtct    420
ctttagtccc acatcgagta attatgcttc atacagtctg tttatataac agagatggaa    480
caaactggtt gtcccttcgg ggacatccga taaaattgga acgatacaga gaagattagc    540

SEQ ID NO: 15            moltype = DNA   length = 540
FEATURE                  Location/Qualifiers
source                   1..540
                         mol_type = genomic DNA
                         organism = Glycine max
SEQUENCE: 15
ctttcaggtc atgattttttt gtttctaaat gatactcaca ctcccttcca gttttttttt     60
tttaaactca gctcccttgc ttcctccacc ggttatcata atactgaacc aaatcaaaca    120
ttacagtcaa ggtactatga atatgaaacc tgaaatccta tgaatgtcat aaatttattt    180
taaataataa atttatttag aataatattt ttttgggtaa gagttataaa ataaaataca    240
aaaaaaaaac ctaatatcaa tttttcactg actccgttta tattgagact tgagaaagat    300
ggttcccgtt tgctcccggt ggaggctccg aggctgtaca tactcgac attactttag    360
cttgttttgt tgtttctttc cctttcccac aagactcagg tctcgttcgc aaacgagtcc    420
cacaccgtct aaacttacca caatattagc gtttataatt agatgcactg catcacttat    480
tgtcccttcg gggacatccg ataaaattgg aacgatacag agaagattag catggcccct    540

SEQ ID NO: 16            moltype = DNA   length = 420
FEATURE                  Location/Qualifiers
source                   1..420
                         mol_type = genomic DNA
                         organism = Glycine max
SEQUENCE: 16
tgcagagcag agtcatgatg atactactta ctacaccgat tcttgtgtgc agaaaaatat     60
gttaaaataa ttgaatcttt ctctagccaa atttgacaac aatgtacacc gttcatattg    120
agagacgatg cttcttgttt gctttcggtg gaagctgcat atactcaaca ttactccttc    180
agcgagtttt ccaactgagt cccacattgc ccagacctaa cacggtattc ttgtttataa    240
tgaaatgtgc caccacatgg attgtcccct cggggacatc cgataaaatt ggaacgatac    300
agagaagatt agcatggccc ctgcgcaagg atgacacgca caaatcgaga aatggtccaa    360
atttttttg aaatttctcg tttagataga tgtctttgct tttccgcact atggttctga    420

SEQ ID NO: 17            moltype = DNA   length = 397
FEATURE                  Location/Qualifiers
source                   1..397
                         mol_type = other DNA
                         note = Recombinant
                         organism = synthetic construct
SEQUENCE: 17
aggaaaagaa gaggtgatta ctgtacctat tcgtctttgt atcggaatat aaatttatca     60
ctattttatg ataaagtaaa tctgtttccc tgtagagtta attaattaat gtaagtataa    120
gcgtaattta tagggcacta gtaggactgt cgactgtgcg ctcggccgg ataatgcgtc    180
aaaagcgaag acgtgcacgt gggatgggaa aacacgaagc gtggtctgct ttttcgcatg    240
atatctgggc cgcaccaaag aatccagccc acgcggcgtg gcgccgtcgt tacggcttgc    300
gggggaagga aacgagggac gaaccgagat ttagtcccac cttgactaat cacaagagtg    360
gagcgtacct tataaaccga ccgcaagca ccgaatt                               397
```

```
SEQ ID NO: 18            moltype = DNA   length = 397
FEATURE                  Location/Qualifiers
source                   1..397
                         mol_type = other DNA
                         note = Recombinant
                         organism = synthetic construct
SEQUENCE: 18
aggaaaagaa gaggtgatta ctgtacctat tcgtctttgt atcggaatat aaatttatca  60
ctattttatg ataaagtaaa tctgtttccc tgtagagtta attaattaat gtaagtataa  120
gcgtaattta tagggcacta gtaggactgt cgactgtgcg ctcggcccgg ataatgcgtc  180
aaaagcgaag acgtgcacgt gggatgggaa aacacgaagc gtggtctgct ttttcgcatg  240
atatctgggc cgcaccaaag aatccagccc acgcggaagc ccaaacagca gtccgtaggt  300
ggagcaaagc gctgggtaat acgcaaacgt tttgtcccac cttgactaat cacaagagtg  360
gagcgtacct tataaaccga gccgcaagca ccgaatt                            397

SEQ ID NO: 19            moltype = DNA   length = 397
FEATURE                  Location/Qualifiers
source                   1..397
                         mol_type = other DNA
                         note = Recombinant
                         organism = synthetic construct
SEQUENCE: 19
aagtcgtaaa atagtggtgt ccaaagaatt tccaggccca gttgtaaaag ctaaaatgct  60
attcgaattt ctactagcag taagtcgtgt ttagaaatta ttttatatac cttttttcct  120
tctatgtaca gtaggacaca gtgtcagcgc cgcgttgacg gagaatattt gcaaaaaagt  180
aaaagagaaa gtcatagcgg cgtatgtgcc aaaaacttcg tcacagagag ggccataaga  240
aacatggccc acggcccaat acgaagcacc gcgacgaagc ccaaacagca gtccgtaggt  300
ggagcaaagc gctgggtaat acgcaaacgt tttgcaccag accggccagc gagcattgca  360
gacaccggct tataagttca gctgcgacta ccactcc                            397

SEQ ID NO: 20            moltype = DNA   length = 397
FEATURE                  Location/Qualifiers
source                   1..397
                         mol_type = other DNA
                         note = Recombinant
                         organism = synthetic construct
SEQUENCE: 20
tcgtaaaata gtggtgtcca aagaatttcc aggcccagtt gtaaaagcta aaatgctatt  60
cgaatttcta ctagcagtaa gtcgtgttta gaaattattt ttttatatac ctttttttcct  120
tctatgtaca gtaggacaca gtgtcagcgc cgcgttgacg gagaatattt gcaaaaaagt  180
aaaagagaaa gtcatagcgg cgtatgtgcc aaaaactgtc acagagaggg ccataagaaa  240
catggcccac ggcccaataa gcccaccagc ccaccgaacg ccaaacagca gtccgtaggt  300
ggagcaaagc gctgggtaat acgcaaacgt tttgtcccac cttgactaat cacaagagtg  360
gagcgtacct tataaaccga gccgcaagca ccgaatt                            397

SEQ ID NO: 21            moltype = DNA   length = 83
FEATURE                  Location/Qualifiers
source                   1..83
                         mol_type = other DNA
                         note = Recombinant
                         organism = synthetic construct
SEQUENCE: 21
gttttagagc tagaaatagc aagttaaaat aaggctagtc cgttatcaac ttgaaaaagt  60
ggcaccgagt cggtgctttt ttt                                           83

SEQ ID NO: 22            moltype = DNA   length = 23
FEATURE                  Location/Qualifiers
source                   1..23
                         mol_type = genomic DNA
                         organism = Zea mays
SEQUENCE: 22
gccggccagc atttgaaaca tgg                                           23

SEQ ID NO: 23            moltype = DNA   length = 20
FEATURE                  Location/Qualifiers
source                   1..20
                         mol_type = genomic DNA
                         organism = Zea mays
SEQUENCE: 23
gccggccagc atttgaaaca                                               20

SEQ ID NO: 24            moltype = DNA   length = 20
FEATURE                  Location/Qualifiers
source                   1..20
                         mol_type = unassigned DNA
                         organism = Zea mays
SEQUENCE: 24
gttatcaatt tactttcaat                                               20
```

```
SEQ ID NO: 25          moltype = DNA   length = 20
FEATURE                Location/Qualifiers
source                 1..20
                       mol_type = unassigned DNA
                       organism = Zea mays
SEQUENCE: 25
gcgcaaggga tcagtaattc                                              20

SEQ ID NO: 26          moltype = AA   length = 1064
FEATURE                Location/Qualifiers
source                 1..1064
                       mol_type = protein
                       organism = Bradyrhizobium sp.
SEQUENCE: 26
MKRTSLRAYR LGVDLGANSL GWFVVWLDDH GQPEGLGPGG VRIFPDGRNP QSKQSNAAGR    60
RLARSARRRR DRYLQRRGKL MGLLVKHGLM PADEPARKRL ECLDPYGLRA KALDEVLPLH   120
HVGRALFHLN QRRGLFANRA IEQGDKDASA IKAAAGRLQT SMQACGARTL GEFLNRRHQL   180
RATVRARSPV GGDVQARYEF YPTRAMVDAE FEAIWAAQAP HHPTMTAEAH DTIREAIFSQ   240
RAMKRPSIGK CSLDPATSQD DVDGFRCAWS HPLAQRFRIW QDVRNLAVVE TGPTSSRLGK   300
EDQDKVARAL LQTDQLSFDE IRGLLGLPSD ARFNLESDRR DHLKGDATGA ILSARRHFGP   360
AWHDRSLDRQ IDIVALLESA LDEAAIIASL GTTHSLDEAA AQRALSALLP DGYCRLGLRA   420
IKRVLPLMEA GRTYAEAASA AGYDHALLPG GKLSPTGYLP YYGQWLQNDV VGSDDERDTN   480
ERRWGRLPNP TVHIGIGQLR RVVNELIRWH GPPAEITVEL TRDLKLSPRR LAELEREQAE   540
NQRKNDKRTS LLRKLGLPAS THNLLKLRLW DEQGDVASEC PYTGEAIGLE RLVSDDVDID   600
HLIPFSISWD DSAANKVVCM RYANREKGNR TPFEAFGHRQ GRPYDWADIA ERAARLPRGK   660
RWRFGPGARA QFEELGDFQA RLLNETSWLA RVAKQYLAAV THPHRIHVLP GRLTALLRAT   720
WELNDLLPGS DDRAAKSRKD HRHHAIDALV AALTDQALLR RMANAHDDTR RKIEVLLPWP   780
TFRIDLETRL KAMLVSHKPD HGLQARLHED TAYGTVEHPE TEDGANLVYR KTFVDISEKE   840
IDRIRDRRLR DLVRAHVAGE RQQGKTLKAA VLSFAQRRDI AGHPNGIRHV RLTKSIKPDY   900
LVPIRDKAGR IYKSYNAGEN AFVDILQAES GRWIARATTV FQANQANESH DAPAAQPIMR   960
VPKGDMLRID HAGAEKFVKI VRLSPSNNLL YLVEHHQAGV FQTRHDDPED SFRWLFASFD  1020
KLREWNAELV RIDTLGQPWR RKRGLETGSE DATRIGWTRP KKWP                   1064

SEQ ID NO: 27          moltype = DNA   length = 3195
FEATURE                Location/Qualifiers
source                 1..3195
                       mol_type = other DNA
                       note = Recombinant
                       organism = synthetic construct
SEQUENCE: 27
atgaagagaa cgagtttacg ggcctaccgt ctgggcgtgg atctcggcgc caattcgctg    60
ggatggttcg tggtctggct cgacgatcac ggacagcccg agggccttgg cccgggcggc   120
gtcaggattt tccccgacgg tcgtaacccg caatccaagc aatccaatgc ggccggtcgc   180
cgcctcgcac gcagtgcacg acgacgacga gaccgctatc tgcagcgacg cggaaagctg   240
atgggcttgc tggtcaagca cggcttgatg cccgccgatg agccggcccg aaagcgattg   300
gaatgcctcg atccctatgg tctccgcgcg aaagcgctta tgaagtgcat ggcctttgcat   360
catgtcggcc gggcgctgtt tcacctcaac cagcggcgcg gcctgtttgc caatcgagcg   420
atcgagcaag cgacaaggag cgccagcgcg atcaaggccg cggccggcag actgcagaca   480
tcgatgcagg cgtgcggcgc gcgcacgctc ggcgaattcc tcaaccgccg tcatcagctc   540
cgcgccacag tgcgcgcccg cagccctgtc ggcggcgacg tccaggcgcg gtatgaattc   600
tatccgacac gcgcgatggt tgatgcggag ttcgaagcca tctgggcggc acaggcaccg   660
catcacccaa cgatgacggc cgaagcgcat gacacgatcc gcgaggcgat cttctctcaa   720
cgcgcgatga agcggccgtc gatcgggaaa tgctcgctcg accccgccac cagccaggac   780
gacgtcgacg gctttcgctg cgcctggtcg catcccctgg cgcagcgttt ccgcatctgg   840
caggacgtcc gcaatctagc cgtggtggag actggcccca cgtcttccag gcttggcaag   900
gaggatcagg acaaggtcgc acgggcactg ctacagaccg accaactcag cttcgatgag   960
atccgcggcc ttctcggatt gccgtcggac gcgcggttca accttgaaag cgaccggcgt  1020
gatcacctca agggcgacgc gaccggccgcg atcctgtccg ccaggaggca ttttggcccg  1080
gcatggcatg accggtccct ggatcgtcag atcgacatcg tcgcgctgct ggagagccga  1140
ctcgatgaag cagcgatcat cgcctcgctc gggacaactc acagccttga tgaagcagct  1200
gcgcagcggg cgttgtccgc cttgctgcct gacggatatt gcaggcttgg actgagggcg  1260
atcaagcggg tcctgccgct catggaagct ggcaggacct acgcggaggc cgccagcgcg  1320
gccggctatg atcacgctct gctgccgggc ggcaagctct ctccaccagg ctacctgccc  1380
tattatggac aatggctgca gaacgatgtc gtgggctcgg acgatgagcg cgacaccaac  1440
gaacggcgct ggggccgctt gccgaatccc accgttcaca tcgggatcgg ccagttgcga  1500
cgcgtcgtca atgagctcat cagatggcat ggaccgccgg ccgagatcac cgtcgagttg  1560
acgcgtgacc tgaagctgtc gccccgacgg ctggcggagc tcgaacgcga gcaggccgag  1620
aaccagcgca agaacgacaa gcgtacctcc ctattgcgga agctcgggct ccccgcgagc  1680
acgcacaatc tcctcaagct tcggctctgg gacgagcaag gcgatgttgc aagcgaatgc  1740
ccctatacgg gcgaggcgat cggcctcgaa cgtctggtct ctgatgatgt ggatatcgat  1800
cacctcatcc cattctcgat cagctgggac gacagcgcgg ccaacaaagt ggtctgcatg  1860
cgctacgcca tcgtgagaa gggcaatcga acgccgttcg aggcctttgg ccatcgccaa  1920
ggcaggcctt acgattgggc ggacattgca gaacgcgaag ccgcctgcc gcgcgccaac  1980
cgctggcgct tcggtccagg cgcgcgggcg caattcgagg agctcggcga ctttcaggca  2040
cgcctgctca cgagaccag ctggctggcg cgcgtcgcca agcaatatct cgcagcggtc  2100
acccaccgc acaggatcca cgttctgccg ggccggctga cagcgctgct ccgcgcaaca  2160
tgggagctca cgatttgct gccccggaagc gacgacagag ccgcgaagag ccgcaaggac  2220
caccgtcatc atgccatcga cgcgctggtg cggcactga cagaccaggc gctgctgcgc  2280
```

-continued

```
cgcatggcga acgcgcatga cgatacgcga cggaagatcg aagttctcct gccctggccg   2340
acgttccgga tcgatctcga gaccaggctg aaggcgatgc tcgtatcgca caagcccgat   2400
cacgggcctcc aggcccgcct gcatgaagac accgcctatg ggaccgtcga acaccccgaa   2460
accgaggatg gtgcaaatct ggtctatcgg aagaccttcg tggacatcag cgaaaaggag   2520
atcgaccgca ttcgcgatcg ccgcttgcgt gacctcgtca gagcccatgt ggccggcgaa   2580
aggcagcagg gcaagacgct caaagcggcg gtgctgtcat tcgcgcagcg cagggacatt   2640
gctggtcacc cgaatggcat tcgccatgtc cgcctgacca aatcgatcaa gccggactat   2700
ctggtaccga tccgcgacaa agccggccgc atctacaagt cctacaatgc aggcgagaat   2760
gccttcgtcg acatcctgca agccgagagt ggccgatgga tcgcgcgggc cacgaccgtc   2820
tttcaggcca atcaagccaa tgagtcgcat gacgcgccag cggcgcaacc gatcatgcgg   2880
gtcttcaagg cgacatgct gcgcatcgat cacgctggcg cggagaagtt cgtgaagatc   2940
gtcaggcttt cgccctcgaa caacctgctc tacctcgtcg aacatcatca ggcgggcgtg   3000
tttcagaccc gccatgacga cccggaagat tcctttcggt ggctcttcgc cagttttgac   3060
aagcttcgcg aatggaacgc cgagcttgtc cggatcgata cgctcgggaca gccctggcgg   3120
cgcaagcgcg gccttgaaac aggaagcgag gacgccactc gcatcggctg gacgcgacca   3180
aaaaaatggc cctga                                                     3195
```

```
SEQ ID NO: 28          moltype = AA  length = 1378
FEATURE                Location/Qualifiers
source                 1..1378
                       mol_type = protein
                       note = Recombinant
                       organism = synthetic construct
SEQUENCE: 28
MDKKYSIGLD IGTNSVGWAV ITDEYKVPSK KFKVLGNTDR HSIKKNLIGA LLFDSGETAE   60
ATRLKRTARR RYTRRKNRIC YLQEIFSNEM AKVDDSFFHR LEESFLVEED KKHERHPIFG   120
NIVDEVAYHE KYPTIYHLRK KLVDSTDKAD LRLIYLALAH MIKFRGHFLI EGDLNPDNSD   180
VDKLFIQLVQ TYNQLFEENP INASGVDAKA ILSARLSKSR RLENLIAQLP GEKKNGLFGN   240
LIALSLGLTP NFKSNFDLAE DAKLQLSKDT YDDDLDNLLA QIGDQYADLF LAAKNLSDAI   300
LLSDILRVNT EITKAPLSAS MIKRYDEHHQ DLTLLKALVR QQLPEKYKEI FFDQSKNGYA   360
GYIDGGASQE EFYKFIKPIL EKMDGTEELL VKLNREDLLR KQRTFDNGSI PHQIHLGELH   420
AILRRQEDFY PFLKDNREKI EKILTFRIPY YVGPLARGNS RFAWMTRKSE ETITPWNFEE   480
VVDKGASAQS FIERMTNFDK NLPNEKVLPK HSLLYEYFTV YNELTKVKYV TEGMRKPAFL   540
SGEQKKAIVD LLFKTNRKVT VKQLKEDYFK KIECFDSVEI SGVEDRFNAS LGTYHDLLKI   600
IKDKDFLDNE ENEDILEDIV LTLTLFEDRE MIEERLKTYA HLFDDKVMKQ LKRRRYTGWG   660
RLSRKLINGI RDKQSGKTIL DFLKSDGFAN RNFMQLIHDD SLTFKEDIQK AQVSGQGDSL   720
HEHIANLAGS PAIKKGILQT VKVVDELVKV MGRHKPENIV IEMARENQTT QKGQKNSRER   780
MKRIEEGIKE LGSQILKEHP VENTQLQNEK LYLYYLQNGR DMYVDQELDI NRLSDYDVDH   840
IVPQSFLKDD SIDNKVLTRS DKNRGKSDNV PSEEVVKKMK NYWRQLLNAK LITQRKFDNL   900
TKAERGGLSE LDKAGFIKRQ LVETRQITKH VAQILDSRMN TKYDENDKLI REVKVITLKS   960
KLVSDFRKDF QFYKVREINN YHHAHDAYLN AVVGTALIKK YPKLESEFVY GDYKVYDVRK   1020
MIAKSEQEIG KATAKYFFYS NIMNFFKTEI TLANGEIRKR PLIETNGETG EIVWDKGRDF   1080
ATVRKVLSMP QVNIVKKTEV QTGGFSKESI LPKRNSDKLI ARKKDWDPKK YGGFDSPTVA   1140
YSVLVVAKVE KGKSKKLKSV KELLGITIME RSSFEKNPID FLEAKGYKEV KKDLIIKLPK   1200
YSLFELENGR KRMLASAGEL QKGNELALPS KYVNFLYLAS HYEKLKGSPE DNEQKQLFVE   1260
QHKHYLDEII EQISEFSKRV ILADANLDKV LSAYNKHRDK PIREQAENII HLFTLTNLGA   1320
PAAFKYFDTT IDRKRYTSTK EVLDATLIHQ SITGLYETRI DLSQLGGDGS KKRRIKQD    1378
```

```
SEQ ID NO: 29          moltype = DNA  length = 4137
FEATURE                Location/Qualifiers
source                 1..4137
                       mol_type = other DNA
                       note = Recombinant
                       organism = synthetic construct
SEQUENCE: 29
atggacaaga agtacagcat tggtctggac atcggaacga actcggtcgg ctgggccgtg   60
attactgacg agtacaaagt tcccagcaaa aaattcaagg ttctaggcaa cacagaccgc   120
cactcgatta aaaagaatct aatcggcgcg cttctgttcg actctggtga aacggccgag   180
gccacacgct aaagaggac cgcgcgccgc cgctacacgc ggcgcaagaa ccgaatctgt   240
tacctccagg agatcttcag taatgagatg gctaaagtcg atgacagctt cttccacagg   300
cttgaagagt cctttctggt cgaagaggac aaaaaacacg aacgtcaccc aatcttcggg   360
aacattgtgg atgaagtcgc ataccacgag aagtatccta cgatctatca cctccgcaag   420
aagctcgtgg atagtaccga caaagccgac ctgcgcttaa tctaccttgc gctcgcgcac   480
atgattaagt tccgaggaca cttccttatt gagggtgatc tgaatccgga caattccgat   540
gtggataaac tgttcattca gttggtccag acatacaatc agctattcga ggagaatccg   600
atcaatgctt ccggcgtgga cgcaaaggct attctgtcag caagactttc aaagagcaga   660
aggttggaga atctgatcgc acaacttccc ggagagaaga gaatgggct cttcggcaac   720
ctcattgcgc tgtctttggg tctgacaccg aactttaagt ctaacttcga cctcgctgag   780
gatgctaaac ttcagcttag caaagcacc tatgatgacg acctcgacaa cctcctcgcc   840
cagattggag accagtacgc ggatctattc ttggctgcca agaacctgtc cgatgcgatt   900
ctgcttagtg acatcctccg agtgaacact gaaattacga agcaccctt gtcggcagt   960
atgattaagc gatacgatga gcaccatcaa gacctgacat tgctaaaggc gctcgtaaga   1020
cagcaacttc ctgagaagta caaggagata ttttttgatc agtctaagaa tggctacgct   1080
ggttacatcg acggtggagc tagtcaggag gaattcatca attcatcaa gcctatcctg   1140
gaaaaaatgg acggtacgga ggaattgctc gttaaactaa atcgagagga tctgctgaga   1200
aagcagcgga ctttcgacaa tggttctatt ccgcatcaga ttcacctcgg agaacttcac   1260
gccatcctga cgacagga ggacttctac ccttttcctga aagacaaccg ggaaaaaatc   1320
gagaagatcc tgacattcag gattcctac tatgtaggcc ctttagcgag aggcaacagt   1380
agattcgcct ggatgaccag aaagtctgag gaaacaatca caccgtggaa cttcgaggaa   1440
```

```
gtggttgata aggggtgctag tgcccaatca ttcattgaga gaatgacgaa cttcgacaag   1500
aatctgccta acgagaaggt tctccctaaa catagcttgc tttacgagta tttcacggtg   1560
tacaatgagc taacgaaggt caagtatgtc acagagggaa tgcggaaacc ggctttcctt   1620
tcgggtgaac agaagaaagc aattgtggat ttgctcttca agacaaaccg aaaggtgaca   1680
gtgaagcagc taaaggagga ctacttcaaa aaaatagagt gcttcgactc agttgagatc   1740
agcggagtgg aggaccggtt taacgcttcc ctcggcactt accacgactt gctcaagatc   1800
atcaaggaca aagacttcct tgataacgag gagaacgaag acatccttga ggacattgtg   1860
ctgacattga cgttgttcga ggatcgggag atgatcgagg aacgcctcaa gacgtacgcc   1920
catctgttcg atgataaggt gatgaagcag ttaaagagga gacgttacac tggctggggc   1980
cgtctctctc gcaaactgat aaacgggata agggataaac aaagcggaaa gacaatcctc   2040
gatttcctta aatccgacgg cttcgctaac cggaacttca tgcagctcat ccatgatgac   2100
tcactgacgt tcaaggagga catccagaaa gctcaagtgt ctggccaggg tgacagcttg   2160
cacgagcaca tcgcaaatct agccggttca ccggcgataa agaagggcat tctacaaacg   2220
gtgaaagtgg tggacgagct tgtgaaggtc atgggtcgcc ataagccaga gaacattgtt   2280
atcgaaatgg cgagggagaa ccagacaacg cagaagggac aaaaaaaacag tagggagcgg   2340
atgaagcgca tcgaggaagg cattaaggaa cttggaagcc aaatcctgaa agagcacccg   2400
gtggagaata cgcagttgca gaacgagaaa ctgtacctct actacttgca gaatggacgt   2460
gatatgtatg tggatcaaga gttggacatc aaccgattgt ctgactatga cgtggatcac   2520
atagtaccac agtccttcct caaggatgat agcatagaca acaaggttct tactcgtagc   2580
gacaagaatc gtggcaaatc ggacaatgtt ccatctgagg aagttgtcaa aaagatgaaa   2640
aattattgga ggcaacttct gaacgcgaag ctaattacac aaaggaaatt cgacaatctc   2700
actaaggccg agagaggagg gttaagtgag ttagacaaag ctggcttcat caagcggcag   2760
ttggtcgaga ctcgtcagat tactaagcac gtggctcaga tcctggattc gcgcatgaac   2820
accaaatacg acgagaatga caactcatc cgtgaagtta aggtgattac actgaaatcc   2880
aagctggtct ctgactttag gaaagacttc caattctaca aggtgagaga gattaacaac   2940
taccaccacg cgcatgacgc ctacttgaat gctgtggttg ggactgccct gataaagaaa   3000
tatcctaaac ttgagtctga gttcgtttac ggtgactaca aggtttatga cgttaggaag   3060
atgatcgcca aatccgaaca ggagattggg aaagcaactg ccaaatattt cttttactcc   3120
aacattatga acttttcaa gacagaaatc acactcgcca atggcgagat tcggaagaga   3180
ccactaatcg aaacaaacgg cgaaactggt gaaatcgttt aggataaggg taggggactc   3240
gcaactgtta ggaaggtctt gtcgatgcct caagtgaaca tagtcaaaaa aacagaggtc   3300
cagaccggtg ggttctcaaa ggagtctatt ctgccaaagc gtaacagcga caaactcatc   3360
gctcgcaaaa aggactgggga tcctaaaaag tacggtggat tcgacagccc gaccgttgct   3420
tattctgttc tcgtagttgc taaagtcgag aagggcaagt ccaaaaaact caaatcggtt   3480
aaggaactgc tcggaatcac gataatggaa cgaagcagtt tcgaaaaaaa tccaattgac   3540
ttcctggaag ctaaaggtta caaggaggtc aagaaggatc ttatcatcaa gctacccaag   3600
tacagtctgt tcgaactgga gaacggtcgc aagagaatgc tggcctcggc tggtgaactc   3660
cagaagggca atgagctggc cctgccgtcc aagtacgtga actttctgta cctggcatct   3720
cattacgaga agctcaaggg ctcaccagag gacaacgagc agaagcagtt gttcgttgaa   3780
cagcacaaac actatcttga tgagatcatt gagcaaatta gcgagttcag taagcgagtt   3840
attctggctg atgctaacct ggataaggtg ctctctgcct acaacaagca ccgggataaa   3900
cctattaggg aacaggcgga gaacataatc cacctcttca ctctgacgaa tctcggcgcg   3960
cctgcggcct tcaaatattt tgataccacc atcgacagga aagtactaaa   4020
gaggtgctgg acgccactct cattcaccag tctattaccg ggctctacga gacacggatt   4080
gacctctccc agctaggtgg cgatggatct aagaagagaa gaattaaaca agattaa     4137
```

SEQ ID NO: 30              moltype = DNA   length = 500
FEATURE                    Location/Qualifiers
source                     1..500
                           mol_type = other DNA
                           note = Recombinant
                           organism = synthetic construct
SEQUENCE: 30

```
aggaaaagaa gaggtgatta ctgtacctat tcgtctttgt atcggaatat aaatttatca   60
ctattttatg ataaagtaaa tctgtttccc tgtagagtta attaattaat gtaagtataa   120
gcgtaattta tagggcacta gtaggactgt cgactgtgcg ctcggcccgg ataatgcgtc   180
aaaagcgaag acgtgcacgt gggatgggaa aacacgaagc gtggtctgct ttttcgcatg   240
atatctgggc cgcaccaaag aatccagccc acgcggcgtg gcgccgtcgt tacggcttgc   300
ggggggaagga aacgagggac gaaccgagat ttagcaccag accggccagc gagcattgca   360
gacaccggct tataagttca gctgcgacta ccactccgcc ggccagcatt tgaaacagtt   420
ttagagctag aaatagcaag ttaaaataag gctagtccgt tatcaacttg aaaaagtggc   480
accgagtcgg tgcttttttt                                               500
```

SEQ ID NO: 31              moltype = DNA   length = 303
FEATURE                    Location/Qualifiers
source                     1..303
                           mol_type = other DNA
                           note = Recombinant
                           organism = synthetic construct
SEQUENCE: 31

```
cgtgggatgg gaaaacacga agcgtggtct gcttttttcgc atgatatctg ggccgcacca   60
aagaatccag cccacgcggc gtggcgccgt cgttacggct gcggggggaa ggaaacgagg   120
gacgaaccga gatttagcac cagaccggcc agcgagcatt gcagacaccg gcttataagt   180
tcagctgcga ctaccactcc gccggccagc atttgaaaca gttttagagc tagaaatagc   240
aagttaaaat aaggctagtc cgttatcaac ttgaaaaagt ggcaccgagt cggtgctttt   300
ttt                                                                 303
```

SEQ ID NO: 32              moltype = DNA   length = 500
FEATURE                    Location/Qualifiers -continued

```
source                   1..500
                         mol_type = other DNA
                         note = Recombinant
                         organism = synthetic construct
SEQUENCE: 32
ttatatgtta ccgttgcaaa gcacgggcac tcacctagta tataatataa catcagtcgt    60
acgtaatgta ctgatgggcg ggttaacaaa tgtcactcac tatcagcacc agcagcgctt   120
agatgcatcc ggccgggcca agacccagga ccagaaagcg cgcacgttca cagcggatgc   180
tgatgggtta gatcgactga tcgaggaaga ggagagctta attaagaaac gccctgttca   240
gctttgctag cttgcgccct gactgtccag cccacgcgct tcggtccgat tcacatgcta   300
ggctggtgca agcgagccga gactttttt tagaaccacc ttgctcagca aaccttagga   360
acaccggctt ataagtcgaa gcgaagcgct gtgcactgcc ggccagcatt tgaaacagtt   420
ttagagctag aaatagcaag ttaaaataag gctagtccgt tatcaacttg aaaaagtggc   480
accgagtcgg tgctttttt                                                500

SEQ ID NO: 33            moltype = DNA  length = 303
FEATURE                  Location/Qualifiers
source                   1..303
                         mol_type = other DNA
                         note = Recombinant
                         organism = synthetic construct
SEQUENCE: 33
tgatcgagga agaggagagc ttaattaaga aacgccctgt tccgctttgc tagcttgcgc    60
cctgactgtc cagcccacgc gcttcggtcc gattcacatg ctaggctggt gcaagcgagc   120
cgagactttt ttttagaacc accttgctca gcaaacctta ggaacaccgg cttataagtc   180
gaagcgaagc gctgtgcact gccggccagc atttgaaaca gttttagagc tagaaatagc   240
aagttaaaat aaggctagtc cgttatcaac ttgaaaaagt ggcaccgagt cggtgctttt   300
ttt                                                                 303

SEQ ID NO: 34            moltype = DNA  length = 500
FEATURE                  Location/Qualifiers
source                   1..500
                         mol_type = other DNA
                         note = Recombinant
                         organism = synthetic construct
SEQUENCE: 34
ggattcggtg ttctttatta ggttctcgcc gaatatggtt ctcagttatg acctaacggt    60
gtccacaaga gttcgccagg atttatacaa ctattttctt atttatttct ttaacatttt   120
ccctctacg cacaatagga gataatgtca agcgttgacg gtgcacatat atttgttttt   180
ttaaaggcgt agtggcgtgt gtgcaaaaac atcctcacag gaaagacacg aagaaacatg   240
gtcaatggcc cattatataa agcaccgcca caaagcccaa ataccagttc gtcggtggag   300
caagtaacgc gctaggcaac aggcaaacag tttgtcccac ctcgtccagt cacaaaggca   360
aagcgtgact tataagccag agcggaagaa ccataccgcc ggccagcatt tgaaacagtt   420
ttagagctag aaatagcaag ttaaaataag gctagtccgt tatcaacttg aaaaagtggc   480
accgagtcgg tgctttttt                                                500

SEQ ID NO: 35            moltype = DNA  length = 303
FEATURE                  Location/Qualifiers
source                   1..303
                         mol_type = other DNA
                         note = Recombinant
                         organism = synthetic construct
SEQUENCE: 35
tgtgtgcaaa aacatcctca caggaaagac acgaagaaac atggtcaatg gcccattata    60
taaagcaccg ccacaaagcc caaataccag ttcgtcggtg gagcaagtaa cgcgctaggc   120
aacaggcaaa cagtttgtcc cacctcgtcc agtcacaaag gcaaagcgtg acttataagc   180
cagagcggaa gaaccatacc gccggccagc atttgaaaca gttttagagc tagaaatagc   240
aagttaaaat aaggctagtc cgttatcaac ttgaaaaagt ggcaccgagt cggtgctttt   300
ttt                                                                 303

SEQ ID NO: 36            moltype = DNA  length = 500
FEATURE                  Location/Qualifiers
source                   1..500
                         mol_type = other DNA
                         note = Recombinant
                         organism = synthetic construct
SEQUENCE: 36
tcgtaaaata gtggtgtcca aagaatttcc aggcccagtt gtaaaagcta aaatgctatt    60
cgaatttcta ctagcagtaa gtcgtgttta gaaattattt ttttatatac ctttttttcct   120
tctatgtaca gtaggacaca gtgtcagcgc cgcgttgacg gagaatattt gcaaaaaagt   180
aaaagagaaa gtcatagcgg cgtatgtgcc aaaaacttcg tcacagagag ggccataaga   240
aacatggccc acgcccaat acgaagcacc gcgacgaagc ccaaacagca gtccgtaggt   300
ggagcaaagc gctgggtaat acgcaaacgt tttgtcccac cttgactaat cacaagagtg   360
gagcgtacct tataaaccga gccgcaagca ccgaattgcc ggccagcatt tgaaacagtt   420
ttagagctag aaatagcaag ttaaaataag gctagtccgt tatcaacttg aaaaagtggc   480
accgagtcgg tgctttttt                                                500

SEQ ID NO: 37            moltype = DNA  length = 303
FEATURE                  Location/Qualifiers
```

-continued

```
source                  1..303
                        mol_type = other DNA
                        note = Recombinant
                        organism = synthetic construct
SEQUENCE: 37
cggcgtatgt gccaaaaact tcgtcacaga gagggccata agaaacatgg cccacggccc   60
aatacgaagc accgcgacga agcccaaaca gcagtccgta ggtggagcaa agcgctgggt  120
aatacgcaaa cgtttgtcc caccttgact aatcacaaga gtggagcgta ccttataaac  180
cgagccgcaa gcaccgaatt gccggccagc atttgaaaca gttttagagc tagaaatagc  240
aagttaaaat aaggctagtc cgttatcaac ttgaaaaagt ggcaccgagt cggtgctttt  300
ttt                                                               303

SEQ ID NO: 38          moltype = DNA  length = 500
FEATURE                Location/Qualifiers
source                 1..500
                       mol_type = other DNA
                       note = Recombinant
                       organism = synthetic construct
SEQUENCE: 38
aggaaaagaa gaggtgatta ctgtacctat tcgtctttgt atcggaatat aaatttatca   60
ctattttatg ataaagtaaa tctgtttccc tgtagagtta attaattaat gtaagtataa  120
gcgtaattta tagggcacta gtaggactgt cgactgtcgg ctcggcccgg ataatgcgtc  180
aaaagcgaag acgtgcacgt gggatgggaa aacacgaagc gtggtctgct ttttcgcatg  240
atatctgggc cgcaccaaag aatccagccc acgcggcgtg gcgccgtcgt tacggcttgc  300
gggggaagga aacgagggac gaaccgagat ttagcaccag accggccagc gagcattgca  360
gacaccggct tataagttca gctgcgacta ccactccgcg caagggatca gtaattcgtt  420
ttagagctag aaatagcaag ttaaaataag gctagtccgt tatcaacttg aaaaagtggc  480
accgagtcgg tgcttttttt                                             500

SEQ ID NO: 39          moltype = DNA  length = 500
FEATURE                Location/Qualifiers
source                 1..500
                       mol_type = other DNA
                       note = Recombinant
                       organism = synthetic construct
SEQUENCE: 39
ttatatgtta ccgttgcaaa gcacgggcac tcacctagta tataatataa catcagtcgt   60
acgtaatgta ctgatgggcg ggttaacaaa tgtcactcac tatcagcacc agcagcgctt  120
agatgcatcc ggccgggcca agacccagga ccagaaagcg cgcacgttca cagcggatgc  180
tgatgggtta gatcgactga tcgaggaaga ggagagctta attaagaaac gccctgttcc  240
gctttgctag cttgcgccct gactgtccag cccacgcgct tcggtccgat tcacatgcta  300
ggctggtgca agcgagccga gactttttt tagaaccacc ttgctcagca aaccttagga  360
acaccggctt ataagtcgaa gcgaagcgct gtgcactgcg caagggatca gtaattcgtt  420
ttagagctag aaatagcaag ttaaaataag gctagtccgt tatcaacttg aaaaagtggc  480
accgagtcgg tgcttttttt                                             500

SEQ ID NO: 40          moltype = DNA  length = 500
FEATURE                Location/Qualifiers
source                 1..500
                       mol_type = other DNA
                       note = Recombinant
                       organism = synthetic construct
SEQUENCE: 40
ggattcggtg ttctttatta ggttctcgcc gaatatggtt ctcagttatg acctaacggt   60
gtccacaaga gttcgccagg atttatacaa ctattttctt ttaacatttt ttaacatttt  120
cccttctacg cacaatagga gataatgtca agcgttgacg gtgcacatat atttgttttt  180
ttaaaggcgt agtggcgtgt gtgcaaaaac atcctcacag gaaagacacg aagaaacatg  240
gtcaatggcc cattatataa agcaccgcca caaagcccaa ataccagttc gtcggtggag  300
caagtaacgc gctaggcaac aggcaaacag tttgtcccac ctcgtccagt cacaaaggca  360
aagcgtgact tataagccag agcggaagaa ccataccgcg caagggatca gtaattcgtt  420
ttagagctag aaatagcaag ttaaaataag gctagtccgt tatcaacttg aaaaagtggc  480
accgagtcgg tgcttttttt                                             500

SEQ ID NO: 41          moltype = DNA  length = 500
FEATURE                Location/Qualifiers
source                 1..500
                       mol_type = other DNA
                       note = Recombinant
                       organism = synthetic construct
SEQUENCE: 41
tcgtaaaata gtggtgtcca aagaatttcc aggcccagtt gtaaaagcta aaatgctatt   60
cgaatttcta ctagcagtaa gtcgtgttta gaaattattt ttttatatac ctttttttcct  120
tctatgtaca gtaggacaca gtgtcagcgc cgcgttgacg gagaatattt gcaaaaaagt  180
aaaagagaaa gtcatagcgg cgtatgtgcc aaaaacttcg tcacagagag ggccataaga  240
aacatggccc acggcccaat acgaagcacc gcgacgaagc ccaaacagca gtccgtaggt  300
ggagcaaagc gctgggtaat acgcaaacgt tttgtcccac cttgactaat cacaagagtg  360
gagcgtacct tataaaccga gccgcaagca ccgaattgcg caagggatca gtaattcgtt  420
ttagagctag aaatagcaag ttaaaataag gctagtccgt tatcaacttg aaaaagtggc  480
accgagtcgg tgcttttttt                                             500
```

-continued

```
SEQ ID NO: 42              moltype = DNA   length = 500
FEATURE                    Location/Qualifiers
source                     1..500
                           mol_type = other DNA
                           note = Recombinant
                           organism = synthetic construct
SEQUENCE: 42
tcgtaaaata gtggtgtcca aagaatttcc aggcccagtt gtaaaagcta aaatgctatt   60
cgaatttcta ctagcagtaa gtcgtgttta gaaattattt ttttatatac cttttttcct  120
tctatgtaca gtaggacaca gtgtcagcgc cgcgttgacg gagaatattt gcaaaaaagt  180
aaaagagaaa gtcatagcgg cgtatgtgcc aaaaacttcg tcacagagag ggccataaga  240
aacatggccc acggcccaat acgaagcacc gcgacgaagc ccaaacagca gtccgtaggt  300
ggagcaaagc gctgggtaat acgcaaacgt tttgtcccac cttgactaat cacaagagtg  360
gagcgtacct tataaaccga gccgcaagca ccgaattgtt atcaatttac tttcaatgtt  420
ttagagctag aaatagcaag ttaaaataag gctagtccgt tatcaacttg aaaaagtggc  480
accgagtcgg tgcttttttt                                              500

SEQ ID NO: 43              moltype = DNA   length = 23
FEATURE                    Location/Qualifiers
source                     1..23
                           mol_type = genomic DNA
                           organism = Zea mays
SEQUENCE: 43
gttatcaatt tactttcaat cgg                                          23

SEQ ID NO: 44              moltype = DNA   length = 23
FEATURE                    Location/Qualifiers
source                     1..23
                           mol_type = genomic DNA
                           organism = Zea mays
SEQUENCE: 44
gcgcaaggga tcagtaattc agg                                          23

SEQ ID NO: 45              moltype = DNA   length = 86
FEATURE                    Location/Qualifiers
source                     1..86
                           mol_type = other DNA
                           note = Recombinant
                           organism = synthetic construct
SEQUENCE: 45
gggataacag ggtaatatag cgtaactata acggtcctaa ggtagcgaat tacgatacaa   60
ggctacctag cttcgcagtt acgcta                                       86

SEQ ID NO: 46              moltype = DNA   length = 86
FEATURE                    Location/Qualifiers
source                     1..86
                           mol_type = other DNA
                           note = Recombinant
                           organism = synthetic construct
SEQUENCE: 46
tagcgtaact gcgaagctag gtagccttgt atcgtaattc gctaccttag gaccgttata   60
gttacgctat attaccctgt tatccc                                       86

SEQ ID NO: 47              moltype = DNA   length = 23
FEATURE                    Location/Qualifiers
source                     1..23
                           mol_type = genomic DNA
                           organism = Zea mays
SEQUENCE: 47
gatatgccaa acggtacttg agg                                          23

SEQ ID NO: 48              moltype = DNA   length = 500
FEATURE                    Location/Qualifiers
source                     1..500
                           mol_type = other DNA
                           note = Recombinant
                           organism = synthetic construct
SEQUENCE: 48
tcgtaaaata gtggtgtcca aagaatttcc aggcccagtt gtaaaagcta aaatgctatt   60
cgaatttcta ctagcagtaa gtcgtgttta gaaattattt ttttatatac cttttttcct  120
tctatgtaca gtaggacaca gtgtcagcgc cgcgttgacg gagaatattt gcaaaaaagt  180
aaaagagaaa gtcatagcgg cgtatgtgcc aaaaacttcg tcacagagag ggccataaga  240
aacatggccc acggcccaat acgaagcacc gcgacgaagc ccaaacagca gtccgtaggt  300
ggagcaaagc gctgggtaat acgcaaacgt tttgtcccac cttgactaat cacaagagtg  360
gagcgtacct tataaaccga gccgcaagca ccgaattgta caaccaact cggcaatgtt  420
ttagagctag aaatagcaag ttaaaataag gctagtccgt tatcaacttg aaaaagtggc  480
accgagtcgg tgcttttttt                                              500
```

-continued

```
SEQ ID NO: 49          moltype = DNA   length = 20
FEATURE                Location/Qualifiers
source                 1..20
                       mol_type = other DNA
                       note = Recombinant
                       organism = synthetic construct
SEQUENCE: 49
gcgtaactgc gaagctaggt                                          20

SEQ ID NO: 50          moltype = DNA   length = 20
FEATURE                Location/Qualifiers
source                 1..20
                       mol_type = other DNA
                       note = Recombinant
                       organism = synthetic construct
SEQUENCE: 50
ctcacgcctt catttcaaag                                          20

SEQ ID NO: 51          moltype = DNA   length = 20
FEATURE                Location/Qualifiers
source                 1..20
                       mol_type = other DNA
                       note = Recombinant
                       organism = synthetic construct
SEQUENCE: 51
gtaatgggta atcacaaagg                                          20

SEQ ID NO: 52          moltype = DNA   length = 22
FEATURE                Location/Qualifiers
source                 1..22
                       mol_type = other DNA
                       note = Recombinant
                       organism = synthetic construct
SEQUENCE: 52
ggattatatt agtttaggct tg                                       22

SEQ ID NO: 53          moltype = DNA   length = 20
FEATURE                Location/Qualifiers
source                 1..20
                       mol_type = other DNA
                       note = Recombinant
                       organism = synthetic construct
SEQUENCE: 53
cgaccaactc tccaccaatc                                          20

SEQ ID NO: 54          moltype = DNA   length = 21
FEATURE                Location/Qualifiers
source                 1..21
                       mol_type = other DNA
                       note = Recombinant
                       organism = synthetic construct
SEQUENCE: 54
taaggagatg agtttgagac c                                        21

SEQ ID NO: 55          moltype = DNA   length = 20
FEATURE                Location/Qualifiers
source                 1..20
                       mol_type = other DNA
                       note = Recombinant
                       organism = synthetic construct
SEQUENCE: 55
tagaggtgga agcatcaaag                                          20

SEQ ID NO: 56          moltype = DNA   length = 20
FEATURE                Location/Qualifiers
source                 1..20
                       mol_type = other DNA
                       note = Recombinant
                       organism = synthetic construct
SEQUENCE: 56
gtaccgtttg gcatatcaac                                          20

SEQ ID NO: 57          moltype = DNA   length = 20
FEATURE                Location/Qualifiers
source                 1..20
                       mol_type = other DNA
                       note = Recombinant
                       organism = synthetic construct
SEQUENCE: 57
```

-continued

```
gagcatctaa ccaccaaaac                                                20

SEQ ID NO: 58              moltype = DNA   length = 500
FEATURE                    Location/Qualifiers
source                     1..500
                           mol_type = other DNA
                           note = Recombinant
                           organism = synthetic construct
SEQUENCE: 58
tcgtaaaata gtggtgtcca aagaatttcc aggcccagtt gtaaaagcta aaatgctatt    60
cgaatttcta ctagcagtaa gtcgtgttta gaaattattt ttttatatac cttttttcct   120
tctatgtaca gtaggacaca gtgtcagcgc cgcgttgacg gagaatattt gcaaaaaagt   180
aaaagagaaa gtcatagcgg cgtatgtgcc aaaaacttcg tcacagagag ggccataaga   240
aacatggccc acggcccaat acgaagcacc gcgacgaagc ccaaacagca gtccgtaggt   300
ggagcaaagc gctgggtaat acgcaaacgt tttgtcccac cttgactaat cacaagagtg   360
gagcgtacct tataaaccga gccgcaagca ccgaattgat atgccaaacg gtacttggtt   420
ttagagctag aaatagcaag ttaaaataag gctagtccgt tatcaacttg aaaaagtggc   480
accgagtcgg tgcttttttt                                               500

SEQ ID NO: 59              moltype = DNA   length = 23
FEATURE                    Location/Qualifiers
source                     1..23
                           mol_type = genomic DNA
                           organism = Zea mays
SEQUENCE: 59
gatatgccaa acggtacttg agg                                            23

SEQ ID NO: 60              moltype = DNA   length = 500
FEATURE                    Location/Qualifiers
source                     1..500
                           mol_type = other DNA
                           note = Recombinant
                           organism = synthetic construct
SEQUENCE: 60
tcgtaaaata gtggtgtcca aagaatttcc aggcccagtt gtaaaagcta aaatgctatt    60
cgaatttcta ctagcagtaa gtcgtgttta gaaattattt ttttatatac cttttttcct   120
tctatgtaca gtaggacaca gtgtcagcgc cgcgttgacg gagaatattt gcaaaaaagt   180
aaaagagaaa gtcatagcgg cgtatgtgcc aaaaacttcg tcacagagag ggccataaga   240
aacatggccc acggcccaat acgaagcacc gcgacgaagc ccaaacagca gtccgtaggt   300
ggagcaaagc gctgggtaat acgcaaacgt tttgtcccac cttgactaat cacaagagtg   360
gagcgtacct tataaaccga gccgcaagca ccgaattgga tctcctatca taacgttgtt   420
ttagagctag aaatagcaag ttaaaataag gctagtccgt tatcaacttg aaaaagtggc   480
accgagtcgg tgcttttttt                                               500

SEQ ID NO: 61              moltype = DNA   length = 23
FEATURE                    Location/Qualifiers
source                     1..23
                           mol_type = genomic DNA
                           organism = Zea mays
SEQUENCE: 61
ggatctccta tcataacgtt tgg                                            23

SEQ ID NO: 62              moltype = DNA   length = 92
FEATURE                    Location/Qualifiers
source                     1..92
                           mol_type = other DNA
                           note = Recombinant
                           organism = synthetic construct
SEQUENCE: 62
ggcgggataa cagggtaata tagcgtaact ataacggtcc taaggtagcg aattacgata    60
caaggctacc tagcttcgca gttacgctaa at                                  92

SEQ ID NO: 63              moltype = DNA   length = 92
FEATURE                    Location/Qualifiers
source                     1..92
                           mol_type = other DNA
                           note = Recombinant
                           organism = synthetic construct
SEQUENCE: 63
atttagcgta actgcgaagc taggtagcct tgtatcgtaa ttcgctacct taggaccgtt    60
atagttacgc tatattaccc tgttatcccg cc                                  92

SEQ ID NO: 64              moltype = DNA   length = 92
FEATURE                    Location/Qualifiers
source                     1..92
                           mol_type = other DNA
                           note = Recombinant
                           organism = synthetic construct
SEQUENCE: 64
```

```
tacgggataa cagggtaata tagcgtaact ataacggtcc taaggtagcg aattacgata   60
caaggctacc tagcttcgca gttacgctat tg                                 92

SEQ ID NO: 65          moltype = DNA   length = 92
FEATURE                Location/Qualifiers
source                 1..92
                       mol_type = other DNA
                       note = Recombinant
                       organism = synthetic construct
SEQUENCE: 65
caatagcgta actgcgaagc taggtagcct tgtatcgtaa ttcgctacct taggaccgtt   60
atagttacgc tatattaccc tgttatcccg ta                                 92

SEQ ID NO: 66          moltype = DNA   length = 92
FEATURE                Location/Qualifiers
source                 1..92
                       mol_type = other DNA
                       note = Recombinant
                       organism = synthetic construct
SEQUENCE: 66
aacgggataa cagggtaata tagcgtaact ataacggtcc taaggtagcg aattacgata   60
caaggctacc tagcttcgca gttacgctag tt                                 92

SEQ ID NO: 67          moltype = DNA   length = 92
FEATURE                Location/Qualifiers
source                 1..92
                       mol_type = other DNA
                       note = Recombinant
                       organism = synthetic construct
SEQUENCE: 67
aactagcgta actgcgaagc taggtagcct tgtatcgtaa ttcgctacct taggaccgtt   60
atagttacgc tatattaccc tgttatcccg tt                                 92

SEQ ID NO: 68          moltype = DNA   length = 3366
FEATURE                Location/Qualifiers
source                 1..3366
                       mol_type = other DNA
                       note = Recombinant
                       organism = synthetic construct
SEQUENCE: 68
atgagtgacc tggtgctagg gttggatata ggcattggct ccgtgggggt tggcattctt   60
aataaggtga ccggcgaaat aattcataaa aactcacgca tctttccagc agcccaggct  120
gagaacaatc tggtccgtag aaccaaccgg cagggtcgaa ggttagccag gcgcaagaag  180
cacagacggg tccggctcaa caggcttttc gaggagtctg gtttgatcac cgatttcact  240
aagatttcta tcaacctgaa tccttatcag ctgcgcgtta aaggtctcac agacgaactt  300
agcaacgaag agttgttcat cgccctgaaa aatatggtca agcatcgcgg cattagctac  360
ctggacgacg cttcggatga tggcaacagt gatgtgaggtg actacgctca gatcgtgaaa  420
gagaactcga agcaattgga gaccaagacc ccgggccaaa ttcaactcga aaggtaccag  480
acgtatggac agttacgagg cgattttacc gttgaaaagg atggtaagaa gcacaggctg  540
attaatgtgt ttccgacctc agcttatcgc tctgaggcgc tgcgtatttt gcagacccaa  600
caggaattta acccgcaaat aacggacgag ttcataaacc gatacttaga gattcttaca  660
ggtaaacgta aatactatca cggcccagga aatgaaaagt ccaggacaga ttatggtcga  720
tatcgcactt ccggagagac tctcgacaat atctttggca ttcttatagg caaatgtacc  780
ttctaccctg acgaatttag agcagcgaag gcttcatata cagcacaaga gtttaatctt  840
ctcaacgacc tcaacaactt gactgtgcct actgaaacca aaaagcttag caaggagcaa  900
aaaaatcaaa tcattaacta tgttaagaat gagaaagcta tggggcccgc aaaattgttc  960
aagtacatag ctaagttact tagctgtgac gttgctgata ttaagggtta ccgtattgac 1020
aagtctggta aagctgaaat tcacaccttt gaggcttata ggaagatgaa gacccttgag 1080
acacttgaca ttgagcagat ggataggag actttggaca aactggcata cgtcttgaca 1140
ttgaacaccg aaagggaagg catccaggaa gctctggaac atgaatttgc agatggttcg 1200
ttcagccaaa aacaggttga cgagctggtc caatttagaa aggcaaactc aagcatattc 1260
ggtaaaggtt ggcacaactt cagcgttaag ctgatgatgg aactcattcc agaattatat 1320
gaaacctctg aggaacagat gacgattctc acaagattgg gtaagcagaa aacaaccagc 1380
tctagcaata agactaaata cattgacgaa aagctcctca ccgaagagat ttataacgca 1440
gtcgtggcaa agagtgtacg gcaagccatc aagatcgtta atgccgctat caaggagtat 1500
ggtgattttg ataatattgt gattgaaatg gcacgcgaga ctaacgagga cgacgagaag 1560
aaagctatac agaagattca aaaggctaat aaggacgaga aggacgccgc aatgctaaag 1620
gcggccaatc aatataatgg gaaggctgaa ctacctcata gcgtcttcca tggacataag 1680
caattagcaa ctaaaataag attatggcac cagcaaggcg aacggtgtct ttatacaggt 1740
aaaacgatat ctattcacga cctgattaac aactctaacc agtttgaagt ggatcatatc 1800
ttaccactaa gtatcacctt cgacgattca cttgctaaca aggtgctcgt ttacgccact 1860
gcgaaccaag agaaagggca gaggactcca taccaggccc ttgacagcat ggacgacgcc 1920
tggagttta gggaattaaa agctttcgta cgtgagtcaa agacgctttc aaataaaaaa 1980
aaggagtact tgctcactga agaagacatc tcaaaattcg acgtgcgcaa aaaattcatt 2040
gagcggaact tagtcgacac tcggtacgca tcaagagtag tgttgaacgc cctccaggag 2100
cactttaggg cacataagat cgacaccaag gtttcagttg ttaggggtca gtttacatcg 2160
cagcttagac gccattgggg tatagaaaaa acacgtgata cctaccatca ccatgcagtt 2220
gacgctctca tcattgcagc atcttctcaa cttaatttgt ggaaaaagca aagaacact 2280
ctggtctcat atagcgaaga tcagctgctt gatattgaaa ccggcgagct gatttctgac 2340
```

-continued

```
gacgaataca aagaatctgt gtttaaggca ccatatcaac actttgtaga cacgcttaaa   2400
tctaaagagt ttgaggattc gatccttttc agttaccaag tcgactcaaa atttaaccgt   2460
aagatctctg atgcaacaat ttatgcgacg aggcaggcca aggtaggtaa ggataaggct   2520
gacgaaacct acgtgctcgg aaaaatcaaa gatatttaca ctcaagatgg atatgatgca   2580
ttcatgaaga tatataaaaa ggacaaatct aaattcctta tgtatcgtca tgacccacag   2640
acattcgaga aagttattga gcctatcctg gagaactatc cgaacaagca aataaatgag   2700
aagggcaaag aagttccatg taatccgttc ctaaagtaca aggaggaaca cggatatatt   2760
agaaaatatac gcaaaaaggg caacggccca gaaatcaaaa gccttaagta ctacgatagt   2820
aaactaggaa accacatcga cattacacca aaagactcta ataataaggt cgtactgcaa   2880
agcgtttccc catggcgcgc cgatgtgtat tttaataaga caacagggaa gtacgaaatc   2940
ttgggggttaa aatatgcgga tctgcaattc gaaaagggaa ccggcacata caaaatttct   3000
caagaaaagt acaacgacat aaagaagaag gaagggggtcg attctgattc tgaattcaag   3060
ttcacactct ataagaatga tcttctgctc gtcaaggaca cagagacaaa ggagcagcag   3120
ttgttcaggt tcttgtctag aactatgcca aaacaaaagc actacgttga actgaagcct   3180
tacgataagc aaaaattcga gggggcgag gcgcttataa aggtcctagg aaatgttgca   3240
aactctgggc agtgtaagaa gggcctgggc aagagcaaca ttagcatcta taaggttcga   3300
acggatgtgc ttgggaacca gcatatcatc aaaaacgagg gagataaacc aaagctggac   3360
ttctag                                                              3366
```

SEQ ID NO: 69          moltype = AA   length = 1121
FEATURE                Location/Qualifiers
source                 1..1121
                       mol_type = protein
                       organism = Streptococcus thermophilus
SEQUENCE: 69
```
MSDLVLGLDI GIGSVGVGIL NKVTGEIIHK NSRIFPAAQA ENNLVRRTNR QGRRLARRKK   60
HRRVRLNRLF EESGLITDFT KISINLNPYQ LRVKGLTDEL SNEELFIALK NMVKHRGISY   120
LDDASDDGNS SVGDYAQIVK ENSKQLETKT PGQIQLERYQ TYGQLRGDFT VEKDGKKHRL   180
INVFPTSAYR SEALRILQTQ QEFNPQITDE FINRYLEILT GKRKYYHGPG NEKSRTDYGR   240
YRTSGETLDN IFGILIGKCT FYPDEFRAAK ASYTAQEFNL LNDLNNLTVP TETKKLSKEQ   300
KNQIINYVKN EKAMGPAKLF KYIAKLLSCD VADIKGYRID KSGKAEIHTF EAYRKMKTLE   360
TLDIEQMDRE TLDKLAYVLT LNTEREGIQE ALEHEFADGS FSQKQVDELV QPRKANSSIF   420
GKGWHNFSVK LMMELIPELY ETSEEQMTIL TRLGKQKTTS SSNKTKYIDE KLLTEEIYNP   480
VVAKSVRQAI KIVNAAIKEY GDFDNIVIEM ARETNEDDEK KAIQKIQKAN KDEKDAAMLK   540
AANQYNGKAE LPHSVFHGHK QLATKIRLWH QQGERCLYTG KTISIHDLIN NSNQFEVDHI   600
LPLSITFDDS LANKVLVYAT ANQEKGQRTP YQALDSMDDA WSFRELKAFV RESKTLSNKK   660
KEYLLTEEDI SKFDVRKKFI ERNLVDTRYA SRVVLNALQE HFRAHKIDTK VSVVRGQFTS   720
QLRRHWGIEK TRDTYHHHAV DALIIAASSQ LNLWKKQKNT LVSYSEDQLL DIETGELISD   780
DEYKESVFKA PYQHFVDTLK SKEFEDSILF SYQVDSKFNR KISDATIYAT RQAKVGKDKA   840
DETYVLGKIK DIYTQDGYDA FMKIYKKDKS KFLMYRHDPQ TFEKVIEPIL ENYPNKQINE   900
KGKEVPCNPF LKYKEEHGYI RKYSKKGNGP EIKSLKYYDS KLGNHIDITP KDSNNKVVLQ   960
SVSPWRADVY FNKTTGKYEI LGLKYADLQF EKGTGTYKIS QEKYNDIKKK EGVDSDSEFK   1020
FTLYKNDLLL VKDTETKEQQ LFRFLSRTMP KQKHYVELKP YDKQKFEGGE ALIKVLGNVA   1080
NSGQCKKGLG KSNISIYKVR TDVLGNQHII KNEGDKPKLD F                      1121
```

SEQ ID NO: 70          moltype = DNA   length = 188
FEATURE                Location/Qualifiers
source                 1..188
                       mol_type = other DNA
                       note = Recombinant
                       organism = synthetic construct
SEQUENCE: 70
```
gacattctcc ccaaaatata gttattgtac tctcaagatt tatttttcca aaagggttat   60
tgtactctca agatttattt ttccaaaagg gttacttaaa tcttgcagaa gctacaaaga   120
taaggcttca tgccgaaatc aacaccctgt cattttatgg cagggtgttt tcgttattta   180
attttttt                                                           188
```

SEQ ID NO: 71          moltype = DNA   length = 20
FEATURE                Location/Qualifiers
source                 1..20
                       mol_type = unassigned DNA
                       organism = Zea mays
SEQUENCE: 71
```
gacattctcc ccaaaatata                                                20
```

SEQ ID NO: 72          moltype = DNA   length = 29
FEATURE                Location/Qualifiers
source                 1..29
                       mol_type = genomic DNA
                       organism = Zea mays
SEQUENCE: 72
```
gtttatcttt catgagcttt ttagagaat                                      29
```

SEQ ID NO: 73          moltype = DNA   length = 29
FEATURE                Location/Qualifiers
source                 1..29
                       mol_type = genomic DNA
                       organism = Zea mays
SEQUENCE: 73
```

-continued

```
gtaatactct atggtctgta aggtagaat                                          29

SEQ ID NO: 74           moltype = DNA    length = 28
FEATURE                 Location/Qualifiers
source                  1..28
                        mol_type = genomic DNA
                        organism = Zea mays
SEQUENCE: 74
gagatccaac gtgttgggac tctagaaa                                           28

SEQ ID NO: 75           moltype = DNA    length = 27
FEATURE                 Location/Qualifiers
source                  1..27
                        mol_type = genomic DNA
                        organism = Zea mays
SEQUENCE: 75
gacattctcc ccaaaatata cgagaaa                                            27

SEQ ID NO: 76           moltype = DNA    length = 103
FEATURE                 Location/Qualifiers
source                  1..103
                        mol_type = other DNA
                        note = Recombinant
                        organism = synthetic construct
SEQUENCE: 76
gccggccagc atttgaaaca gttttagagc tagaaatagc aagttaaaat aaggctagtc        60
cgttatcaac ttgaaaaagt ggcaccgagt cggtgctttt ttt                         103

SEQ ID NO: 77           moltype = DNA    length = 103
FEATURE                 Location/Qualifiers
source                  1..103
                        mol_type = other DNA
                        note = Recombinant
                        organism = synthetic construct
SEQUENCE: 77
gcgcaaggga tcagtaattc gttttagagc tagaaatagc aagttaaaat aaggctagtc        60
cgttatcaac ttgaaaaagt ggcaccgagt cggtgctttt ttt                         103

SEQ ID NO: 78           moltype = DNA    length = 103
FEATURE                 Location/Qualifiers
source                  1..103
                        mol_type = other DNA
                        note = Recombinant
                        organism = synthetic construct
SEQUENCE: 78
gttatcaatt tactttcaat gttttagagc tagaaatagc aagttaaaat aaggctagtc        60
cgttatcaac ttgaaaaagt ggcaccgagt cggtgctttt ttt                         103

SEQ ID NO: 79           moltype = RNA    length = 103
FEATURE                 Location/Qualifiers
source                  1..103
                        mol_type = other RNA
                        note = Recombinant
                        organism = synthetic construct
SEQUENCE: 79
gccggccagc atttgaaaca gttttagagc tagaaatagc aagttaaaat aaggctagtc        60
cgttatcaac ttgaaaaagt ggcaccgagt cggtgctttt ttt                         103

SEQ ID NO: 80           moltype = RNA    length = 103
FEATURE                 Location/Qualifiers
source                  1..103
                        mol_type = other RNA
                        note = Recombinant
                        organism = synthetic construct
SEQUENCE: 80
gcgcaaggga tcagtaattc gttttagagc tagaaatagc aagttaaaat aaggctagtc        60
cgttatcaac ttgaaaaagt ggcaccgagt cggtgctttt ttt                         103

SEQ ID NO: 81           moltype = RNA    length = 103
FEATURE                 Location/Qualifiers
source                  1..103
                        mol_type = other RNA
                        note = Recombinant
                        organism = synthetic construct
SEQUENCE: 81
gttatcaatt tactttcaat gttttagagc tagaaatagc aagttaaaat aaggctagtc        60
cgttatcaac ttgaaaaagt ggcaccgagt cggtgctttt ttt                         103

SEQ ID NO: 82           moltype = DNA    length = 103
```

-continued

```
FEATURE             Location/Qualifiers
source              1..103
                    mol_type = other DNA
                    note = Recombinant
                    organism = synthetic construct
SEQUENCE: 82
gtacaaacca actcggcaat gttttagagc tagaaatagc aagttaaaat aaggctagtc   60
cgttatcaac ttgaaaaagt ggcaccgagt cggtgctttt ttt                    103

SEQ ID NO: 83          moltype = DNA   length = 103
FEATURE             Location/Qualifiers
source              1..103
                    mol_type = other DNA
                    note = Recombinant
                    organism = synthetic construct
SEQUENCE: 83
gatatgccaa acggtacttg gttttagagc tagaaatagc aagttaaaat aaggctagtc   60
cgttatcaac ttgaaaaagt ggcaccgagt cggtgctttt ttt                    103

SEQ ID NO: 84          moltype = DNA   length = 103
FEATURE             Location/Qualifiers
source              1..103
                    mol_type = other DNA
                    note = Recombinant
                    organism = synthetic construct
SEQUENCE: 84
ggatctccta tcataacgtt gttttagagc tagaaatagc aagttaaaat aaggctagtc   60
cgttatcaac ttgaaaaagt ggcaccgagt cggtgctttt ttt                    103

SEQ ID NO: 85          moltype = RNA   length = 103
FEATURE             Location/Qualifiers
source              1..103
                    mol_type = other RNA
                    note = Recombinant
                    organism = synthetic construct
SEQUENCE: 85
gtacaaacca actcggcaat gttttagagc tagaaatagc aagttaaaat aaggctagtc   60
cgttatcaac ttgaaaaagt ggcaccgagt cggtgctttt ttt                    103

SEQ ID NO: 86          moltype = RNA   length = 103
FEATURE             Location/Qualifiers
source              1..103
                    mol_type = other RNA
                    note = Recombinant
                    organism = synthetic construct
SEQUENCE: 86
gatatgccaa acggtacttg gttttagagc tagaaatagc aagttaaaat aaggctagtc   60
cgttatcaac ttgaaaaagt ggcaccgagt cggtgctttt ttt                    103

SEQ ID NO: 87          moltype = RNA   length = 103
FEATURE             Location/Qualifiers
source              1..103
                    mol_type = other RNA
                    note = Recombinant
                    organism = synthetic construct
SEQUENCE: 87
ggatctccta tcataacgtt gttttagagc tagaaatagc aagttaaaat aaggctagtc   60
cgttatcaac ttgaaaaagt ggcaccgagt cggtgctttt ttt                    103

SEQ ID NO: 88          moltype = DNA   length = 190
FEATURE             Location/Qualifiers
source              1..190
                    mol_type = other DNA
                    note = Recombinant
                    organism = synthetic construct
SEQUENCE: 88
gtttatcttt catgagcttt ttgttattgt actctcaaga tttattttc caaaagggtt    60
attgtactct caagatttat ttttccaaaa gggttactta atcttgcag aagctacaaa    120
gataaggctt catgccgaaa tcaacaccct gtcattttat ggcagggtgt tttcgttatt    180
taatttttt                                                           190

SEQ ID NO: 89          moltype = DNA   length = 190
FEATURE             Location/Qualifiers
source              1..190
                    mol_type = other DNA
                    note = Recombinant
                    organism = synthetic construct
SEQUENCE: 89
gtaatactct atggtctgta aggttattgt actctcaaga tttattttc caaaagggtt     60
```

-continued

```
attgtactct caagatttat ttttccaaaa gggttactta aatcttgcag aagctacaaa   120
gataaggctt catgccgaaa tcaacaccct gtcattttat ggcagggtgt tttcgttatt   180
taattttttt                                                          190

SEQ ID NO: 90              moltype = DNA   length = 189
FEATURE                    Location/Qualifiers
source                     1..189
                           mol_type = other DNA
                           note = Recombinant
                           organism = synthetic construct
SEQUENCE: 90
gagatccaac gtgttgggac tgttattgta ctctcaagat ttattttttcc aaaagggtta   60
ttgtactctc aagatttatt tttccaaaag ggttacttaa atcttgcaga agctacaaag   120
ataaggcttc atgccgaaat caacaccctg tcattttatg gcagggtgtt ttcgttattt   180
aattttttt                                                           189

SEQ ID NO: 91              moltype = DNA   length = 188
FEATURE                    Location/Qualifiers
source                     1..188
                           mol_type = other DNA
                           note = Recombinant
                           organism = synthetic construct
SEQUENCE: 91
gacattctcc ccaaaatata gttattgtac tctcaagatt tattttttcca aaagggttat   60
tgtactctca agatttattt ttccaaaagg gttacttaaa tcttgcagaa gctacaaaga   120
taaggcttca tgccgaaatc aacaccctgt cattttatgg cagggtgttt tcgttattta   180
attttttt                                                            188

SEQ ID NO: 92              moltype = RNA   length = 190
FEATURE                    Location/Qualifiers
source                     1..190
                           mol_type = other RNA
                           note = Recombinant
                           organism = synthetic construct
SEQUENCE: 92
gtttatcttt catgagcttt ttgttattgt actctcaaga tttatttttc caaaagggtt   60
attgtactct caagatttat ttttccaaaa gggttactta aatcttgcag aagctacaaa   120
gataaggctt catgccgaaa tcaacaccct gtcattttat ggcagggtgt tttcgttatt   180
taattttttt                                                          190

SEQ ID NO: 93              moltype = RNA   length = 190
FEATURE                    Location/Qualifiers
source                     1..190
                           mol_type = other RNA
                           note = Recombinant
                           organism = synthetic construct
SEQUENCE: 93
gtaatactct atggtctgta aggttattgt actctcaaga tttatttttc caaaagggtt   60
attgtactct caagatttat ttttccaaaa gggttactta aatcttgcag aagctacaaa   120
gataaggctt catgccgaaa tcaacaccct gtcattttat ggcagggtgt tttcgttatt   180
taattttttt                                                          190

SEQ ID NO: 94              moltype = RNA   length = 189
FEATURE                    Location/Qualifiers
source                     1..189
                           mol_type = other RNA
                           note = Recombinant
                           organism = synthetic construct
SEQUENCE: 94
gagatccaac gtgttgggac tgttattgta ctctcaagat ttattttttcc aaaagggtta   60
ttgtactctc aagatttatt tttccaaaag ggttacttaa atcttgcaga agctacaaag   120
ataaggcttc atgccgaaat caacaccctg tcattttatg gcagggtgtt ttcgttattt   180
aattttttt                                                           189

SEQ ID NO: 95              moltype = RNA   length = 188
FEATURE                    Location/Qualifiers
source                     1..188
                           mol_type = other RNA
                           note = Recombinant
                           organism = synthetic construct
SEQUENCE: 95
gacattctcc ccaaaatata gttattgtac tctcaagatt tattttttcca aaagggttat   60
tgtactctca agatttattt ttccaaaagg gttacttaaa tcttgcagaa gctacaaaga   120
taaggcttca tgccgaaatc aacaccctgt cattttatgg cagggtgttt tcgttattta   180
attttttt                                                            188

SEQ ID NO: 96              moltype = AA   length = 1368
FEATURE                    Location/Qualifiers
source                     1..1368
```

```
                         mol_type = protein
                         organism = Streptococcus pyogenes
SEQUENCE: 96
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD            1368

SEQ ID NO: 97            moltype = DNA   length = 4107
FEATURE                  Location/Qualifiers
source                   1..4107
                         mol_type = other DNA
                         note = Recombinant
                         organism = synthetic construct
SEQUENCE: 97
atggacaaga agtacagcat tggtctggac atcggaacga actcggtcgg ctgggccgtg  60
attactgacg agtacaaagt tcccagcaaa aaattcaagg ttctaggcaa cacagaccgc  120
cactcgatta aaaagaatct aatcggcgcg cttctgttcg actctggtga aacggccgag  180
gccacacgct taaagaggac cgcgcgccgc cgctacacgg ggcgcaagaa ccgaatctgt  240
tacctccagg agatcttcag taatgagatg gctaaggtcg atgacagctt cttccacagg  300
cttgaagagt cctttctggt cgaagaggac aaaaaacacg aacgtcaccc aatcttcggg  360
aacattgtgg atgaagtcgc ataccacgag aagtatccta cgatctatca cctccgcaag  420
aagctcgtgg atagtaccga caaagccgac ctgcgcttaa tctaccttgc gctcgcgcac  480
atgattaagt tccgaggaca cttccttatt gagggtgatc tgaatccgga caattccgat  540
gtggataaac tgttcattca gttggtccag acatacaatc agctattcga ggagaatccg  600
atcaatgctt ccggcgtgga cgcaaaggct attctgtcag caagactttc aaagagcaga  660
aggttggaga atctgatcgc acaacttccc ggagagaaga agaatgggct cttcggcaac  720
ctcattgcgc tgtctttggg tctgacaccg aactttaagt ctaacttcga cctcgctgag  780
gatgctaaac ttcagcttag caaagacacc tatgatgatg acctggacaa cctcctcgcc  840
cagattggag accagtacgc ggatctattc ttggctgcca gaaacctgtc cgatgcgatt  900
ctgcttagtg acatcctccg agtgaacact gaaattacga agcacccctt gtcggctagt  960
atgattaagc gatacgatga gcaccatcaa gacctgacat tgctaaaggc gctcgtaaga  1020
cagcaacttc ctgagaagta caaggagata ttttttgatc agtctaagaa tggctacgct  1080
ggttacatcg acggtggagc tagtcaggag gaattctata aattcatcaa gcctatcctg  1140
gaaaaaatgg acggtacgga ggaattgctc gttaaactaa atcgagagga tctgctgaga  1200
aagcagcgaa ctttcgacaa tggttctatt ccgcatcaga ttcacctcgg agaacttcac  1260
gccatcctga cgcacaggga ggacttctac cctttcctga aagacaaccg ggaaaaaatc  1320
gagaagatcc tgacattcag gattccttac tatgtaggcc ctttagcgag aggcaacagt  1380
agattcgcct ggatgaccag aaagtctgag gaaacaatca caccgtggaa cttcgaggaa  1440
gtggttgata agggtgctag tgcccaatca ttcattgaga gaatgacgaa cttcgacaag  1500
aatctgccta cgagaaggt tctccctaaa catagcttgc tttacgagta tttcacggtg  1560
tacaatgagc taacgaaggt caagtatgtc acagagggaa tgcggaaacc ggctttcctt  1620
tcgggtgaac agaagaaagc aattgtggat ttgctcttca agacaaaccg aaaggtgaca  1680
gtgaagcagc taaaggagga ctacttcaaa aaaatagagt gcttcgactc agttgagatc  1740
agcggagtgg aggaccggtt taacgcttcc ctcggcactt accacgactt gctcaagatc  1800
atcaaggaca aagacttcct tgataacgag gagaacgaag acatccttga ggacattgtg  1860
ctgacattga cgttgttcga ggatcgggag atgatcgagg aacgcctcaa gacgtacgcc  1920
catctgttcg atgataaggt gatgaagcag ttaaagagga gacgttacac tggctggggc  1980
cgtctctctc gcaaactgat aaacgggata agggataaac aaagcggaaa gacaatcctc  2040
gatttcctta atccgacgg cttcgctaac cggaacttca tgcagctcat ccatgatgac  2100
tcactgacgt tcaaggagga catccagaaa gctcaagtgt ctggccaggg tgacagcttg  2160
cacgagcaca tcgcaaatct agccggttca ccggcgataa agaagggcat tctacaaacg  2220
gtgaaagtgg tggacgagct tgtgaaggtc atgggtcgcc ataagccaga gaacattgtt  2280
atcgaaatgc cgaggagaa ccagacaacg cagaagggac aaaaaaacag tagggagcgg  2340
atgaagcgca tcgaagaagg cattaaggaa cttggaagcc aatcctgaa agacaccacc  2400
gtggagaata cgcagttgca gaacgagaaa ctgtacctct actacttgca gaatggacgt  2460
gatatgtatg tggatcaaga gttggacatc aaccgattgt ctgactatga cgtggatcac  2520
atagtaccac agtccttcct caaggatgat agcatagaca caaggttct tactcgtagc  2580
gacaagaatc gtggcaaatc ggacaatgtt ccatctgagg aagttgtcaa aaagatgaaa  2640
aattattgga ggcaacttct gaacgcgaag ctaattcac aaaggaaatt cgacaatctc  2700
```

-continued

```
actaaggccg agagaggagg gttaagtgag ttagacaagg ctggcttcat caagcggcag   2760
ttggtcgaga ctcgtcagat tactaagcac gtggctcaga tcctggattc gcgcatgaac   2820
accaaatacg acgagaatga caaactcatc cgtgaagtta aggtgattac actgaaatcc   2880
aagctggtct ctgactttag gaaagacttc caattctaca aggtgagaga gattaacaac   2940
taccaccacg cgcatgacgc ctacttgaat gctgtggttg ggactgccct gataaagaaa   3000
tatcctaaac ttgagtctga gttcgtttac ggtgactaca aggtttatga cgttaggaag   3060
atgatcgcca aatccgaaca ggagattggg aaagcaactg ccaaatattt cttttactcc   3120
aacattatga acttttttcaa gacagaaatc acactcgcca atggcgagat cggaagagaa   3180
ccactaatcg aaacaaacgg cgaaactggt gaaatcgttt gggataaggg tagggacttc   3240
gcaactgtta ggaaggtctt gtcgatgcct caagtgaaca tagtcaaaaa aacagaggtc   3300
cagaccggtg ggttctcaaa ggagtctatt ctgccaaagc gtaacagcga caaactcatc   3360
gctcgcaaaa aggactggga tcctaaaaag tacggtggat tcgacagccc gaccgttgct   3420
tattctgttc tcgtagttgc taaagtcgag aagggcaagt ccaaaaaact caaatcggtt   3480
aaggaactgc tcggaatcac gataatggaa cgaagcagtt tcgaaaaaa tccaattgac   3540
ttcctggaag ctaaaggtta caaggaggtc aagaaggatc ttatcatcaa gctacccaag   3600
tacagtctgt tcgaactgga gaacggtcgc aagagaatgc tggcctcggc tggtgaactc   3660
cagaagggca atgagctggc cctgccgtcc aagtacgtga actttctgta cctggcatct   3720
cattacgaga agctcaaggg ctcaccagag gacaaccgag agaagcagtt gttcgttgaa   3780
cagcacaaac actatcttga tgagatcatt gagcaaatta gcgagttcag taagcgagtt   3840
attctggctg atgctaacct ggataaggtg ctctctgcct acaacaagca ccgggataaa   3900
cctattaggg aacaggcgga gaacataatc cacctcttca ctctgacgaa tctcggcgcg   3960
cctgcggcct tcaaatattt tgataccacc atcgacagga agcgctacac aagcactaaa   4020
gaggtgctgg acgccactct cattcaccag tctattaccg ggctctacga gacacggatt   4080
gacctctccc agctaggtgg cgattaa                                       4107

SEQ ID NO: 98              moltype = DNA   length = 469
FEATURE                    Location/Qualifiers
source                     1..469
                           mol_type = other DNA
                           note = Recombinant
                           organism = synthetic construct
SEQUENCE: 98
cgtctttgta tcggaatata aatttatcac tattttatga taaagtaaat ctgtttccct   60
gtagagttaa ttaattaatg taagtataag cgtaatttat agggcactag taggactgtc   120
gactgtgcgc tcggcccgga taatgcgtca aaagcgaaga cgtgcacgtg ggatgggaaa   180
acacgaagcg tggtctgctt tttcgcatga tatctgggcc gcaccaaaga atccagccca   240
cgcggcgtgg cgccgtcgtt acttgcgggg gaaggaaacg agggacgaac cgagatttag   300
caccagaccg gccagcgagc attgcagaca ccggcttata agttcagctg cgactaccac   360
tccgtctctt cggagacatc cgataaaatt ggaacgatac agagaagatt agcatggccc   420
ctgcgcaagg atgacacgca caaatcgaga aatggtccaa attttttg              469

SEQ ID NO: 99              moltype = DNA   length = 268
FEATURE                    Location/Qualifiers
source                     1..268
                           mol_type = other DNA
                           note = Recombinant
                           organism = synthetic construct
SEQUENCE: 99
cctgttccgc tttgctagct tgcgccctga ctgtccagcc cacgcgcttc ggtccgattc   60
tgctaggctg gtgcaagcga gccgagactt ttttttagaa ccaccttgct cagcaaacct   120
taggaacacc ggcttataag tcgaagcgaa gcgctgtgca ctgtctcttc ggagacatcc   180
gataaaattg gaacgataca gagaagatta gcatggcccc tgcgcaagga tgacacgcac   240
aaatcgagaa atggtccaaa ttttttg                                       268

SEQ ID NO: 100             moltype = DNA   length = 426
FEATURE                    Location/Qualifiers
source                     1..426
                           mol_type = other DNA
                           note = Recombinant
                           organism = synthetic construct
SEQUENCE: 100
gccaggattt atacaactat tttcttattt atttctttaa cattttccct tctacgcaca   60
ataggagata atgtcaagcg ttgacggtgc acatatattt gttttttaa aggcgtagtg   120
gcgtgtgtgc aaaaacatcc tcacaggaaa gacacgaaga aacatggtca atgcccatt   180
atataaagca ccgccacaaa gcccaaatac cagttcgttg gagcaagtaa cgcgctaggc   240
aacaggcaaa cagtttgtcc cacctcgtcc agtcacaaag gcaaagcgtg acttataagc   300
cagagcggaa gaaccatacc gtctcttcgg agacatccga taaaattgga acgatacaga   360
gaagattagc atggcccctg cgcaaggatg acacgcacaa atcgagaaat ggtccaaatt   420
tttttg                                                              426

SEQ ID NO: 101             moltype = DNA   length = 469
FEATURE                    Location/Qualifiers
source                     1..469
                           mol_type = other DNA
                           note = Recombinant
                           organism = synthetic construct
SEQUENCE: 101
ggcccagttg taaaagctaa aatgctattc gaatttctac tagcagtaag tcgtgtttag   60
aaattatttt tttatatacc ttttttcctt ctatgtacag taggacacag tgtcagcgcc   120
```

-continued

```
gcgttgacgg agaatatttg caaaaaagta aaagagaaag tcatagcggc gtatgtgcca   180
aaaacttcgt cacagagagg gccataagaa acatggccca cggcccaata cgaagcaccg   240
cgacgaagcc caaacagcag ttaggtggag caaagcgctg ggtaatacgc aaacgttttg   300
tcccaccttg actaatcaca agagtggagc gtaccttata aaccgagccg caagcaccga   360
attgtctctt cggagacatc cgataaaatt ggaacgatac agagaagatt agcatggccc   420
ctgcgcaagg atgacacgca caaatcgaga aatggtccaa attttttttg              469

SEQ ID NO: 102          moltype = DNA   length = 80
FEATURE                 Location/Qualifiers
source                  1..80
                        mol_type = other DNA
                        note = Recombinant
                        organism = synthetic construct
SEQUENCE: 102
acacttaatc ggctctcaag aagtcctcaa gggataacag ggtaatatag cgtaactata   60
acggtcctaa ggtagcgaat                                              80

SEQ ID NO: 103          moltype = DNA   length = 80
FEATURE                 Location/Qualifiers
source                  1..80
                        mol_type = other DNA
                        note = Recombinant
                        organism = synthetic construct
SEQUENCE: 103
acacttaatc ggctctcaag aagtcctcaa gggataacag ggtaatatag cgtaactata   60
acggtcctaa ggtagcgaat                                              80

SEQ ID NO: 104          moltype = DNA   length = 59
FEATURE                 Location/Qualifiers
source                  1..59
                        mol_type = other DNA
                        note = Recombinant
                        organism = synthetic construct
SEQUENCE: 104
acacttaatc ggctctcaag aagtcctcaa gtaactataa cggtcctaag gtagcgaat   59

SEQ ID NO: 105          moltype =    length =
SEQUENCE: 105
000

SEQ ID NO: 106          moltype =    length =
SEQUENCE: 106
000

SEQ ID NO: 107          moltype = DNA   length = 155
FEATURE                 Location/Qualifiers
source                  1..155
                        mol_type = other DNA
                        note = Recombinant
                        organism = synthetic construct
SEQUENCE: 107
gtttatcttt catgagcttt ttgttattgt actctcaaga tttatttttc caaaagggtt   60
acttaaatct tgcagaagct acaaagataa ggcttcatgc cgaaatcaac accctgtcat  120
tttatggcag ggtgttttcg ttatttaatt ttttt                            155

SEQ ID NO: 108          moltype = DNA   length = 155
FEATURE                 Location/Qualifiers
source                  1..155
                        mol_type = other DNA
                        note = Recombinant
                        organism = synthetic construct
SEQUENCE: 108
gtaatactct atggtctgta aggttattgt actctcaaga tttatttttc caaaagggtt   60
acttaaatct tgcagaagct acaaagataa ggcttcatgc cgaaatcaac accctgtcat  120
tttatggcag ggtgttttcg ttatttaatt ttttt                            155

SEQ ID NO: 109          moltype = DNA   length = 154
FEATURE                 Location/Qualifiers
source                  1..154
                        mol_type = other DNA
                        note = Recombinant
                        organism = synthetic construct
SEQUENCE: 109
gagatccaac gtgttgggac tgttattgta ctctcaagat ttatttttcc aaaagggtta   60
cttaaatctt gcagaagcta caaagataag gcttcatgcc gaaatcaaca ccctgtcatt  120
ttatggcagg gtgttttcgt tatttaattt tttt                             154

SEQ ID NO: 110          moltype = DNA   length = 153
FEATURE                 Location/Qualifiers
```

-continued

```
source                    1..153
                          mol_type = other DNA
                          note = Recombinant
                          organism = synthetic construct
SEQUENCE: 110
gacattctcc ccaaaatata gttattgtac tctcaagatt tatttttcca aaagggttac    60
ttaaatcttg cagaagctac aaagataagg cttcatgccg aaatcaacac cctgtcattt   120
tatggcaggg tgttttcgtt atttaatttt ttt                                153

SEQ ID NO: 111             moltype = RNA   length = 155
FEATURE                   Location/Qualifiers
source                    1..155
                          mol_type = other RNA
                          note = Recombinant
                          organism = synthetic construct
SEQUENCE: 111
gtttatcttt catgagcttt ttgttattgt actctcaaga tttatttttc caaaagggtt    60
acttaaatct tgcagaagct acaaagataa ggcttcatgc cgaaatcaac accctgtcat   120
tttatggcag ggtgttttcg ttatttaatt ttttt                              155

SEQ ID NO: 112             moltype = RNA   length = 155
FEATURE                   Location/Qualifiers
source                    1..155
                          mol_type = other RNA
                          note = Recombinant
                          organism = synthetic construct
SEQUENCE: 112
gtaatactct atggtctgta aggttattgt actctcaaga tttatttttc caaaagggtt    60
acttaaatct tgcagaagct acaaagataa ggcttcatgc cgaaatcaac accctgtcat   120
tttatggcag ggtgttttcg ttatttaatt ttttt                              155

SEQ ID NO: 113             moltype = RNA   length = 154
FEATURE                   Location/Qualifiers
source                    1..154
                          mol_type = other RNA
                          note = Recombinant
                          organism = synthetic construct
SEQUENCE: 113
gagatccaac gtgttgggac tgttattgta ctctcaagat ttatttttcc aaaagggtta    60
cttaaatctt gcagaagcta caaagataag gcttcatgcc gaaatcaaca ccctgtcatt   120
ttatggcagg gtgttttcgt atttaatttt tttt                               154

SEQ ID NO: 114             moltype = RNA   length = 153
FEATURE                   Location/Qualifiers
source                    1..153
                          mol_type = other RNA
                          note = Recombinant
                          organism = synthetic construct
SEQUENCE: 114
gacattctcc ccaaaatata gttattgtac tctcaagatt tatttttcca aaagggttac    60
ttaaatcttg cagaagctac aaagataagg cttcatgccg aaatcaacac cctgtcattt   120
tatggcaggg tgttttcgtt atttaatttt ttt                                153

SEQ ID NO: 115             moltype = DNA   length = 90
FEATURE                   Location/Qualifiers
source                    1..90
                          mol_type = other DNA
                          note = Recombinant
                          organism = synthetic construct
SEQUENCE: 115
ttaagggata acaggguaat atagcgtaac tataacggtc ctaaggtagc gaattacgat    60
acaaggctac ctagcttcgc agttacgcta                                     90

SEQ ID NO: 116             moltype = DNA   length = 90
FEATURE                   Location/Qualifiers
source                    1..90
                          mol_type = other DNA
                          note = Recombinant
                          organism = synthetic construct
SEQUENCE: 116
tagcgtaact gcgaagctag gtagccttgt atcgtaattc gctaccttag gaccgttata    60
gttacgctat attaccctgt tatcccttaa                                     90

SEQ ID NO: 117             moltype = DNA   length = 20
FEATURE                   Location/Qualifiers
source                    1..20
                          mol_type = other DNA
                          note = Recombinant
                          organism = synthetic construct
```

```
SEQUENCE: 117
ctatattacc ctgttatccc                                                    20

SEQ ID NO: 118          moltype = AA   length = 1388
FEATURE                 Location/Qualifiers
source                  1..1388
                        mol_type = protein
                        note = Recombinant
                        organism = synthetic construct
SEQUENCE: 118
MGSKKRRIKQ DDKKYSIGLD IGTNSVGWAV ITDEYKVPSK KFKVLGNTDR HSIKKNLIGA  60
LLFDSGETAE ATRLKRTARR RYTRRKNRIC YLQEIFSNEM AKVDDSFFHR LEESFLVEED  120
KKHERHPIFG NIVDEVAYHE KYPTIYHLRK KLVDSTDKAD LRLIYLALAH MIKFRGHFLI  180
EGDLNPDNSD VDKLFIQLVQ TYNQLFEENP INASGVDAKA ILSARLSKSR RLENLIAQLP  240
GEKKNGLFGN LIALSLGLTP NFKSNFDLAE DAKLQLSKDT YDDDLDNLLA QIGDQYADLF  300
LAAKNLSDAI LLSDILRVNT EITKAPLSAS MIKRYDEHHQ DLTLLKALVR QQLPEKYKEI  360
FFDQSKNGYA GYIDGGASQE EFYKFIKPIL EKMDGTEELL VKLNREDLLR KQRTFDNGSI  420
PHQIHLGELH AILRRQEDFY PFLKDNREKI EKILTFRIPY YVGPLARGNS RFAWMTRKSE  480
ETITPWNFEE VVDKGASAQS FIERMTNFDK NLPNEKVLPK HSLLYEYFTV YNELTKVKYV  540
TEGMRKPAFL SGEQKKAIVD LLFKTNRKVT VKQLKEDYFK KIECFDSVEI SGVEDRFNAS  600
LGTYHDLLKI IKDKDFLDNE ENEDILEDIV LTLTLFEDRE MIEERLKTYA HLFDDKVMKQ  660
LKRRRYTGWG RLSRKLINGI RDKQSGKTIL DFLKSDGFAN RNFMQLIHDD SLTFKEDIQK  720
AQVSGQGDSL HEHIANLAGS PAIKKGILQT VKVVDELVKV MGRHKPENIV IEMARENQTT  780
QKGQKNSRER MKRIEEGIKE LGSQILKEHP VENTQLQNEK LYLYYLQNGR DMYVDQELDI  840
NRLSDYDVDH IVPQSFLKDD SIDNKVLTRS DKNRGKSDNV PSEEVVKKMK NYWRQLLNAK  900
LITQRKFDNL TKAERGGLSE LDKAGFIKRQ LVETRQITKH VAQILDSRMN TKYDENDKLI  960
REVKVITLKS KLVSDFRKDF QFYKVREINN YHHAHDAYLN AVVGTALIKK YPKLESEFVY  1020
GDYKVYDVRK MIAKSEQEIG KATAKYFFYS NIMNFFKTEI TLANGEIRKR PLIETNGETG  1080
EIVWDKGRDF ATVRKVLSMP QVNIVKKTEV QTGGFSKESI LPKRNSDKLI ARKKDWDPKK  1140
YGGFDSPTVA YSVLVVAKVE KGKSKKLKSV KELLGITIME RSSFEKNPID FLEAKGYKEV  1200
KKDLIIKLPK YSLFELENGR KRMLASAGEL QKGNELALPS KYVNFLYLAS HYEKLKGSPE  1260
DNEQKQLFVE QHKHYLDEII EQISEFSKRV ILADANLDKV LSAYNKHRDK PIREQAENII  1320
HLFTLTNLGA PAAFKYFDTT IDRKRYTSTK EVLDATLIHQ SITGLYETRI DLSQLGGDGS  1380
KKRRIKQD                                                           1388

SEQ ID NO: 119          moltype = DNA   length = 4542
FEATURE                 Location/Qualifiers
source                  1..4542
                        mol_type = other DNA
                        note = Recombinant
                        organism = synthetic construct
SEQUENCE: 119
atgggatcta agaagagaag aattaaacaa gatgacaaga agtacagcat tggtctggac  60
atcggaacga actcggtcgg ctgggccgtg attactgacg agtacaaagt tcccagcaaa  120
aaattcaagg ttctaggcaa cacagaccgc cactcgatta aaaagaatct aatcggtgcg  180
cttctgttcg actctggtga aacggccgag gccacgcgct aaagaggac cgcgcgccgc   240
cgctacacgc ggcgcaagaa ccgaatctgt tacctccagg aagtttctg cttctacctt   300
tgatatatat ataataatta tcattaatta gtagtaataat aatatttcaa atatttttt   360
caaaataaaa gaatgtagta tatagcaatt gctttttctgt agtttataag tgtgtatatt   420
ttaatttata acttttctaa tatatgacca aaatttgttg atgtgcaggt aagtttctgc   480
ttctacctt gatatatat taataattat cattaattag tagtaatata atatttcaaa   540
tatttttttc aaaataaaag aatgtagtat atagcaattg ctttttctgta gtttataagt   600
gtgtatattt taatttataa cttttctaat atatgaccaa aatttgttga tgtgcaggag   660
atcttcagta atgagatggc taaggtcgat gacagcttct tccacaggct tgaagagtcc   720
tttctggtcg aagaggacaa aaaacacgaa cgtcacccaa tcttcgggaa cattgtggat   780
gaagtcgcat accacgagaa gtatcctacg atctatcacc tccgcaagaa gctcgtggat   840
agtaccgaca aagccgacct gcgcttaatc taccttgcgc tcgcgcacat gattaagttc   900
cgaggacact tccttattga gggtgatctg aatccggaca attccgatgt ggataaactg   960
ttcattcagt tggtccagac atacaatcag ctattcgagg agaatccgat caatgcttcc   1020
ggcgtggacg caaaggctat tctgtcagca agactttcaa agagcagaag gttggagaat   1080
ctgatcgcac aacttcccgg agagaagaag aatgggctct cggcaacct cattgcgctg    1140
tctttgggtc tgacaccgaa ctttaagtct aacttcgacc tcgctgagga tgctaaactt   1200
cagcttagca aagacaccta tgatgatgac ctggacaacc tcctcgccca gattggagac   1260
cagtacgcgg atctattctt ggctgccaag aacctgtccg atgcgattct gcttagtgac   1320
atcctccgag tgaacactga aattacgaaa gcacccttgt cggctagtat gattaagcga   1380
tacgatgagc accatcaaga cctgacattg ctaaaggcgc tcgtaagaca gcaacttcct   1440
gagaagtaca aggagatatt ttttgatcag tctaagaatg ctacgctgg ttacatcgac    1500
ggtggagcta gtcaggagga attctataaa ttcatcaagc ctatcctgga aaaaatggac   1560
ggtacggagg aattgctcgt taaactaaat cgagaggatc tgctcgagaa gcagcgaact   1620
ttcgacaatg gttctattcc gcatcagatt cacctcggag aacttcacgc catcctgaga   1680
cgacaggagg acttctaccc ttttcctgaaa gacaaccggg aaaaatcga gaagatcctg    1740
acattcagga ttccttacta tgtaggccct ttagcgagag caacagtag attcgcctgg     1800
atgaccagaa agtctgagga acaatcaca ccgtggaact cgaggaagt ggttgataag      1860
gctgtagtg cccaatcatt cattgagaga atgacgaact tcgacaagaa tctgcctaac     1920
gagaaggttc tccctaaaca tagcttgctt tacgagtatt tcacggtgta caatgagcta    1980
acgaaggtca agtatgtcac agagggaatg cggaaaccgg ctttcctttc gggtgaacag     2040
aagaaagcaa ttgtggattt gctcttcaag acaaaccgaa aggtgacagt gaagcagcta     2100
aaggaggact acttcaaaaa aatagagtgc ttcgactcag ttgagatcag cggagtggag     2160
gaccggttta acgcttccct cggcacttac cacgacttgc tcaagatcat caaggacaaa     2220
```

```
gacttccttg ataacgagga gaacgaagac atccttgagg acattgtgct gacattgacg    2280
ttgttcgagg atcgggagat gatcgaggaa cgcctcaaga cgtacgccca tctgttcgat    2340
gataaggtga tgaagcagtt aaagaggaga cgttacactg gctggggccg tctctctcgc    2400
aaactgataa acgggataag ggataaacaa agcggaaaga caatcctcga tttccttaaa    2460
tccgacggct tcgctaaccg gaacttcatg cagctcatcc atgatgactc actgacgttc    2520
aaggaggaca tccagaaagc tcaagtgtct ggccagggtg acagcttgca cgagcacatc    2580
gcaaatctag ccggttcacc ggcgataaag aagggcattc tacaaacggt gaaagtggtg    2640
gacgagcttg tgaaggtcat gggtcgccat aagccagaga acattgttat cgaaatggcg    2700
agggagaacc agacaacgca gaagggacaa aaaaacagta gggagcggat gaagcgcatc    2760
gaggaaggca ttaaggaact tggaagccaa atcctgaaag agcacccggt ggagaatacg    2820
cagttgcaga acgagaaact gtacctctac tacttgcaga atggacgtga tatgtatgtg    2880
gatcaagagt tggacatcaa ccgattgtct gactatgacg tggatcacat agtaccacag    2940
tccttcctca aggatgatag catagacaac aaggttctta ctcgtagcga caagaatcgt    3000
ggcaaatcgg acaatgttcc atctgaggaa gttgtcaaaa agatgaaaaa ttattggagg    3060
caacttctga acgcgaagct aattacacaa aggaaattcg acaatctcac taaggccgag    3120
agaggagggt taagtgagtt agacaaggct ggcttcatca agcggcagtt ggtcgagact    3180
cgtcagatta ctaagcacgt ggctcagatc ctggattcgc gcatgaacac caaatacgac    3240
gagaatgaca aactcatccg tgaagttaag gtgattacac tgaaatccaa gctggtctct    3300
gactttagga aagacttcca attctacaag gtgagagaga ttaacaacta ccaccacgcg    3360
catgacgcct acttgaatgc tgtggttggg actgccctga taaagaaata tcctaaactt    3420
gagtctgagt tcgtttacgg tgactacaag gtttatgacg ttaggaagat gatcgccaaa    3480
tccgaacagg agattgggaa agcaactgcc aaatatttct tttactccaa cattatgaac    3540
tttttcaaga cagaaatcac actcgccaat ggcgagattc ggaagagacc actaatcgaa    3600
acaaacggcg aaactggtga aatcgtttgg gataagggta gggacttcgc aactgttagg    3660
aaggtcttgt cgatgcctca agtgaacata gtcaaaaaaa cagaggtcca gaccggtggg    3720
ttctcaaagg agtctattct gccaaagcgt aacagcgaca aactcatcgc tcgcaaaaag    3780
gactgggatc ctaaaaagta cggtggattc gacagcccga ccgttgctta ttctgttctc    3840
gtagttgcta aagtcgagaa gggcaagtcc aaaaaactca aatcggttaa ggaactgctc    3900
ggaatcacga taatggaacg aagcagtttc gaaaaaaatc caattgactt cctggaagct    3960
aaaggttaca aggaggtcaa gaaggatctt atcatcaagc tacccaagta cagtctgttc    4020
gaactggaga acgtcgcaa gagaatgctg gcctcggctg gtgaactcca gaagggcaat    4080
gagctggccc tgccgtccaa gtacgtgaac tttctgtacc tggcatctca ttacgagaag    4140
ctcaagggct caccagagga caacgagcag aagcagttgt tcgttgaaca gcacaaacac    4200
tatcttgatg agatcattga gcaaattagc gagttcagta agcgagttat tctggctgat    4260
gctaacctgg ataaggtgct ctctgcctac aacaagcacc gggataaacc tattagggaa    4320
caggcggaga acataatcca cctcttcact ctgacgaatc tcggcgcgcc tgcggccttc    4380
aaatattttg ataccaccat cgacaggaag cgctacacaa gcactaaaga ggtgctggac    4440
gccactctca ttcaccagtc tattaccggg ctctacgaga cacggattga cctctcccag    4500
ctaggtggcg atggatctaa gaagagaaga attaaacaag at                      4542
```

```
SEQ ID NO: 120              moltype = AA   length = 10
FEATURE                     Location/Qualifiers
source                      1..10
                            mol_type = protein
                            note = Recombinant
                            organism = synthetic construct
SEQUENCE: 120
GSKKRRIKQD                                                          10

SEQ ID NO: 121              moltype = DNA   length = 92
FEATURE                     Location/Qualifiers
source                      1..92
                            mol_type = other DNA
                            note = Recombinant
                            organism = synthetic construct
SEQUENCE: 121
caagggataa cagggtaata tagcgtaact ataacggtcc taaggtagcg aattacgata    60
caaggctacc tagcttcgca gttacgctag ta                                 92

SEQ ID NO: 122              moltype = DNA   length = 92
FEATURE                     Location/Qualifiers
source                      1..92
                            mol_type = other DNA
                            note = Recombinant
                            organism = synthetic construct
SEQUENCE: 122
tactagcgta actgcgaagc taggtagcct tgtatcgtaa ttcgctacct taggaccgtt    60
atagttacgc tatattaccc tgttatccct tg                                 92

SEQ ID NO: 123              moltype = DNA   length = 73
FEATURE                     Location/Qualifiers
source                      1..73
                            mol_type = other DNA
                            note = Recombinant
                            organism = synthetic construct
SEQUENCE: 123
catgccctct taggcagtag ccggccagca tttgaattaa gggataacag ggtaatatag    60
cgtaactata acg                                                      73
```

-continued

```
SEQ ID NO: 124          moltype = DNA   length = 73
FEATURE                 Location/Qualifiers
source                  1..73
                        mol_type = other DNA
                        note = Recombinant
                        organism = synthetic construct
SEQUENCE: 124
catgccctct taggcagtag ccggccagca tttgaattaa gggataacag ggtaatatag   60
cgtaactata acg                                                      73

SEQ ID NO: 125          moltype = DNA   length = 68
FEATURE                 Location/Qualifiers
source                  1..68
                        mol_type = other DNA
                        note = Recombinant
                        organism = synthetic construct
SEQUENCE: 125
catgccctct taggcagtag ccggccagca tttaagggat aacagggtaa tatagcgtaa   60
ctataacg                                                            68

SEQ ID NO: 126          moltype = DNA   length = 73
FEATURE                 Location/Qualifiers
source                  1..73
                        mol_type = other DNA
                        note = Recombinant
                        organism = synthetic construct
SEQUENCE: 126
aaagcaacac ttaatcggct ctcaagaagt cctcaaggga taacagggta atatagcgta   60
actataacgg tcc                                                      73

SEQ ID NO: 127          moltype = DNA   length = 73
FEATURE                 Location/Qualifiers
source                  1..73
                        mol_type = other DNA
                        note = Recombinant
                        organism = synthetic construct
SEQUENCE: 127
aaagcaacac ttaatcggct ctcaagaagt cctcaaggga taacagggta atatagcgta   60
actataacgg tcc                                                      73

SEQ ID NO: 128          moltype = DNA   length = 52
FEATURE                 Location/Qualifiers
source                  1..52
                        mol_type = other DNA
                        note = Recombinant
                        organism = synthetic construct
SEQUENCE: 128
aaagcaacac ttaatcggct ctcaagaagt cctcaagtaa ctataacggt cc           52

SEQ ID NO: 129          moltype = DNA   length = 73
FEATURE                 Location/Qualifiers
source                  1..73
                        mol_type = other DNA
                        note = Recombinant
                        organism = synthetic construct
SEQUENCE: 129
aaagcaacac ttaatcggct ctcaagaagt cctcaaggga taacagggta atatagcgta   60
actataacgg tcc                                                      73

SEQ ID NO: 130          moltype = DNA   length = 71
FEATURE                 Location/Qualifiers
source                  1..71
                        mol_type = other DNA
                        note = Recombinant
                        organism = synthetic construct
SEQUENCE: 130
aaagcaacac ttaatcggct ctcaagaagt cctcaaggga taacagggta atatagcgta   60
actataagtc c                                                        71

SEQ ID NO: 131          moltype = DNA   length = 69
FEATURE                 Location/Qualifiers
source                  1..69
                        mol_type = other DNA
                        note = Recombinant
                        organism = synthetic construct
SEQUENCE: 131
aaagcaacac ttaatcggct ctcaagaagt cctcaagata acagggtaat atagcgtaac   60
tataagtcc                                                           69
```

-continued

```
SEQ ID NO: 132              moltype = DNA   length = 18
FEATURE                     Location/Qualifiers
source                      1..18
                            mol_type = other DNA
                            note = Recombinant
                            organism = synthetic construct
SEQUENCE: 132
gaaacggttc ggcatgca                                                     18

SEQ ID NO: 133              moltype = DNA   length = 15
FEATURE                     Location/Qualifiers
source                      1..15
                            mol_type = other DNA
                            note = Recombinant
                            organism = synthetic construct
SEQUENCE: 133
tgagctggca cgaac                                                        15

SEQ ID NO: 134              moltype = DNA   length = 20
FEATURE                     Location/Qualifiers
source                      1..20
                            mol_type = other DNA
                            note = Recombinant
                            organism = synthetic construct
SEQUENCE: 134
ccctgtcgtc cgtccaagta                                                   20

SEQ ID NO: 135              moltype = AA   length = 1142
FEATURE                     Location/Qualifiers
source                      1..1142
                            mol_type = protein
                            note = Recombinant
                            organism = synthetic construct
SEQUENCE: 135
MGSKKRRIKQ DMSDLVLGLD IGIGSVGVGI LNKVTGEIIH KNSRIFPAAQ AENNLVRRTN  60
RQGRRLARRK KHRRVRLNRL FEESGLITDF TKISINLNPY QLRVKGLTDE LSNEELFIAL  120
KNMVKHRGIS YLDDASDDGN SSVGDYAQIV KENSKQLETK TPGQIQLERY QTYGQLRGDF  180
TVEKDGKKHR LINVFPTSAY RSEALRILQT QQEFNPQITD EFINRYLEIL TGKRKYYHGP  240
GNEKSRTDYG RYRTSGETLD NIFGILIGKC TFYPDEFRAA KASYTAQEFN LLNDLNNLTV  300
PTETKKLSKE QKNQIINYVK NEKAMGPAKL FKYIAKLLSC DVADIKGYRI DKSGKAEIHT  360
FEAYRKMKTL ETLDIEQMDR ETLDKLAYVL TLNTEREGIQ EALEHEFADG SFSQKQVDEL  420
VQFRKANSSI FGKGWHNFSV KLMMELIPEL YETSEEQMTI LTRLGKQKTT SSSNKTKYID  480
EKLLTEEIYN PVVAKSVRQA IKIVNAAIKE YGDFDNIVIE MARETNEDDE KKAIQKIQKA  540
NKDEKDAAML KAANQYNGKA ELPHSVFHGH KQLATKIRLW HQQGERCLYT GKTISIHDLI  600
NNSNQFEVDH ILPLSITFDD SLANKVLVYA TANQEKGQRT PYQALDSMDD AWSFRELKAF  660
VRESKTLSNK KKEYLLTEED ISKFDVRKKF IERNLVDTRY ASRVVLNALQ EHFRAHKIDT  720
KVSVVRGQFT SQLRRHWGIE KTRDTYHHHA VDALIIAASS QLNLWKKQKN TLVSYSEDQL  780
LDIETGELIS DDEYKESVFK APYQHFVDTL KSKEFEDSIL FSYQVDSKFN RKISDATIYA  840
TRQAKVGKDK ADETYVLGKI KDIYTQDGYD AFMKIYKKDK SKFLMYRHDP QTFEKVIEPI  900
LENYPNKQIN EKGKEVPCNP FLKYKEEHGY IRKYSKKGNG PEIKSLKYYD SKLGNHIDIT  960
PKDSNNKVVL QSVSPWRADV YFNKTTGKYE ILGLKYADLQ FEKGTGTYKI SQEKYNDIKK  1020
KEGVDSDSEF KFTLYKNDLL LVKDTETKEQ QLFRFLSRTM PKQKHYVELK PYDKQKFEGG  1080
EALIKVLGNV ANSGQCKKGL GKSNISIYKV RTDVLGNQHI IKNEGDKPKL DFGSKKRRIK  1140
QD                                                                    1142

SEQ ID NO: 136              moltype = DNA   length = 3618
FEATURE                     Location/Qualifiers
source                      1..3618
                            mol_type = other DNA
                            note = Recombinant
                            organism = synthetic construct
SEQUENCE: 136
atgggatcta agaagagaag aattaaacaa gatatgagtg acctggtgct agggttggat  60
ataggcattg gctccgtggg ggttggcatt cttaataagg tgaccggcga aataattcat  120
aaaaactcac gcatctttcc agcagcccag gctgagaaca atctggtccg tagaaccaac  180
cggcagggtc gaaggttagc caggcgcaag aagcacagac gggtccggct caacaggctt  240
ttcgaggagt ctggtttgat caccgatttc actaagattt ctatcaacct gaatccttat  300
cagctgcgcg ttaaaggtct cacagacgaa cttagcaacg aagagttgtt catcgccatg  360
aaaaatatgg tcaagcatcg cggcattagc tacctggacg acgcttcgga tgatggcaac  420
agtagtgtag gtgactacgc tcagatcgtg aaagagaact cgaagcaatt ggagaccaag  480
accccgggcc aaattcaact cgaaaggtaa gtttctgctt ctacctttga tatatata  540
ataattatca ttaattagta gtaatataat atttcaaata ttttttttcaa aataaaagaa  600
tgtagtatat agcaattgct tttctgtagt ttataagtgt gtatatttta atttataact  660
tttctaatat atgaccaaaa tttgttgatg tgcaggtacc agacgtatgg acagttacga  720
ggcgatttta ccgttgaaaa ggatggtaag aagcacaggc tgattaatgt gtttccgacc  780
tcagcttatc gctctgaggc gctgcgtatt ttgcagaccc aacaggaatt taaccccgcaa  840
ataacggacg agttcataaa ccgatactta gagattctta caggtaaacg taaatactat  900
cacggcccag gaaatgaaaa gtccaggaca gattatggtc gatatcgcac ttccggagag  960
actctcgaca atatctttgg cattcttata ggcaaatgta ccttctaccc tgacgaattt  1020
```

```
agagcagcga aggcttcata tacagcacaa gagtttaatc ttctcaacga cctcaacaac   1080
ttgactgtgc ctactgaaac caaaaagctt agcaaggagc aaaaaaatca aatcattaac   1140
tatgttaaga atgagaaagc tatggggccc gcaaaattgt tcaagtacat agctaagtta   1200
cttagctgtg acgttgctga tattaagggt taccgtattg acaagtctgg taaagctgaa   1260
attcacacct ttgaggctta taggaagatg aagacccttg agacacttga cattgagcag   1320
atggataggg agactttgga caaactggca tacgtcttga cattgaacac cgaaagggaa   1380
ggcatccagg aagctctgga acatgaattt gcagatggtt cgttcagcca aaaacaggtt   1440
gacgagctgc tccaatttag aaaggcaaac tcaagcatat tcggtaaagg ttggcacaac   1500
ttcagcgtta agctgatgat ggaactcatt ccagaattat atgaaacctc tgaggaacag   1560
atgacgattc tcacaagatt gggtaagcag aaaacaacca gctctagcaa taagactaaa   1620
tacattgacg aaaagctcct caccgaagag atttataacc cggtcgtggc aaagagtgta   1680
cggcaagcca tcaagatcgt taatgccgct atcaaggagt atggtgattt tgataatatt   1740
gtgattgaaa tggcacgcga gactaacgag gacgacgaga agaaagctat acagaagatt   1800
caaaaggcta ataaggacga gaaggacgcc gcaatgctaa aggcggccaa tcaatataat   1860
gggaaggctg aactacctca tagcgtcttc catggacata agcaattagc aactaaaata   1920
agattatggc accagcaagg cgaacggtgt ctttatacag gtaaaacgat atctattcac   1980
gacctgatta acaactctaa ccagtttgaa gtggatcata tcttaccact aagtatcacc   2040
ttcgacgatt cacttgctaa caaggtgctc gtttacgcca ctgcgaacca agagaaaggg   2100
cagaggactc cataccaggc ccttgacagc atggacgacg cctggagttt tagggaatta   2160
aaagctttcg tacgtgagtc aaagacgctt tcaaataaaa aaaaggagta cttgctcact   2220
gaagaagaca tctcaaaatt cgacgtgcgc aaaaaattca ttgagcggaa cttagtcgac   2280
actcggtacg catcaaagagt agtgttgaac gccctccagg agcactttag ggcacataag   2340
atcgacacca aggtttcagt tgttaggggt cagtttacat cgcagcttag acgccattgg   2400
ggtatagaaa aaacacgtga tacctaccat caccatgcag ttgacgctct catcattgca   2460
gcatcttctc aacttaattt gtggaaaaag caaaagaaca ctctggtctc atatagcgaa   2520
gatcgctgc ttgatattga aaccggcgag ctgatttctg acgacgaata caaagaatct   2580
gtgtttaagg caccatatca acactttgta gacacgctta aatctaaaga gtttgaggat   2640
tcgatccttt tcagttacca agtcgactca aaatttaacc gtaagatctc tgatgcaaca   2700
atttatgcga cgaggcaggc caaggtaggt aaggataagg ctgacgaaac ctacgtgctc   2760
ggaaaaatca aagatattta cactcaagat ggatatgatg cattcatgaa gatatataaa   2820
aaggacaaat ctaaattcct tatgtatcgt catgacccac agacattcga gaaagttatt   2880
gagcctatcc tggagaacta tccgaacaag caaatacatg agaagggcaa agaagttcca   2940
tgtaatccgt tcctaaagta caaggaggaa cacggatata ttagaaaata cagcaaaaag   3000
ggcaacggcc cagaaatcaa aagccttaag tactacgata gtaaactagg aaaccacatc   3060
gacattacac caaaagactc taataataag gtcgtactgc aaagcgtttc cccatggcgc   3120
gccgatgtgt atttttaataa gacaacaggg aagtacgaaa tcttggggtt aaaatatgcg   3180
gatctgcaat tcgaaaaggg aaccggcaca tacaaaattt ctcaagaaaa gtacaacgac   3240
ataaagaaga aggaaggggt cgattctgat tctgaattca agttcacact ctataagaat   3300
gatcttctgc tcgtcaagga cacagagaca aaggagcagc agttgttcag gttcttgtct   3360
agaactatgc caaaacaaaa gcactacgtt gaactgaagc cttacgataa gcaaaaattc   3420
gagggggggcg aggcgcttat aaaggtccta ggaaatgttg caaactctgg gcagtgtaag   3480
aagggcctgg gcaagagcaa cattagcatc tataaggttc gaacggatgt gcttgggaac   3540
cagcatatca tcaaaaacga gggagataaa ccaaagctgg acttcggatc taagaagaga   3600
agaattaaac aagattag                                                 3618
```

SEQ ID NO: 137          moltype = DNA   length = 26
FEATURE                 Location/Qualifiers
source                  1..26
                        mol_type = other DNA
                        note = Recombinant
                        organism = synthetic construct
SEQUENCE: 137
ccttgtatcg taattcgcta ccttag                                        26

SEQ ID NO: 138          moltype = DNA   length = 20
FEATURE                 Location/Qualifiers
source                  1..20
                        mol_type = other DNA
                        note = Recombinant
                        organism = synthetic construct
SEQUENCE: 138
ctatattacc ctgttatccc                                               20

SEQ ID NO: 139          moltype = DNA   length = 20
FEATURE                 Location/Qualifiers
source                  1..20
                        mol_type = other DNA
                        note = Recombinant
                        organism = synthetic construct
SEQUENCE: 139
taatcggctc tcaagaagtc                                               20

SEQ ID NO: 140          moltype = DNA   length = 20
FEATURE                 Location/Qualifiers
source                  1..20
                        mol_type = other DNA
                        note = Recombinant
                        organism = synthetic construct
SEQUENCE: 140

-continued

```
gggactctag aaaaaacttg                                              20

SEQ ID NO: 141          moltype = DNA   length = 21
FEATURE                 Location/Qualifiers
source                  1..21
                        mol_type = other DNA
                        note = Recombinant
                        organism = synthetic construct
SEQUENCE: 141
taaggagatg agtttgagac c                                            21

SEQ ID NO: 142          moltype = DNA   length = 20
FEATURE                 Location/Qualifiers
source                  1..20
                        mol_type = other DNA
                        note = Recombinant
                        organism = synthetic construct
SEQUENCE: 142
aacatttcag taatcacgag                                              20

SEQ ID NO: 143          moltype = DNA   length = 20
FEATURE                 Location/Qualifiers
source                  1..20
                        mol_type = other DNA
                        note = Recombinant
                        organism = synthetic construct
SEQUENCE: 143
taatatgatg gcatgccctc                                              20

SEQ ID NO: 144          moltype = DNA   length = 68
FEATURE                 Location/Qualifiers
source                  1..68
                        mol_type = other DNA
                        note = Recombinant
                        organism = synthetic construct
SEQUENCE: 144
ctatctagtg aagatgtaat actctatggt ctgtttaagg gataacaggg taatatagcg  60
taactata                                                           68

SEQ ID NO: 145          moltype = DNA   length = 55
FEATURE                 Location/Qualifiers
source                  1..55
                        mol_type = other DNA
                        note = Recombinant
                        organism = synthetic construct
SEQUENCE: 145
ctatctagtg aagatgtaat actctatggt ctgtgggtaa tatagcgtaa ctata       55

SEQ ID NO: 146          moltype = DNA   length = 397
FEATURE                 Location/Qualifiers
source                  1..397
                        mol_type = genomic DNA
                        organism = Solanum lycopersicum
SEQUENCE: 146
aataaatata ttatctatca ttagaacttg aattataagt gaataataga ttattttttg  60
taatatgaat taaaagtgta ttaaacatgt attaacggtg atcaattggt taaaaaaaag  120
tttattatta aaatgataaa tcttttaat ttatagtata tttatgtaag ttttcacgtt  180
gagtaaatag cgaagaagtt gggcccaacc aagtaaaata agaaggccgg gccattacaa  240
ttaagtcgtc acacaactgg gcttcattga aaaaagcgca aaaccgattc caggcccgtg  300
ttagcatgaa gactcaactc aaccagagat ttctccctca tcgcttacag aaaaaagcta  360
tatgctgttt atattgcgaa atctaacagt gtagttt                          397

SEQ ID NO: 147          moltype = DNA   length = 397
FEATURE                 Location/Qualifiers
source                  1..397
                        mol_type = genomic DNA
                        organism = Solanum lycopersicum
SEQUENCE: 147
tacttatgag aagaagtaac tgatttaaaa ttttcactaa tagggttcga aaaatgaaaa  60
tgtaatacgt ggaacttgaa tgtaaaacct caaggaattc ttgtgtttaa gaaattcaaa  120
atctctctaa atgtatacaa aagatgattt cttttacct tatatatagt aaaataaaat  180
tgtcggataa attcgagtga acaccctagc accccctaaa tcctcccccg tagtcggccc  240
attacagtta aagtccaggt acaacaaaat gggcttcgat taagatggaa taaaaggagt  300
ccaggcccat gagcccaaca aacaagctat ttctccctca tcggcgcaca aagaagcttt  360
attctcttat tatagctgaa tattagcatg tgtgttt                          397

SEQ ID NO: 148          moltype = DNA   length = 397
FEATURE                 Location/Qualifiers
source                  1..397
```

```
                         mol_type = genomic DNA
                         organism = Solanum lycopersicum
SEQUENCE: 148
ttctatttgt gctacatata ttagacaagg aaaataacat atgttatttt gaaatcacgt    60
atatttacta taaattacaa tgattaacaa cttaaaaat ttaaatgaaa atcatattaa    120
tgactctcta aattttatct gtgtcacata aatgaaaaac aaaaaaataac aaatattgta   180
ttcgcacggg cgcatgtgtc tagttagtta taaacgaaga aataagggggc tgatttcgaa   240
ataaacgttc ttagaattgg aagaaatgtt cagtttctaa acttgtagga ctaaagcaat   300
aactttattt taatttattt tcttttatgt ttctcccaca tcgatcatac atataactat   360
acagcagtat aagaactcta gcgaagcaat aatgctc                            397

SEQ ID NO: 149        moltype = DNA   length = 261
FEATURE               Location/Qualifiers
source                1..261
                      mol_type = genomic DNA
                      organism = Solanum lycopersicum
SEQUENCE: 149
ataaatcttt ttaatttata gtatatttat gtaagttttc acgttgagta aatagcgaag    60
aagttgggcc caaccaagta aaataagaag gccgggccat tacaattaag tcgtcacaca   120
actgggcttc attgaaaaaa gcgcaaaacc gattccaggc ccgtgttagc atgaagactc    180
aactcaacca gagatttctc cctcatcgct tacagaaaaa agctatatgc tgtttatatt    240
gcgaatctaa cagtgtagtt t                                             261

SEQ ID NO: 150        moltype = DNA   length = 103
FEATURE               Location/Qualifiers
source                1..103
                      mol_type = unassigned DNA
                      organism = Solanum lycopersicum
SEQUENCE: 150
ggatctttcc aagcttgagg gttttagagc tagaaatagc aagttaaaat aaggctagtc    60
cgttatcaac ttgaaaaagt ggcaccgagt cggtgctttt ttt                     103

SEQ ID NO: 151        moltype = DNA   length = 119
FEATURE               Location/Qualifiers
source                1..119
                      mol_type = other DNA
                      organism = Solanum lycopersicum
SEQUENCE: 151
aagctaatca agctgctaat actatttcaa aacttaggca ttctaatcct cctcaagctt    60
ggaaagatcc tttgaagaat tgtgcctttt cgtataaggt aatgtttatt cgttcgtcg    119

SEQ ID NO: 152        moltype = DNA   length = 120
FEATURE               Location/Qualifiers
source                1..120
                      mol_type = other DNA
                      note = Recombinant
                      organism = synthetic construct
SEQUENCE: 152
aagctaatca agctgctaat actatttcaa aacttaggca ttctaatcct cctacaagct    60
tggaaagatc ctttgaagaa ttgtgccttt cgtataaggt aatgtttat tcgttcgtcg    120

SEQ ID NO: 153        moltype = DNA   length = 120
FEATURE               Location/Qualifiers
source                1..120
                      mol_type = other DNA
                      note = Recombinant
                      organism = synthetic construct
SEQUENCE: 153
aagctaatca agctgctaat actatttcaa aacttaggca ttctaatcct cctgcaagct    60
tggaaagatc ctttgaagaa ttgtgccttt cgtataaggt aatgtttat tcgttcgtcg    120

SEQ ID NO: 154        moltype = DNA   length = 117
FEATURE               Location/Qualifiers
source                1..117
                      mol_type = other DNA
                      note = Recombinant
                      organism = synthetic construct
SEQUENCE: 154
aagctaatca agctgctaat actatttcaa aacttaggca ttctaatcct cctagcttgg    60
aaagatcctt tgaagaattg tgccttttcg tataaggtaa tgtttattcg ttcgtcg     117

SEQ ID NO: 155        moltype = DNA   length = 116
FEATURE               Location/Qualifiers
source                1..116
                      mol_type = other DNA
                      note = Recombinant
                      organism = synthetic construct
SEQUENCE: 155
aagctaatca agctgctaat actatttcaa aacttaggca ttctaatcct cctgcttgga    60
```

-continued

```
aagatccttt gaagaattgt gccttttcgt ataaggtaat gtttattcgt tcgtcg         116

SEQ ID NO: 156          moltype = DNA   length = 114
FEATURE                 Location/Qualifiers
source                  1..114
                        mol_type = other DNA
                        note = Recombinant
                        organism = synthetic construct
SEQUENCE: 156
aagctaatca agctgctaat actatttcaa aacttaggca ttctaatcct cctttggaaa     60
gatcctttga agaattgtgc cttttcgtat aaggtaatgt ttattcgttc gtcg           114

SEQ ID NO: 157          moltype = DNA   length = 20
FEATURE                 Location/Qualifiers
source                  1..20
                        mol_type = other DNA
                        note = Recombinant
                        organism = synthetic construct
SEQUENCE: 157
tagagacaac atgcaagaac                                                 20

SEQ ID NO: 158          moltype = DNA   length = 20
FEATURE                 Location/Qualifiers
source                  1..20
                        mol_type = other DNA
                        note = Recombinant
                        organism = synthetic construct
SEQUENCE: 158
taagcaacca gtaagatagg                                                 20

SEQ ID NO: 159          moltype = DNA   length = 380
FEATURE                 Location/Qualifiers
source                  1..380
                        mol_type = other DNA
                        note = Recombinant
                        organism = synthetic construct
SEQUENCE: 159
tagagacaac atgcaagaac acaccaaatt ataatttgtg tgtgaaaact ttgtctttag     60
acaaaagaag tgaaaaagca ggagatatta caacattagc attaattatg gttgatgcta     120
ttaaatctaa agctaatcaa gctgctaata ctatttcaaa acttaggcat tctaatcctc     180
ctcaagcttg gaaagatcct ttgaagaatt gtgccttttc gtataaggta atgtttattc     240
gttcgtcgtt tcaatttgtt tgtcctaaca aaactcgact atgatgaatt aggattttat     300
gtttattttt tctgtctcaa tttgcttgtc ttacttcttt ttttggctaa aagtttcgac     360
cctatcttac tggttgctta                                                 380

SEQ ID NO: 160          moltype = DNA   length = 246
FEATURE                 Location/Qualifiers
source                  1..246
                        mol_type = genomic DNA
                        organism = Glycine max
SEQUENCE: 160
ggaaacttct gtttgtcccc atactccaaa aacaaaacca tttttttttt atcttcgttt     60
ttgtttgctt tgactgtgag ttgaggccca actttctgct tctgtccgac tctatttgat     120
gaattttgtt tgcctcctgt gatgtgaagg atgtatcatt gaaagggaac gtgtctcaat     180
gatcccacat cggccaaata tgctcattac attgcgttta tatagtccca ggaaaacata     240
tggatt                                                                246

SEQ ID NO: 161          moltype = DNA   length = 493
FEATURE                 Location/Qualifiers
source                  1..493
                        mol_type = genomic DNA
                        organism = Glycine max
SEQUENCE: 161
tctacaaaac attataaaaa gtaagatata acaacttttt ttttaaaaaa atcaatagga     60
aatattatcg gttcagttaa tttacagaga gatatttatt tcatatgtgc cagaagtatt     120
tcagttcctt atgaaaaatc agaaaaatgt atggaataaa atataataat cgatactaat     180
aatagaacaa aataaatggt aaaatgtcaa atcaaaacta ggctgcagta tgcagagcag     240
agtcatgatg atactactta ctacaccgat tcttgtgtgc agaaaaatat gttaaaataa     300
ttgaatcttt ctctagccaa atttgacaac aatgtacacc gttcatattg agagacgatg     360
cttcttgttt gctttcggtg gaagctgcat atactcaaca ttactccttc agcgagtttt     420
ccaactgagt cccacattgc ccagacctaa cacggtattc ttgtttataa tgaaatgtgc     480
caccacatgg att                                                        493

SEQ ID NO: 162          moltype = DNA   length = 559
FEATURE                 Location/Qualifiers
source                  1..559
                        mol_type = genomic DNA
                        organism = Glycine max
SEQUENCE: 162
```

```
aggtggagtt gttccagatt tagttttcga cttagatgat gcatggaact ggctagtgac   60
gtggatggtg gtaggttact ttcaggtcat gattttttgt ttctaaatga tactcacact  120
cccttccagt tttttttttt taaactcagc tcccttgctt cctccaccgg ttatcataat  180
actgaaccaa atcaaacatt acagtcaagg tactatgaat atgaaacctg aaatcctatg  240
aatgtcataa atttatttta aataataaat ttatttagaa taatattttt ttgggtaaga  300
gttataaaat aaaatacaaa aaaaaaacct aatatcaatt tttcactgac tccgtttata  360
ttgagacttg agaaagatgg ttcccgtttg ctcccggtgg aggctccgag gctgtgtata  420
tactcgacat tactttagct tgttttgttg tttctttccc tttcccacaa gactcaggtc  480
tcgttcgcaa acgagtccca caccgtctaa acttaccaca atattagcgt ttataattag  540
atgcactgca tcacttatt                                                559
```

```
SEQ ID NO: 163         moltype = DNA   length = 596
FEATURE                Location/Qualifiers
source                 1..596
                       mol_type = genomic DNA
                       organism = Glycine max
SEQUENCE: 163
aaattacacg gtagtacatc ctattataga tcgatgaatt cttaactact cgtgtccctt   60
aggccaggcc tgtttttcttg cacaatttct gaaatgtata cggtttccac ttcaacctttt  120
ttaaccgcac aaagtttttaa ccagatttat ataatttatt tttgaatccc caatacatat  180
cattataaca tatcaattat caaatatttc aataacctca tgatatggca atgaatacat  240
cttcttctca atgaacagag atttctgaaa aagattagga aagtgaaagc atactcgttt  300
gcaatgtaaa actgatactt ccccaaaatc atcatattcc aaatatgccc tggtgttact  360
gaccaaaacc agaaaaaaga aacggaagac atatacgtct aaacggagaa atttcaaaaa  420
acaaaaattg gatcatttct cgatttgtgg gtgtcatctt gtgcagggca tgctaatctt  480
ctctttaccc tttcccacaa gactcagcgc atgttgtctc gtctcatcca agtcccacac  540
cgcctaaact taacacaata ttagtattta taatgacata caacattcaa gatgtt       596
```

```
SEQ ID NO: 164         moltype = DNA   length = 737
FEATURE                Location/Qualifiers
source                 1..737
                       mol_type = genomic DNA
                       organism = Glycine max
SEQUENCE: 164
aattatttaa tcctaaaaat caatcttaca aggaaccact ataaaactag ttgaacccat   60
cgaaaactaa ctacagttga caaaatctat ttggttggtt gatttttttt aattaaaaac  120
atccaatctt aatgatataa ttatagctta atattataag atttttataa aaattatatt  180
tattttgttt ctaattatgc taagagatat tattatttgt tatttaactt aaatattatc  240
acaaacttga ttgaaactta tgtttaattt aaaatattat atgtcatgag ttatgactcc  300
aataatcaca attataaagt gaagtttaat ttttagtatt acaaatattt ttttgttgtt  360
taattttaat tacttaatgt attatgttaa taattaaaaa tacaaattat ttattattaa  420
tgcaatcaca gtttgtggat ttgacaaaag aaataggggga tctaaaattg tagataagc  480
aaagttaaaa cttgaattga ctattttttg ctctttactc tgcaccaact ttactattcc  540
ttcttttagt gtgagcttca tgcatccttgt tcaccgcaat tccgctcggt gaaagttgca  600
caattcactc acaatctgtt tctggtctgt taggtttgtt acttggagtg acacgatgac  660
gcaacagtac aagtcccaca tcgtttgagt atacagtttt caagcagttt atattcccat  720
agccttagca gagagctt                                                737
```

```
SEQ ID NO: 165         moltype = DNA   length = 484
FEATURE                Location/Qualifiers
source                 1..484
                       mol_type = genomic DNA
                       organism = Glycine max
SEQUENCE: 165
ttttttaata aaaaaaattc aatgggagat actatggatt caattacctt actgatttta   60
tttcatatgt gccagaagta tttcagttta ttttgaaaaa tcagaaaaaa aatgtctgga  120
ataaaatata ataagcgata ctaataaata attgaacaag ataaatggta aaatgtcaaa  180
tcaaaactag gctacagagt gcagagcaga gtcatgatga atgacagcta gttctactta  240
ctacaccgat tcttgtgtac ataaaaaatat tttaaaataa tcttttagccag           300
ctttgacaac aatgtacacc gttcgtactt cttactggta ggcaatgctt cttgtttgct  360
ttcggtggaa ggtgtatata ctcaacatta cttcttttttc agcgtgtttt cttacgggag  420
tcccacaccg cccaaaacta atacagtatt cttgtttata aagaagtgca ccacttcaat  480
tgtt                                                                484
```

```
SEQ ID NO: 166         moltype = DNA   length = 427
FEATURE                Location/Qualifiers
source                 1..427
                       mol_type = genomic DNA
                       organism = Glycine max
SEQUENCE: 166
cgataaaaat gttttaaacg atatatatta taaaaaaaaa cgtttcaaaa ataaatacaa   60
aaatgttttt aaatatatat aatttaactc attaaagaaa ataaaaatgc aagtgcggtg  120
acaagacaag ctaaaagttg caaaagaaat ggcagggcta taaggctcac ctactcctgg  180
atttaccaaa ttttggttcg tccctatact cgaaaaataa aacaaaataa atttcagtat  240
cttcgttttt gtatgctttg actgtgaggc gaggccaact ttcttcttct gtctgagatg  300
aattttgttt gcctcctgtg aaggatgtat cattcaaagt gaatgttttg caactgccag  360
tagtcccaca tcgaccaaat attcttatta cagtgtgttt atatagcacc tggagaagga  420
atgggtt                                                             427
```

-continued

```
SEQ ID NO: 167          moltype = DNA  length = 400
FEATURE                 Location/Qualifiers
source                  1..400
                        mol_type = genomic DNA
                        organism = Glycine max
SEQUENCE: 167
gaaaagcatt cagaatattt gagcctctaa aaacttttct tctttttctt tgaggagtgt   60
aatgtggatc ccaagtaacc aagaaaagca atccgaaaat tcaatttcaa gcaaactgtt  120
ctcaagtttt cgagggatat agtaatagca gagcaaaaaa acactggaaa aagcttgtac  180
ctattgaaac aaaggataat taaaaatcca aaatgtatca aaagcctaga caattttaat  240
cactattgcc tcttaacaat ttgcgcacta tgacaatcat gctctcataa tgtaacaaaa  300
gacacattag gatactagta ctgacactga caccaaggtt acatagtccc acatcgaagg  360
agtttaggta gagacatcgg tttatataac taagcgtgac                         400

SEQ ID NO: 168          moltype = DNA  length = 434
FEATURE                 Location/Qualifiers
source                  1..434
                        mol_type = genomic DNA
                        organism = Glycine max
SEQUENCE: 168
ttgccaacaa gatataacaa gaagcctaat atttcaaaag gccttttggt ccttaaaaac   60
taaggaatgc atctccagaa agaagtacaa tcataatagt tgctaagaat gcagcaaaat  120
tgataaatta atcgagaaac cacaccacaa atcacacatg gccattagag aaaaagaaag  180
gtttcaggaa aataaaagaa aagaaaaagt caattactgc ttagctacct ctctatattc  240
ccatgtgccc cttgcttgaa attggaacca ctaccaggca acagagttgt tccctttcaa  300
gcaataagag ttagaaatat ttttatatca accgaagtgg caaaaagtca gaaaccatga  360
catacgttta ctttgttagt cccacattgg atagtttttag taaaacacag gtcattatat  420
agctaaacgc taac                                                    434

SEQ ID NO: 169          moltype = DNA  length = 436
FEATURE                 Location/Qualifiers
source                  1..436
                        mol_type = genomic DNA
                        organism = Glycine max
SEQUENCE: 169
aatatttcaa agcacactta ggtccttaaa aatgcaatgt tacaattcca aaaggaagta   60
taatcatagt agaagccaag aatgcagaaa aattaacaaa gtgatcgagg aatcattgcc  120
acaaatcact catggctatt agagaaaaaa aaaagtttca agaaaagaaa agaaaaagtt  180
aattactact tagctacttc tttgtaaact caggtgcccc ttgcatgcaa ttgataccac  240
accaggcacc agagctgttc ctttttcatgc aataagagta agagacattt ttttatgaac  300
tcagatggcg aagtgtttga aaccatgaca ggcgttactc tggtagtccg acatagagag  360
ttttaataaa acacaaatgt agtcccacat tgaacagttt taataaaaca cagtctttat  420
ataactaaac gctgag                                                  436

SEQ ID NO: 170          moltype = DNA  length = 428
FEATURE                 Location/Qualifiers
source                  1..428
                        mol_type = genomic DNA
                        organism = Glycine max
SEQUENCE: 170
cttaggtggc tcttgcttga aatgggtact gtactggaat tagagtttat cttttcatgc   60
acaaagtttt ggccctcgtt ctactacagt atacagcagt atggatatgg ttcacattaa  120
ttctccgaaa gtaatctatc cctgcgggct agcctgagaa agggtgttta taatcttgta  180
gtgatagaat caagcatcat aagagctttc aaagcctcta atgagtattt cttttttctag  240
aaaagatgaa tatttgggat caatgctgct gctgttatga aggaaacacc gtggcaggaa  300
gattgtattt gtatccttgt gcaatactca gaccaattct gttagaaaaa tgacacaaag  360
gccgtgatgc tagtcccaca tcgagtgttt ttaacaaaac aggcgcatat atattactgg  420
acgctgag                                                           428

SEQ ID NO: 171          moltype = DNA  length = 432
FEATURE                 Location/Qualifiers
source                  1..432
                        mol_type = genomic DNA
                        organism = Glycine max
SEQUENCE: 171
catgctgtgt agtgaaagac atagacagtc aaaaggcctg agaagggtat atattgtaaa   60
gatgatgatt tttcttacag atggtttata ccgctttatg cttcttcagc gtagaactta  120
tcaaagagaa cactatccat agctgaatca agttggttca ggcttttgtt ataatcacag  180
tctaggagtc taggacactt ttattttgca ttcattttcg gattgttgac gcctttgtat  240
aaattttaca atctctcagt aaaagatcga acacttctga taatgtttta ggaatttaac  300
tctcattcta taagctttga ccaagtctga accctagaca attgcctctt taacaacttg  360
acacagaaat aataatagtc ccacatcgag agcgtttagc tacaaacatg tgtttatata  420
attaagcata ac                                                      432

SEQ ID NO: 172          moltype = DNA  length = 434
FEATURE                 Location/Qualifiers
source                  1..434
                        mol_type = genomic DNA
                        organism = Glycine max
```

```
SEQUENCE: 172
gtttatgttt ggcattcttt aatctttagt atcagaataa ttgatcacat tttgaaatgc    60
caatagaaag acactcctta aacaaaagct atcgtgtatg aaaagctgca gagaaaaatc   120
aaatgtacaa gattttaaat aaagacatgc taaactgtcc aatatgtaac tagttgaaca   180
ggctgcattt ctctgtgttt ttgcttccgc agggaggaat acaaacatct aacaacttat   240
accaaagcat atagtacaaa ttacaatctt ttgtttttccc caaattaatc caatttatct   300
ttcatttcat ccagaaagaa gctctttgag attgttagtg ttaaactgca aactttcttc   360
ttacttatgt cccacatagg aaagaaaagg agacaacaaa atctttatat gccctctgac   420
aaagttgtct gaat                                                     434

SEQ ID NO: 173         moltype = DNA   length = 417
FEATURE                Location/Qualifiers
source                 1..417
                       mol_type = genomic DNA
                       organism = Glycine max
SEQUENCE: 173
catttaaaat aatgaatgac taatccatta actaataact atagttgatt acttttttagt   60
taattaggat gttaggaata cctgaatcca ccgacttaac tattatcata atcagttcat   120
tcaatttgaa tttgtaggat gcacctctat gttttcctct tcactttcta gtggacacaa   180
gaccctgtgt cacacacagt taatagaaga agatcattta catgtaagcg gaacccattg   240
cattctacag caatattttg gggttggtgt tataatacaa gacggataaa atagctagag   300
agaatccaat caaatcccac attccaaatt agactatcca ttgtaggcca agtcccacat   360
tggttagaat attaggcaac gaaaccttta taaatcttct gacaagcact tcagcat      417

SEQ ID NO: 174         moltype = DNA   length = 439
FEATURE                Location/Qualifiers
source                 1..439
                       mol_type = genomic DNA
                       organism = Glycine max
SEQUENCE: 174
ggcatgtgac ttttttattta aattattctc agaaatatta aaatataatc aaatatattt   60
ttttataaga tactggaaat aacattttta ggaatgtaac gaaagcccca ttacaaacac   120
ttgaactcag ggatcgatcc aacttaatta ttatctgcta cttcaaattc aaatttatag   180
gccctacctt tatgttttgc tctgcacttt cttaaatgga acaagtaac acaatagagt   240
aagatcattt acttgtaagc ggaaactgtt gcatcaactg caatattttc gggttagttt   300
tataatataa caatgaagag aattgccgag aagatcatat caagtcccat attccattta   360
ttggcctttta caagtcccac atcggtccaa atattagaca aagaaacatt tatatatcgt   420
ctgacaaacc tgtaagatt                                                439

SEQ ID NO: 175         moltype = DNA   length = 169
FEATURE                Location/Qualifiers
source                 1..169
                       mol_type = genomic DNA
                       organism = Zea mays
SEQUENCE: 175
ggattgtgcg ggcaaagtat tttcgtcgaa agagaagcaa cgaaaaagcc cactgctccg    60
agacaccgtt ccacgaaacc tgtccgcact catctcatcg tttagcacca cctcgccagt   120
ccgcagtcct ctatacctgc ttaaatattc gtccagaccc cccaccctc                169

SEQ ID NO: 176         moltype = DNA   length = 200
FEATURE                Location/Qualifiers
source                 1..200
                       mol_type = genomic DNA
                       organism = Zea mays
SEQUENCE: 176
ctgttttcat ccggcctgtg atggaaattg tgctgcaaag tgcgcagggc cgttggcccg    60
acgacaagta ttttttcgtcg agagaagcaa cgaaagccca ctcctccaag ccaccccttcg   120
ctcaagtcat atttagcacc acctcggcag tcgacactgc agcacaccaa cttaaatatt   180
catcccgatc tccctcactc                                               200

SEQ ID NO: 177         moltype = DNA   length = 200
FEATURE                Location/Qualifiers
source                 1..200
                       mol_type = genomic DNA
                       organism = Zea mays
SEQUENCE: 177
aaactgtgct tgtgcagggc cgttgggcca cgtgcccacg tcaaagtatt ctagtcgaaa    60
gagaagcaac gaaagcccac tactactcct aggcaccgtt gccacgagac ctgtccgcac   120
tcatctcatc gtttagcacc aatgcgccag tccgcagtcc gctgtaccag cttaaatatt   180
cgtccctacc gcgctccatc                                               200

SEQ ID NO: 178         moltype = DNA   length = 200
FEATURE                Location/Qualifiers
source                 1..200
                       mol_type = genomic DNA
                       organism = Zea mays
SEQUENCE: 178
catatagggga tcagctaagc ttatcatacc ttccttttttt tttctcattc agccactact    60
gcagcctaca aaggatatca taatgggccg acccagtcac ccaggacgca atatgttggt   120
```

-continued

```
caatcccacc agttagtacc acctcggtag ctcagatgag tagaagatac cttaaaagtt   180
cagctcaggc aacttgcagc                                               200

SEQ ID NO: 179        moltype = DNA   length = 200
FEATURE               Location/Qualifiers
source                1..200
                      mol_type = genomic DNA
                      organism = Zea mays
SEQUENCE: 179
catggtccat aggtatcaag atccagcatt gcacttgggc caaagattga gctctgcgaa   60
gtgtcaacta caatcatcta gatgggctcg acctgaaagg ccacacgatt tgccagaact   120
cccaccaatt aattagtacc acctcggttg ctcgatttag tagaagccag cttaaaagtt   180
cagctctggg gtccggtagc                                               200

SEQ ID NO: 180        moltype = DNA   length = 181
FEATURE               Location/Qualifiers
source                1..181
                      mol_type = genomic DNA
                      organism = Zea mays
SEQUENCE: 180
catccaggtg aggcatcaag ctactactgc ctcgattggc tggacccgaa gcccacatgt   60
aggataccag aatgggccga cccaggacgc agtatgttgg ccagtcccac cggttagtgc   120
catctcggtt gctcacatgc gtagaagcca gcttaaaaat ttagctttgg taactcacag   180
c                                                                   181

SEQ ID NO: 181        moltype = DNA   length = 200
FEATURE               Location/Qualifiers
source                1..200
                      mol_type = genomic DNA
                      organism = Zea mays
SEQUENCE: 181
catcaataag ataaagctgg tgcaggctct cgacctgaag cccacacact ggagagcaac   60
gatataccag aatggagcgg cccagtacac gatctgctgg gattgctggc cagtggccag   120
tcccgcagcc gattagcacc acctcggtgg cacagacgaa cgaacgctaa tttaaaagct   180
tagctctgga gcttggcacc                                               200

SEQ ID NO: 182        moltype = DNA   length = 200
FEATURE               Location/Qualifiers
source                1..200
                      mol_type = genomic DNA
                      organism = Zea mays
SEQUENCE: 182
gcgaggcatc aacaagataa agctggtgca ggctctcgac ctgaagccca cacacaggag   60
agcaacaata taccaggaat ggagcggccc agtacgcgat ctgctgggat tgctggctag   120
tcccgcaccc gattagcacc acctcgcttg ctcatacgag cgaacgcaaa tttaaaaggt   180
tagctctgga gtttggcagc                                               200

SEQ ID NO: 183        moltype = DNA   length = 200
FEATURE               Location/Qualifiers
source                1..200
                      mol_type = genomic DNA
                      organism = Zea mays
SEQUENCE: 183
cctaactaat aagtatcgga ggcaacaacg cccgctgggc tgcggcccat taacatagca   60
ctagacggac accgccgcag tcagcgttca gccggatgca gtgcgatcgg cttcatccgt   120
ttagtcccac ctcgcccagc caaagcagcg gggaggcccg gactcgctac aaaaggagac   180
ggaggttggc tgtttagagc                                               200

SEQ ID NO: 184        moltype = DNA   length = 200
FEATURE               Location/Qualifiers
source                1..200
                      mol_type = genomic DNA
                      organism = Zea mays
SEQUENCE: 184
gccagctgcg gtggaaacga ctgcggaccg ggctagcatc gacgtattgc cgtattagta   60
gcccagaaag cccacgcaac cagatagagg tctgaatgcc tgtactttgt ggtgcttcag   120
tttagtccca cctcggtggc tttcagcggg agagagcaga gaaggcttat aaaagcagac   180
ctcagtcaac ataacaattc                                               200

SEQ ID NO: 185        moltype = DNA   length = 200
FEATURE               Location/Qualifiers
source                1..200
                      mol_type = genomic DNA
                      organism = Zea mays
SEQUENCE: 185
tcaataaaca attggagcga gagagactct gctgaccggg ccatcattga cgtattggta   60
gcccagaaag cccacacagt catacagagg tctgaatgtc tgtgctttat ggtgcttgag   120
tttagtccca cctcggtggc tttcagcggg agagagcaga gaaggcttat aaaagcagac   180
ctcagtcaac ataacaattc                                               200
```

```
SEQ ID NO: 186              moltype = DNA   length = 200
FEATURE                     Location/Qualifiers
source                      1..200
                            mol_type = genomic DNA
                            organism = Zea mays
SEQUENCE: 186
gaccccatct atgccgtaat tctggcttca cccctgatca agctatcgta ccttaaatgc   60
gtcgtttcac gttttttcacc ttgttggagg tctgaatgtc tgtgctttgt ggtgcttcaa  120
tttagtccca ccttgtcggc tttcaacggg agggagcgga gaaggcttat aaaagcagac  180
cctagtcaac ataacaattc                                               200

SEQ ID NO: 187              moltype = DNA   length = 200
FEATURE                     Location/Qualifiers
source                      1..200
                            mol_type = genomic DNA
                            organism = Zea mays
SEQUENCE: 187
ggtggaaacg gactcgagcg agagagactc tgcggaccgg gccagcatcg atgtattggt   60
agcccagaaa gcccacgcaa ccagacagag gtatgaatgt tgtgctttgt ggtgcttcag  120
tttagtccca cctcggcggt tttcagcgga agggagcaga gaaggcttat aaaagcagac  180
ctcagtcaac ataacaattc                                               200

SEQ ID NO: 188              moltype = DNA   length = 200
FEATURE                     Location/Qualifiers
source                      1..200
                            mol_type = genomic DNA
                            organism = Zea mays
SEQUENCE: 188
tccctttgtc gccttgctgt tcgctccgtt tgttgggccg gacatgtggc tttctgggcc   60
gcgcacgtag agtcctcctg gccagtgtcg ggctctggct ggctgcctgc tctttttct   120
gtagtcccaa accgcttgct gaggctaata tcagccggga acaacgctat ttaggattga  180
ctgaactctg tgtaagaggc                                               200

SEQ ID NO: 189              moltype = DNA   length = 200
FEATURE                     Location/Qualifiers
source                      1..200
                            mol_type = genomic DNA
                            organism = Zea mays
SEQUENCE: 189
cctttgtggc ttcgcttcat tctcttcatc cgtttgtgac cggagtcagc ggctgtcgac   60
cgcggcgcat cctctgacta gcactgcgtc tggctggctc tggctgcttc agcttgcttt  120
agttcccaaa cccgcttgct gtagctaata ccagcaggga gcgctgctat ttaggatgga  180
ctgggcgctg cgagagaagc                                               200

SEQ ID NO: 190              moltype = DNA   length = 200
FEATURE                     Location/Qualifiers
source                      1..200
                            mol_type = genomic DNA
                            organism = Zea mays
SEQUENCE: 190
ggccttcgct tcctcgctct tcgctccttt gttgggccgg acaacaagcg gctgtctggg   60
ccgcgcacgc agtcctctgg tccagtgggc aactgcctct ggctgcttgc tctttttctt  120
aatcccaaac cgctcgatga agctaatacc agctggggggg cgctgctatt taggagagac  180
taagcgccac ccgtagatgc                                               200

SEQ ID NO: 191              moltype = DNA   length = 200
FEATURE                     Location/Qualifiers
source                      1..200
                            mol_type = genomic DNA
                            organism = Zea mays
SEQUENCE: 191
ttcgcttcat ttctcttcac tccgtttgtt gggccggaca tcaagcggct gtctgggccg   60
cgcacgcagt cctcttgact agcactgcgt ctggctggct ctggctgctt cagctttgct  120
ttagttccaa accgcttgct gtagctaata ccagcaggga gcgctgctat ttaggatgga  180
ctgggcgctg cgagagaagc                                               200

SEQ ID NO: 192              moltype = DNA   length = 200
FEATURE                     Location/Qualifiers
source                      1..200
                            mol_type = genomic DNA
                            organism = Zea mays
SEQUENCE: 192
tcaataaaca attggagcaa gagagactct gctgaccggg ccatcatcga cgtattggta   60
gcccagaaag cccacgcagt catacagagg tctgaatgtc tgtgctttgt ggtgcttgag  120
tttagtccca cctcgacggc tttcagcggg agagagcaga gaaggcttat aaaagcagac  180
ctcagtcaac ataacaattc                                               200

SEQ ID NO: 193              moltype = DNA   length = 200
```

```
FEATURE                    Location/Qualifiers
source                     1..200
                           mol_type = genomic DNA
                           organism = Zea mays
SEQUENCE: 193
gactcgagaa cttagagcta gagagactct gcggaccggg ccagcatcga cgtattggta    60
gcccagaaag cccacgcaac cagacagagg tctgaatgca tgtgctttgt ggtgcttcag   120
tttagtccca cctcggcggc tttcagcggg agagagcaga gaaggcttat aaaagcagac   180
ctcagttaac ataacaattc                                               200

SEQ ID NO: 194            moltype = DNA   length = 200
FEATURE                    Location/Qualifiers
source                     1..200
                           mol_type = genomic DNA
                           organism = Zea mays
SEQUENCE: 194
ggcccccttct atgtcgtaaa tctaggtcca cccccaatca agcaatccta ccttaaatac    60
atcgtttcac gttttttgagc ttgttggagg tgtgaaagtt tgtgctttgt ggtgcttcac   120
tttagtccca cctcggtggc tttcagtgag agggagcgaa gaaggcttat aaaagcacac   180
cccaatcaac ataacaattc                                               200

SEQ ID NO: 195            moltype = DNA   length = 200
FEATURE                    Location/Qualifiers
source                     1..200
                           mol_type = genomic DNA
                           organism = Zea mays
SEQUENCE: 195
tcaatataca attggagcga gagagactct gctgaccggg ccagcatcga cgtattggta    60
gcccagaaag cccacgcagt catacagagg tctgaatgta tgtgctttgt ggtgcttgag   120
tttagtccca cctcggaggc tttcagcggg agagagcaaa gaaggcttat aaaagcagac   180
ctcagtcagc ataacaattc                                               200

SEQ ID NO: 196            moltype = DNA   length = 200
FEATURE                    Location/Qualifiers
source                     1..200
                           mol_type = genomic DNA
                           organism = Zea mays
SEQUENCE: 196
gccagctgcg gtggaaacga ctgcggaccg agccagcatc gacgtattgc cgtattggta    60
gcccagaaag cccacgcaac cggacagagg tctgaatgcc tgtactttgt ggtgcttcag   120
tttagtccca cctcggtggc tttcagcggg agagagcaga gaaggcttat aaaagcagac   180
ctcagtcaat ataacaattc                                               200

SEQ ID NO: 197            moltype = DNA   length = 200
FEATURE                    Location/Qualifiers
source                     1..200
                           mol_type = genomic DNA
                           organism = Zea mays
SEQUENCE: 197
gagtccagaa cttggagcga gagagactct gctgaccggg ccagcatgga cgtattggta    60
gcccagaaag cccacgcaac cagatagagg tcttaatgcc ctttctttgt ggtgcttag   120
tttagtccca cctcgacggc tttcagcggg agggagcaga gaaggcttat aaaagaagat   180
ctcaatcaaa ttaacaattc                                               200

SEQ ID NO: 198            moltype = DNA   length = 200
FEATURE                    Location/Qualifiers
source                     1..200
                           mol_type = genomic DNA
                           organism = Zea mays
SEQUENCE: 198
gactcgagaa cttggagcga gagagactct gctgaccggg ccagcatgga cgtattggta    60
gcccagaaag cccacgctac cagacagagg tctgaatgac tgttctttgt ggtgcttcag   120
tttagtccca cctcgacggc tttcagcggg aggaagcaga gaaggcttat aaaagcagat   180
cctagtcaac ataacaattc                                               200

SEQ ID NO: 199            moltype = DNA   length = 192
FEATURE                    Location/Qualifiers
source                     1..192
                           mol_type = genomic DNA
                           organism = Zea mays
SEQUENCE: 199
aacggactcg agcgagagag actctgcgga ccgggccagc atcgatgtat ttggtagccc    60
agagcccacg caaccagaca gaggtatgaa tgttgtgctt tgtggtgctt cagtttagtc   120
ccacctcggc ggttttcagc ggaagggagc agagaaggct tataaaagca gacctcagtc   180
aacataacaa tt                                                       192

SEQ ID NO: 200            moltype = DNA   length = 199
FEATURE                    Location/Qualifiers
source                     1..199
```

```
                        mol_type = genomic DNA
                        organism = Zea mays
SEQUENCE: 200
ggcgtatgtg ccaaaaactt cgtcacagag agggccataa gaaacatggc ccacggccca    60
atacgaagca ccgcgacgaa gcccaaacag cagtccgtag gtggagcaaa gcgctgggta   120
atacgcaaac gttttgtccc accttgacta atcacaagag tggagcgtac cttataaacc   180
gagccgcaag caccgaatt                                                199

SEQ ID NO: 201          moltype = DNA  length = 418
FEATURE                 Location/Qualifiers
source                  1..418
                        mol_type = genomic DNA
                        organism = Zea mays
SEQUENCE: 201
aggaaaagaa gaggtgatta ctgtacctat tcgtctttgt atcggaatat aaatttatca    60
ctattttatg ataaagtaaa tctgtttccc tgtagagtta attaattaat gtaagtataa   120
gcgtaattta tagggcacta gtaggactgt cgactgtgcg ctcggcccgg ataatgcgtc   180
aaaagcgaag acgtgcacgt gggatgggaa aacacgaagc gtggtctgct ttttcgcatg   240
atatctgggc cgcaccaaag aatccagccc acgcggcgtg gcgccgtcgt tacggcttgc   300
ggggggaagga aacgagggac gaaccgagat ttagcaccag accggccagc gagcattgca   360
gacaccggct tataagttca gctgcgacta ccactccggg aggtccgagt tccactcg     418

SEQ ID NO: 202          moltype = DNA  length = 625
FEATURE                 Location/Qualifiers
source                  1..625
                        mol_type = other DNA
                        note = Recombinant
                        organism = synthetic construct
SEQUENCE: 202
ttctatttgt gctacatata ttagacaagg aaaataacat atgttatttt gaaatcacgt    60
atatttacta taaattacaa tgattaacaa cttaaaatat ttaaatgaaa atcatattaa   120
tgactctcta aattttatct gtgtcacata aatgaaaaac aaaaaataac aaatattgta   180
ttcgcacggg cgcatgtgtc tagttagtta taaacgaaga aataaggggc tgatttcgaa   240
ataaacgttc ttagaattgg aagaaatgtt cagtttctaa acttgtagga ctaaagcaat   300
aactttattt taatttattt tcttttatgt ttctcccaca tcgatcatac atataactat   360
acagcagtat aagaactcta gcgaagcaat aatgctccaa gctgactcta gcagatctcc   420
atgacggcag agaaggtact ggaaaaagaa cttctggcct ggcaggagaa actgcatcag   480
ccgattatca tcaccgaata cggcgtggat acgttagccg ggctgcactc aatgtacacc   540
gacatgtgga gtgaagagta tcagtgtgca tggctggata tgtatcaccg cgtctttgat   600
cgcgtcagcg ccgtcgtctt tttt                                          625

SEQ ID NO: 203          moltype = DNA  length = 474
FEATURE                 Location/Qualifiers
source                  1..474
                        mol_type = other DNA
                        note = Recombinant
                        organism = synthetic construct
SEQUENCE: 203
ggaaacttct gtttgtcccc atactccaaa aacaaaacca tttttttttt atcttcgttt    60
ttgtttgctt tgactgtgag ttgaggccca actttctgct tctgtccgac tctatttgat   120
gaattttgtt tgcctcctgt gatgtgaagg atgtatcatt gaaagggaac gtgtctcaat   180
gatcccacat cggccaaata tgctcattac attgcgttta tatagtccca ggaaaacata   240
tggattcaag ctgactctag cagatctcca tgacggcaga gaaggtactg gaaaaagaac   300
ttctggcctg gcaggagaaa ctgcatcagc cgattatcat caccgaatac ggcgtggata   360
cgttagccgg gctgcactca atgtacaccg acatgtggag tgaagagtat cagtgtgcat   420
ggctggatat gtatcaccgc gtctttgatc gcgtcagcgc cgtcgtcttt tttt          474

SEQ ID NO: 204          moltype = DNA  length = 721
FEATURE                 Location/Qualifiers
source                  1..721
                        mol_type = other DNA
                        note = Recombinant
                        organism = synthetic construct
SEQUENCE: 204
tctacaaaac attataaaaa gtaagatata acaacttttt ttttaaaaaa atcaatagga    60
aatattatcg gttcagttaa tttacagaga gatatttatt tcatatgtgc cagaagtatt   120
tcagttcctt atgaaaaatc agaaaaatgt atggaataaa atataataat cgatactaat   180
aatagaacaa aataaatggt aaaatgtcaa atcaaaacta ggctgcagta tgcagagcag   240
agtcatgatg atactactta ctacaccgat tcttgtgtgc agaaaaatat gttaaaataa   300
ttgaatcttt ctctagccaa atttgacaac aatgtacacc gttcatattg agagacgatg   360
cttcttgttt gctttcggtg gaagctgcat atactcaaca ttactccttc agcgagtttt   420
ccaactgagt cccacattgc ccagacctaa cacggtattc ttgtttataa tgaaatgtgc   480
caccacatgg attcaagctg actctagcag atctccatga cggcagagaa ggtactggaa   540
aaagaacttc tggcctggca ggagaaactg catcagccga ttatcatcac cgaatacggc   600
gtggatacgt tagccgggct gcactcaatg tacaccgaca tgtggagtga agagtatcag   660
tgtgcatggc tggatatgta tcaccgcgtc tttgatcgcg tcagcgccgt cgtctttttt   720
t                                                                   721

SEQ ID NO: 205          moltype = DNA  length = 787
```

```
FEATURE            Location/Qualifiers
source             1..787
                   mol_type = other DNA
                   note = Recombinant
                   organism = synthetic construct
SEQUENCE: 205
aggtggagtt gttccagatt tagttttcga cttagatgat gcatggaact ggctagtgac    60
gtggatggtg gtaggttact ttcaggtcat gatttttgt ttctaaatga tactcacact   120
cccttccagt tttttttttt taaactcagc tcccttgctt cctccaccgg ttatcataat   180
actgaaccaa atcaaacatt acagtcaagg tactatgaat atgaaacctg aaatcctatg   240
aatgtcataa atttatttta aataataaat ttatttagaa taatatttt ttgggtaaga   300
gttataaaat aaaatacaaa aaaaaaacct aatatcaatt tttcactgac tccgtttata   360
ttgagacttg agaaagatgg ttcccgtttg ctcccggtgg aggctccgag gctgtgtata   420
tactcgacat tactttagct tgttttgttg tttctttccc tttcccacaa gactcaggtc   480
tcgttcgcaa acgagtccca caccgtctaa acttaccaca atattagcgt ttataattag   540
atgcactgca tcacttattc aagctgactc tagcagatct ccatgacggc agagaaggta   600
ctggaaaaag aacttctggc ctggcaggag aaactgcatc agccgattat catcaccgaa   660
tacggcgtgg atacgttagc cgggctgcac tcaatgtaca ccgacatgtg gagtgaagag   720
tatcagtgtg catggctgga tatgtatcac cgcgtctttg atcgcgtcag cgccgtcgtc   780
ttttttt                                                             787
```

```
SEQ ID NO: 206          moltype = DNA  length = 824
FEATURE            Location/Qualifiers
source             1..824
                   mol_type = other DNA
                   note = Recombinant
                   organism = synthetic construct
SEQUENCE: 206
aaattacacg gtagtacatc ctattataga tcgatgaatt cttaactact cgtgtccctt    60
aggccaggcc tgttttcttg cacaatttct gaaatgtata cggtttccac ttcaaccttt   120
ttaaccgcac aaagttttaa ccagatttat ataatttatt tttgaatccc caatacatat   180
cattataaca tatcaattat caaatatttc aataacctca tgatatggca atgaatacat   240
cttcttctca atgaacagag atttctgaaa aagattagga aagtgaaagc atactcgttt   300
gcaatgtaaa actgatactt ccccaaaatc atcatattcc aaatatgccc tggtgttact   360
gaccaaaacc agaaaaaaga aacggaagac atatacgtct aaacggagaa atttcaaaaa   420
acaaaaattg gatcatttct cgatttgtgg gtgtcatctt gtgcagggca tgctaatctt   480
ctctttaccc tttcccacaa gactcagcgc atgttgtctc gtctcatcca agtcccacac   540
cgcctaaact taacacaata ttagtattta taatgacata caacattcaa gatgttcaag   600
ctgactctag cagatctcca tgacggcaga gaaggtactg gaaaaagac ttctggcctg   660
gcaggagaaa ctgcatcagc cgattatcat caccgaatac ggcgtggata cgttagccgg   720
gctgcactca atgtacaccg acatgtggag tgaagagtat cagtgtgcat ggctggatat   780
gtatcaccgc gtctttgatc gcgtcagcgc cgtcgtcttt tttt                    824
```

```
SEQ ID NO: 207          moltype = DNA  length = 965
FEATURE            Location/Qualifiers
source             1..965
                   mol_type = other DNA
                   note = Recombinant
                   organism = synthetic construct
SEQUENCE: 207
aattatttaa tcctaaaaat caatcttaca aggaaccact ataaaactag ttgaacccat    60
cgaaaactaa ctacagttga caaaatctat ttggttggtt gatttttttt aattaaaaac   120
atccaatctt aatgatataa ttatagctta atattataag atttttataa aaattatatt   180
tattttgttt ctaattatgc taagagatat tattatttgt tatttaactt aaatattatc   240
acaaacttga ttgaaactta tgtttaattt aaaatattat atgtcatgag ttatgactcc   300
aataatcaca attatataagt gaagtttaat ttttagtatt acaaatattt tttgttgtt   360
taattttaat tacttaatgt attatgttaa taattaaaaa tacaaattat ttattattaa   420
tgcaatcaca gtttgtggat ttgacaaaag aaataggggga tctaaaattg tagataagcc   480
aaagttaaaa cttgaattga ctatttttg ctctttactc tgcaccaact ttactattcc   540
ttcttttagt gtgagcttca tgcatcttgt tcaccgcaat tccgctcggt gaaagttgca   600
caattcactc acaatctgtt tctggtctgt taggttgtt acttggagtg acacgatgac   660
gcaacagtac aagtcccaca tcgtttgagt atacagtttt caagcagttt atattcccat   720
agccttagca agagcttcaa gctgactcta gcagatctcc atgacggcag agaaggtact   780
ggaaaaagaa cttctggcct ggcaggagaa actgcatca tccgcttatca tcaccgaata   840
cggcgtggat acgttagccg ggctgcactc aatgtacacc gacatgtgga gtgaagagta   900
tcagtgtgca tggctggata tgtatcaccg tctcttgat cgcgtcagcg ccgtcgtctt   960
ttttt                                                               965
```

```
SEQ ID NO: 208          moltype = DNA  length = 712
FEATURE            Location/Qualifiers
source             1..712
                   mol_type = other DNA
                   note = Recombinant
                   organism = synthetic construct
SEQUENCE: 208
ttttttaata aaaaaaattc aatgggagat actatggatt caattccctt actgatttta    60
tttcatatgt gccagaagta tttcagttta ttttgaaaaa tcagaaaaaa aatgtctgga   120
ataaaatata ataagcgata ctaataaata attgaacaag ataaatggta aaatgtcaaa   180
tcaaaactag gctacagagt gcagagcaga gtcatgatga atgacagcta gttctactta   240
```

-continued

```
ctacaccgat tcttgtgtac ataaaaatat tttaaaataa ttgaatcttc ctttagccag   300
ctttgacaac aatgtacacc gttcgtactc cttactggta ggcaatgctt cttgtttgct   360
ttcggtggaa ggtgtatata ctcaacatta cttctttttc agcgtgtttt cttacgggag   420
tcccacaccg cccaaaacta atacagtatt cttgtttata aagaagtgca ccacttcaat   480
tgttcaagct gactctagca gatctccatg acggcagaga aggtactgga aaaagaactt   540
ctggcctggc aggagaaact gcatcagccg attatcatca ccgaatacgg cgtggatacg   600
ttagccgggc tgcactcaat gtacaccgac atgtggagtg aagagtatca gtgtgcatgg   660
ctggatatgt atcaccgcgt ctttgatcgc gtcagcgccg tcgtcttttt tt           712
```

SEQ ID NO: 209          moltype = DNA   length = 655
FEATURE                 Location/Qualifiers
source                  1..655
                        mol_type = other DNA
                        note = Recombinant
                        organism = synthetic construct
SEQUENCE: 209

```
cgataaaaat gttttaaacg atatatatta taaaaaaaaa cgtttcaaaa ataaatacaa   60
aaatgttttt aaatatatat aatttaactc attaaagaaa ataaaaatgc aagtgcggtg   120
acaagacaag ctaaaagttg caaaagaaat ggcagggcta taaggctcac ctactcctgg   180
atttaccaaa tttttggttcg tccctatact cgaaaaataa aacaaaataa atttcagtat   240
cttcgttttt gtatgctttg actgtgaggc gaggccaact ttcttcttct gtctgagatg   300
aattttgttt gcctcctgtg aaggatgtat cattcaaagt gaatgttttg caactgccag   360
tagtcccaca tcgaccaaat attcttatta cagtgtgtttt atatagcacc tggagaagga   420
atgggttcaa gctgactcta gcagatctcc atgacggcag agaaggtact ggaaaaagaa   480
cttctggcct ggcaggagaa actgcatcag ccgattatca tcaccgaata cggcgtggat   540
acgttagccg ggctgcactc aatgtacacc gacatgtgga gtgaagagta tcagtgtgca   600
tggctggata tgtatcaccg cgtctttgat cgcgtcagcc ccgtcgtctt ttttt        655
```

SEQ ID NO: 210          moltype = DNA   length = 628
FEATURE                 Location/Qualifiers
source                  1..628
                        mol_type = other DNA
                        note = Recombinant
                        organism = synthetic construct
SEQUENCE: 210

```
gaaaagcatt cagaatattt gagcctctaa aaacttttct tcttttttctt tgaggagtgt   60
aatgtggatc ccaagtaacc aagaaaagca atccgaaaat tcaatttcaa gcaaactgtt   120
ctcaagtttt cgagggatat agtaatagca gagcaaaaaa acactggaaa aagcttgtac   180
ctattgaaac aaaggataat taaaaatcca aaatgtatca aaagcctaga caattttaat   240
cactattgcc tcttaacaat ttgcgcacta tgacaatcat gctctcataa tgtaacaaaa   300
gacacattag gatactagta ctgacactga caccaaggtt acatagtccc acatcgaagg   360
agtttaggta gagacatcgg tttatataac taagcgtgac caagctgact ctagcagatc   420
tccatgacgg cagagaaggt actggaaaaa gaacttctgg cctggcagga gaaactgcat   480
cagccgatta tcatcaccga atacggcgtg gatacgttag ccgggctgca ctcaatgtac   540
accgacatgt ggagtgaaga gtatcagtgt gcatggctgg atatgtatca ccgcgtcttt   600
gatcgcgtca gcgccgtcgt cttttttt                                       628
```

SEQ ID NO: 211          moltype = DNA   length = 662
FEATURE                 Location/Qualifiers
source                  1..662
                        mol_type = other DNA
                        note = Recombinant
                        organism = synthetic construct
SEQUENCE: 211

```
ttgccaacaa gatataacaa gaagcctaat atttcaaaag gccttttggt ccttaaaaac   60
taaggaatgc atctccagaa agaagtacaa tcataatagt tgctaagaat gcagcaaaat   120
tgataaatta atcgagaaac cacaccacaa atcacacatg gccattagag aaaaagaaag   180
gtttcaggaa aataaaagaa aagaaaaagt caattactgc ttagctacct ctctatattc   240
ccatgtgccc cttgcttgaa attggaacca ctaccaggca acagagttgt tcccttttcaa   300
gcaataagag ttagaaatat ttttatatca accgaagtgg caaaaagtca gaaaccatga   360
catacgttta ctttgttagt cccacattgg atagtttttag taaaacacag gtcattatat   420
agctaaacgc taaccaagct gactctagca gatctccatg acggcagaga aggtactgga   480
aaaagaactt ctggcctggc aggagaaact gcatcagccg attatcatca ccgaatacgg   540
cgtggatacg ttagccgggc tgcactcaat gtacaccgac atgtggagtg aagagtatca   600
gtgtgcatgg ctggatatgt atcaccgcgt ctttgatcgc gtcagcgccg tcgtcttttt   660
tt                                                                   662
```

SEQ ID NO: 212          moltype = DNA   length = 664
FEATURE                 Location/Qualifiers
source                  1..664
                        mol_type = other DNA
                        note = Recombinant
                        organism = synthetic construct
SEQUENCE: 212

```
aatatttcaa agcacactta ggtccttaaa aatgcaatgt tacaattcca aaaggaagta   60
taatcatagt agaagccaag aatgcagaaa aattaacaaa gtgatcgagg aatcattgcc   120
acaaatcact catggctatt agagaaaaaa aaaagtttca agaaaagaaa agaaaaagtt   180
aattactact tagctacttc tttgtaaact caggtgcccc ttgcatgcaa ttgataccac   240
accaggcacc agagctgttc cttttcatgc aataagagta gagacatttt ttttatgaac   300
```

```
tcagatggcg aagtgtttga aaccatgaca ggcgttactc tggtagtccg acatagagag   360
ttttaataaa acacaaatgt agtcccacat tgaacagttt taataaaaca cagtctttat   420
ataactaaac gctgagcaag ctgactctag cagatctcca tgacggcaga gaaggtactg   480
gaaaaagaac ttctggcctg gcaggagaaa ctgcatcagc cgattatcat caccgaatac   540
ggcgtggata cgttagccgg gctgcactca atgtacaccg acatgtggag tgaagagtat   600
cagtgtgcat ggctggatat gtatcaccgc gtctttgatc gcgtcagcgc cgtcgtcttt   660
tttt                                                                664

SEQ ID NO: 213           moltype = DNA   length = 656
FEATURE                  Location/Qualifiers
source                   1..656
                         mol_type = other DNA
                         note = Recombinant
                         organism = synthetic construct
SEQUENCE: 213
cttaggtggc tcttgcttga aatgggtact gtactggaat tagagtttat cttttcatgc   60
acaaagtttt ggccctcgtt ctactacagt atacagcagt atggatatgg ttcacattaa   120
ttctccgaaa gtaatctatc cctgcgggct agcctgagaa agggtgttta taatcttgta   180
gtgatagaat caagcatcat aagagctttc aaagcctcta atgagtattt cttttttctag   240
aaaagatgaa tatttgggat caatgctgct gctgttatgt aggaaacacc gtggcaggaa   300
gattgtattt gtatccttgt gcaatactca gaccaattct gttagaaaaa tgacacaaag   360
gccgtgatgc tagtcccaca tcgagtgttt ttaacaaaac aggcgcatat atattactgg   420
acgctgagca agctgactct agcagatctc catgacggca gagaaggtac tggaaaaaga   480
acttctggcc tggcaggaga aactgcatca gccgattatc atcaccgaat acggcgtgga   540
tacgttagcc gggctgcact caatgtacac cgacatgtgg agtgaagagt atcagtgtgc   600
atggctggat atgtatcacc gcgtctttga tcgcgtcagc gccgtcgtct tttttt       656

SEQ ID NO: 214           moltype = DNA   length = 660
FEATURE                  Location/Qualifiers
source                   1..660
                         mol_type = other DNA
                         note = Recombinant
                         organism = synthetic construct
SEQUENCE: 214
catgctgtgt agtgaaagac atagacagtc aaaaggcctg agaagggtat atattgtaaa   60
gatgatgatt tttcttacag atggtttata ccgctttatg cttcttcagc gtagaactta   120
tcaaagagaa cactatccat agctgaatca agttggttca ggctttttgtt ataatcacag   180
tctaggagtc taggacactt ttattttgca ttcattttcg gattgttgac gcctttgtat   240
aaattttaca atctctcagt aaaagatcga acacttctga taatgtttta ggaatttaac   300
tctcattcta taagctttga ccaagtctga accctagaca attgcctctt taacaacttg   360
acacagaaat aataatagtc ccacatcgag agcgtttagc tacaaacatg tgtttatata   420
attaagcata accaagctga ctctagcaga tctccatgcc ggcagagaag gtactggaaa   480
aagaacttct ggcctggcag gagaaactgc atcagccgat tatcatcacc gaatacggcg   540
tggatacgtt agccgggctg cactcaatgt acaccgacat gtggagtgaa gagtatcagt   600
gtgcatggct ggatatgtat caccgcgtct ttgatcgcgt cagcgccgtc gtctttttt   660

SEQ ID NO: 215           moltype = DNA   length = 662
FEATURE                  Location/Qualifiers
source                   1..662
                         mol_type = other DNA
                         note = Recombinant
                         organism = synthetic construct
SEQUENCE: 215
gtttatgttt ggcattcttt aatctttagt atcagaataa ttgatcacat tttgaaatgc   60
caatagaaag acactcctta aacaaaagct atcgtgtatg aaaagctgca gagaaaaatc   120
aaatgtacaa gattttaaat aaagacatgc taaactgtcc aatatgtaac tagttgaaca   180
ggctgcattt ctctgtgttt ttgcttccgc agggaggaat acaaacatct aacaacttat   240
accaaagcat atagtacaaa ttacaatctt ttgtttttccc caaattaatc caatttatct   300
ttcatttcat ccagaaagaa gctctttgag attgttagtg ttaaactgaca aactttcttc   360
ttacttatgt cccacatagg aaagaaaagg agacaacaaa atctttatat gccctctgac   420
aaagttgtct gaatcaagct gactctagca gatctccatg acggcagaga aggtactgga   480
aaaagaactt ctggcctggc aggagaaact gcatcagccg attatcatca ccgaatacgg   540
cgtggatacg ttagccgggc tgcactcaat gtacaccgac atgtggagtg aagagtatca   600
gtgtgcatgg ctggatatgt atcaccgcgt ctttgatcgc gtcagcgccg tcgtcttttt   660
tt                                                                  662

SEQ ID NO: 216           moltype = DNA   length = 645
FEATURE                  Location/Qualifiers
source                   1..645
                         mol_type = other DNA
                         note = Recombinant
                         organism = synthetic construct
SEQUENCE: 216
catttaaaat aatgaatgac taatccatta actaataact atagttgatt acttttttagt   60
taattaggat gttaggaata cctgaatcca ccgacttaac tattatcata atcagttcat   120
tcaatttgaa tttgtaggat gcacctctat gttttcctct tcactttcta gtggacacaa   180
gaccctgtgt cacacacagt taatagagaa agatcattta catgtaagcg gaacccattg   240
cattctacag caatattttg gggttggtgt tataatacaa gacggataaa atagctagag   300
agaatccaat caaatcccac attccaaatt agactatcca ttgtaggcca agtcccacat   360
```

```
tggttagaat attaggcaac gaaaccttta taaatcttct gacaagcact tcagcatcaa    420
gctgactcta gcagatctcc atgacggcag agaaggtact ggaaaaagaa cttctggcct    480
ggcaggagaa actgcatcag ccgattatca tcaccgaata cggcgtggat acgttagccg    540
ggctgcactc aatgtacacc gacatgtgga gtgaagagta tcagtgtgca tggctggata    600
tgtatcaccg cgtctttgat cgcgtcagcg ccgtcgtctt ttttt                    645

SEQ ID NO: 217              moltype = DNA   length = 667
FEATURE                     Location/Qualifiers
source                      1..667
                            mol_type = other DNA
                            note = Recombinant
                            organism = synthetic construct
SEQUENCE: 217
ggcatgtgac tttttattta aattattctc agaaatatta aaatataatc aaatatattt    60
ttttataaga tactggaaat aacattttta ggaatgtaac gaaagcccca ttacaaacac   120
ttgaactcag ggatcgatcc aacttaatta ttatctgcta cttcaaattc aaatttatag   180
gccctacctt tatgtttttgc tctgcacttt cttaaatgga aacaagtaac acaatagagt   240
aagatcattt acttgtaagc ggaaactgtt gcatcaactg caatattttc gggttagttt   300
tataatataa caatgaagag aattgccgag aagatcatat caagtcccat attccattta   360
ttggccctta caagtcccac atcggtccaa atattagaca aagaaacatt tatatatcgt   420
ctgacaaacc tgtaagattc aagctgactc tagcagatct ccatgacggc agagaaggta   480
ctggaaaaag aacttctggc ctggcaggag aaactgcatc agccgattat catcaccgaa   540
tacggcgtgg atacgttagc cgggctgcac tcaatgtaca ccgacatgtg gagtgaagag   600
tatcagtgtg catggctgga tatgtatcac cgcgtctttg atcgcgtcag cgccgtcgtc   660
ttttttt                                                            667

SEQ ID NO: 218              moltype = DNA   length = 398
FEATURE                     Location/Qualifiers
source                      1..398
                            mol_type = other DNA
                            note = Recombinant
                            organism = synthetic construct
SEQUENCE: 218
ggattgtgcg ggcaaagtat tttcgtcgaa agagaagcaa cgaaaaagcc cactgctccg    60
agacaccgtt ccacgaaacc tgtccgcact catctcatcg tttagcacca cctcgccagt   120
ccgcagtcct ctatacctgc ttaaatattc gtccagaccg cccaccctcc aagctgactc   180
tagcagatct ccatgacggc agagaaggta ctggaaaaag aacttctggc ctggcaggag   240
aaactgcatc agccgattat catcaccgaa tacggcgtgg atacgttagc cgggctgcac   300
tcaatgtaca ccgacatgtg gagtgaagag tatcagtgtg catggctgga tatgtatcac   360
cgcgtctttg atcgcgtcag cgccgtcgtc tttttttt                           398

SEQ ID NO: 219              moltype = DNA   length = 429
FEATURE                     Location/Qualifiers
source                      1..429
                            mol_type = other DNA
                            note = Recombinant
                            organism = synthetic construct
SEQUENCE: 219
ctgtttttcat ccggcctgtg atggaaattg tgctgcaaag tgcgcagggc cgttggcccg    60
acgacaagta tttttcgtcg agagaagcaa cgaaagccca ctcctccaag ccaccccttcg   120
ctcaagtcat atttagcacc acctcggcag tcgacactgc agcacaccaa cttaaatatt   180
catcccgatc tccctcactc caagctgact ctagcagatc tccatgacgg cagagaaggt   240
actggaaaaa gaacttctgg cctggcagga gaaactgcat cagccgatta tcatcaccga   300
atacggcgtg gatacgttag ccgggctgca ctcaatgtac accgacatgt ggagtgaaga   360
gtatcagtgt gcatggctgg atatgtatca ccgcgtcttt gatcgcgtca gcgccgtcgt   420
cttttttttt                                                          429

SEQ ID NO: 220              moltype = DNA   length = 429
FEATURE                     Location/Qualifiers
source                      1..429
                            mol_type = other DNA
                            note = Recombinant
                            organism = synthetic construct
SEQUENCE: 220
aaactgtgct tgtgcagggc cgttgggcca cgtgcccacg tcaaagtatt ctagtcgaaa    60
gagaagcaac gaaagcccac tactactcct aggcaccgtt gccacgagac ctgtccgcac   120
tcatctcatc gtttagcacc aatgcgccag tccgcagtcc gctgtaccag cttaaatatt   180
cgtccctacc gcgctccatc caagctgact ctagcagatc tccatgacgg cagagaaggt   240
actggaaaaa gaacttctgg cctggcagga gaaactgcat cagccgatta tcatcaccga   300
atacggcgtg gatacgttag ccgggctgca ctcaatgtac accgacatgt ggagtgaaga   360
gtatcagtgt gcatggctgg atatgtatca ccgcgtcttt gatcgcgtca gcgccgtcgt   420
cttttttttt                                                          429

SEQ ID NO: 221              moltype = DNA   length = 429
FEATURE                     Location/Qualifiers
source                      1..429
                            mol_type = other DNA
                            note = Recombinant
                            organism = synthetic construct
```

```
SEQUENCE: 221
catatataggga tcagctaagc ttatcatacc ttcctttttt tttctcattc agccactact    60
gcagcctaca aaggatatca taatgggccg acccagtcac ccaggacgca atatgttggt   120
caatcccacc agttagtacc acctcggtag ctcagatgag tagaagatac cttaaaagtt   180
cagctcaggc aacttgcagc caagctgact ctagcagatc tccatgacgg cagagaaggt   240
actggaaaaa gaacttctgg cctggcagga gaaactgcat cagccgatta tcatcaccga   300
atacggcgtg gatacgttag ccgggctgca ctcaatgtac accgacatgt ggagtgaaga   360
gtatcagtgt gcatggctgg atatgtatca ccgcgtcttt gatcgcgtca gcgccgtcgt   420
cttttttttt                                                          429

SEQ ID NO: 222             moltype = DNA   length = 429
FEATURE                    Location/Qualifiers
source                     1..429
                           mol_type = other DNA
                           note = Recombinant
                           organism = synthetic construct
SEQUENCE: 222
catggtccat aggtatcaag atccagcatt gcacttgggc caaagattga gctctgcgaa    60
gtgtcaacta caatcatcta gatgggctcg acctgaaagg ccacacgatt tgccagaact   120
cccaccaatt aattagtacc acctcggttg ctcgatttag tagaagccag cttaaaagtt   180
cagctctggg gtccggtagc caagctgact ctagcagatc tccatgacgg cagagaaggt   240
actggaaaaa gaacttctgg cctggcagga gaaactgcat cagccgatta tcatcaccga   300
atacggcgtg gatacgttag ccgggctgca ctcaatgtac accgacatgt ggagtgaaga   360
gtatcagtgt gcatggctgg atatgtatca ccgcgtcttt gatcgcgtca gcgccgtcgt   420
cttttttttt                                                          429

SEQ ID NO: 223             moltype = DNA   length = 410
FEATURE                    Location/Qualifiers
source                     1..410
                           mol_type = other DNA
                           note = Recombinant
                           organism = synthetic construct
SEQUENCE: 223
catccaggtg aggcatcaag ctactactgc ctcgattggc tggacccgaa gcccacatgt    60
aggataccag aatgggccga cccaggacgc agtatgttgg ccagtcccac cggttagtgc   120
catctcggtt gctcacatgc gtagaagcca gcttaaaaat ttagctttgg taactcacag   180
ccaagctgac tctagcagat ctccatgacg gcagagaagg tactggaaaa agaacttctg   240
gcctggcagg agaaactgca tcagccgatt atcatcaccg aatacggcgt ggatacgtta   300
gccgggctgc actcaatgta caccgacatg tggagtgaag agtatcagtg tgcatggctg   360
gatatgtatc accgcgtctt tgatcgcgtc agcgccgtcg tctttttttt             410

SEQ ID NO: 224             moltype = DNA   length = 429
FEATURE                    Location/Qualifiers
source                     1..429
                           mol_type = other DNA
                           note = Recombinant
                           organism = synthetic construct
SEQUENCE: 224
catcaataag ataaagctgg tgcaggctct cgacctgaag cccacacact ggagagcaac    60
gatataccag aatggagcgg cccagtacac gatctgctgg gattgctggc cagtggccag   120
tcccgcagcc gattagcacc acctcggtgg cacagacgaa cgaacgctaa tttaaaagct   180
tagctctgga gcttggcacc caagctgact ctagcagatc tccatgacgg cagagaaggt   240
actggaaaaa gaacttctgg cctggcagga gaaactgcat cagccgatta tcatcaccga   300
atacggcgtg gatacgttag ccgggctgca ctcaatgtac accgacatgt ggagtgaaga   360
gtatcagtgt gcatggctgg atatgtatca ccgcgtcttt gatcgcgtca gcgccgtcgt   420
cttttttttt                                                          429

SEQ ID NO: 225             moltype = DNA   length = 429
FEATURE                    Location/Qualifiers
source                     1..429
                           mol_type = other DNA
                           note = Recombinant
                           organism = synthetic construct
SEQUENCE: 225
gcgaggcatc aacaagataa agctggtgca ggctctcgac ctgaagccca cacacaggag    60
agcaacaata taccaggaat ggagcggccc agtacgcgat ctgctgggat tgctggctag   120
tcccgcaccc gattagcacc acctcgcttg ctcatacgag cgaacgcaaa tttaaaaggt   180
tagctctgga gtttggcagc caagctgact ctagcagatc tccatgacgg cagagaaggt   240
actggaaaaa gaacttctgg cctggcagga gaaactgcat cagccgatta tcatcaccga   300
atacggcgtg gatacgttag ccgggctgca ctcaatgtac accgacatgt ggagtgaaga   360
gtatcagtgt gcatggctgg atatgtatca ccgcgtcttt gatcgcgtca gcgccgtcgt   420
cttttttttt                                                          429

SEQ ID NO: 226             moltype = DNA   length = 442
FEATURE                    Location/Qualifiers
source                     1..442
                           mol_type = other DNA
                           note = Recombinant
                           organism = synthetic construct
```

```
SEQUENCE: 226
cctaactaat aagtatcgga ggcaacaacg cccgctgggc tgcggcccat taacatagca    60
ctagacggac accgccgcag tcagcgttca gccggatgca gtcgatcgg cttcatccgt    120
ttagtcccac ctcgcccagc caaagcagcg gggaggcccg gactcgctac aaaaggagac   180
ggaggttggc tgtttagagc caagctgact ctagcagatc tccatgacgg cagagaaggt   240
actggaaaaa gaacttctgg cctggcagga gaaactgcat cagccgatta tcatcaccga   300
atacggcgtg gatacgttag ccgggctgca ctcaatgtac accgacatgt ggagtgaaga   360
gtatcagtgt gcatggctgg atatgtatca ccgcgtcttt gatcgcgtca gcgccgtcgt   420
cacaattcaa aacaagtttt at                                           442

SEQ ID NO: 227        moltype = DNA   length = 442
FEATURE               Location/Qualifiers
source                1..442
                      mol_type = other DNA
                      note = Recombinant
                      organism = synthetic construct
SEQUENCE: 227
gccagctgcg gtggaaacga ctgcggaccg ggctagcatc gacgtattgc cgtattagta    60
gcccagaaag cccacgcaac cagatagagg tctgaatgcc tgtactttgt ggtgcttcag   120
tttagtccca cctcggtggc tttcagcggg agagagcaga gaaggcttat aaaagcagac   180
ctcagtcaac ataacaattc caagctgact ctagcagatc tccatgacgg cagagaaggt   240
actggaaaaa gaacttctgg cctggcagga gaaactgcat cagccgatta tcatcaccga   300
atacggcgtg gatacgttag ccgggctgca ctcaatgtac accgacatgt ggagtgaaga   360
gtatcagtgt gcatggctgg atatgtatca ccgcgtcttt gatcgcgtca gcgccgtcgt   420
cacaattcaa aacaagtttt at                                           442

SEQ ID NO: 228        moltype = DNA   length = 442
FEATURE               Location/Qualifiers
source                1..442
                      mol_type = other DNA
                      note = Recombinant
                      organism = synthetic construct
SEQUENCE: 228
tcaataaaca attggagcga gagagactct gctgaccggg ccatcattga cgtattggta    60
gcccagaaag cccacacagt catacagagg tctgaatgtc tgtgctttat ggtgcttgag   120
tttagtccca cctcggtggc tttcagcggg agagagcaga gaaggcttat aaaagcagac   180
ctcagtcaac ataacaattc caagctgact ctagcagatc tccatgacgg cagagaaggt   240
actggaaaaa gaacttctgg cctggcagga gaaactgcat cagccgatta tcatcaccga   300
atacggcgtg gatacgttag ccgggctgca ctcaatgtac accgacatgt ggagtgaaga   360
gtatcagtgt gcatggctgg atatgtatca ccgcgtcttt gatcgcgtca gcgccgtcgt   420
cacaattcaa aacaagtttt at                                           442

SEQ ID NO: 229        moltype = DNA   length = 442
FEATURE               Location/Qualifiers
source                1..442
                      mol_type = other DNA
                      note = Recombinant
                      organism = synthetic construct
SEQUENCE: 229
gaccccatct atgccgtaat tctggcttca cccctgatca agctatcgta ccttaaatgc    60
gtcgtttcac gttttttcacc ttgttggagg tctgaatgtc tgtgcttttgt ggtgcttcaa   120
tttagtccca ccttgtcggc tttcaacggg agggagcgga gaaggcttat aaaagcagac   180
cctagtcaac ataacaattc caagctgact ctagcagatc tccatgacgg cagagaaggt   240
actggaaaaa gaacttctgg cctggcagga gaaactgcat cagccgatta tcatcaccga   300
atacggcgtg gatacgttag ccgggctgca ctcaatgtac accgacatgt ggagtgaaga   360
gtatcagtgt gcatggctgg atatgtatca ccgcgtcttt gatcgcgtca gcgccgtcgt   420
cacaattcaa aacaagtttt at                                           442

SEQ ID NO: 230        moltype = DNA   length = 442
FEATURE               Location/Qualifiers
source                1..442
                      mol_type = other DNA
                      note = Recombinant
                      organism = synthetic construct
SEQUENCE: 230
ggtggaaacg gactcgagcg agagagactc tgcggaccgg gccagcatcg atgtattggt    60
agcccagaaa gcccacgcaa ccagacagag gtatgaatgt tgtgctttgt ggtgcttcag   120
tttagtccca cctcggcggt tttcagcgga agggagcaga gaaggcttat aaaagcagac   180
ctcagtcaac ataacaattc caagctgact ctagcagatc tccatgacgg cagagaaggt   240
actggaaaaa gaacttctgg cctggcagga gaaactgcat cagccgatta tcatcaccga   300
atacggcgtg gatacgttag ccgggctgca ctcaatgtac accgacatgt ggagtgaaga   360
gtatcagtgt gcatggctgg atatgtatca ccgcgtcttt gatcgcgtca gcgccgtcgt   420
cacaattcaa aacaagtttt at                                           442

SEQ ID NO: 231        moltype = DNA   length = 442
FEATURE               Location/Qualifiers
source                1..442
                      mol_type = other DNA
                      note = Recombinant
```

```
                         organism = synthetic construct
SEQUENCE: 231
tccctttgtc gccttgctgt tcgctccgtt tgttgggccg gacatgtggc tttctgggcc   60
gcgcacgtag agtcctcctg gccagtgtcg ggctctggct ggctgcctgc tcttttttct  120
gtagtcccaa accgcttgct gaggctaata tcagccggga acaacgctat ttaggattga  180
ctgaactctg tgtaagaggc caagctgact ctagcagatc tccatgacgg cagagaaggt  240
actggaaaaa gaacttctgg cctggcagga gaaactgcat cagccgatta tcatcaccga  300
atacggcgtg gatacgttag ccgggctgca ctcaatgtac accgacatgt ggagtgaaga  360
gtatcagtgt gcatggctgg atatgtatca ccgcgtcttt gatcgcgtca gcgccgtcgt  420
cacaattcaa aacaagtttt at                                           442

SEQ ID NO: 232          moltype = DNA   length = 442
FEATURE                 Location/Qualifiers
source                  1..442
                        mol_type = other DNA
                        note = Recombinant
                        organism = synthetic construct
SEQUENCE: 232
cctttgtggc ttcgcttcat tctcttcatc cgtttgtgac cggagtcagc ggctgtcgac   60
cgcggcgcat cctctgacta gcactgcgtc tggctggctc tggctgcttc agcttgcttt  120
agttcccaaa cccgcttgct gtagctaata ccagcaggga gcgctgctat ttaggatgga  180
ctgggcgctg cgagagaagc caagctgact ctagcagatc tccatgacgg cagagaaggt  240
actggaaaaa gaacttctgg cctggcagga gaaactgcat cagccgatta tcatcaccga  300
atacggcgtg gatacgttag ccgggctgca ctcaatgtac accgacatgt ggagtgaaga  360
gtatcagtgt gcatggctgg atatgtatca ccgcgtcttt gatcgcgtca gcgccgtcgt  420
cacaattcaa aacaagtttt at                                           442

SEQ ID NO: 233          moltype = DNA   length = 442
FEATURE                 Location/Qualifiers
source                  1..442
                        mol_type = other DNA
                        note = Recombinant
                        organism = synthetic construct
SEQUENCE: 233
ggccttcgct tcctcgctct tcgctccttt gttgggccgg acaacaagcg gctgtctggg   60
ccgcgcacgc agtcctctgg tccagtgggc aactgcctct ggctgcttgc tcttttcctt  120
aatcccaaac cgctcgatga agctaatacc agctggggg cgctgctatt taggagagac  180
taagcgccac ccgtagatgc caagctgact ctagcagatc tccatgacgg cagagaaggt  240
actggaaaaa gaacttctgg cctggcagga gaaactgcat cagccgatta tcatcaccga  300
atacggcgtg gatacgttag ccgggctgca ctcaatgtac accgacatgt ggagtgaaga  360
gtatcagtgt gcatggctgg atatgtatca ccgcgtcttt gatcgcgtca gcgccgtcgt  420
cacaattcaa aacaagtttt at                                           442

SEQ ID NO: 234          moltype = DNA   length = 442
FEATURE                 Location/Qualifiers
source                  1..442
                        mol_type = other DNA
                        note = Recombinant
                        organism = synthetic construct
SEQUENCE: 234
ttcgcttcat ttctcttcac tccgtttgtt gggccggaca tcaagcggct gtctgggccg   60
cgcacgcagt cctcttgact agcactgcgt ctggctggct ctggctgctt cagctttgct  120
ttagttccaa accgcttgct gtagctaata ccagcaggga gcgctgctat ttaggatgga  180
ctgggcgctg cgagagaagc caagctgact ctagcagatc tccatgacgg cagagaaggt  240
actggaaaaa gaacttctgg cctggcagga gaaactgcat cagccgatta tcatcaccga  300
atacggcgtg gatacgttag ccgggctgca ctcaatgtac accgacatgt ggagtgaaga  360
gtatcagtgt gcatggctgg atatgtatca ccgcgtcttt gatcgcgtca gcgccgtcgt  420
cacaattcaa aacaagtttt at                                           442

SEQ ID NO: 235          moltype = DNA   length = 427
FEATURE                 Location/Qualifiers
source                  1..427
                        mol_type = other DNA
                        note = Recombinant
                        organism = synthetic construct
SEQUENCE: 235
ggcgtatgtg ccaaaaactt cgtcacagag agggccataa gaaacatggc ccacggccca   60
atacgaagca ccgcgacgaa gcccaaacag cagtccgtag gtggagcaaa gcgctgggta  120
atacgcaaac gttttgtccc accttgacta atcacaagg tggagcgtac cttataaacc  180
gagccgcaag caccgaattc aagctgactc tagcagatct ccatgacggc agagaaggta  240
ctggaaaaag aacttctggc ctggcaggag aaactgcatc agccgattat catcaccgaa  300
tacggcgtgg atacgttagc cgggctgcac tcaatgtaca ccgacatgtg gagtgaagag  360
tatcagtgtg catggctgga tatgtatcac cgcgtctttg atcgcgtcag cgccgtcgtc  420
tttttttt                                                           427

SEQ ID NO: 236          moltype = DNA   length = 428
FEATURE                 Location/Qualifiers
source                  1..428
                        mol_type = other DNA
```

-continued

```
                        note = Recombinant
                        organism = synthetic construct
SEQUENCE: 236
gcgtggtctg ctttttcgca tgatatctgg gccgcaccaa agaatccagc ccacgcggcg    60
tggcgccgtc gttacggctt gcgggggaag gaaacgaggg acgaaccgag atttagcacc   120
agaccggcca gcgagcattg cagacaccgg cttataagtt cagctgcgac taccactccg   180
ggaggtccga gttccactcg caagctgact ctagcagatc tccatgacgg cagagaaggt   240
actggaaaaa gaacttctgg cctggcagga gaaactgcat cagccgatta tcatcaccga   300
atacggcgtg gatacgttag ccgggctgca ctcaatgtac accgacatgt ggagtgaaga   360
gtatcagtgt gcatggctgg atatgtatca ccgcgtcttt gatcgcgtca gcgccgtcgt   420
cttttttt                                                           428

SEQ ID NO: 237          moltype = DNA  length = 21
FEATURE                 Location/Qualifiers
source                  1..21
                        mol_type = other DNA
                        note = Recombinant
                        organism = synthetic construct
SEQUENCE: 237
acaattcaaa acaagtttta t                                              21

SEQ ID NO: 238          moltype = DNA  length = 4622
FEATURE                 Location/Qualifiers
source                  1..4622
                        mol_type = other DNA
                        note = Recombinant
                        organism = synthetic construct
SEQUENCE: 238
atgggatcta agaagagaag aattaaacaa gatatgagtg acctggtgct agggttggct    60
ataggcattg gctccgtggg ggttggcatt cttaataagg tgaccggcga aataattcat   120
aaaaactcac gcatctttcc agcagcccga gctgagaaca atctggtccg tagaaccaac   180
cggcagggtc gaaggttagc caggcgcaag aagcacagac gggtccggct caacaggctt   240
ttcgaggagt ctggtttgat caccgatttc actaagattt ctatcaacct gaatccttat   300
cagctgcgcg ttaaaggtct cacagacgaa cttagcaacg aagagttgtt catcgccctg   360
aaaaatatgg tcaagcatcg cggcattagc tacctggacg acgcttcgga tgatggcaac   420
agtagtgtag gtgactacgc tcagatcgtg aaagagaact cgaagcaatt gggagaccaag   480
accccgggcc aaattcaact cgaaaggtaa gtttctgctt ctacctttga tatatatata   540
ataattatca ttaattagta gtaatataat atttcaaata tttttttcaa aataaaagaa   600
tgtagtatat agcaattgct tttctgtagt ttataagtgt gtatatttta atttataact   660
tttctaatat atgaccaaaa tttgttgatg tgcaggtacc agacgtatgg acagttacga   720
ggcgatttta ccgttgaaaa ggatggtaag aagcacaggc tgattaatgt gtttccgacc   780
tcagcttatc gctctgaggc gctgcgtatt ttgcagaccc aacaggaatt taacccgcaa   840
ataacggacg agttcataaa ccgatactta gagattctta caggtaaacg taaatactat   900
cacggcccag gaaatgaaaa gtccaggaca gattatggtc gatatcgcac ttccggagag   960
actctcgaca atatctttgg cattcttata ggcaaatgta ccttctaccc tgacgaattt  1020
agagcagcga aggcttcata tacagcacaa gagtttaatc ttctcaacga cctcaacaac  1080
ttgactgtgc ctactgaaac caaaaagctt agcaaggagc aaaaaaatca aatcattaac  1140
tatgttaaga atgagaaagc tatgggggccc gcaaaattgt tcaagtacat agctaagtta  1200
cttagctgtg acgttgctga tattaagggt taccgtattg acaagtctgg taaagctgaa  1260
attcacacct ttgaggctta taggaagatg aagacccttg agacacttga cattgagcag  1320
atggataggg agactttgga caaactggca tacgtcttga cattgaacac cgaaagggaa  1380
ggcatccagg aagctctgga acatgaattt gcagatggtt cgttcagcca aaaacaggtt  1440
gacgagctgg tccaatttag aaaaggcaaac tcaagcatat tcggtaaagg ttggcacaac  1500
ttcagcgtta agctgatgat ggaactcatt ccagaattat atgaaacctc tgaggaacag  1560
atgacgattc tcacaagatt gggtaagcag aaaacaacca gctctagcaa taagactaaa  1620
tacattgacg aaaagctcct caccgaagag atttataacc cggtcgtggc aaagagtgta  1680
cggcaagcca tcaagatcgt taatgccgct atcaaggagt atggtgattt tgataatatt  1740
gtgattgaaa tggcacgcga gactaacgag gacgacgaga agaaagctat acagaagatt  1800
caaaaggcta ataaggacga gaaggacgcc gcaatgctaa aggcggccaa tcaatataat  1860
gggaaggctg aactacctca tagcgtcttc catggacata agcaattagc aactaaaata  1920
agattatggc accagcaagg cgaacggtgt ctttatacag gtaaaacgat atctattcac  1980
gacctgatta caactctaa ccagtttgaa gtggatgcta tcttaccact aagtatcacc  2040
ttcgacgatt cacttgctaa caaggtgctc gtttacgcca ctgcgaacca agagaaaggg  2100
cagaggactc cataccaggc ccttgacagc atggcagac cctggagttt tagggaatta  2160
aaagctttcg tacgtgagtc aaagacgctt tcaaataaaa aaaaggagta cttgctcact  2220
gaagaagaca tctcaaaatt cgacgtgcgc aaaaaattca ttgagcggaa cttagtcgac  2280
actcggtacg catcaagagt agtgttgaac gccctccagg agcactttag ggcacataag  2340
atcgacacca aggtttcagt tgttaggggt cagtttacat cgcagcttag acgccattgg  2400
ggtatagaaa aaacacgtga tacctaccat caccatgcag ttgacgctct catcattgca  2460
gcatcttctc aacttaattt gtggaaaaag caaaagaaca ctctggtctc atatagcgaa  2520
gatcagctgc ttgatattga aaccggcgag ctgatttctg acgacgaata caagaatct  2580
gtgtttaagg caccatatca acacttttgta gacacgctta aatctaaaga gtttgaggat  2640
tcgatccttt tcagttacca agtcgactca aaatttaacc gtaagatctc tgatgcaaca  2700
atttatgcga cgaggcaggc caaggtaggt aaggataagg ctgacgaaac ctacgtgctc  2760
ggaaaaatca aagatatta cactcaagat ggatatgatg cattcatgaa gatatataaa  2820
aaggacaaat ctaaattcct tatgtatcgt catgacccac agacattcga gaagttatt  2880
gagcctatcc tggagaacta tccgaacaag caaataaatg agaagggcaa agaagttcca  2940
tgtaatccgt tcctaaagta caagaggaa cacggatata ttagaaaata cagcaaaaag  3000
ggcaacggcc cagaaatcaa aagccttaag tactacgata gtaaactagg aaaccacatc  3060
```

```
gacattacac caaaagactc taataataag gtcgtactgc aaagcgtttc cccatggcgc   3120
gccgatgtgt attttaataa gacaacaggg aagtacgaaa tcttggggtt aaaatatgcg   3180
gatctgcaat tcgaaaaggg aaccggcaca tacaaaattt ctcaagaaaa gtacaacgac   3240
ataaagaaga aggaaggggt cgattctgat tctgaattca agttcacact ctataagaat   3300
gatcttctgc tcgtcaagga cacagagaca aaggagcagc agttgttcag gttcttgtct   3360
agaactatgc caaaacaaaa gcactacgtt gaactgaagc cttacgataa gcaaaaattc   3420
gagggggggcg aggcgcttat aaaggtccta ggaaatgttg caaactctgg gcagtgtaag   3480
aagggcctgg gcaagagcaa cattagcatc tataaggttc gaacggatgt gcttgggaac   3540
cagcatatca tcaaaaacga gggagataaa ccaaagctgg acttcggatc ttctattgtg   3600
gcgcagctct caagaaggga cccggcgcta gcggctctga ctaatgacca tctcgtggtg   3660
ctggcttgcc tgggggggcg gcctgctctg gacgctgtga agaaggggct cccacacgct   3720
ccagagttca tccgcagggt gaacaggagg attgctgagc ggacaagcca cagggtcgct   3780
gactacgctc atgtggtccg cgttctggag ttcttccagt gccactcgca tccggctcac   3840
gccttcgatg aggccatgac ccagttcggc atgtctcggc atgggctggt ccagctcttc   3900
aggcggggttg gcgtgactga gttcgaggct cgctacggga ccctgccacc agcgtcccag   3960
cgctgggaca ggatcctcca ggcgagcggc atgaagaggg ctaagccaag ccctacctcg   4020
gctcagacgc agaccagac atctctccac gcgttcgctg attcactgga gagggacctc   4080
gatgctccat ccccaatgca tgagggcgac cagaccagg cgtccagccg caagaggtca   4140
cggtccgata gggctgtgac ggggccatcg gctcagcagg ctgtcgaggt tagggtgcct   4200
gagcagaggg acgctctcca cctgccactc tcctggaggg tcaagcgccc taggacgagg   4260
atctggggcg ggctgccaga ccctggcaca ccgattgccg cggatctcgc tgcctcgtct   4320
actgttatgt gggagcagga cgctgctcca ttcgctgcgg ctgctgacga tttcccagcc   4380
ttcaatgagg aggagctggc ttggctgatg gagctgctgc ctcagtcggg gtcggttggc   4440
gggacaatcg ctgccgacct ggcggcttcg tctaccgtca tgtgggagca ggacgccgcg   4500
ccgttcgctg gcgctgccga cgatttccct gcgttcaacg aggaggagct ggcgtggctg   4560
atggagctgc tgcccagag cgggagcgtc ggcgggacaa tctgaagcag aacacgcgct   4620
ga                                                                  4622
```

```
SEQ ID NO: 239          moltype = AA  length = 1471
FEATURE                 Location/Qualifiers
source                  1..1471
                        mol_type = protein
                        note = Recombinant
                        organism = synthetic construct
SEQUENCE: 239
MGSKKRRIKQ DMSDLVLGLA IGIGSVGVGI LNKVTGEIIH KNSRIFPAAQ AENNLVRRTN   60
RQGRRLARRK KHRRVRLNRL FEESGLITDF TKISINLNPY QLRVKGLTDE LSNEELFIAL   120
KNMVKHRGIS YLDDASDDGN SSVGDYAQIV KENSKQLETK TPGQIQLERY QTYGQLRGDF   180
TVEKDGKKHR LINVFPTSAY RSEALRILQT QQEFNPQITD EFINRYLEIL TGKRKYYHGP   240
GNEKSRTDYG RYRTSGETLD NIFGILIGKC TFYPDEFRAA KASYTAQEFN LLNDLNNLTV   300
PTETKKLSKE QKNQIINYVK NEKAMGPAKL FKYIAKLLSC DVADIKGYRI DKSGKAEIHT   360
FEAYRKMKTL ETLDIEQMDR ETLDKLAYVL TLNTEREGIQ EALEHEFADG SFSQKQVDEL   420
VQFRKANSSI FGKGWHNFSV KLMMELIPEL YETSEEQMTI LTRLGKQKTT SSSNKTKYID   480
EKLLTEEIYN PVVAKSVRQA IKIVNAAIKE YGDFDNIVIE MARETNEDDE KKAIQKIQKA   540
NKDEKDAAML KAANQYNGKA ELPHSVFHGH KQLATKIRLW HQQGERCLYT GKTISIHDLI   600
NNSNQFEVDA ILPLSITFDD SLANKVLVYA TANQEKGQRT PYQALDSMDD AWSFRELKAF   660
VRESKTLSNK KKEYLLTEED ISKFDVRKKF IERNLVDTRY ASRVVLNALQ EHFRAHKIDT   720
KVSVVRGQFT SQLRRHWGIE KTRDTYHHHA VDALIIAASS QLNLWKKQKN TLVSYSEDQL   780
LDIETGELIS DDEYKESVFK APYQHFVDTL KSKEFEDSIL FSYQVDSKFN RKISDATIYA   840
TRQAKVGKDK ADETYVLGKI KDIYTQDGYD AFMKIYKKDK SKFLMYRHDP QTFEKVIEPI   900
LENYPNKQIN EKGKEVPCNP FLKYKEEHGY IRKYSKKGNG PEIKSLKYYD SKLGNHIDIT   960
PKDSNNKVVL QSVSPWRADV YFNKTTGKYE ILGLKYADLQ FEKGTGTYKI SQEKYNDIKK  1020
KEGVDSDSEF KFTLYKNDLL LVKDTETKEQ QLFRFLSRTM PKQKHYVELK PYDKQKFEGG  1080
EALIKVLGNV ANSGQCKKGL GKSNISIYKV RTDVLGNQHI IKNEGDKPKL DFGSSIVAQL  1140
SRRDPALAAL TNDHLVALAC LGGRPALDAV KKGLPHAPEF IRRVNRRIAE RTSHRVADYA  1200
HVVRVLEFFQ CHSHPAHAFD EAMTQFGMSR HGLVQLFRRV GVTEFEARYG TLPPASQRWD  1260
RILQASGMKR AKPSPTSAQT PDQTSLHAFA DSLERDLDAP SPMHEGDQTR ASSRKRSRSD  1320
RAVTGPSAQQ AVEVRVPEQR DALHLPLSWR VKRPRTRIWG GLPDPGTPIA ADLAASSTVM  1380
WEQDAAPFAG AADDFPAFNE EELAWLMELL PQSGSVGGTI AADLAASSTV MWEQDAAPFA  1440
GAADDFPAFN EEELAWLMEL LPQSGSVGGT I                                1471
```

```
SEQ ID NO: 240          moltype = DNA  length = 27
FEATURE                 Location/Qualifiers
source                  1..27
                        mol_type = other DNA
                        note = Recombinant
                        organism = synthetic construct
SEQUENCE: 240
ggaggtccga gttccactcg caagaat                                       27
```

```
SEQ ID NO: 241          moltype = DNA  length = 353
FEATURE                 Location/Qualifiers
source                  1..353
                        mol_type = other DNA
                        note = Recombinant
                        organism = synthetic construct
SEQUENCE: 241
ggcgtatgtg ccaaaaactt cgtcacagag agggccataa gaaacatggc ccacggccca   60
atacgaagca ccgcgacgaa gcccaaacag cagtccgtag gtggagcaaa cgctgggta  120
```

```
atacgcaaac gttttgtccc accttgacta atcacaagag tggagcgtac cttataaacc  180
gagccgcaag caccgaattg ggaggtccga gttccactcg gttattgtac tctcaagatt  240
tattttttcca aaagggttac ttaaatcttg cagaagctac aaagataagg cttcatgccg  300
aaatcaacac cctgtcattt tatggcaggg tgttttcgtt atttaatttt ttt          353

SEQ ID NO: 242              moltype = DNA   length = 350
FEATURE                    Location/Qualifiers
source                     1..350
                           mol_type = other DNA
                           note = Recombinant
                           organism = synthetic construct
SEQUENCE: 242
tttcatccgg cctgtgatgg aaattgtgct gcaaagtgcg cagggccgtt ggcccgacga  60
caagtatttt tcgtcgagag aagcaacgaa agcccactcc tccaagccac ccttcgctca  120
agtcatattt agcaccacct cggcagtcga cactgcagca caccaactta aatattcatc  180
ccgatctccc tcactcggga ggtccgagtt ccactcggtt attgtactct caagatttat  240
ttttccaaaa gggttactta aatcttgcag aagctacaaa gataaggctt catgccgaaa  300
tcaacaccct gtcattttat ggcagggtgt tttcgttatt taattttttt              350

SEQ ID NO: 243              moltype = DNA   length = 360
FEATURE                    Location/Qualifiers
source                     1..360
                           mol_type = other DNA
                           note = Recombinant
                           organism = synthetic construct
SEQUENCE: 243
aacggactcg agcgagagag actctgcgga ccgggccagc atcgatgtat ttggtagccc  60
agagcccacg caaccagaca gaggtatgaa tgttgtgctt tgtggtgctt cagtttagtc  120
ccacctcggc ggttttcagc ggaagggagc agagaaggct tataaaagca gacctcagtc  180
aacataacaa ttaggaggtc cgagttccac tcggttattg tactctcaag atttattttt  240
ccaaaagggt tacttaaatc ttgcagaagc tacaaagata aggcttcatg ccgaaatcaa  300
caccctgtca ttttatggca gggtgttttc gttatttaat caaattcaaa tttttttttaa  360

SEQ ID NO: 244              moltype = DNA   length = 373
FEATURE                    Location/Qualifiers
source                     1..373
                           mol_type = other DNA
                           note = Recombinant
                           organism = synthetic construct
SEQUENCE: 244
aggcgttcgc ttcatttctc ttcactccgt ttgttgggcc ggacatcaag cggctgtctg  60
ggccgcgcac gcagtcctct tgactagcac tgcgtctggc tggctctggc tgcttcagct  120
ttgctttagt tccaaaccgc ttgctgtagc taataccagc agggagcgct gctatttagg  180
atggactggg cgctgcgaga gaagcaggag gtccgagttc cactcggtta ttgtactctc  240
aagatttatt tttccaaaag ggttacttaa atcttgcaga agctacaaag ataaggcttc  300
atgccgaaat caacaccctg tcattttatg gcagggtgtt ttcgttattt aatcaaattc  360
aaatttttttt taa                                                     373

SEQ ID NO: 245              moltype = DNA   length = 348
FEATURE                    Location/Qualifiers
source                     1..348
                           mol_type = other DNA
                           note = Recombinant
                           organism = synthetic construct
SEQUENCE: 245
caataagata aagctggtgc aggctctcga cctgaagccc acacactgga gagcaacgat  60
ataccagaat ggagcggccc agtacacgat ctgctgggat tgctggccag tggccagtcc  120
cgcagccgat tagcaccacc tcggtggcac agacgaacga acgctaattt aaaagcttag  180
ctctggagct tggcaggagg tccgagttcc actcggttat tgtactctca agatttattt  240
ttccaaaagg gttacttaaa tcttgcagaa gctacaaaga taaggcttca tgccgaaatc  300
aacaccctgt cattttatgg cagggtgttt tcgttattta atttttttt                348

SEQ ID NO: 246              moltype = DNA   length = 3131
FEATURE                    Location/Qualifiers
source                     1..3131
                           mol_type = other DNA
                           note = Recombinant
                           organism = synthetic construct
SEQUENCE: 246
gaattcctat gataaagttg ctctgtaaca gaaaacacca tctaggtcga cttacttgcg  60
gccgcttact tggcgcgccg gaggtccgag ttccactcgc aagaatttgc ttcttgggag  120
gtccgagttc cactcgcaag aatcctctca ttaggaggtc cgagttccac tcgcaagaat  180
attattcgca gacccttcc tctatataag gaagttcatt tcatttggag aggacacgct  240
gaaatcacca gtctctctct acaaatctat ctctctctat tttccggacc gaccgtcttc  300
ggtacgcgct cactccgccc tctgcctttg ttactgccac gtttctctga atgctctctt  360
gtgtggtgat tgctgagagt ggtttagctg gatctagaat tacactctga aatcgtgttc  420
tgcctgtgct gattacttgc cgtcctttgt agcagcaaaa tatagggaca tggtagtacg  480
aaacgaagat agaacctaca cagcaatacg agaaatgtgt aatttggtgc ttagcggtat  540
ttatttaagc acatgttggt gttataggggc acttggattc agaagtttgc tgttaattta  600
```

```
ggcacaggct tcatactaca tgggtcaata gtatagggat tcatattata ggcgatacta    660
taataatttg ttcgtctgca gagcttatta tttgccaaaa ttagatattc ctattctgtt    720
tttgtttgtg tgctgttaaa ttgttaacgc ctgaaggaat aaatataaat gacgaaattt    780
tgatgtttat ctctgctcct ttattgtgac cataagtcaa gatcagatgc acttgtttta    840
aatattgttg tctgaagaaa taagtactga cagtattttg atgcattgat ctgcttgttt    900
gttgtaacaa aatttaaaaa taaagagttt ccttttttgtt gctctcctta cctcctgatg    960
gtatctagta tctaccaact gacactatat tgcttctctt tacatacgta tcttgctcga   1020
tgccttctcc ctagtgttga ccagtgttac tcacatagtc tttgctcatt tcattgtaat   1080
gcagatacca agcgggtac cctcagcgct gtgcctgttg cgatcgcacc atggtccgtc   1140
ctgtagaaac cccaacccgt gaaatcaaaa aactcgacgg cctgtgggca ttcagtctgg   1200
atcgcgaaaa ctgtggaatt gatcagcgtt ggtgggaaag cgcgttacaa gaaagccggg   1260
caattgctgt gccaggcagt tttaacgatc agttcgccga tgcagatatt cgtaattatg   1320
cgggcaacgt ctggtatcag cgcgaagtct ttataccgaa aggttgggca ggccagcgta   1380
tcgtgctgcg tttcgatgcg gtcactcatt acggcaaagt gtgggtcaat aatcaggaag   1440
tgatggagca tcagggcggc tatacgccat ttgaagccga tgtcacgccg tatgttattg   1500
ccgggaaaag tgtacgtaag tttctgcttc tacctttgat atatatataa taattatcat   1560
taattagtag taatataata tttcaaatat tttttttcaaa ataaaagaat gtagtatata   1620
gcaattgctt ttctgtagtt tataagtgtg tatattttaa tttataactt ttctaatata   1680
tgaccaaaat ttgttgatgt gcaggtatca ccgtttgtgt gaacaacgaa ctgaactggc   1740
agactatccc gccgggaatg gtgattaccg acgaaaacgg caagaaaaag cagtcttact   1800
tccatgattt cttttaactat gccggaatcc atcgcagcgc aatgctctac accacgccga   1860
acacctgggt ggacgatatc accgtggtga cgcatgtcgc gcaagactgt aaccacgcgt   1920
ctgttgactg gcaggtggtg gccaatggtg atgtcagcgt tgaactgcgt gatgcggatc   1980
aacaggtggt tgcaactgga caaggcacta gcgggacttt gcaagtggtg aatccgcacc   2040
tctggcaacc gggtgaaggt tatctctatg aactgtgcgt cacagccaaa agccagacag   2100
agtgtgatat ctacccgctt cgcgtcggca tccggtcagt ggacgaagag ggcgaacagt   2160
tcctgattaa ccacaaaccg ttctacttta ctggctttgg tcgtcatgaa gatgcggact   2220
tgcgtggcaa aggattcgat aacgtgctga tggtgcacga ccacgcatta atggactgga   2280
ttggggccaa ctcctaccgt acctcgcatt acccttacgc tgaagagatg ctcgactggg   2340
cagatgaaca tggcatcgtg gtgattgatg aaactgctgc tgtcggcttt aacctctctt   2400
taggcattgg tttcgaagcg ggcaacaagc cgaaagaact gtacagcgaa gaggcagtca   2460
acggggaaac tcagcaagcg cacttacagg cgattaaaga gctgatagcg cgtgacaaaa   2520
accacccaag cgtggtgatg tggagtattg ccaacgaacc ggatacccgt ccgcaaggtg   2580
cacggaaata tttcgcgcca ctggcggaag caacgcgtaa actcgacccg acgcgtccga   2640
tcacctgcgt caatgtaatg ttctgcgacg ctcacaccga taccatcagc gatctctttg   2700
atgtgctgtg cctgaaccgt tattacggat ggtatgtcca aagcggcgat ttggaaacgg   2760
cagagaaggt actggaaaaa gaacttctgg cctggcagga gaaactgcat cagccgatta   2820
tcatcaccga atacggcgtg gatacgttag ccgggctgca ctcaatgtac accgacatgt   2880
ggagtgaaga gtatcagtgt gcatggctag atatgtatca ccgcgtcttt gatcgcgtca   2940
gcgccgtcgt cggtgaacag gtatggaatt cgccgatttt gcgacctcg caaggcatat   3000
tgcgcgttgg cggtaacaag aaagggatct tcactcgcga ccgcaaaccg aagtcggcgg   3060
cttttctgct gcaaaaacgc tggactggca tgaacttcgg tgaaaaaccg cagcagggag   3120
gcaaacaatg a                                                         3131
```

```
SEQ ID NO: 247             moltype = DNA  length = 200
FEATURE                    Location/Qualifiers
source                     1..200
                           mol_type = genomic DNA
                           organism = Glycine max
SEQUENCE: 247
atccaagcaa aatacttgga agatacgaaa gtgtttgaaa tcagttatta gtttcacgtt    60
tgataaaatt gctgatttaa attttttgact gttgctctcg gctaggaatg ttgcaagcga   120
agaagtccca catttgtcag aacattggca ggcagctgaa gctcactgta taaaaatgga   180
gtacttggat agttgaaagc                                                200
```

```
SEQ ID NO: 248             moltype = DNA  length = 200
FEATURE                    Location/Qualifiers
source                     1..200
                           mol_type = genomic DNA
                           organism = Glycine max
SEQUENCE: 248
acttgtttga actcaattat tagtctcaag ttcgaagaat attggataaa ctcaactgcc    60
gatttaaatt tgaaaatgtt gttcttgtgt agagatttta ggagcatctg acaccagtga   120
caaagtccca catttgtcag aacactgaca atcagctaat gctgacagta taaaagtgga   180
gtacttggaa ggttgaaagc                                                200
```

```
SEQ ID NO: 249             moltype = DNA  length = 200
FEATURE                    Location/Qualifiers
source                     1..200
                           mol_type = genomic DNA
                           organism = Glycine max
SEQUENCE: 249
aacgtgtttg aactcaatta ttagtctcaa gtttgaagag tactggataa actcaactgc    60
tgcattaaat ttgaaactgt tagttcttgt ttggagattt tagaagcatc ttacacaagt   120
cagagcccca cattcgtcag aacactgaca agcagctaat gctcacagta taaaagttga   180
atacttagac gtttcaaagc                                                200
```

```
SEQ ID NO: 250             moltype = DNA  length = 200
FEATURE                    Location/Qualifiers
```

```
source                    1..200
                          mol_type = genomic DNA
                          organism = Glycine max
SEQUENCE: 250
tagttatctg gtttcgttaa ttgtggttga agcctgaagg catccattat ccctaactat    60
cctggatggt tgcaaatact gtcctaagta ctacagaaac aagaagactg acagtgtaac   120
gaagtaccac gtctctcaag agaaataaca agcgttgaag actaaactat aaataaaaac   180
attatttcat tgtacaaagc                                               200

SEQ ID NO: 251            moltype = DNA   length = 200
FEATURE                   Location/Qualifiers
source                    1..200
                          mol_type = genomic DNA
                          organism = Glycine max
SEQUENCE: 251
aaataaaccc gttgaatgaa tggaccgaag acaatctgaa tccaaaaaag atagctatca    60
ttgcttgtga ttgaactggc tcatgctctg catccgaaca aaacttggag acacttataa   120
cgaagtccca cattgctgag atgagataac actcgcttca gatttttatta taaaaaacgc   180
attacatatt gtggaaactc                                               200

SEQ ID NO: 252            moltype = DNA   length = 200
FEATURE                   Location/Qualifiers
source                    1..200
                          mol_type = genomic DNA
                          organism = Glycine max
SEQUENCE: 252
attaattgtg gatgatggca tccattatcc gtggtatttg ttagacttgg atggttgctg    60
gtcgaccaaa caaatactgt cctaaggact acaaaaacaa gaagactgac agtgcaacaa   120
agtatccact cattcaagag aaataacaag cgctaaagac taaactttta aaaaaaatgc   180
attattccat tgttcaaagc                                               200

SEQ ID NO: 253            moltype = DNA   length = 200
FEATURE                   Location/Qualifiers
source                    1..200
                          mol_type = genomic DNA
                          organism = Glycine max
SEQUENCE: 253
tgttaattgt gtttgaggac atccattatc caacattaga acaagatttg ttagacttgg    60
atagttgcta atcgagaagt cccagcaaat actacagaaa ctagaaagct attgatgtaa   120
tgaagtccca catcgctcaa gagaaataac aagcactgaa gactgaagta taaaacaagc   180
attatttcat tgtgcaaagc                                               200

SEQ ID NO: 254            moltype = DNA   length = 200
FEATURE                   Location/Qualifiers
source                    1..200
                          mol_type = genomic DNA
                          organism = Glycine max
SEQUENCE: 254
atgaatggaa cggcttgagt ttcgctcaac tgcaggaaaa tgtggattgc agacaatctg    60
aatcccaaaa agatagttat ccttgcttgt tatcagaact agacttggac acacttatta   120
cgatggccca tatcgcttag atgagataac actcgcttca gatttttatta taaaaaatgc   180
attgtatgtt gtgtaaactc                                               200

SEQ ID NO: 255            moltype = DNA   length = 200
FEATURE                   Location/Qualifiers
source                    1..200
                          mol_type = genomic DNA
                          organism = Glycine max
SEQUENCE: 255
gtttcatgat tccgatcaaa gcaagagcat ccagtctcaa ttttgtcttc tcaattcact    60
cattcatcaa aatcagcagt tttatgcatc aacaagcatg gaatgttgaa ccacccatga   120
ttaagcccca tatcgttgtg ttgagataac tatcacctga agttgtctta taaaaaacac   180
atctgaatac ttttataatc                                               200

SEQ ID NO: 256            moltype = DNA   length = 200
FEATURE                   Location/Qualifiers
source                    1..200
                          mol_type = genomic DNA
                          organism = Glycine max
SEQUENCE: 256
agtaaaatat caacgggaag attataatgt gtttgaactt tcattagtct cagatttgaa    60
cttttatgtt gctgatctaa atttttaacc atgttgctct tggctaggat gttgggatga   120
attagtccca catttgtcag aactttgtca ggaagctgaa gctcccagta taaaatttga   180
atacttacat tgtacaaagc                                               200

SEQ ID NO: 257            moltype = DNA   length = 200
FEATURE                   Location/Qualifiers
source                    1..200
                          mol_type = genomic DNA
```

```
                                   organism = Glycine max
SEQUENCE: 257
attcactcat tttcagaatt atcagtgtgt ctacactcta cactctacac tcagaaacaa      60
gcttgaaaca ttggtgccca ttgtcgaaga ctccatggct aagtcaaatt gtcaccatga     120
ctaagtccca tatcgattag aagagaggac aatcactcca gagcttatta taaaacagac     180
attataacac cgttgtactc                                                 200

SEQ ID NO: 258               moltype = DNA   length = 200
FEATURE                      Location/Qualifiers
source                       1..200
                             mol_type = genomic DNA
                             organism = Glycine max
SEQUENCE: 258
tgtggctgaa ggcatcaatt atccatagtt agaacaaaga tttgttagac atggatagtt      60
gctggtcgac caaacaaata ctgtcctaag gactacaaaa caagaagacc ttcagtgtaa     120
cgaagtccca cattgcgcaa gagaaataac aagcactgaa gactgaagta taaaaacaac     180
attatttcat tgaacaaatc                                                 200

SEQ ID NO: 259               moltype = DNA   length = 200
FEATURE                      Location/Qualifiers
source                       1..200
                             mol_type = genomic DNA
                             organism = Glycine max
SEQUENCE: 259
agtaaaatat caacgggaag attataatgt gtttgaactt ttattagtct caggtttgaa      60
cttttatgtt gctgatctaa atttttaacc atgttgctct tggctaggat gttgggatga     120
attagtccca catttgtcag aactttgtca ggcagctgaa gctcccagta taaaatttga     180
atacctacaa tgtacaaagc                                                 200

SEQ ID NO: 260               moltype = DNA   length = 200
FEATURE                      Location/Qualifiers
source                       1..200
                             mol_type = genomic DNA
                             organism = Glycine max
SEQUENCE: 260
agtaaaatat caacgggaag attataatgt gtttgaactt ttattagtct caggtttgaa      60
cttttatgtt gctgatctaa atttttaacc atgttgctct tggctaggat gttgggatga     120
attagtccca catttgtcag gactttgtca ggcagctgaa gctcccagta taaaatttga     180
atacttacat tgtacaaagc                                                 200

SEQ ID NO: 261               moltype = DNA   length = 200
FEATURE                      Location/Qualifiers
source                       1..200
                             mol_type = genomic DNA
                             organism = Glycine max
SEQUENCE: 261
ggtgccccat ctggtggcag cagagtattg taatgtgggt gtttggagac tggagtgtcc      60
atggatttct gtacggagaa atggaagatt taacacataa gggtgcgcgt tgaagtacta     120
atatggccca tatcgtttag aagagataga aataactcta tatcttatta taaaagaaga     180
ttttgaagcc atgtatactc                                                 200

SEQ ID NO: 262               moltype = DNA   length = 200
FEATURE                      Location/Qualifiers
source                       1..200
                             mol_type = genomic DNA
                             organism = Glycine max
SEQUENCE: 262
tgttcatgga tttgttctgt gtggagaaat tattgatcgt cacaactaca ttttctagac      60
tctgctttgc cattgtagta gaggaattac tgtttctctg ttccaggcgt tacaagtata     120
aacagtccca tatcgtttag aagagataga aataactcta tatcttatta taaaagaaga     180
ttttgaagca tagcaaactc                                                 200

SEQ ID NO: 263               moltype = DNA   length = 200
FEATURE                      Location/Qualifiers
source                       1..200
                             mol_type = genomic DNA
                             organism = Glycine max
SEQUENCE: 263
gttatagggg tttagcatta atccagatgg gttgtgaaat atgcaagtgt aagtgtaatc      60
taattaggat acgttataga cacaaaggtc acttgatgtt caatgtggaa ccacccatga     120
gtgagtccca catcgctgag ttaagataag aatcacctga agtttttatta taaaacaaac     180
gtttcaacag ttaaaaattc                                                 200

SEQ ID NO: 264               moltype = DNA   length = 200
FEATURE                      Location/Qualifiers
source                       1..200
                             mol_type = genomic DNA
                             organism = Glycine max
SEQUENCE: 264
```

-continued

```
ttttgcagga atcaggataa tggaagaatg aagaaaagat atagagacgt agaggttgaa    60
gagaaggtag tagcagaaaa tccaagttct tatgtatgtt ggcgcttaac tccttattgc   120
ccaagtccca caccggcgat gagaaagaat ctgcgccaaa gacttggcta taaaacaaac   180
aatccttgaa attcttaagc                                               200

SEQ ID NO: 265          moltype = DNA   length = 200
FEATURE                 Location/Qualifiers
source                  1..200
                        mol_type = genomic DNA
                        organism = Glycine max
SEQUENCE: 265
ggtttggact ctgtacgcac tgtcacatcc taaataagaa aacacatttc gaagaaagac    60
cggatattag aagaattaac atttcaaatt gttactattg caacagcaac gtagtcgcca   120
aagagtccca catcagtcag tcaagaaagc agtagaacta gtaacagaaa taaaagcaac   180
aacaatatac tgatcaaagc                                               200

SEQ ID NO: 266          moltype = DNA   length = 200
FEATURE                 Location/Qualifiers
source                  1..200
                        mol_type = genomic DNA
                        organism = Glycine max
SEQUENCE: 266
ctatgtaaca agtacaattt cacagacccg gtgttgttct ggtcttttga gaagtggtat    60
tgtattgtgc agaatgcatg agttatgtag aaacaagctt gccctgaaga gctatcctac   120
ctaagtccca cactggtaag gagaaagaat atgcaaaaat agtttgacta taaaagaaac   180
agtctatgat agaacaaatc                                               200

SEQ ID NO: 267          moltype = DNA   length = 200
FEATURE                 Location/Qualifiers
source                  1..200
                        mol_type = genomic DNA
                        organism = Glycine max
SEQUENCE: 267
gtagcttcag attactcgtg tgttaactgg gtcatgaatc cgtgatccaa cgttagaaca    60
agaacaaaac ctgaatagaa gagaaaggct atttggtgga tgttgcagaa atactagcga   120
tgaagtctca cattgctgag aagagaaaac aatgacctga tattttatta taaaagacaa   180
ctctggagcc ttaaaagctc                                               200

SEQ ID NO: 268          moltype = DNA   length = 400
FEATURE                 Location/Qualifiers
source                  1..400
                        mol_type = genomic DNA
                        organism = Glycine max
SEQUENCE: 268
aagaatgtcc actctcaatc actaagttgt tgtttccttt ttaattcact catttttaga    60
attatcagtg ttatactgaa tctagattga aacatttgtg cccgaagact ccatccatga   120
caaagcccca tatcgtctag aagagatgac aatcactcca gggcttatca taaaaaagac   180
tttttgcagc tgtaacactc aagaatgtcc actctcaatc actaagttgt tgtttccttt   240
ttaattcact cattttaga attatcagtg ttatactgaa tctagattga aacatttgtg   300
cccgaagact ccatccatga caaagcccca tatcgtctag aagagatgac aatcactcca   360
gggcttatca taaaaaagac tttttgcagc tgtaacactc                         400

SEQ ID NO: 269          moltype = DNA   length = 200
FEATURE                 Location/Qualifiers
source                  1..200
                        mol_type = genomic DNA
                        organism = Glycine max
SEQUENCE: 269
agctgaggaa ggtagcttca gattactcgt gtgttaactg ggtcatgaat ccgtgatcca    60
acgtttgaac aagagcaaaa tctgaataga agagaaaggc tgttgcagaa atactagtga   120
tgaagtctca cattgctgag aagagaaaac aatgacctga tattttatta taaaacacaa   180
ctctggagcc ttaacaactc                                               200

SEQ ID NO: 270          moltype = DNA   length = 200
FEATURE                 Location/Qualifiers
source                  1..200
                        mol_type = genomic DNA
                        organism = Glycine max
SEQUENCE: 270
gttaatatta ttactcgtgt gttaactggg tcatgaatcc gcgatccaac gttagcacaa    60
gaacaaaatc tgaatagaag agaaaaggcg atttggtgga tatagcagaa gaactagtga   120
gaaagtccca cattgctgag aagagaaaac aataacatga tgtttattta taaaacgcaa   180
ctctggagtg tgaacaactc                                               200

SEQ ID NO: 271          moltype = DNA   length = 200
FEATURE                 Location/Qualifiers
source                  1..200
                        mol_type = genomic DNA
                        organism = Glycine max
```

```
SEQUENCE: 271
tctgtggaaa gattgaagat tcaatacaaa ccagaccctg tcttgtttttg ttttggaatt        60
atcagttctc tattgcagcc agacccagag caagcgtgga tgttgcggaa gtactagtta       120
tgaagtccca cattgctgag aagagaaaac aatgacctga tgtttttatta taaaatgcaa       180
ctctggaaca tgaacaactc                                                     200

SEQ ID NO: 272              moltype = DNA    length = 200
FEATURE                     Location/Qualifiers
source                      1..200
                            mol_type = genomic DNA
                            organism = Glycine max
SEQUENCE: 272
agtaaaatat caacgggaag attataatgt gtttgaactt tcattagtct caggtttgaa        60
cttttatgtt gctgatctaa atttttaacc atgttgctct tggctaggat gttgggatga       120
attagtccca catttgtcag aactttgtca ggcagctgaa gctcccagta taaaatttga       180
atacttacat tgtacaaagc                                                     200

SEQ ID NO: 273              moltype = DNA    length = 200
FEATURE                     Location/Qualifiers
source                      1..200
                            mol_type = genomic DNA
                            organism = Glycine max
SEQUENCE: 273
agttcttgtt tctttttaa ttaattcatt ttcagaatta ttatacacaa aaactagctt         60
gaaaaatttg tgcccattgt ccaagactcc atccatgact aggcgtctaa gccgcatcga       120
ttaagtccca tatcgcttag aaaatatgac aatcactcca gagcttatta taaaagagac       180
atttttagac taaggcattc                                                     200

SEQ ID NO: 274              moltype = DNA    length = 200
FEATURE                     Location/Qualifiers
source                      1..200
                            mol_type = genomic DNA
                            organism = Glycine max
SEQUENCE: 274
ctaaattctt gtttcttttt taattcactc attttcagaa ttattataca caaactagct        60
tgaaaatttt gtgcccattg tcgaagactc caccatgact aagggtctaa gccccatcga       120
ataagtccca tatcacttag aaaagatgaa aatgactcca gagcttatta taaaataaac       180
attttttacac tgttatattc                                                    200

SEQ ID NO: 275              moltype = DNA    length = 200
FEATURE                     Location/Qualifiers
source                      1..200
                            mol_type = genomic DNA
                            organism = Glycine max
SEQUENCE: 275
ctggatccaa cttataaatc agttataggg ggtttagcat gactccagat gggttgtgaa        60
atatgcatgt gagtgcaatc acattaggac acttgaagtt taatgttaaa ccacccacga       120
ttaagtcccg tatcgatgag taaagataac aatcatctga agtattttta taaaacgcac       180
gtttcaaagc atagaaattc                                                     200

SEQ ID NO: 276              moltype = DNA    length = 200
FEATURE                     Location/Qualifiers
source                      1..200
                            mol_type = genomic DNA
                            organism = Glycine max
SEQUENCE: 276
tgataggtga attaattatt tttaatatac gaatgaggaa gaaagaaaaa ctattataac        60
aatctgctaa gttggggccg aagttgaagt atcaagcgca cgagtgcctc tgtatagtga       120
aaaaagccca catcgagcag cttactaagt tgaagtaaac tctaggctat aaaatgagag       180
agctactcgt cagttcaacc                                                     200

SEQ ID NO: 277              moltype = DNA    length = 200
FEATURE                     Location/Qualifiers
source                      1..200
                            mol_type = genomic DNA
                            organism = Glycine max
SEQUENCE: 277
catgttgaga tgaaagatca agtattcgta ttgcattgat gagtcagatc attgactttg        60
gagatgctct acatagagaa gagaaagtga aggatcaagt gtcattcttt gtttctggcg       120
aaggtccaca tcgagccgca tactgaggga aagtgagctg cttgtactat aaatttcaaa       180
ggtgcatctg taaacaaatc                                                     200

SEQ ID NO: 278              moltype = DNA    length = 200
FEATURE                     Location/Qualifiers
source                      1..200
                            mol_type = genomic DNA
                            organism = Glycine max
SEQUENCE: 278
caagctagtt gtcccaagcc tgcatagagt gataacagca tgctaataac tcccaaagaa        60
```

```
cacagatgaa aaatcaagta tcaagtgtgt gggtgctaac atttcagatt ctgactaaat    120
aaagcccaca tcgaatggta tacttagagc tagtaagctg cttacgctat aaaatgaaag    180
gctcattgct attgatattc                                                200

SEQ ID NO: 279          moltype = DNA   length = 200
FEATURE                 Location/Qualifiers
source                  1..200
                        mol_type = genomic DNA
                        organism = Glycine max
SEQUENCE: 279
aacaccatca gaagctatga agaagaacaa aaggctcctg gagatattcc atttttcatt     60
gattccctat cttcatgata ttaacagtgt gggagccttg cctgagttta catttctgac    120
caaagcccac atcgactggt attgtaatag caagtgaact ggttatacaa taaaaggaaa    180
gggctgttag ctcattactt                                                200

SEQ ID NO: 280          moltype = DNA   length = 200
FEATURE                 Location/Qualifiers
source                  1..200
                        mol_type = genomic DNA
                        organism = Glycine max
SEQUENCE: 280
caacaataag ttggtacctt tagagaaaag acatgctttc tgtgtatagc attattagcg     60
cacagttgat agaaaatgaa gtattgtata tgggtatgat cgagtgtcta tttcttgagc    120
aaagcccaca ttgagtaata taccaaatag aagtgaactg cttatgctat aaaatggaag    180
agctgcattt agtttttaagc                                               200

SEQ ID NO: 281          moltype = DNA   length = 200
FEATURE                 Location/Qualifiers
source                  1..200
                        mol_type = genomic DNA
                        organism = Glycine max
SEQUENCE: 281
atgtgagatg aaaaatcaag tattcataat gggtggacga gactgtgaca acttcattca     60
ggggtattac aggtgactgg aaagaaagta ttaagtgtgc gggtgctaac ttttctgact    120
aaagtccaca tcgaagggta taccaagagc aagtaagcag cttatgctat aaaatgaaag    180
ggtcgtttgt tttgttactc                                                200

SEQ ID NO: 282          moltype = DNA   length = 200
FEATURE                 Location/Qualifiers
source                  1..200
                        mol_type = genomic DNA
                        organism = Glycine max
SEQUENCE: 282
aaagatcaag tattcatatt gcattgatga gtgagaccat tgactttgta gatgctaccg     60
ttgatagaag agaaagtgaa ggatcaagta tggtcatttc tttgtttccg tcttctaacg    120
aaggtccaca tcgagccgta ttctgagtga gagtgagctg cttataatat aaaattcgaa    180
ggtgtttact tactaaaaca                                                200

SEQ ID NO: 283          moltype = DNA   length = 389
FEATURE                 Location/Qualifiers
source                  1..389
                        mol_type = genomic DNA
                        organism = Glycine max
SEQUENCE: 283
tagagagaat cgttaagaaa aaaataaata gtaaagtaaa tgaaaaccca aataatatca     60
ttattatgtc aataagtcgg agaggatagt aatcaaatgg tctatgaggt ggtggttcat    120
tcaacatata gcacctattc attgttccta aaacataatt taagaacaaa aacttaaact    180
taaataataa taataaaaga gtacatcgaa gtatctgtgt tctctatcct tctgactaac    240
attcatgttg tttgtattca gcaaagggcc gtgcaggatt tgtgcgtcgc gctccggtta    300
gttattgcag tgaccgtctc tttagtccca catcgagtaa ttatgcttca tacagtctgt    360
ttatataaca gagatggaac aaactggtt                                      389

SEQ ID NO: 284          moltype = AA   length = 9
FEATURE                 Location/Qualifiers
source                  1..9
                        mol_type = protein
                        note = Synthetic peptide
                        organism = synthetic construct
SEQUENCE: 284
LAGLIDADG                                                              9

SEQ ID NO: 285          moltype = DNA   length = 28
FEATURE                 Location/Qualifiers
source                  1..28
                        mol_type = other DNA
                        note = consensus sequence
                        organism = synthetic construct
SEQUENCE: 285
agctannatg ttntacaaat ttctncta                                        28
```

```
SEQ ID NO: 286          moltype = DNA  length = 22
FEATURE                 Location/Qualifiers
source                  1..22
                        mol_type = other DNA
                        note = consensus sequence
                        organism = synthetic construct
SEQUENCE: 286
ctatttnntt ctatagcttt tt                                             22

SEQ ID NO: 287          moltype = DNA  length = 16
FEATURE                 Location/Qualifiers
source                  1..16
                        mol_type = other DNA
                        note = consensus sequence
                        organism = synthetic construct
SEQUENCE: 287
atccntctan gnacaa                                                    16

SEQ ID NO: 288          moltype = DNA  length = 20
FEATURE                 Location/Qualifiers
source                  1..20
                        mol_type = other DNA
                        note = consensus sequence
                        organism = synthetic construct
SEQUENCE: 288
naggacanag tgtcancnag                                                20

SEQ ID NO: 289          moltype = DNA  length = 71
FEATURE                 Location/Qualifiers
source                  1..71
                        mol_type = other DNA
                        note = consensus sequence
                        organism = synthetic construct
SEQUENCE: 289
gcgcgttgac cgtgcanant nannggntag ttcnacagaa ngncntagng gcgtgtgtga    60
tcnaaaaaca n                                                         71

SEQ ID NO: 290          moltype = DNA  length = 53
FEATURE                 Location/Qualifiers
source                  1..53
                        mol_type = other DNA
                        note = consensus sequence
                        organism = synthetic construct
SEQUENCE: 290
cntnannggc ntngccnnaa gaaacatggg ccanggccca nnatncaang cac           53

SEQ ID NO: 291          moltype = DNA  length = 48
FEATURE                 Location/Qualifiers
source                  1..48
                        mol_type = other DNA
                        note = consensus sequence
                        organism = synthetic construct
SEQUENCE: 291
cgcnnncaag cccanatacc agttcgtngg tggagcaanc gaggcgct                 48

SEQ ID NO: 292          moltype = DNA  length = 187
FEATURE                 Location/Qualifiers
source                  1..187
                        mol_type = other DNA
                        note = consensus sequence
                        organism = synthetic construct
SEQUENCE: 292
aacagncaaa catttngtnc cacctngncc agncacnatt gcnnannnng gcttataagn    60
cganncgcaa cgcaccncac ngtctcttcg gagacatccg ataaaattgg aacgatacag    120
agaagattag catggcccct gcgcaaggat gacacgcaca aatcgagaaa tggtccaaat    180
ttttttg                                                              187

SEQ ID NO: 293          moltype = DNA  length = 24
FEATURE                 Location/Qualifiers
source                  1..24
                        mol_type = other DNA
                        note = blunt-end oligonucleotide
                        organism = synthetic construct
SEQUENCE: 293
agaagtcctc aagtaccgtt tggc                                           24

SEQ ID NO: 294          moltype = DNA  length = 14
FEATURE                 Location/Qualifiers
```

-continued

```
source                  1..14
                        mol_type = other DNA
                        note = blunt-end oligonucleotide
                        organism = synthetic construct
SEQUENCE: 294
aagtcctcaa ggga                                                      14

SEQ ID NO: 295          moltype = DNA   length = 14
FEATURE                 Location/Qualifiers
source                  1..14
                        mol_type = other DNA
                        note = blunt-end oligonucleotide
                        organism = synthetic construct
SEQUENCE: 295
gctagtaccg tttg                                                      14
```